US012679838B2

(12) United States Patent
Zhang et al.

(10) Patent No.: US 12,679,838 B2
(45) Date of Patent: Jul. 14, 2026

(54) AROMATIC COMPOUND AND APPLICATION THEREOF IN ANTITUMOR DRUG

(71) Applicant: Shanghai Zheye Biotechnology Co., Ltd., Shanghai (CN)

(72) Inventors: Qiang Zhang, Shanghai (CN); Fengtian Du, Shanghai (CN); Haibo Wang, Shanghai (CN); Na Guo, Shanghai (CN); Tao Zhang, Shanghai (CN)

(73) Assignee: Shanghai Zheye Biotechnology Co., Ltd., Shanghai (CN)

( * ) Notice: Subject to any disclaimer, the term of this patent is extended or adjusted under 35 U.S.C. 154(b) by 646 days.

(21) Appl. No.: 18/157,397

(22) Filed: Jan. 20, 2023

(65) Prior Publication Data

US 2023/0159529 A1 May 25, 2023

Related U.S. Application Data

(63) Continuation of application No. PCT/CN2021/109963, filed on Aug. 2, 2021.

(30) Foreign Application Priority Data

| | | |
|---|---|---|
| Aug. 2, 2020 | (CN) | 202010764149.2 |
| Sep. 10, 2020 | (CN) | 202010948887.2 |
| Oct. 11, 2020 | (CN) | 202011080255.5 |
| Oct. 19, 2020 | (CN) | 202011114321.6 |
| Dec. 5, 2020 | (CN) | 202011412233.4 |

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
USPC .......................................................... 546/113
See application file for complete search history.

(56) References Cited

U.S. PATENT DOCUMENTS

| | | | | |
|---|---|---|---|---|
| 2019/0343838 | A1 | 11/2019 | Allen et al. | |
| 2019/0374542 | A1* | 12/2019 | Allen | A61K 31/519 |

FOREIGN PATENT DOCUMENTS

| | | | |
|---|---|---|---|
| CN | 106488910 | A | 3/2017 |
| CN | 110366550 | A | 10/2019 |
| CN | 111205286 | A | 5/2020 |
| CN | 111377918 | A | 7/2020 |
| WO | WO-2018/217651 | A1 | 11/2018 |
| WO | WO-2019/051291 | A1 | 3/2019 |
| WO | WO-2020/239077 | A1 | 12/2020 |
| WO | WO-2021/143693 | A1 | 7/2021 |
| WO | WO-2021/175199 | A1 | 9/2021 |
| WO | WO-2021/249563 | A1 | 12/2021 |
| WO | WO-2022/111644 | A1 | 6/2022 |

OTHER PUBLICATIONS

International Search Report issued in connection with PCT Appl. Ser. No. PCT/CN2021/109963 dated Nov. 1, 2021.
Extended European Search Report issued in connection with EP Appl. No. 21854249.6 dated Jul. 24, 2024.
Chan et al., "Structure-Activity Relationships Study of Two Series of Leukotriene B4 Antagonists: Novel Indolyl and Naphthyl Compounds Substituted with a 2-[Methyl(2-phenethyl)amino]-2-oxoethyl Side Chain", J. Med. Chem. 1996, 39, pp. 3756-3768.
Meco-Navas et al., "SAR of 4-Alkoxybenzoic Acid Inhibitors of the Trypanosome Alternative Oxidase", ACS Med. Chem. Lett., 2018, 9, pp. 923-928.

* cited by examiner

*Primary Examiner* — Jeffrey H Murray
*Assistant Examiner* — Rilla Marie Samsell
(74) *Attorney, Agent, or Firm* — Foley & Lardner LLP

(57) ABSTRACT

An aromatic compound protein inhibitor, a stereoisomer, a tautomer, or a pharmaceutically acceptable salt thereof, a method related to the preparation and use of the compound, a pharmaceutical composition comprising the compound, and a relevant cancer treatment method. The aromatic compound has selective and significant inhibitory activity on a protein, and has a wide application prospect in the field of tumor treatment.

15 Claims, 1 Drawing Sheet

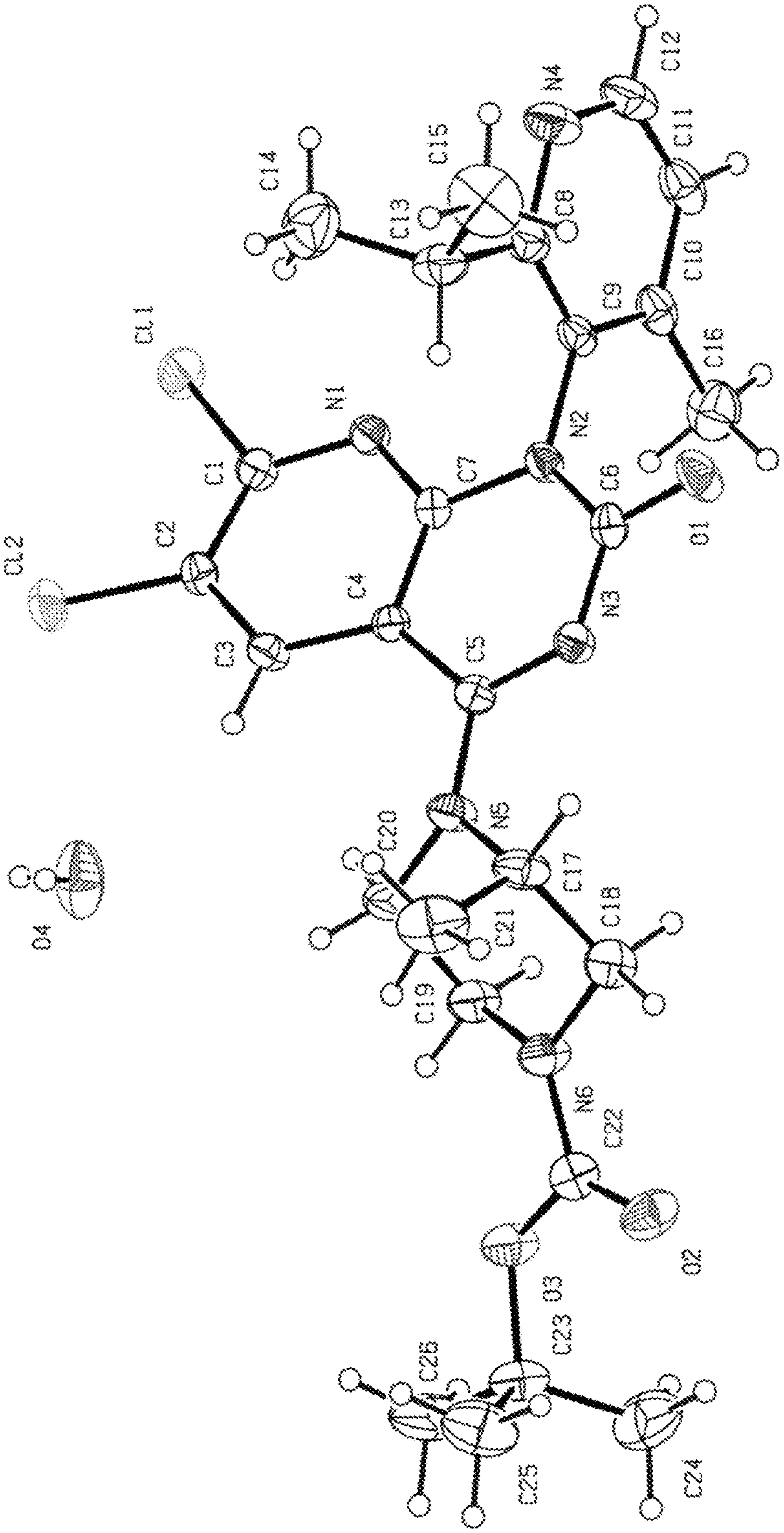

AROMATIC COMPOUND AND APPLICATION THEREOF IN ANTITUMOR DRUG

CROSS-REFERENCE TO RELATED APPLICATIONS

This is a Continuation of International Application PCT/CN2021/109963, filed Aug. 2, 2021, which claims priority to and the benefit of each of the following Chinese applications: (1) CN 202010764149.2, filed Aug. 2, 2020; (2) CN 202010948887.2, filed Sep. 10, 2020; (3) CN 202011080255.5, filed Oct. 11, 2020; (4) CN 202011114321.6, filed Oct. 19, 2020; and (5) CN 202011412233.4, filed Dec. 5, 2020. The disclosures of each of the aforementioned applications are incorporated by reference herein in their entireties.

TECHNICAL FIELD

The present invention relates to an aromatic compound, a preparation method thereof, and an application of the aromatic compound in a drug for treating diseases.

BACKGROUND

Aromatic ring has a conjugated planar ring system, which is covered by delocalized π electron cloud. As a structural unit commonly used in pharmaceutical chemistry design, the aromatic ring widely exists in molecular structures of drugs and plays an important role in improving hydrophilic and hydrophobic properties of the drug molecules.

In drug molecular design, introducing other functional groups into the aromatic ring to form large π bond can effectively regulate a density of abundant electron cloud on the aromatic ring, affect the effective chimerism between the aromatic ring and amino acid residues of a drug target protein, improve the action efficiency of the drug molecule and the target protein, and regulate an ability of the drug molecules in exciting or inhibiting the target protein.

Other functional groups commonly introduced into the aromatic ring include carbonyl compounds (aldehydes, ketones, carboxylic acids and carboxylic acid derivative groups, or the like) and unsaturated alkanes (olefins, alkynes, or the like). For example, introducing other functional groups (for example, carbonyls, unsaturated alkanes, or the like) into the aromatic rings of the molecular structures of the following listed drugs or candidate drugs in clinical stage has achieved ideal results in improving the drug-likeness of the drug molecules, enhancing the drug effect and reducing toxic and side effects.

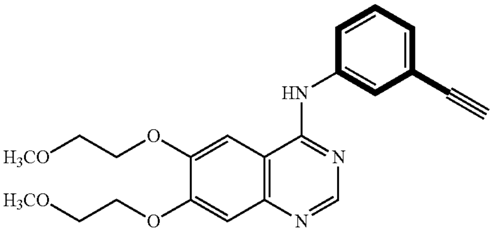

Erlotinib

-continued

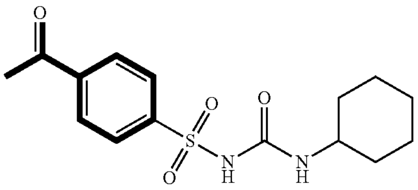

Acetohexamide

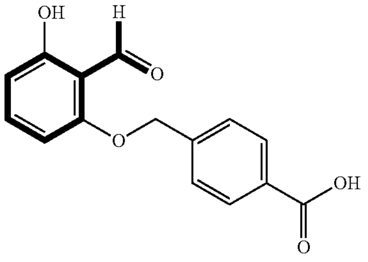

Tucaresol

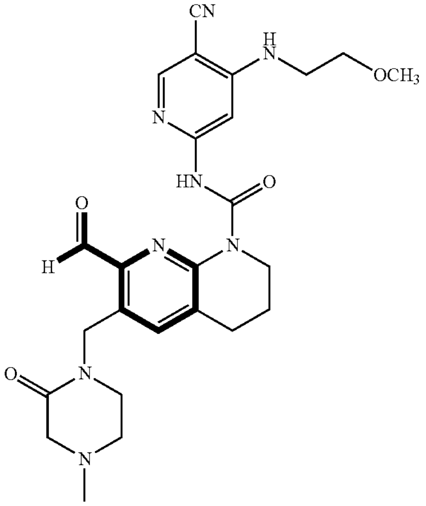

Roblitinib

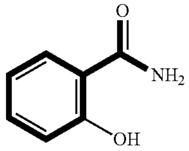

Salicylamide

In recent years, a series of compounds with aromatic structures have been disclosed, which can inhibit the growth of tumor cells by inhibiting the activity of RAS protein. However, there is still a need to find and develop new compounds with better drug effect and pharmacological properties. The invention designs a compound with an aromatic structure, and finds that the compound with such aromatic structures shows excellent antitumor effects.

SUMMARY

The present invention provides a compound represented by formula (I), or a stereoisomer, a tautomer, or a pharmaceutically acceptable salt thereof,

I

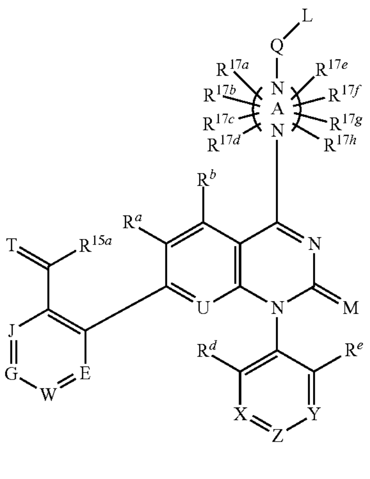

wherein, U is a nitrogen atom or $CR^U$, wherein $R^U$ is hydrogen or deuterium;

M is an oxygen atom or a sulfur atom;

X is a nitrogen atom or $CR^1$, Y is a nitrogen atom or $CR^2$, and Z is a nitrogen atom or $CR^3$;

E is a nitrogen atom or $CR^{11}$, W is a nitrogen atom or $CR^{12}$, G is a nitrogen atom or $CR^{13}$, and J is nitrogen atom or $CR^{11}$;

$R^a$ and $R^b$ are each independently hydrogen, deuterium or halogen;

$R^d$ and $R^e$ are each independently hydrogen, deuterium, halogen, alkyl, deuterated alkyl, haloalkyl, cycloalkyl, hydroxyl, amino, sulfuryl, sulfonamido, carbonamido, alkenyl or alkynyl;

ring A is a 5-7 membered nitrogen-containing heterocyclyl;

$R^1$, $R^2$, $R^3$, $R^{11}$, $R^{12}$, $R^{13}$, $R^{14}$, $R^{17a}$, $R^{17b}$, $R^{17c}$, $R^{17a}$, $R^{17e}$, $R^{17f}$, $R^{17g}$, and $R^{17h}$ are each independently selected from hydrogen, deuterium, halogen, alkyl or deuterated alkyl;

$R^{15a}$ is hydrogen or deuterium;

Q is —C(O)—, —C(S)—, —S(O)—, or —$S(O)_2$—;

T is an oxygen atom or a sulfur atom; and

L is alkynyl, alkenyl, deuterated alkynyl, deuterated alkenyl, chloroalkenyl, or haloalkyl.

The present invention provides the compound represented by the formula (I), or the stereoisomer, the tautomer, or the pharmaceutically acceptable salt thereof, wherein the following structural segment:

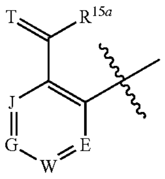

is selected from the following groups:

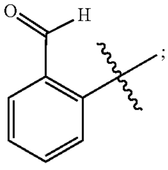 ; 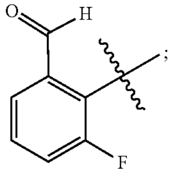 ;

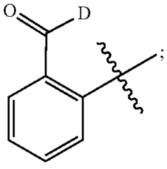 ; 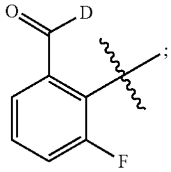 ;

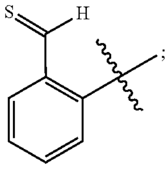 ; 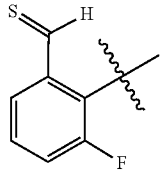 ;

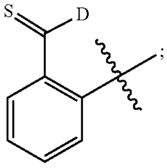 ; 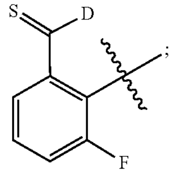 ;

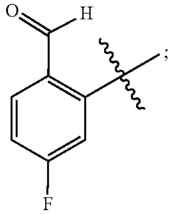 ; 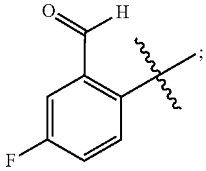 ;

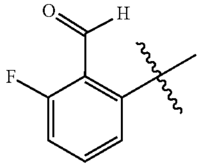 ; 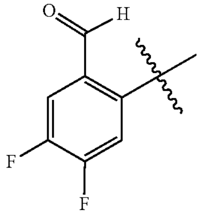 ;

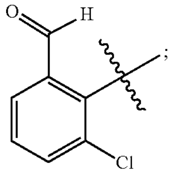 ; or 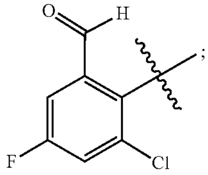 ;

ring A is selected from the following groups:

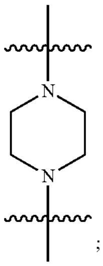 ; 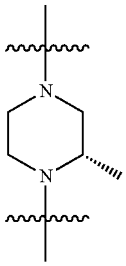 ; 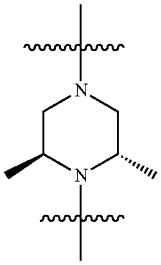 ;

-continued
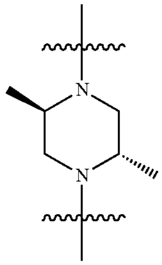 ; 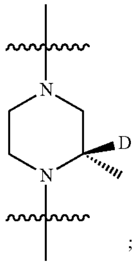 ; 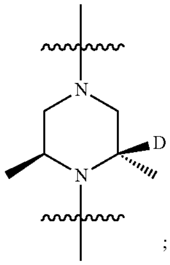 ;
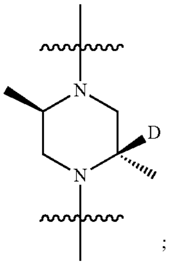 ; 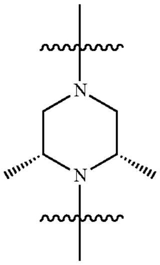 ; 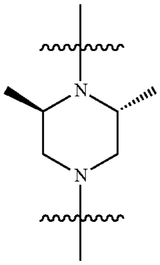 ;
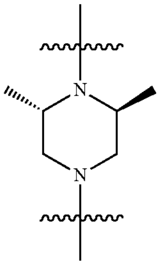 ; 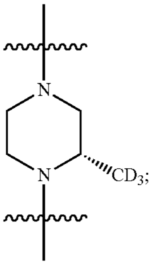 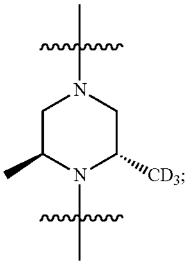
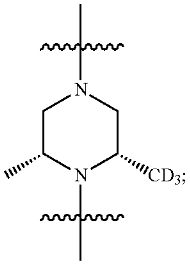 or 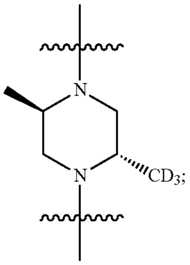
wherein,
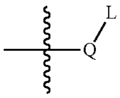
is selected from the following groups:
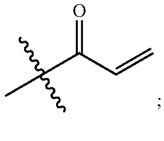 ; or 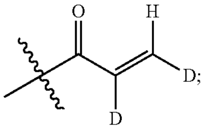
and
wherein,
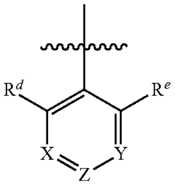
is selected from the following groups:
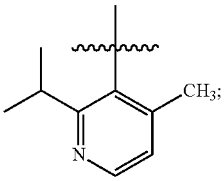 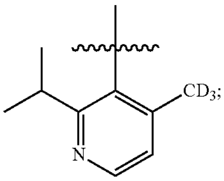
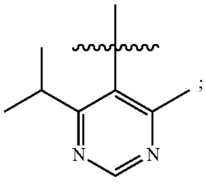 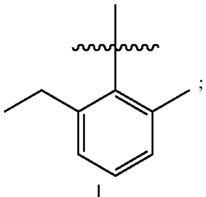
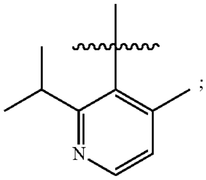 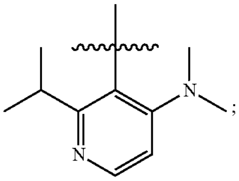
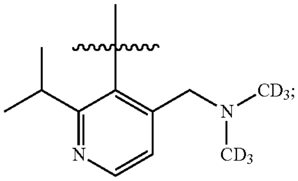 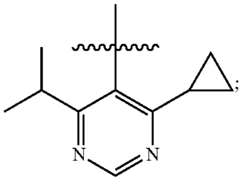
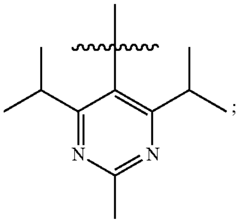 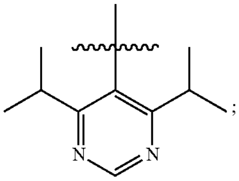
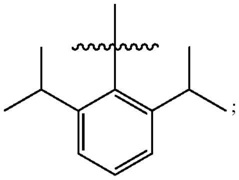 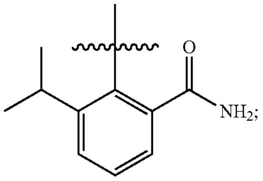
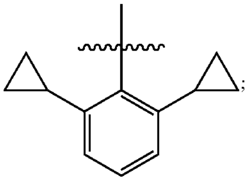 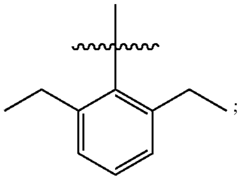

-continued

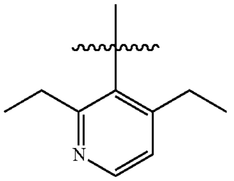
;
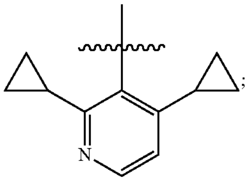
;

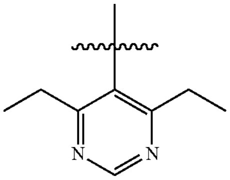
;

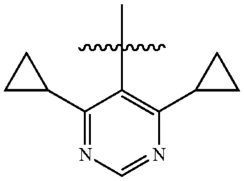
; or

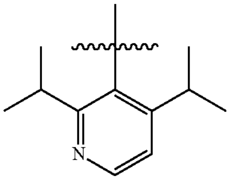
.

The present invention provides a compound represented by formula (II), or a stereoisomer, a tautomer, or a pharmaceutically acceptable salt thereof,

II

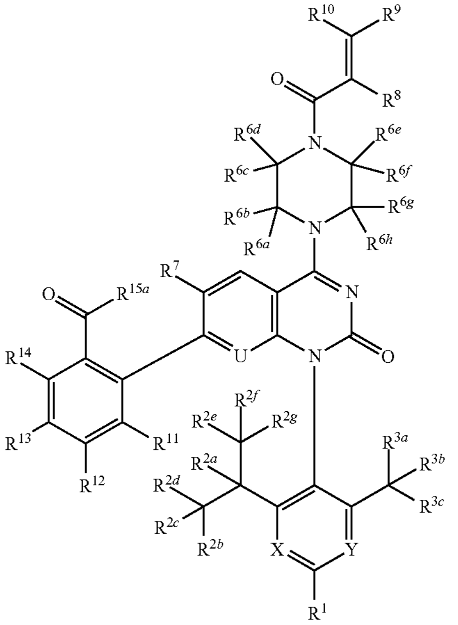

wherein, X is a nitrogen atom or $CR^4$, and Y is a nitrogen atom or $CR^5$;

U is a nitrogen atom or $CR^U$, wherein $R^U$ is hydrogen or deuterium;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{11}$, $R^{12}$, $R^{13}$, and $R^{14}$ are each independently selected from hydrogen, deuterium, halogen, alkyl or deuterated alkyl;

$R^{15a}$ is hydrogen or deuterium;

$R^{6a}$, $R^{6b}$, $R^{6c}$, $R^{6d}$, $R^{6e}$, $R^{6f}$, $R^{6g}$, and $R^{6h}$ are each independently selected from hydrogen, deuterium, methyl or trideuteriomethyl;

$R^7$ is fluorine or chlorine; and $R^8$, $R^9$, and $R^{10}$ are each independently selected from hydrogen, deuterium or fluorine;

wherein, the structural segment

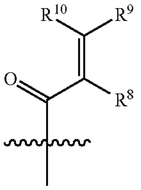

is selected from the following structures:

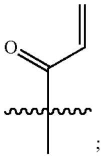
; or
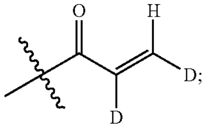
;

wherein, the structural segment

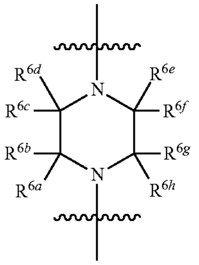

is selected from the following structures:

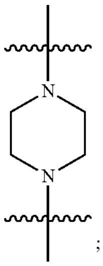
;
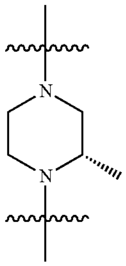
;
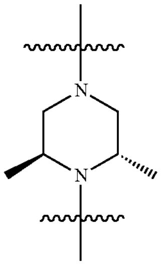
;

-continued
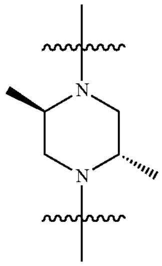
;
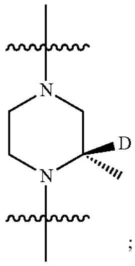
;
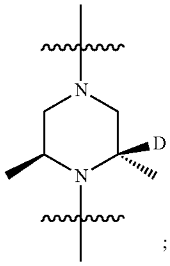
;
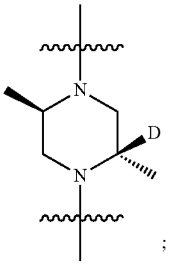
;
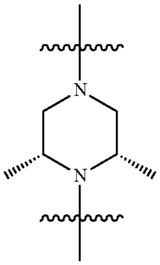
;
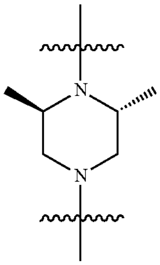
;
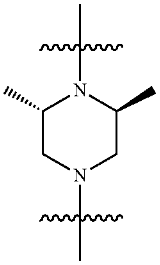
;
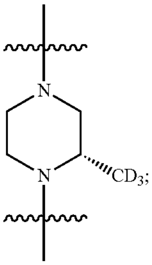
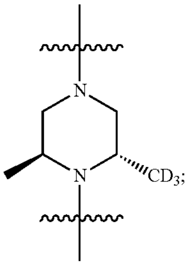
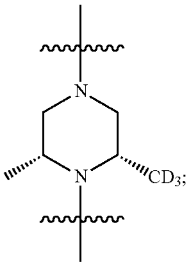
or
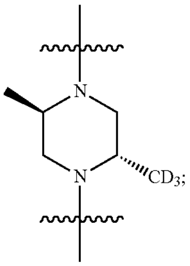
wherein, the structural segment
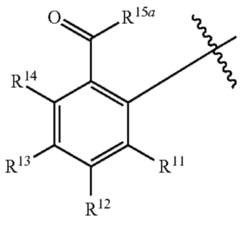
is selected from the following structures:
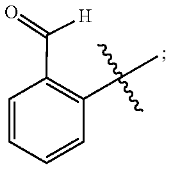
;
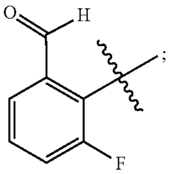
;
-continued
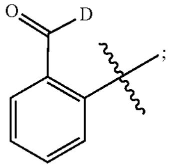
;
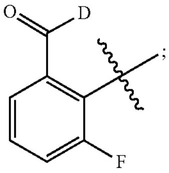
;
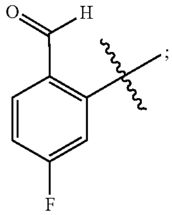
;
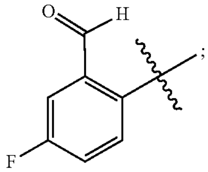
;
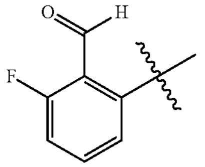
;
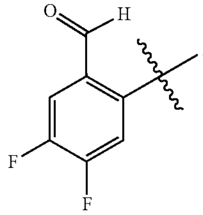
;
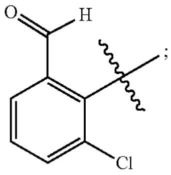
; or
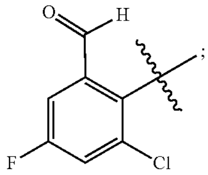
;
and
wherein, the structural segment
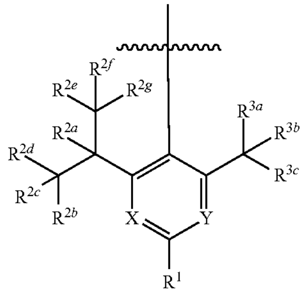
is selected from the following structures:
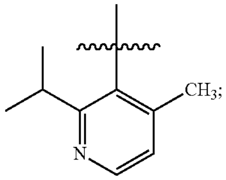
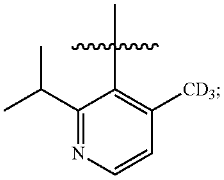
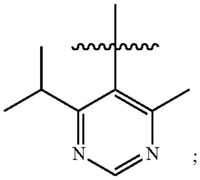
;
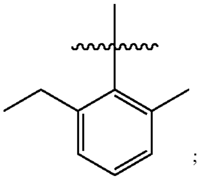
;

-continued

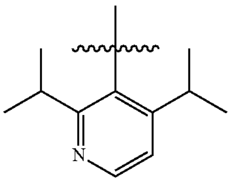

;

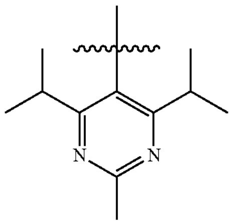

;

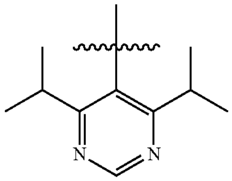

;

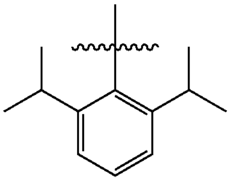

;

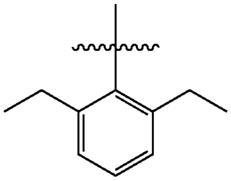

;

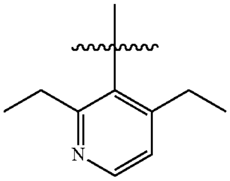

;

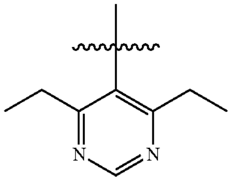

; or

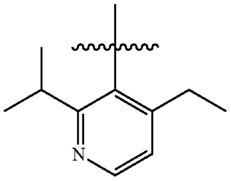

.

The present invention provides a compound represented by formula (III), or a stereoisomer, a tautomer, or a pharmaceutically acceptable salt thereof,

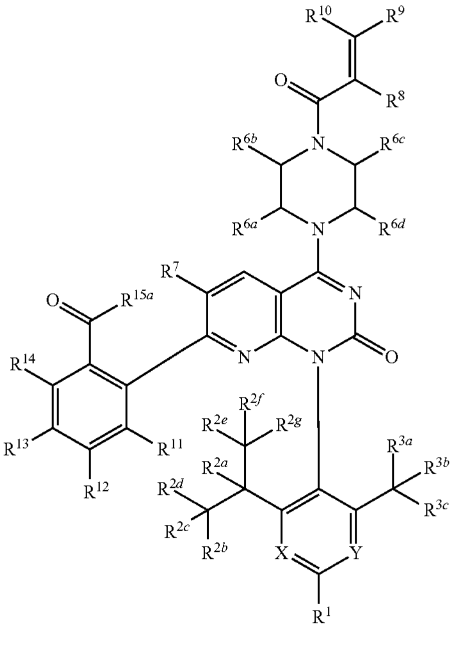

III wherein, X is a nitrogen atom or $CR^4$, and Y is a nitrogen atom or $CR^5$;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{11}$, $R^{12}$, $R^{13}$, and $R^{14}$ are each independently selected from hydrogen, deuterium, halogen, alkyl or deuterated alkyl;

$R^{15a}$ is hydrogen or deuterium;

$R^{6a}$, $R^{6b}$, $R^{6C}$, and $R^{6d}$ are each independently selected from hydrogen, deuterium, methyl or trideuteriomethyl;

$R^7$ is fluorine or chlorine; and $R^8$, $R^9$, and $R^{10}$ are each independently selected from hydrogen, deuterium or fluorine;

wherein, the structural segment

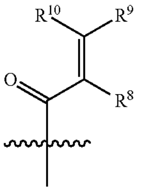

is selected from the following structures:

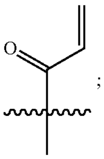

;

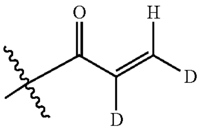

;

wherein, the structural segment

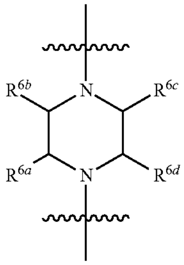

is selected from the following structures:

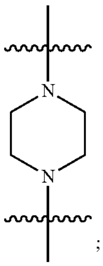

;

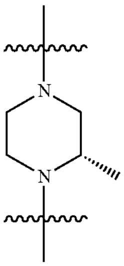

;

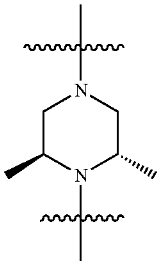

;

-continued
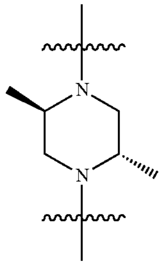 ; 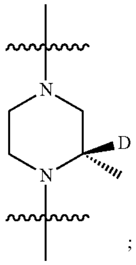 ; 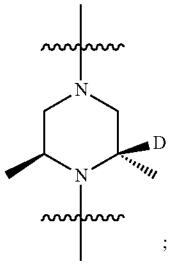 ;
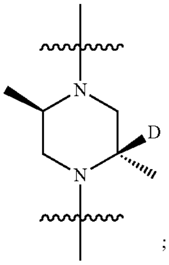 ; 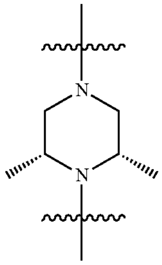 ; 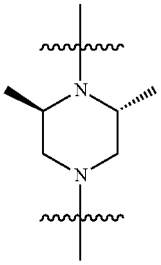 ;
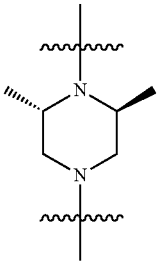 ; 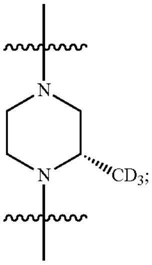 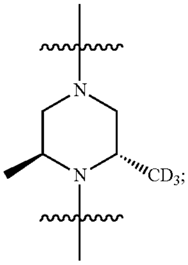
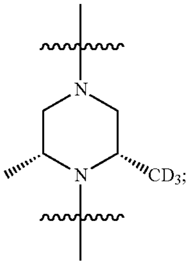 or 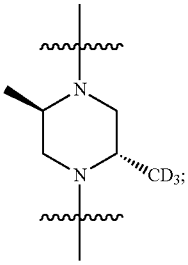
wherein, the structural segment
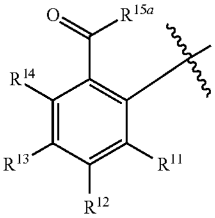
selected from the following structures:
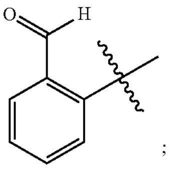 ; 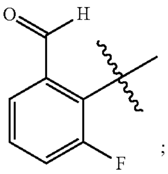 ; 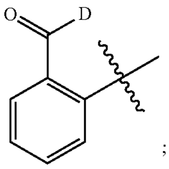 ;
-continued
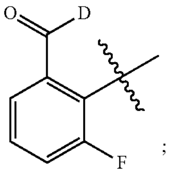 ; 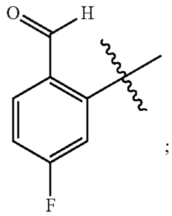 ; 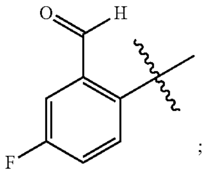 ;
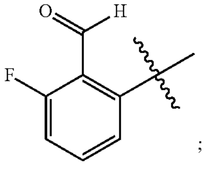 ; 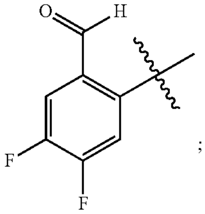 ;
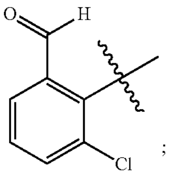 ; or 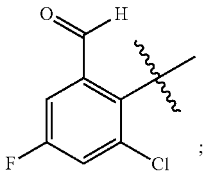 ;
wherein, the structural segment
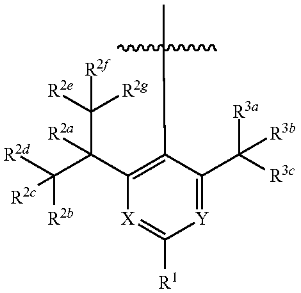
selected from the following structures:
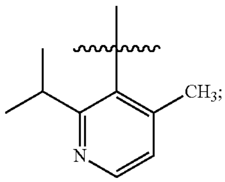 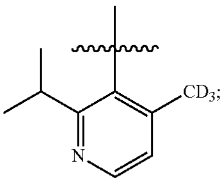
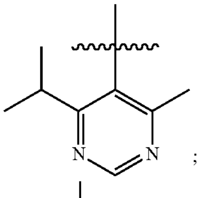 ; 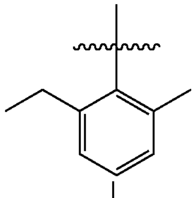 ;
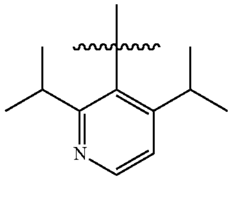 ; 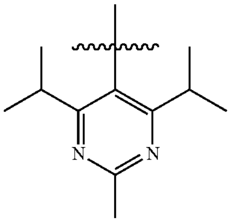 ;

-continued
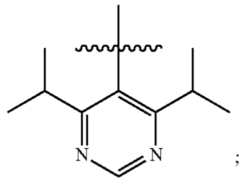 ; 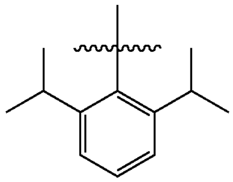 ;
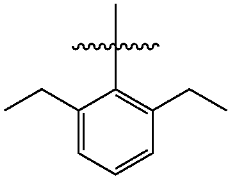 ; 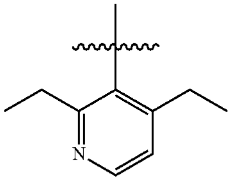 ;
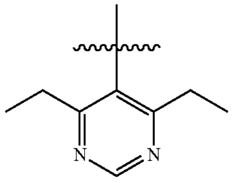 ; or 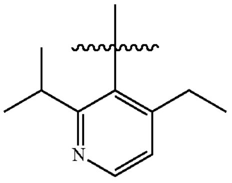 .
The present invention provides the following compounds, or stereoisomers, tautomers, or pharmaceutically acceptable salts thereof,
3-1
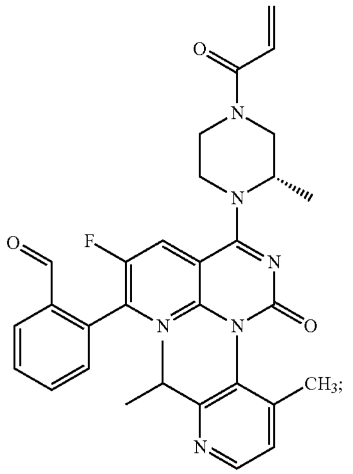
3-2
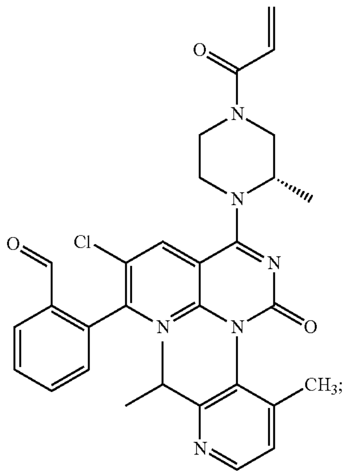
-continued
3-3
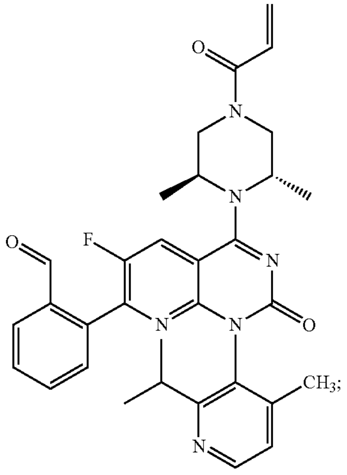
3-4
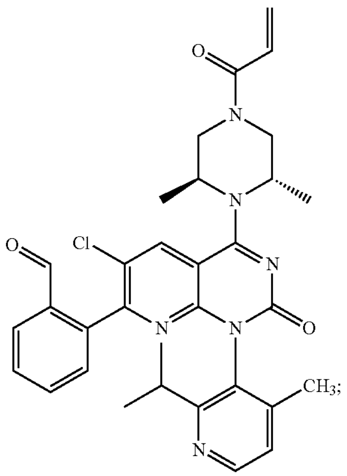
3-5
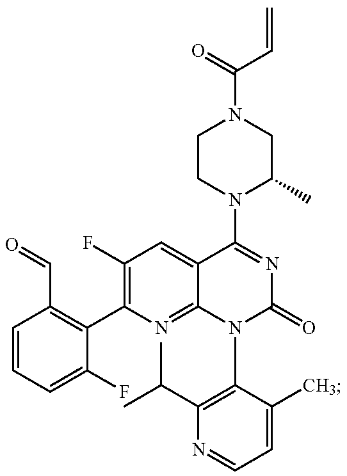

-continued
3-6
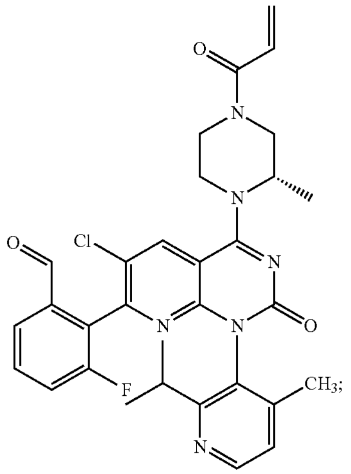
3-7
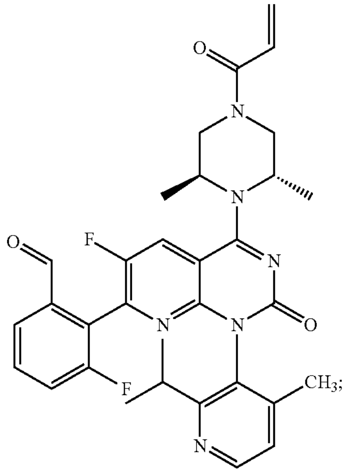
3-8
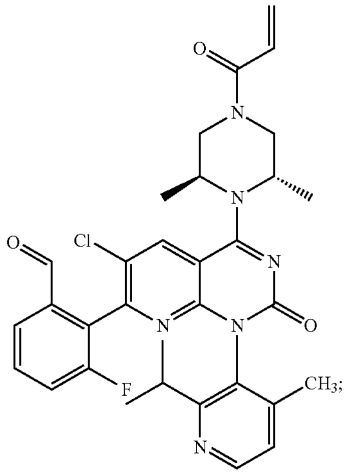
-continued
3-9
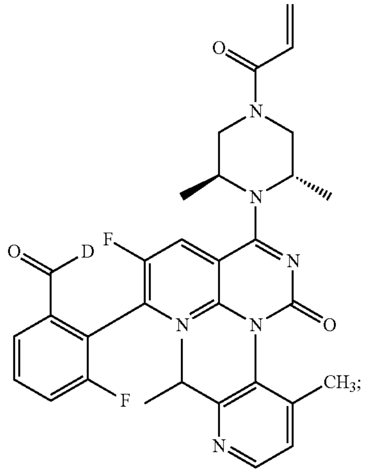
3-10
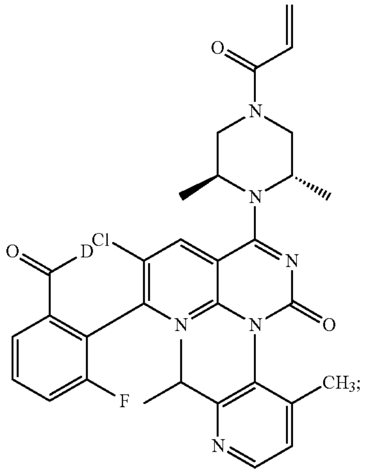
3-11
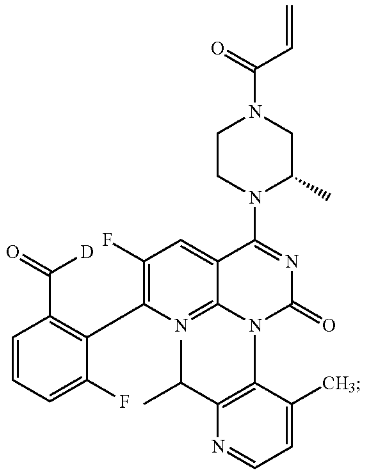

-continued
3-12
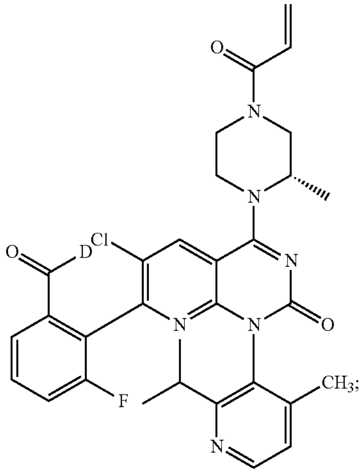
3-13
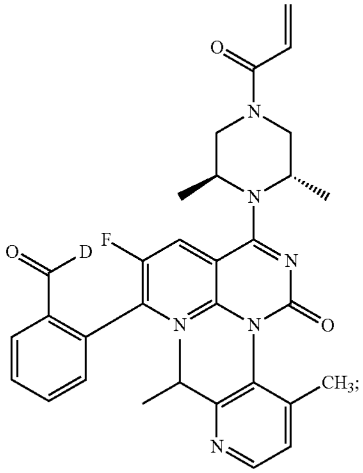
3-14
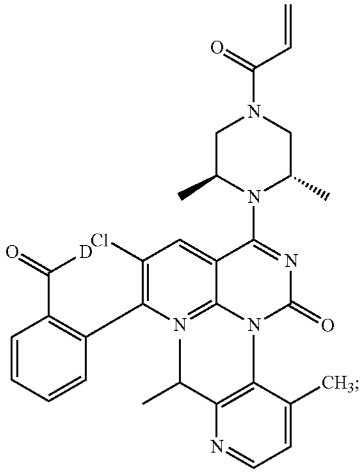
-continued
3-15
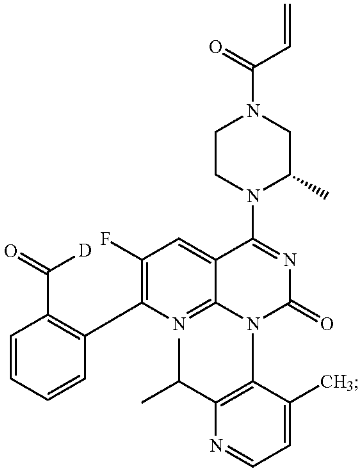
3-16
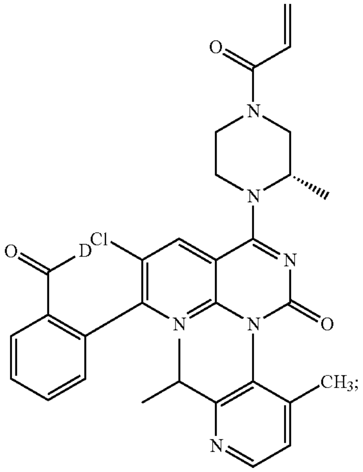
3-17
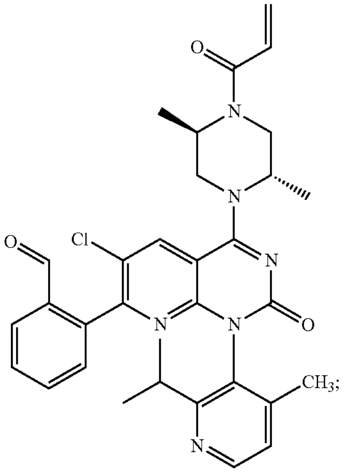

-continued
3-18
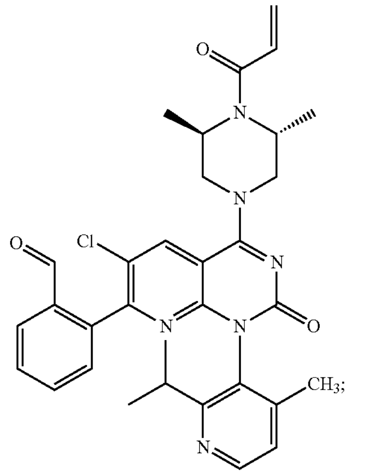
3-19
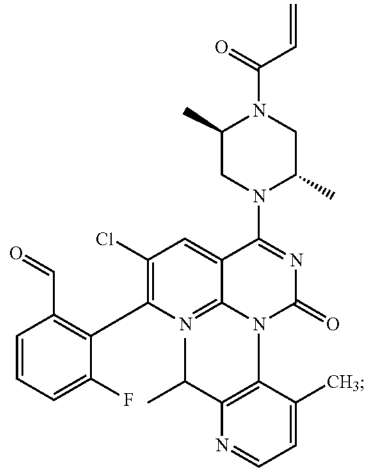
3-20
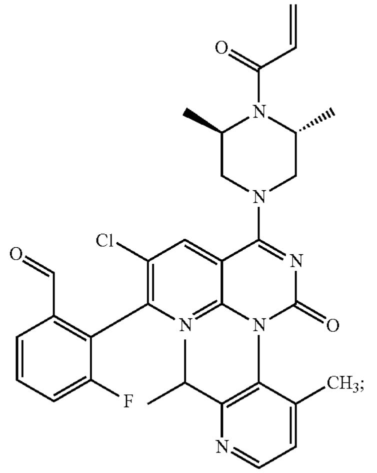
-continued
3-21
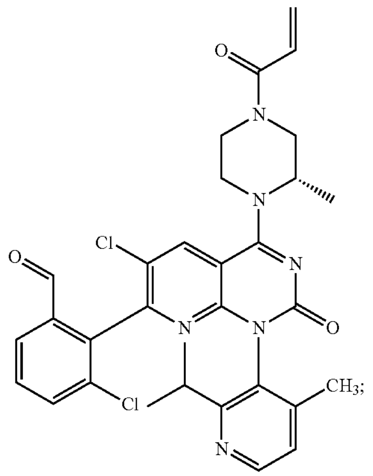
3-22
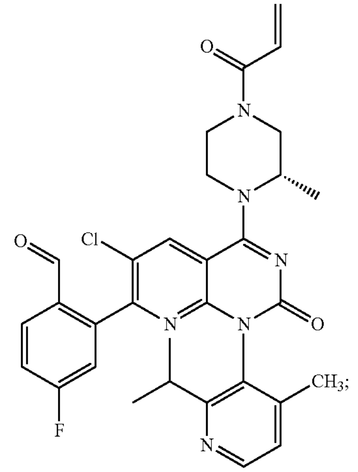
3-23
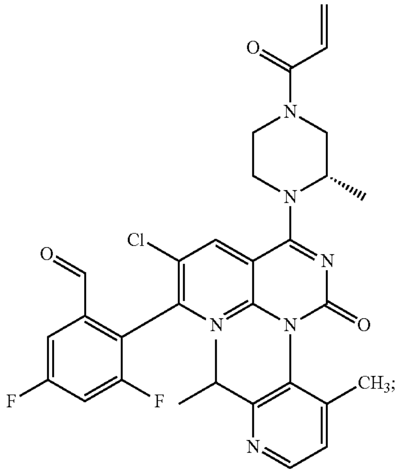

-continued
3-24
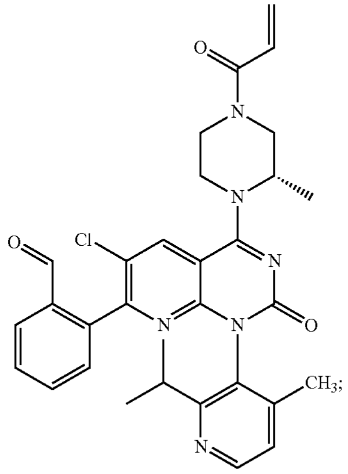
3-25
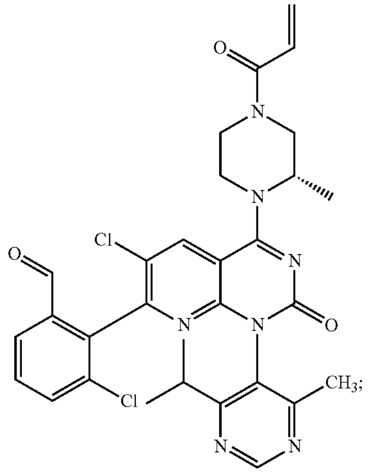
3-26
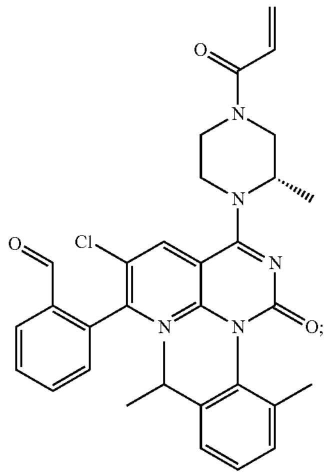
-continued
3-27
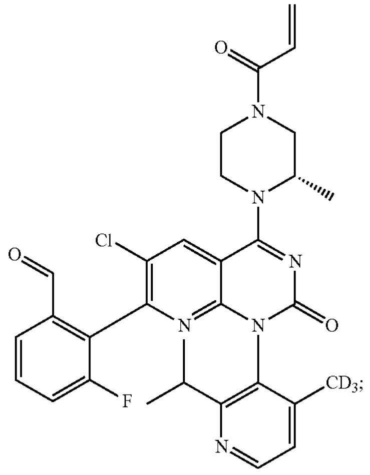
or
3-28
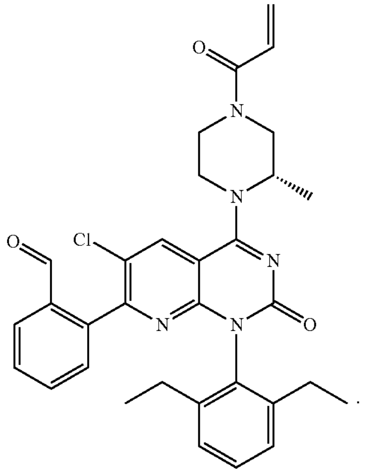
The present invention provides the following compounds, or stereoisomers, tautomers, or pharmaceutically acceptable salts thereof,
3-1B
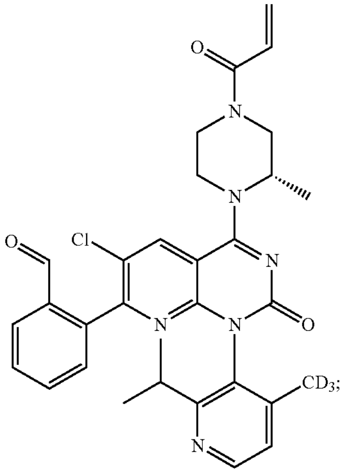

-continued
3-2B
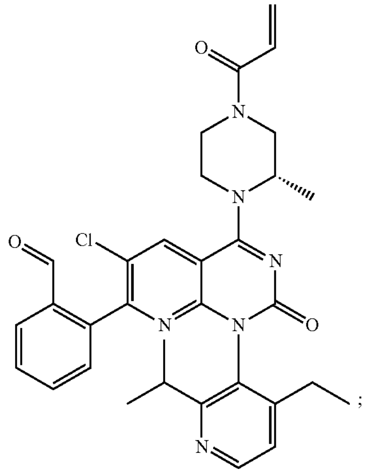
3-3B
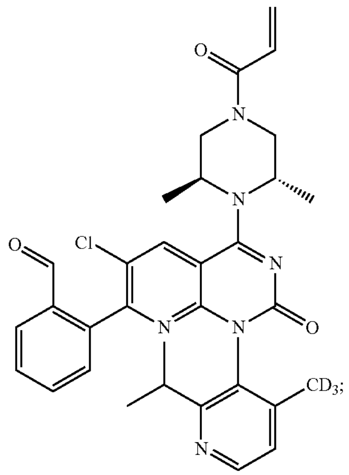
3-4B
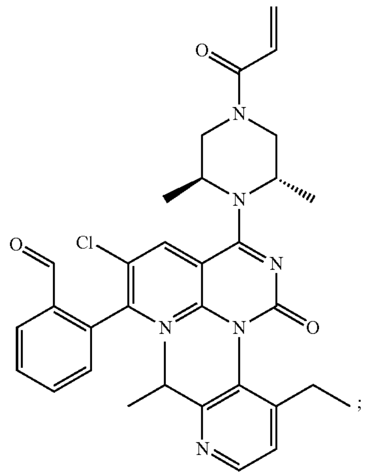
-continued
3-5B
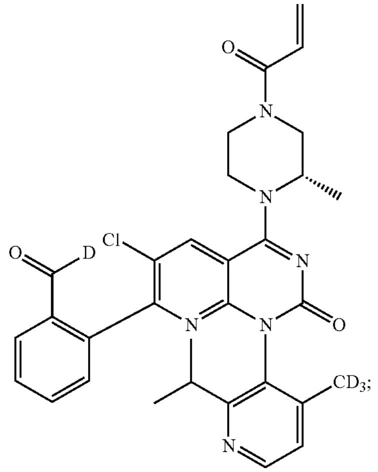
3-6B
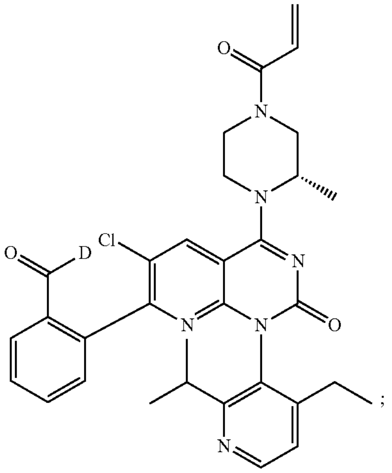
3-7B
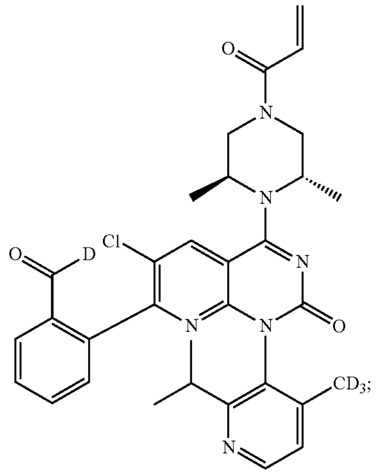

-continued
3-8B
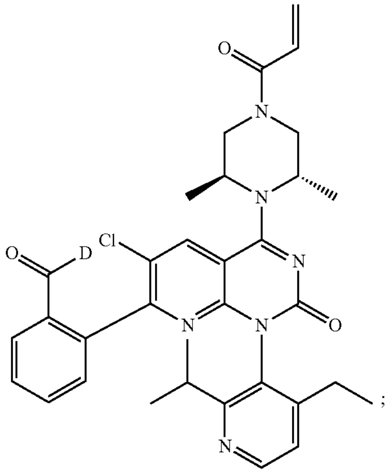
3-9B
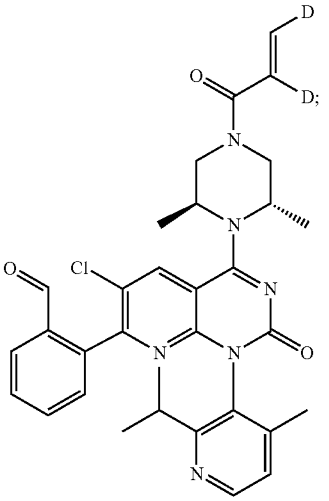
3-10B
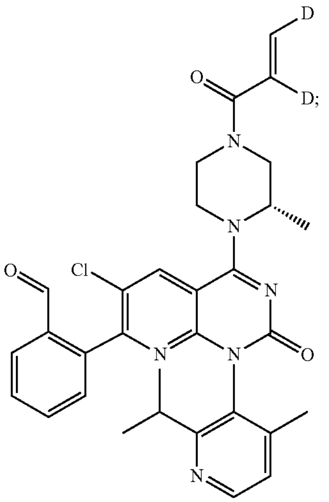
-continued
3-11B
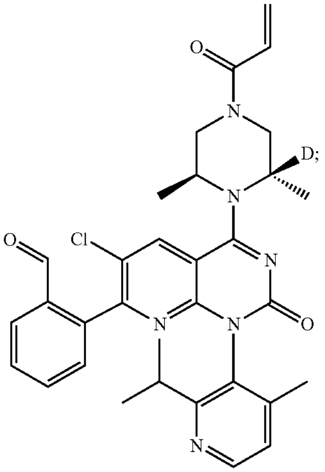
3-12B
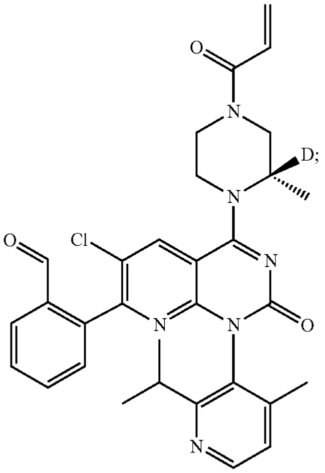
3-13B
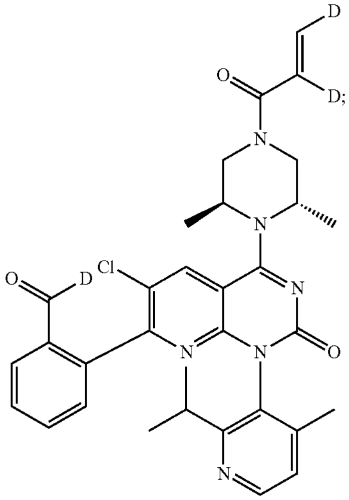

-continued
3-14B
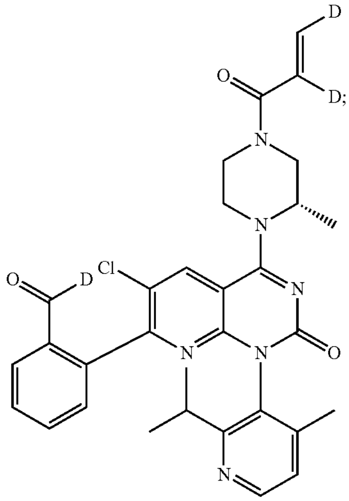
3-15B
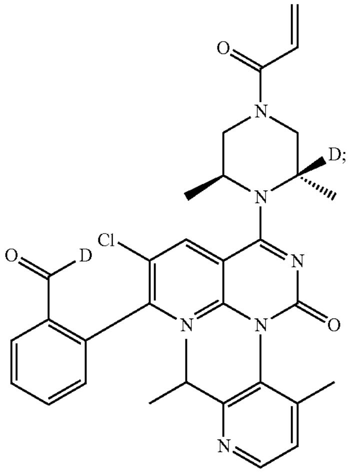
or
3-16B
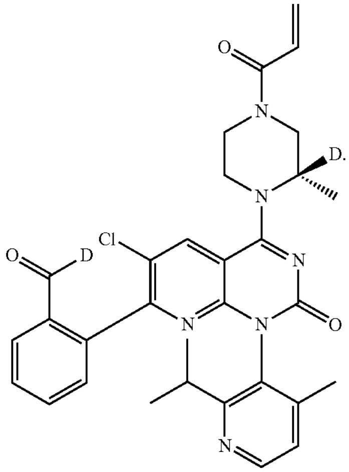
The present invention provides the following compounds, or stereoisomers, tautomers, or pharmaceutically acceptable salts thereof,
3-1MS
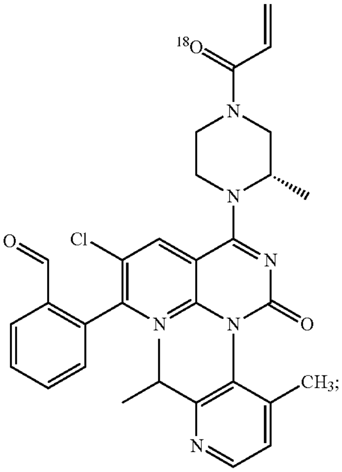
3-2MS
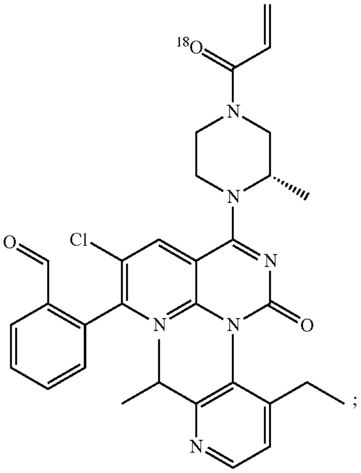
3-3MS
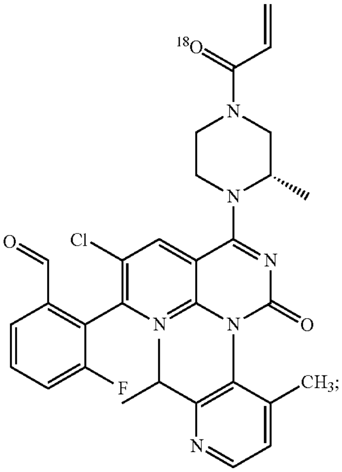

-continued
3-4MS
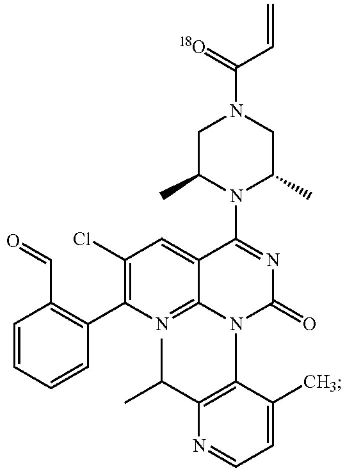
;
3-5MS
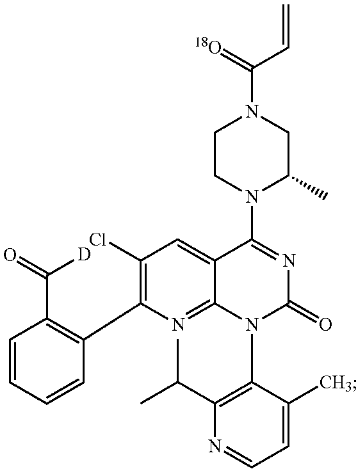
;
3-6MS
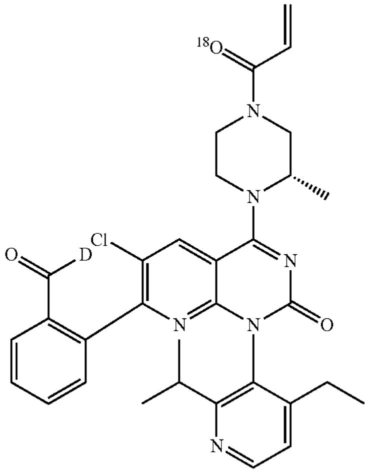
;
-continued
3-7MS
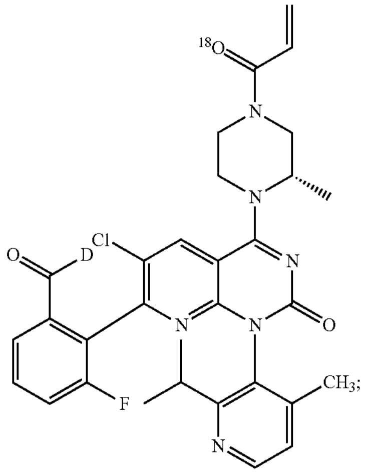
; or
3-8MS
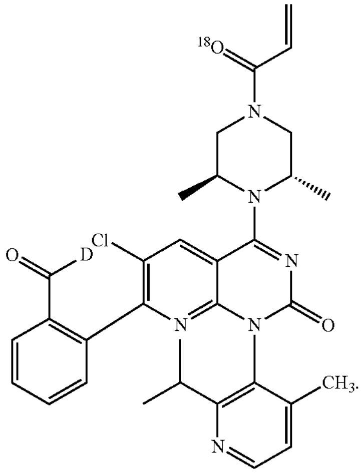
.
The present invention provides the following compounds, or stereoisomers, tautomers, or pharmaceutically acceptable salts thereof,
3K-1
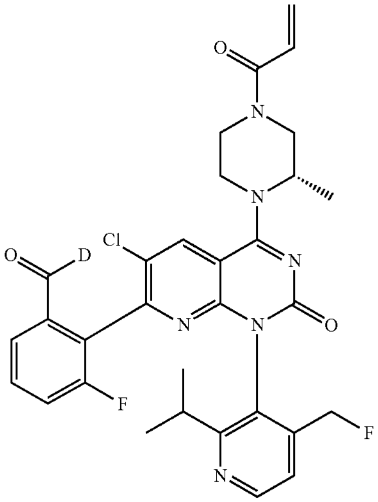
;

-continued
3K-2
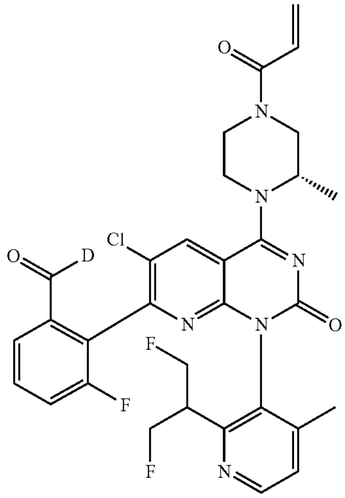
;
3K-3
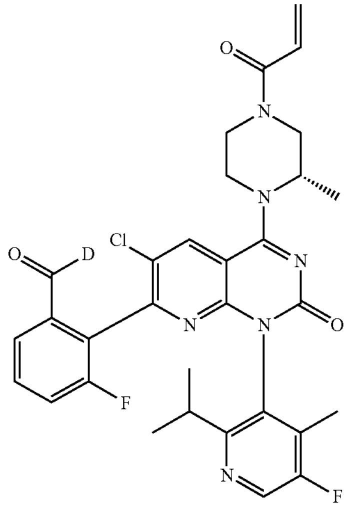
;
3k-4
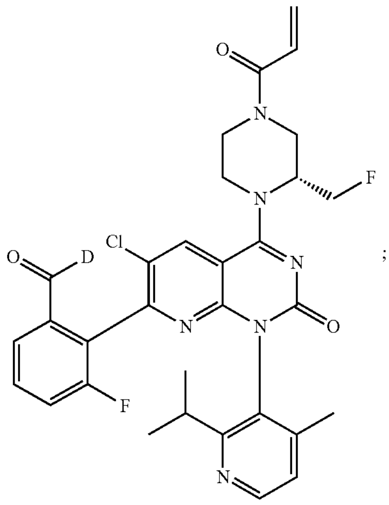
;
-continued
3K-5
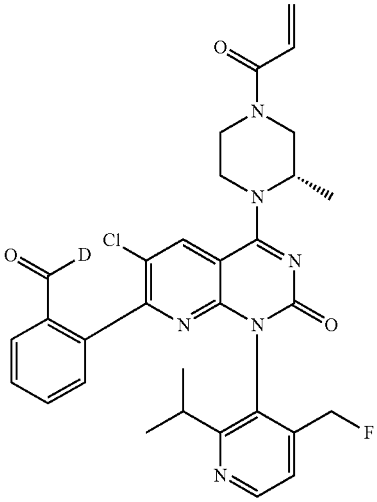
;
3K-6
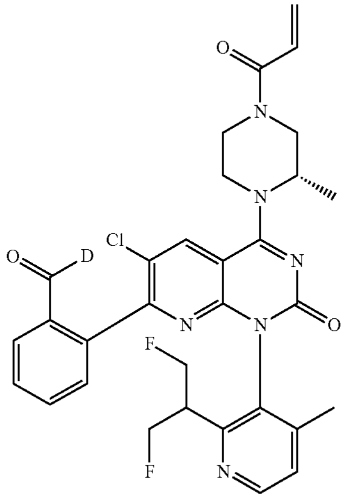
;
3K-7
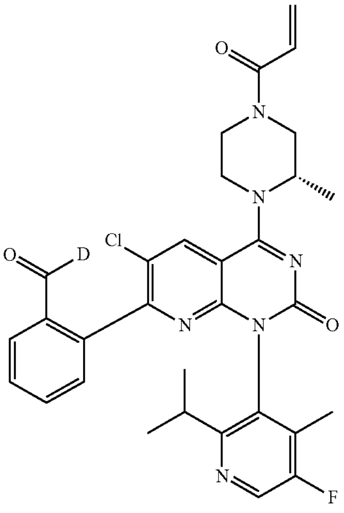
; or -continued 3K-8

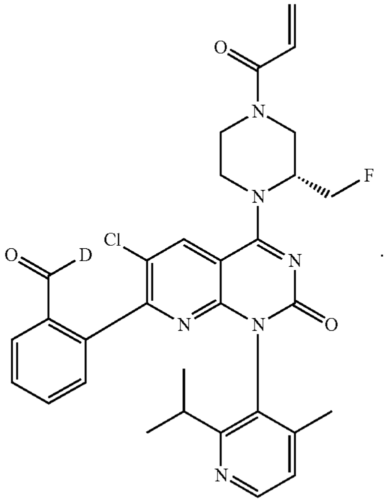

The present invention provides a compound represented by formula (IIIM), or a stereoisomer, a tautomer, or a pharmaceutically acceptable salt thereof,

IIIM

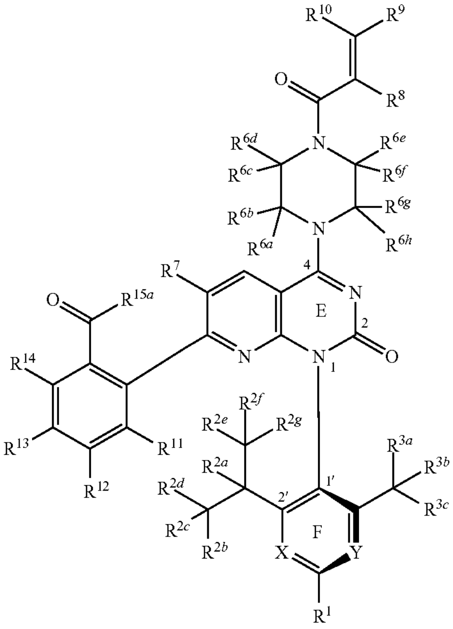

wherein, an axial chiral stereoconfiguration formed by connecting a nitrogen atom at the 1 position of the ring E with a carbon atom at the 1' position of the ring F is optically pure;

X is a nitrogen atom or $CR^4$, and Y is a nitrogen atom or $CR^5$;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{11}$, $R^{12}$, $R^{13}$, and $R^{14}$ are each independently selected from hydrogen, deuterium, alkyl or deuterated alkyl;

$R^{15a}$ is hydrogen or deuterium;

$R^{6a}$, $R^{6b}$, $R^{6c}$, $R^{6d}$, $R^{6e}$, $R^6$, $R^{6g}$, and $R^{6h}$ are each independently selected from hydrogen, deuterium, methyl or trideuteriomethyl;

$R^7$ is fluorine or chlorine; and $R^8$, $R^9$, and $R^{10}$ are each independently selected from hydrogen, deuterium or fluorine;

wherein, the structural segment

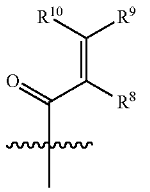

selected from the following structures:

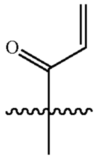
;
and
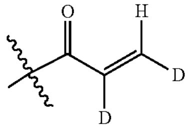
;

wherein, the structural segment

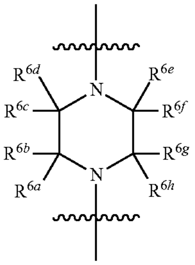

selected from the following structures:

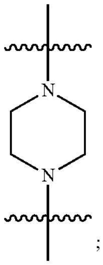
;
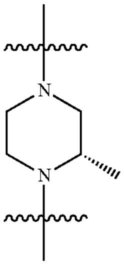
;
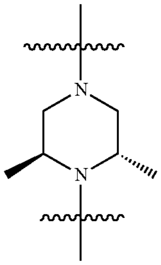
;
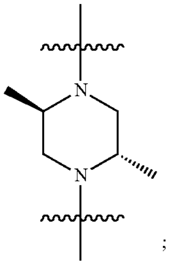
;
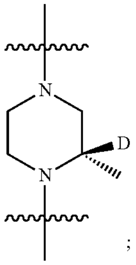
;
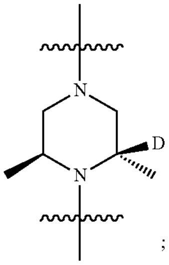
;

-continued
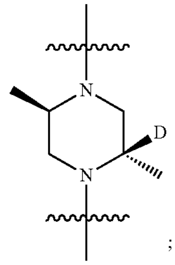 ; 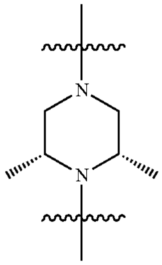 ; 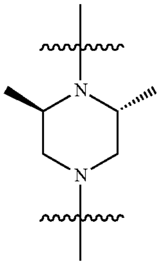 ;
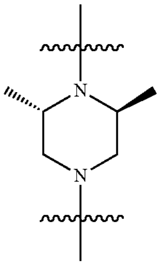 ; 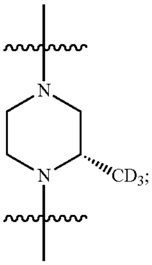 ; 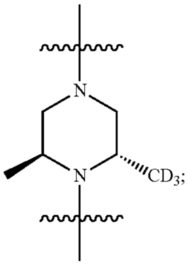
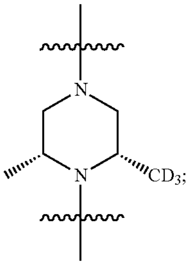 or 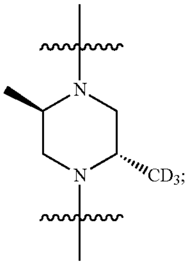
wherein, the structural segment
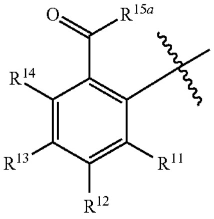
selected from the following structures:
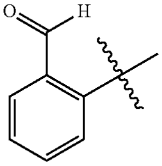 ; 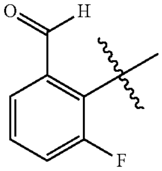 ; 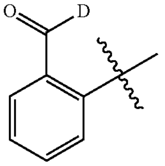 ;
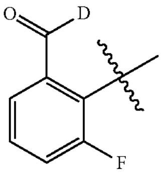 ; 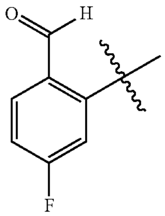 ;
-continued
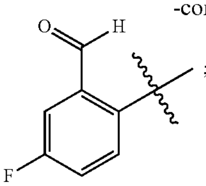 ; 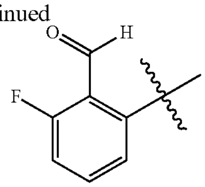 ;
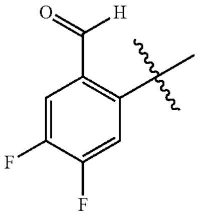 ; 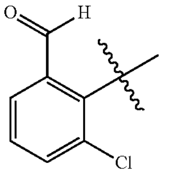 ; or
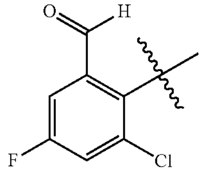 ;
and
wherein, the structural segment
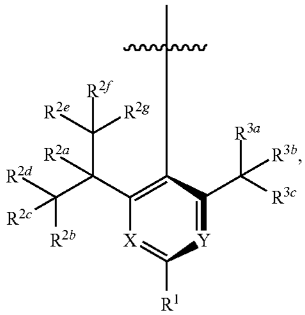
selected from the following structures:
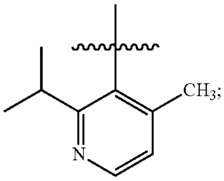 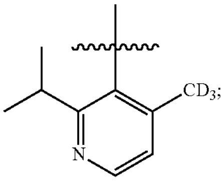
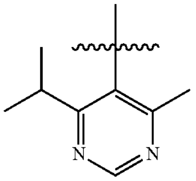 ; 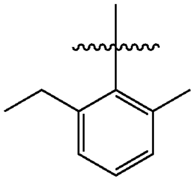 ;
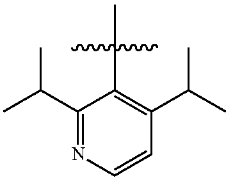 ; 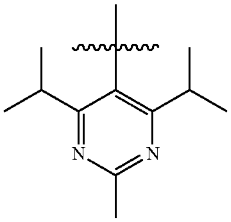 ;

-continued

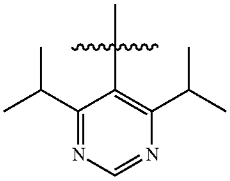 ; 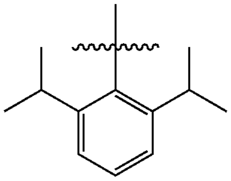 ;

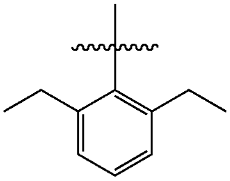 ; 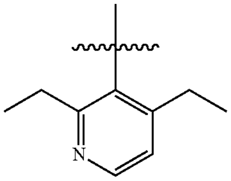 ;

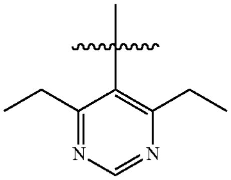 ; or 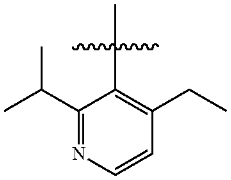 .

The present invention provides a compound represented by formula (IIIM-1), or a stereoisomer, a tautomer, or a pharmaceutically acceptable salt thereof,

IIIM-1

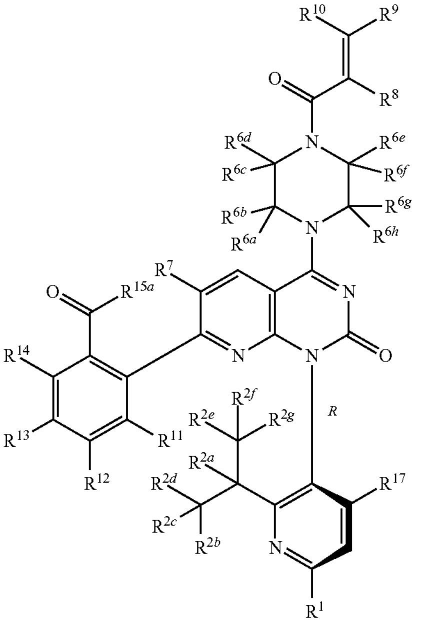

wherein:

$R^1$, $R^{2a}$, $R^{2b}$, $R^{2c}$, $R^{2d}$, $R^{2e}$, $R^{2f}$, $R^{2g}$, $R^{11}$, $R^{12}$, $R^{13}$, and $R^{14}$ are each independently selected from hydrogen, deuterium, alkyl or deuterated alkyl;

$R^{15a}$ is hydrogen or deuterium;

$R^{6a}$, $R^{6b}$, $R^{6c}$, $R^{6d}$, $R^{6e}$, $R^{6f}$, $R^{6g}$, and $R^{6h}$ are each independently selected from hydrogen, deuterium, methyl or trideuteriomethyl;

$R^7$ is fluorine or chlorine;

$R^1$, $R^9$, and $R^{10}$ are each independently selected from hydrogen, deuterium or fluorine; and $R^{17}$ is hydrogen, deuterium, methyl, ethyl, deuterated methyl or deuterated ethyl;

wherein, the structural segment

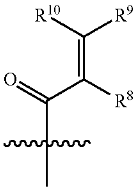

selected from the following structures:

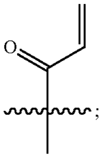 ; or 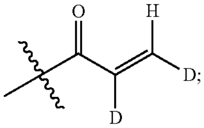 ;

wherein, the structural segment

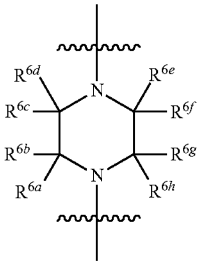

selected from the following structures:

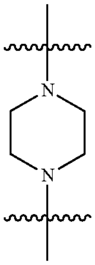 ; 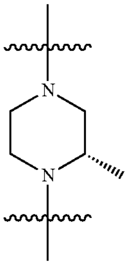 ; 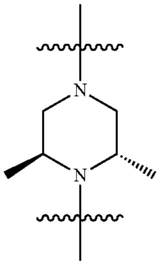 ;

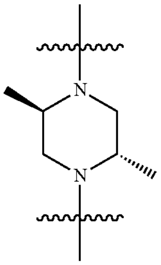 ; 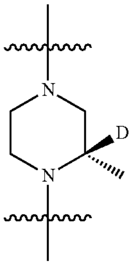 ; 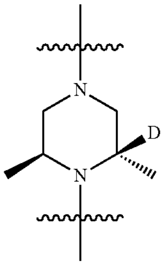 ;

-continued
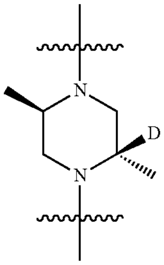 ; 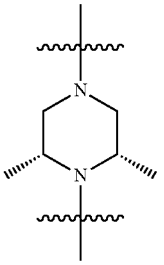 ; 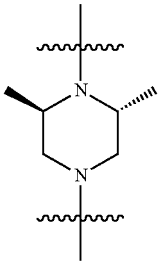 ;
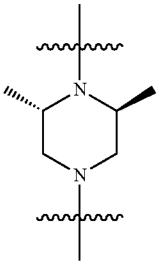 ; 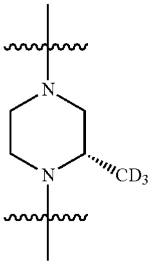 ; 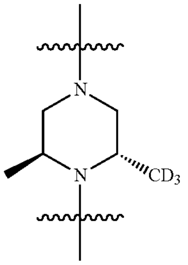 ;
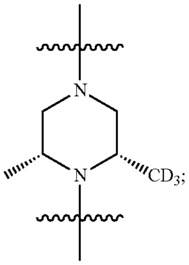 or 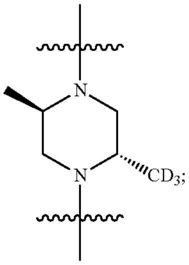
and
wherein, the structural segment
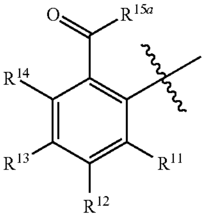
selected from the following structures:
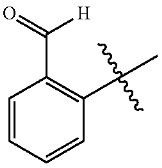 ; 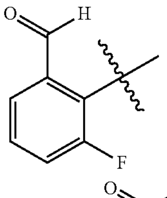 ; 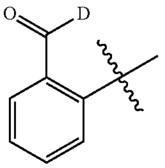 ;
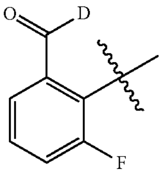 ; 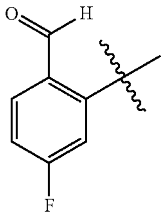 ;
-continued
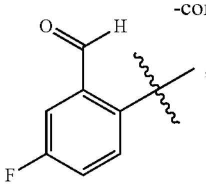 ; 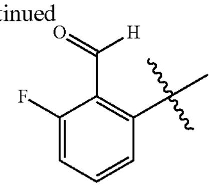 ;
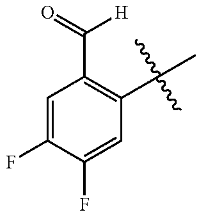 ; 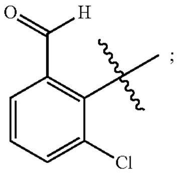 ; or
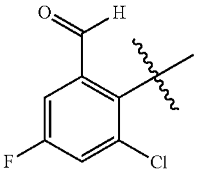 .
The present invention provides the following compounds, or stereoisomers, tautomers, or pharmaceutically acceptable salts thereof,
3-1M
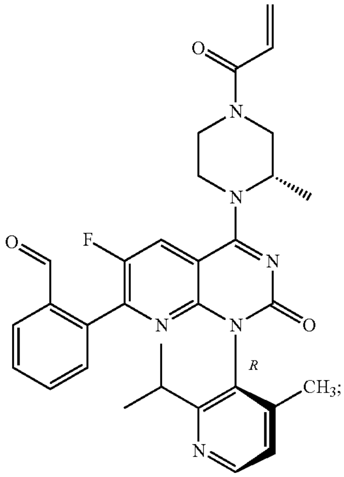
3-2M
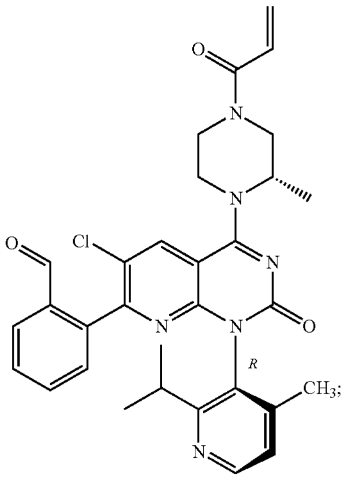

-continued
3-3M
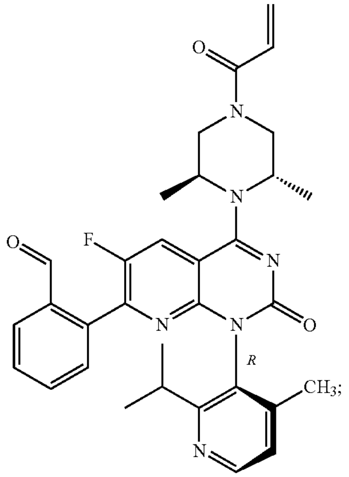
3-4M
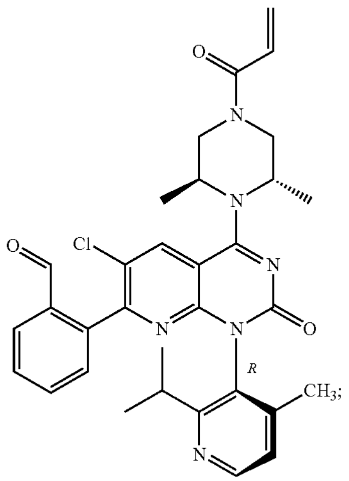
3-5M
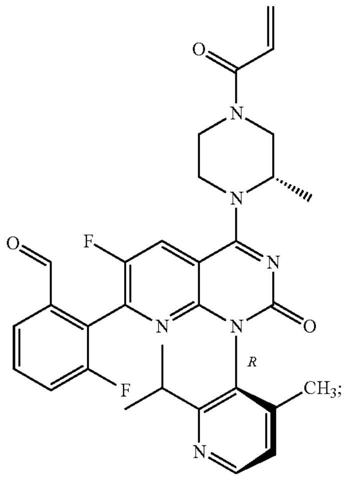
-continued
3-6M
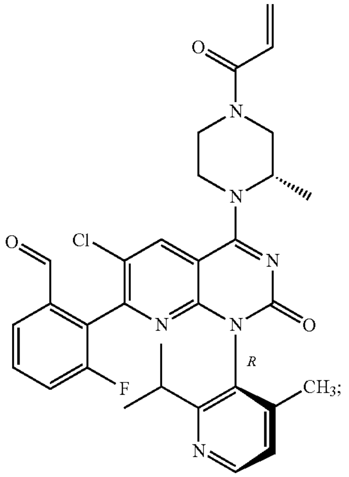
3-7M
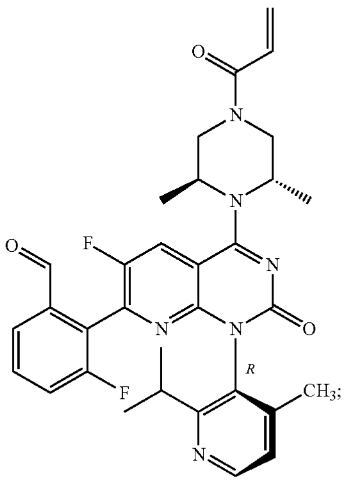
3-8M
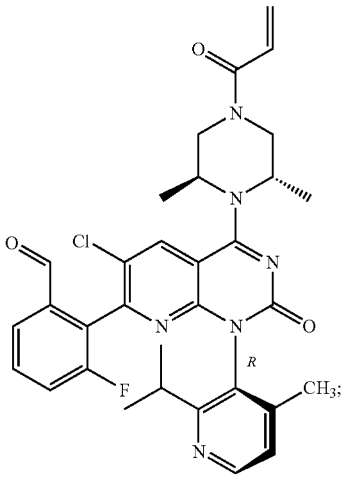

-continued
3-9M
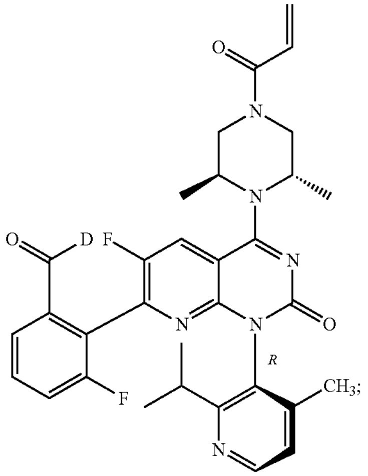
3-10M
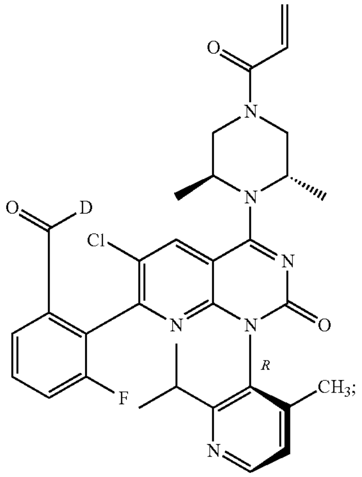
3-11M
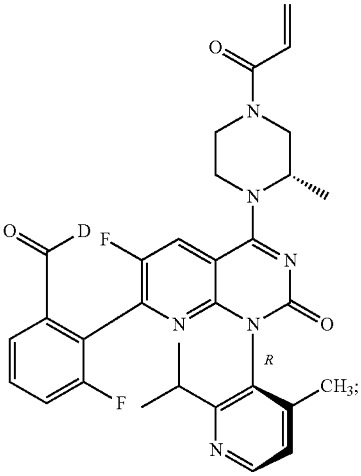
-continued
3-12M
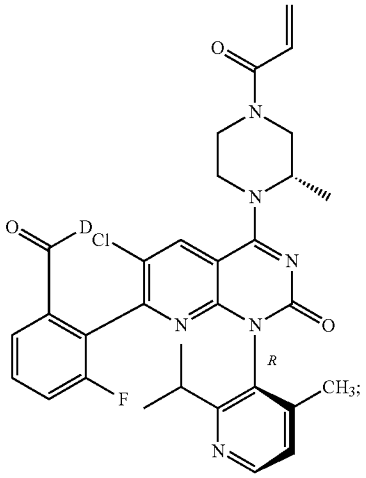
3-13M
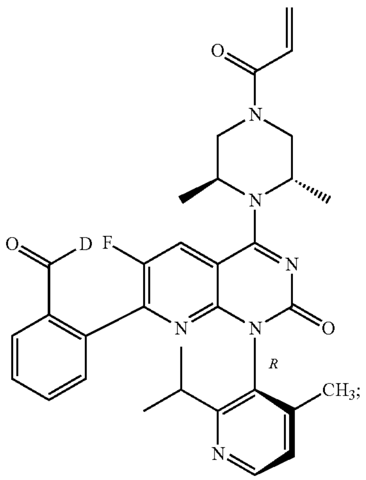
3-14M
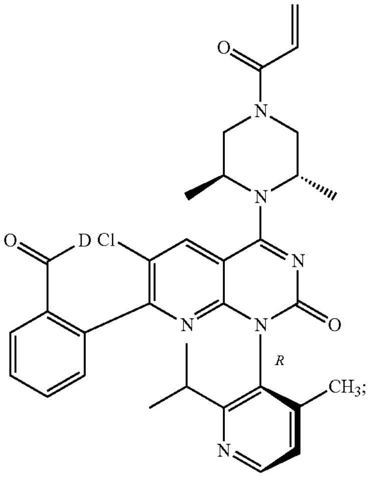

-continued
3-15M
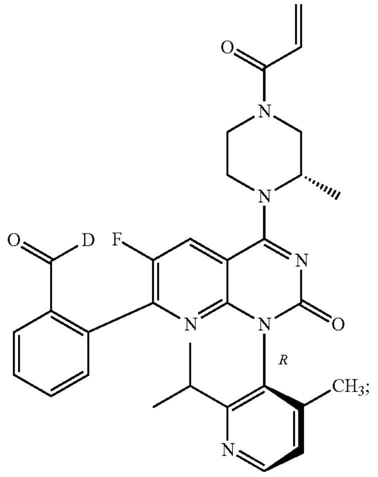
3-16M
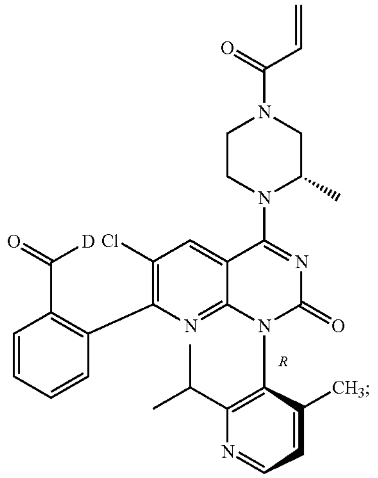
3-17M
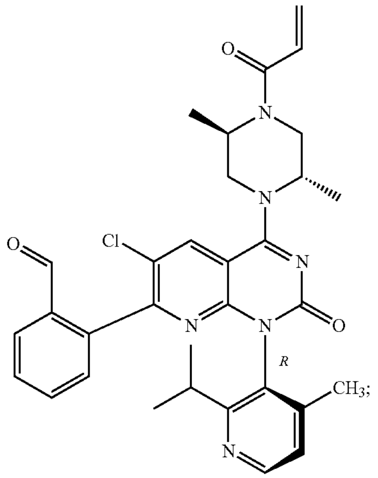
-continued
3-18M
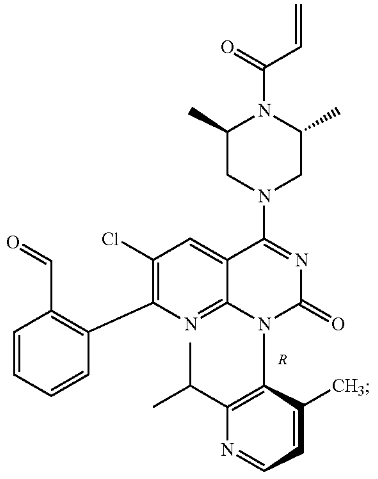
3-19M
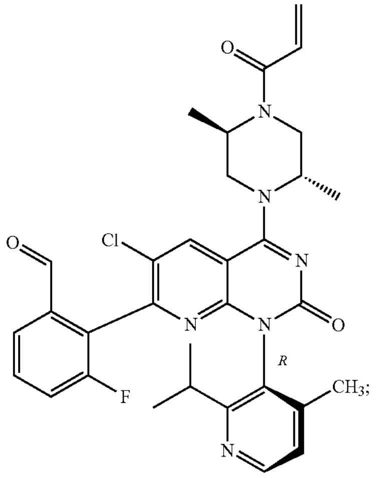
3-20M
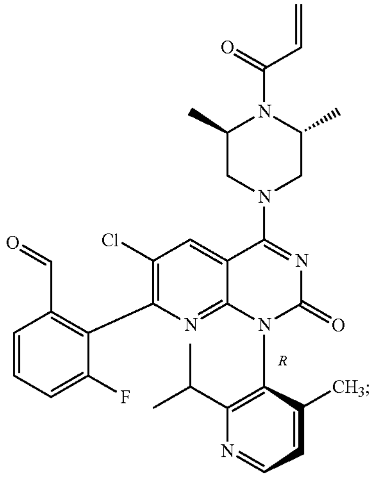

-continued
3-21M
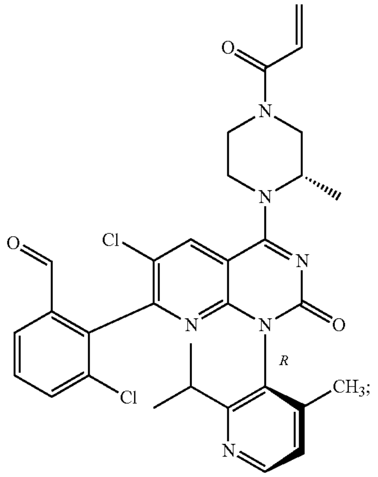
3-22M
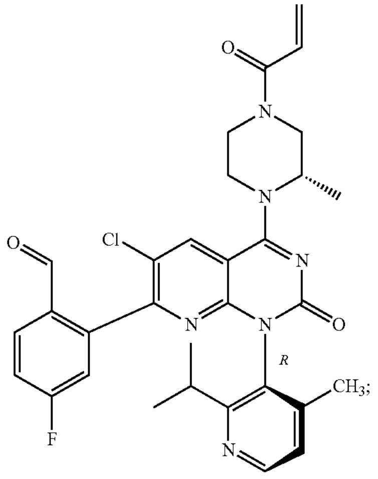
3-23M
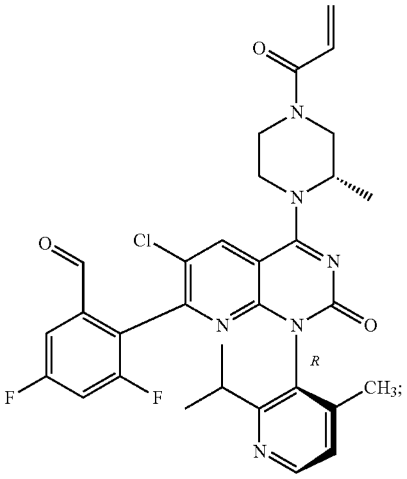
-continued
3-24M
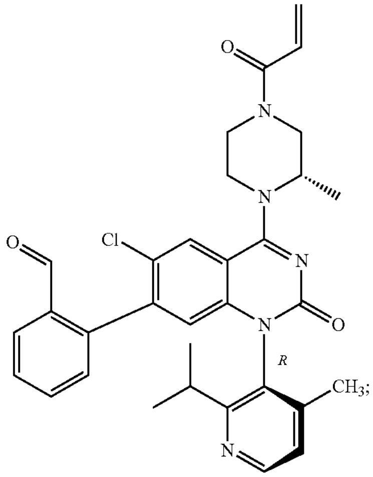
3-25M
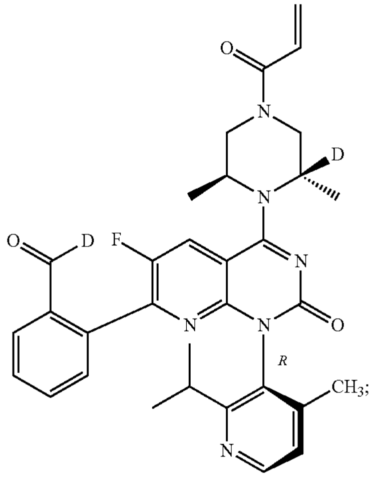
3-26M
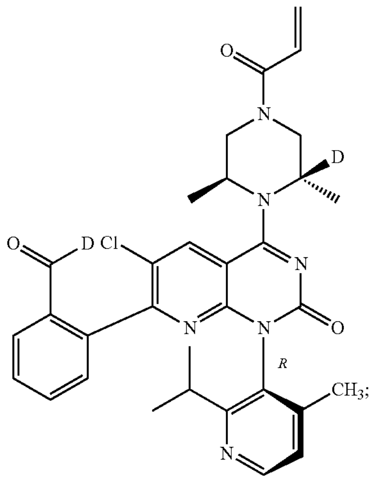

-continued
3-27M
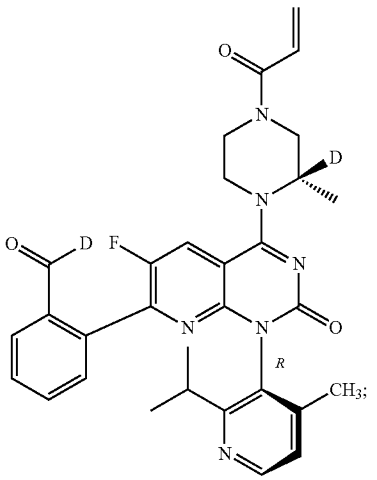
or
3-28M
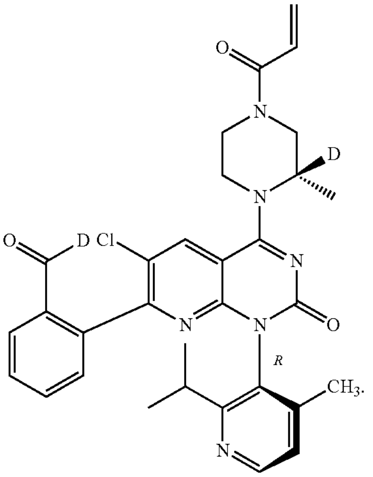
The present invention provides the following compounds with an axial chiral stereoconfiguration as R configuration, or tautomers or pharmaceutically acceptable salts thereof,
3-1MIS
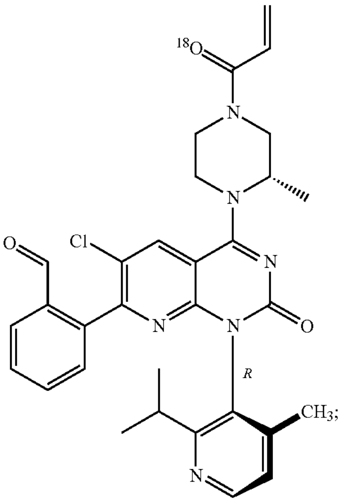
-continued
3-2MIS
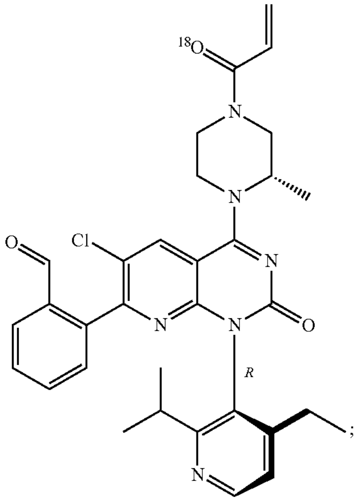
3-3MIS
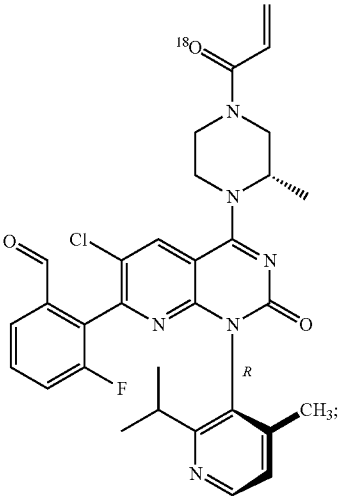
3-4MIS
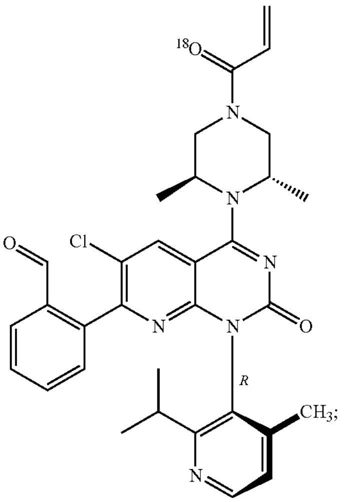

3-5MIS
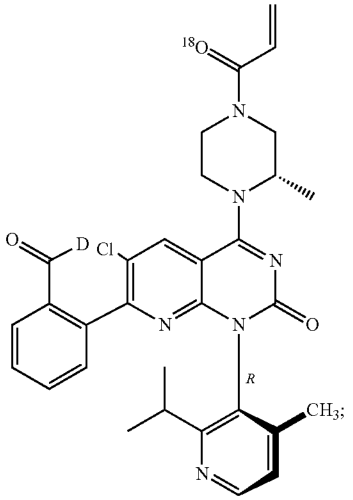
3-6MIS
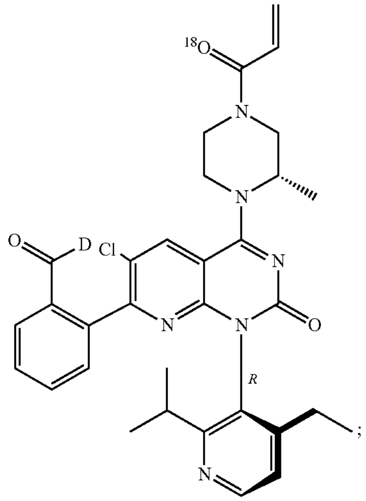
3-7MIS
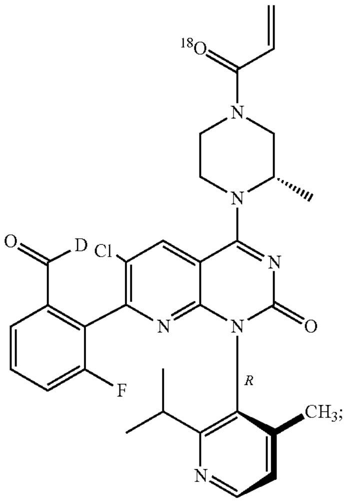
or
3-8MIS
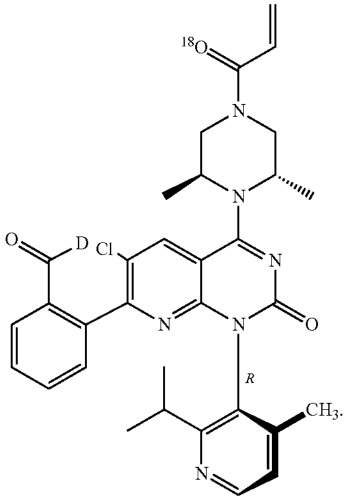
The present invention provides the following compounds with an axial chiral stereoconfiguration as R configuration, or tautomers or a pharmaceutically acceptable salts thereof,
3K-1M
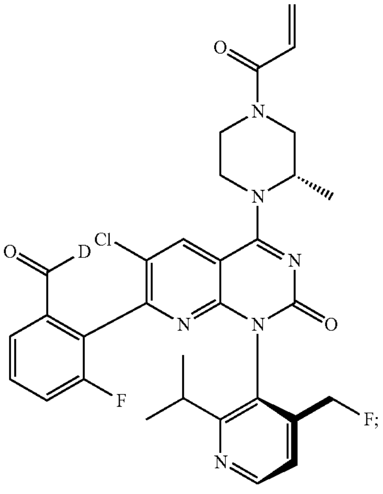

-continued
3K-2M
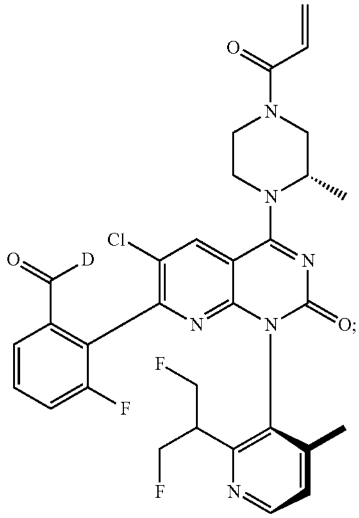
3K-3M
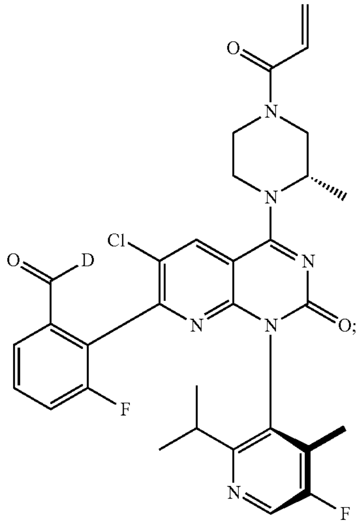
3K-4M
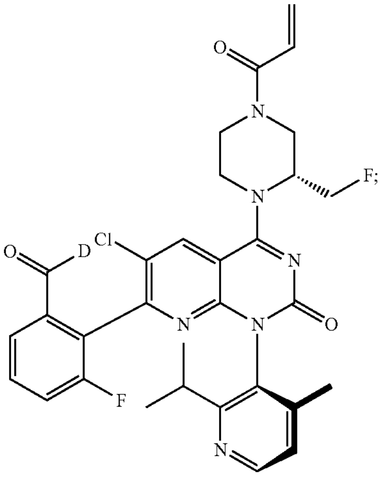
-continued
3K-5M
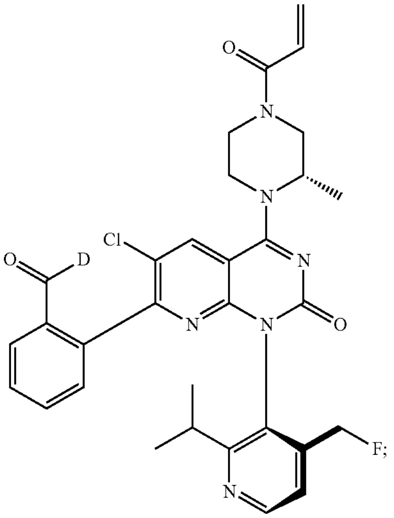
3K-6M
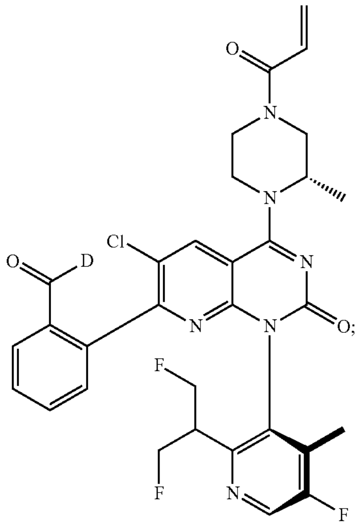
3K-7M
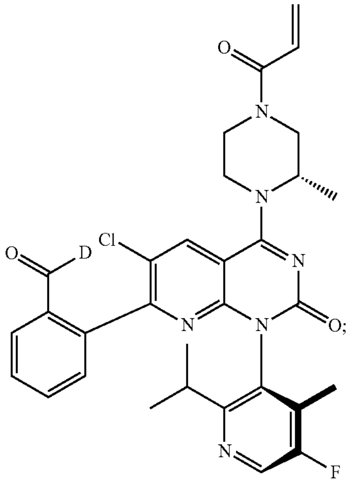

-continued
3K-8M
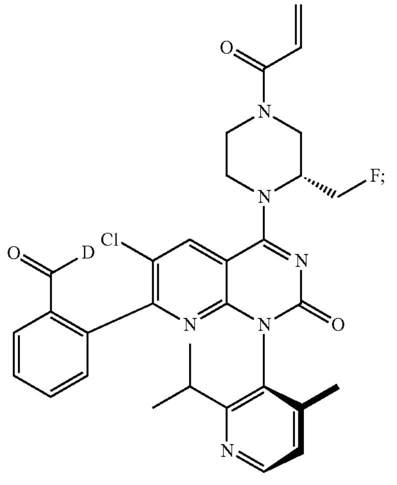
3K-9M
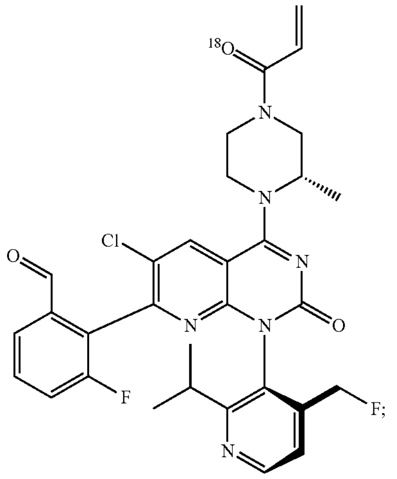
3K-10M
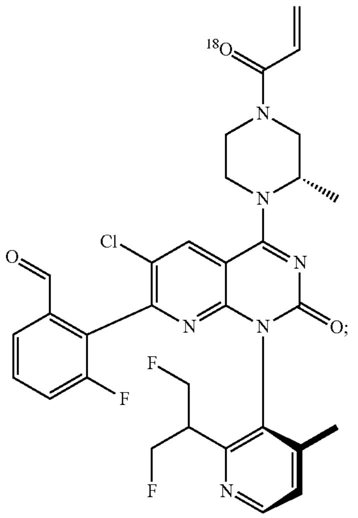
-continued
3K-11M
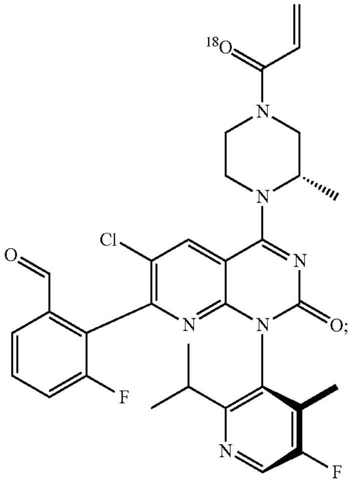
3K-12M
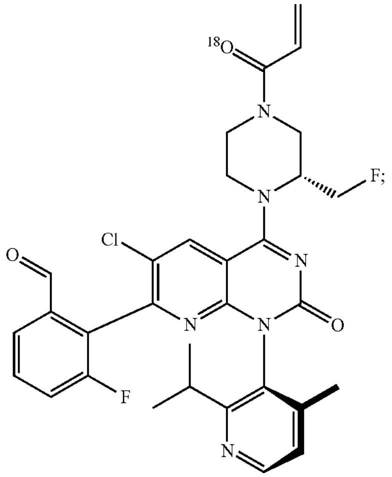
3K-13M
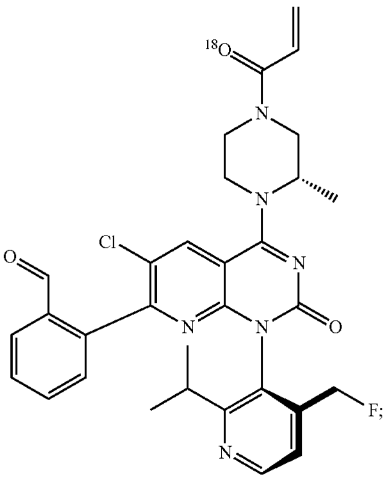

-continued
3K-14M
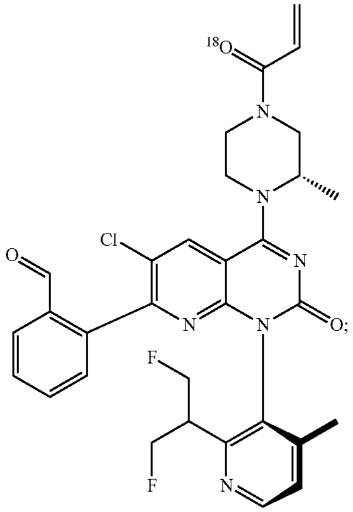
3K-15M
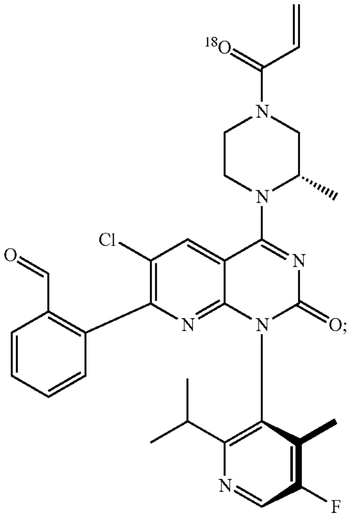
or
3K-16M
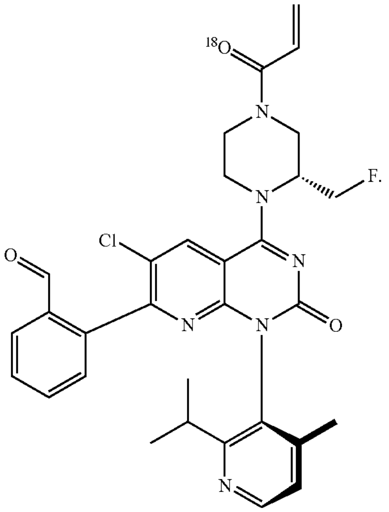
The present invention provides the following compounds, or stereoisomers, tautomers, or pharmaceutically acceptable salts thereof,
3-29
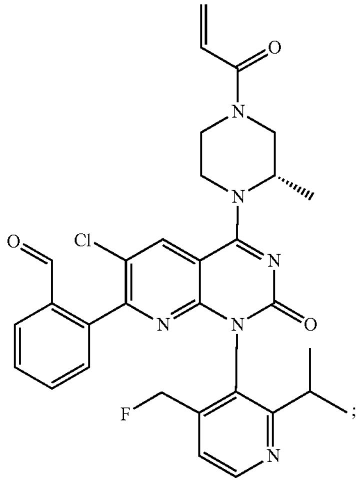
3-30M
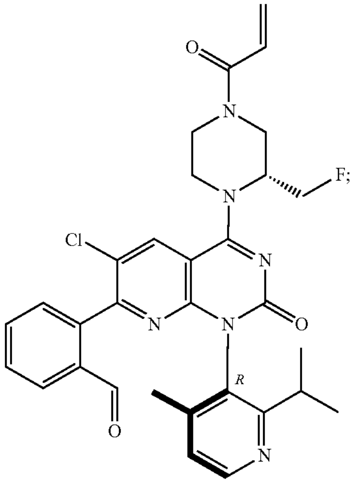
3-31
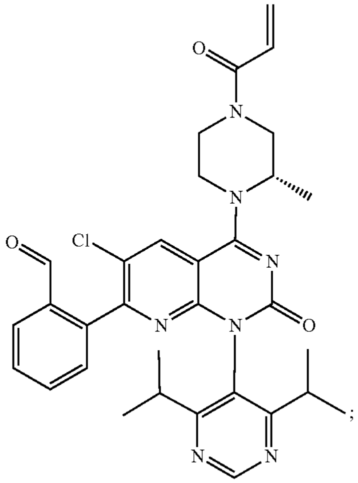
or -continued 3-32

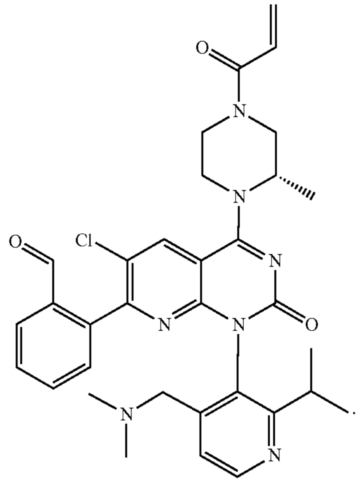

The present invention provides a pharmaceutical composition, comprising an effective dose of any of the compound, or the stereoisomer, the tautomer, or the pharmaceutically acceptable salt thereof according to the present invention, and a pharmaceutically acceptable carrier.

The present invention provides use of the compound or the pharmaceutically acceptable salt thereof according to the present invention, or the pharmaceutical composition according to the present invention in preparing a medicament for preventing and/or treating a disease related to a cancer mediated by mutations of KRAS G12C, HRAS or NRAS, wherein the use includes that any one of the compound or the pharmaceutically acceptable salt thereof according to the present invention, or the pharmaceutical composition according to the present invention is capable of being used alone or in combination with other therapeutic methods comprising immunotherapy to prevent and/or treat a disease related to a cancer mediated by mutations of KRAS G12C, HRAS or NRAS.

In the use according to the present invention, the various cancers of diseases related to KRAS function are liver cancer, esophageal cancer, gastric cancer, renal cell cancer, sarcoma, cholangiocarcinoma, colon cancer, prostate cancer, ovarian cancer, breast cancer, hematological cancer, pancreatic cancer, MYH-related polyp cancer, colorectal cancer or lung cancer.

DESCRIPTION OF THE DRAWINGS

FIG. 1 shows single crystal diffraction results of an intermediate 3M.

DETAILED DESCRIPTION

All technological and scientific terms used in this specification have the same meanings as general terms understood by those of ordinary skilled in the art.

The term “hydrogen” refers to —H herein.

The term “deuterium” refers to -D herein.

The term “halogen” refers to —F, —Cl, —Br and —I herein.

The term “fluorine” refers to —F herein.

The term “chlorine” refers to —Cl herein.

The term “bromine” refers to —Br herein.

The term “iodine” refers to —I herein.

The term “cyano” refers to —CN herein.

The term “amino” refers to $—NH_2$ herein.

The term “hydroxyl” refers to —OH herein.

The term “alkyl” herein refers to a saturated aliphatic hydrocarbon group having 1 to 10 carbon atoms, and the term includes straight-chain and branched-chain hydrocarbyls. Non-limiting examples of alkyl include methyl, ethyl, n-propyl, isopropyl, n-butyl, isobutyl, sec-butyl, tert-butyl, n-pentyl, neopentyl, n-hexyl, and the like. The alkyl herein may be optionally substituted by one or more of the following substituents: deuterium, fluorine, chlorine, bromine, iodine, cyano, nitro, hydroxyl, carboxyl, amino, alkyl, alkoxy, acyl, acyloxy, oxo, acylamino, ester, amido, cycloalkyl, cycloalkenyl, heterocycloalkyl, alkenyl, alkenyloxy, alkynyl, cycloalkoxy, heterocycloalkyloxy, aryloxy, heteroaryloxy, aryl or heteroaryl.

The term “aryl” herein refers to a 6-to-10-membered all-carbon monocyclic or fused polycyclic group (i.e., a ring sharing adjacent pairs of carbon atoms), a polycyclic group having a conjugated π electron system (i.e., a ring with adjacent pairs of carbon atoms). The aryl may be covalently linked to a defined chemical structure on any carbon atom that produces a stable structure. The aryl herein may be optionally substituted by one or more of the following substituents: fluorine, chlorine, bromine, iodine, cyano, nitro, hydroxyl, carboxyl, amino, alkyl, alkoxy, acyl, acylamino, ester, amido, sulfonyl, sulfinyl, cycloalkyl, cycloalkenyl, heterocycloalkyl, alkenyl, alkynyl and cycloalkoxy.

The term “heteroaryl” herein refers to an aromatic group consisting of 5 to 10 atoms and containing at least one heteroatom selected from N, O or S etc. The term may have a single ring (non-limiting examples include furan, thiophene, imidazole, pyrazole, pyridine, pyrazine, oxazole, thiazole, or the like) or multiple fused rings (non-limiting examples include benzothiophene, benzofuran, indole, isoindole, or the like), wherein the fused ring may or may not be an aromatic group containing heteroatoms, assuming that a connection point is an atom through an aromatic heteroaryl group. The heteroaryl herein may be optionally substituted by one or more of the following substituents: fluorine, chlorine, bromine, iodine, cyano, nitro, hydroxyl, amino, alkyl, alkoxy, acyl, acyloxy, acylamino, ester, amido, sulfonyl, sulfinyl, cycloalkyl, cycloalkenyl, heterocycloalkyl, alkenyl, alkynyl and cycloalkoxy.

The term “alkenyl” herein refers to an alkenyl group having 2 to 8 carbon atoms and at least one alkenyl unsaturated site. Non-limiting examples of alkenyl include ethenyl, propenyl, allyl, isopropenyl, butenyl, isobutenyl and the like. The alkenyl herein may be optionally substituted by one or more of the following substituents: deuterium, fluorine, chlorine, bromine, iodine, cyano, nitro, hydroxyl, carboxyl, amino, alkyl, alkoxy, acyl, acylamino, ester, amido, sulfonyl, sulfinyl, cycloalkyl, cycloalkenyl, heterocycloalkyl, cycloalkoxy, sulfydryl, alkylmercapto, deuterated alkylmercapto, sulfuryl, sulfoxide, amino, silyl, phosphoryl, deuterated alkyl, heterocycloalkyl, aryl, heteroaryl, alkynyl, alkenyl, arylalkyl, and ester.

The term “alkynyl” herein refers to an alkyl in which two adjacent carbon atoms are joined by a triple bond, wherein the alkyl is as defined herein. The alkynyl refers to an unsaturated alkyl as defined above consisting of at least two carbon atoms and at least one carbon-carbon triple bond, for example, ethynyl, 1-propinyl, 2-propinyl, 1-, 2- or 3-butynyl, or the like. The alkynyl may be substituted or unsubstituted, and when the alkynyl is substituted, the substituents are preferably one or more of the following groups, the substituents are independently selected from deuterium, fluorine, chlorine, bromine, iodine, cyano, nitro, hydroxyl, carboxyl, amino, alkyl, alkoxy, acyl, acylamino, ester, amido, sulfonyl, sulfinyl, cycloalkyl, cycloalkenyl, heterocycloalkyl, cycloalkoxy, sulfydryl, alkylmercapto, deuterated alkylmercapto, sulfuryl, sulfoxide, amino, silyl, phosphoryl, deuterated alkyl, heterocycloalkyl, aryl, heteroaryl, alkynyl, alkenyl, arylalkyl, and ester.

The term "heterocyclyl" refers to a substituted or unsubstituted and saturated or unsaturated aromatic ring containing at least 1 to 5 heteroatoms selected from N, O or S, and a non-aromatic ring. The aromatic ring and the non-aromatic ring may be a 3-to-10-membered single ring, a 4-to-20-membered spiro ring, fused ring or bridged ring, and the optionally substituted N and S in the heterocyclyl ring may be oxidized to various oxidation states. A 3-to-12-membered heterocycle is preferred. Non-limiting examples include oxiranyl, oxetanyl, oxylanyl, oxacyclohexyl, oxacyclohexyl, oxecanyl, aziridine, azetidinyl, azacyclopcntyl, azacyclohexyl, aziridinyl, 1,3-dioxolany, 1,4-dioxolany, 1,3-dioxolany, 1,3-dioxanyl, 1,3-dithianyl, azepinyl, morpholinyl, piperazinyl, pyridinyl, furanyl, thienyl, pyrrolyl, pyranyl, N-alkylpyrrolyl, pyrimidinyl, pyrazinyl, pyridazinyl, imidazolyl, piperidinyl, thiomorpholinyl, dihydropyran, thiadiazolyl, oxazolyl, oxadiazolyl, pyrazolyl, 1,4-dioxadienyl, and the like.

The term "haloalkyl" refer to the alkyl obtained by substituting the "alkyl" defined above with halogen. The halogen includes: fluorine, chlorine, bromine, iodine, or the like.

The term "alkenylalkyl" refers to the alkyl obtained by substituting the "alkyl" defined above with the "alkenyl" defined above.

The term "alkynylalkyl" refers to the alkyl obtained by substituting the "alkyl" defined above with the "alkynyl" defined above.

The term "nitrogen-containing heterocyclyl" refers to a ring system containing nitrogen atom(s), which may "fused" aromatic and non-aromatic ring systems, or link other ring systems through "spiro carbon atoms", such as the following structures:

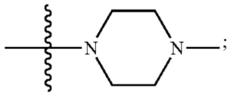
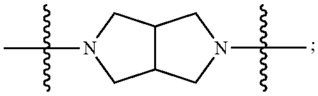
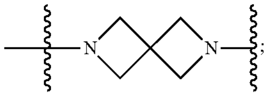
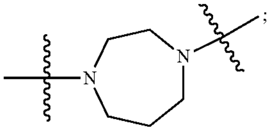
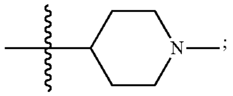
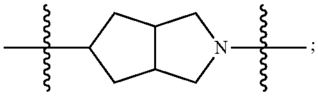
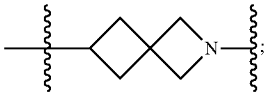
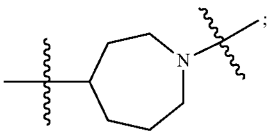
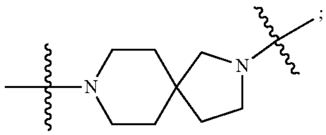

-continued

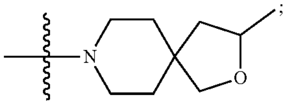
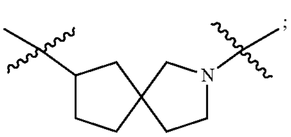
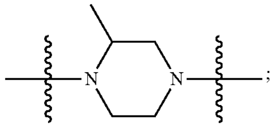
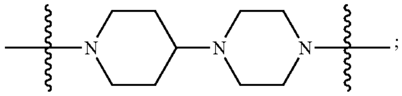
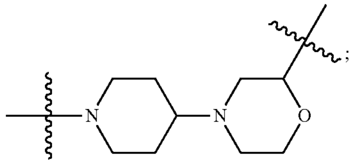
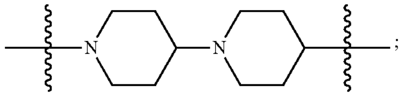
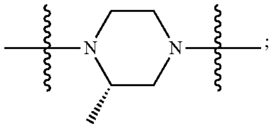
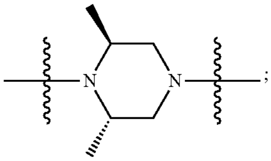
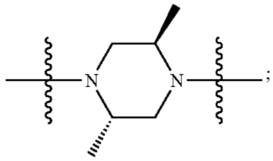
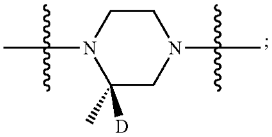
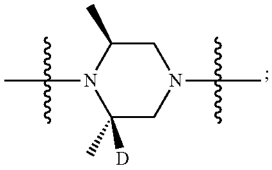
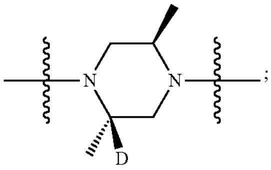
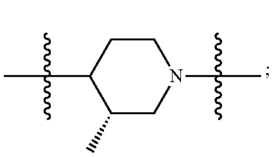
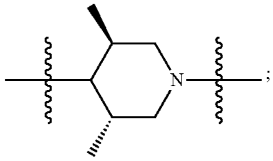
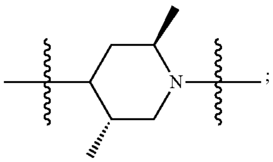
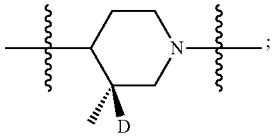
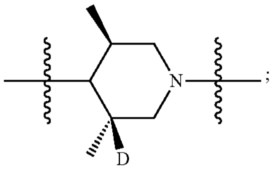
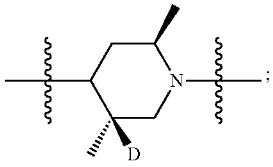

-continued

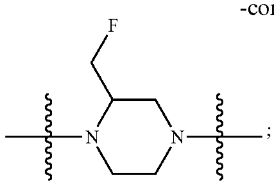
;
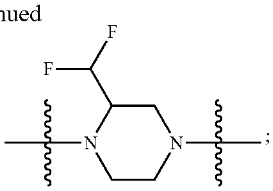
;
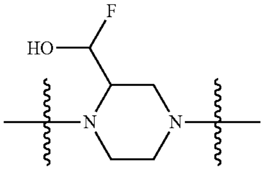
;
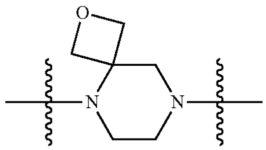
;
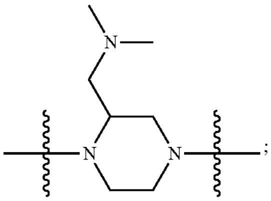
;
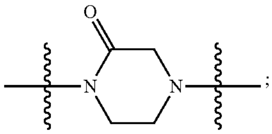
;
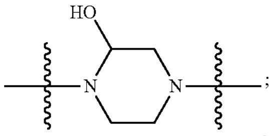
;
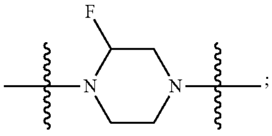
; or
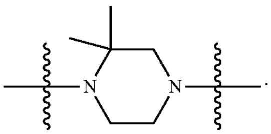
.

The term "amide" (or "acylamino") includes C-amide group and N-amide group, i.e. —C(O)NR$^A$R$^B$ and —NR$^A$C(O)R$^B$ groups, respectively. R$^A$ and R$^B$ are independently hydrogen or substituted or unsubstituted alkyl, alkenyl, alkynyl, cycloalkyl, aryl, arylalkyl, heterocycloalkyl or heterocyclyl as defined herein. Therefore, the acylamino includes, but is not limited to, carbamoyl (—C(O)$NH_2$) and formamido (—NHC(O)H). In some embodiments, the amide is —NR$^A$C(O)—($C_{1-5}$ alkyl), which is called "carbonylamino", and in some other embodiments, the amide is —NHC(O)— alkyl, which is called "alkanoylamino".

The term "sulfonamide" includes S— sulfonamido group and N— sulfonamido group, i.e., —$SO_2$NR$^C$R$^D$ and —NR$^C$$SO_2$R$^D$ groups, respectively. R$^C$ and R$^D$ are independently hydrogen or substituted or unsubstituted alkyl, alkenyl, alkynyl, cycloalkyl, aryl, arylalkyl, heterocycloalkyl or heterocyclyl as defined herein. Therefore, the sulfonamido group includes, but is not limited to, sulfonyl (—$SO_2NH_2$). In some embodiments herein, sulfonamide is —$NHSO_2$—alkyl, which is referred to as "alkylsulfonylamino".

The present invention further includes isotope-labeled compounds of the present invention, i.e., compounds with the same structure as that disclosed above, but in which one or more atoms are replaced by atoms with the same proton number but different neutron number. Isotope examples of the compounds of the present invention include isotopes of hydrogen, carbon, nitrogen, oxygen, sulfur, fluorine, chlorine and iodine, such as $^2$H, $^3$H, $^{13}$C, $^{14}$C, $^{15}$N, $^{18}$O, $^{17}$O, $^{35}$S, $^{18}$F, $^{36}$Cl, and $^{131}$I or the like. The compound, the stereoisomer, the tautomer, or the pharmaceutically acceptable salt thereof according to the present invention, and the compounds of the above forms containing the above isotopes and/or other atomic isotopes are all within the scope of the present invention. Some isotope-labeled compounds of the present invention, such as those labeled with $^3$H or $^{14}$C, may be used in drug tissue distribution tests, so 3H or $^{14}$C isotopes are particularly preferred due to ease of preparation and detection thereof.

Some compounds of the present invention substituted by heavier isotopes, such as $^2$H and $^{18}$O, have some therapeutic advantages due to better metabolic stability thereof, such as increasing a half-life in vivo and reducing a dosage. Therefore, $^2$H and $^{18}$O are also preferred in some cases.

In the molecular structures of compounds 3-6B, 3-16M and the like, "deuterated formyl" is a structural feature thereof. It is reported in literature (Journal of American. Chemistry. Society. 1999, 121, 326-334; Tetrahedron Letter, 1976, 3013-3016) that in an organic chemical reaction (reaction of reducing benzaldehyde carbonyl to alcohol hydroxyl by sodium borohydride), the "Secondary deuterium kinetic isotope effects" (i.e., SDKIEs) of "deuterated formyl" has a value that is kH/kD=1/1.13. Therefore, it is speculated that the compounds 3-6B, 3-16M, and the like, which have the structural features of "deuterated formyl", have potential advantages in metabolism and biological activity in vitro and in vivo.

EMBODIMENTS

The present invention will be further explained in detail with reference to the embodiments below, but the present invention is not limited thereto. Throughout the present application, various embodiments of the compounds and methods of the present invention are mentioned herein. The present invention is not limited to these examples. The following examples only provide methods for practicing the present invention, and do not limit the scope of the present invention in any way.

The compounds provided by the present invention may be prepared by standard synthesis methods known in the art. This specification provides a general method for preparing the compounds of the present invention. The starting materials may usually be obtained commercially or prepared by methods well known to those skilled in the art.

The process is as follows:

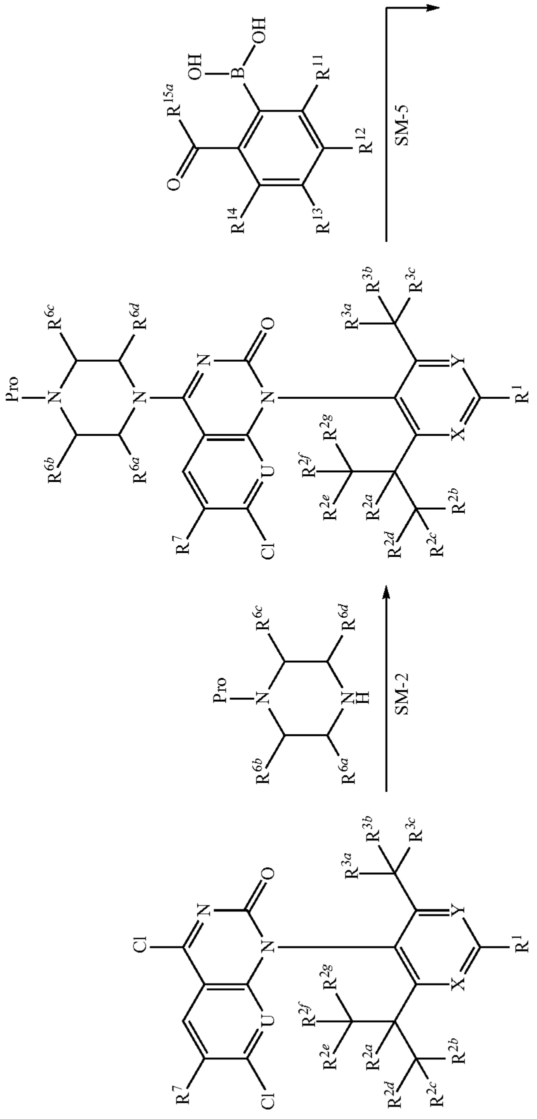
SM-1
M-1

-continued
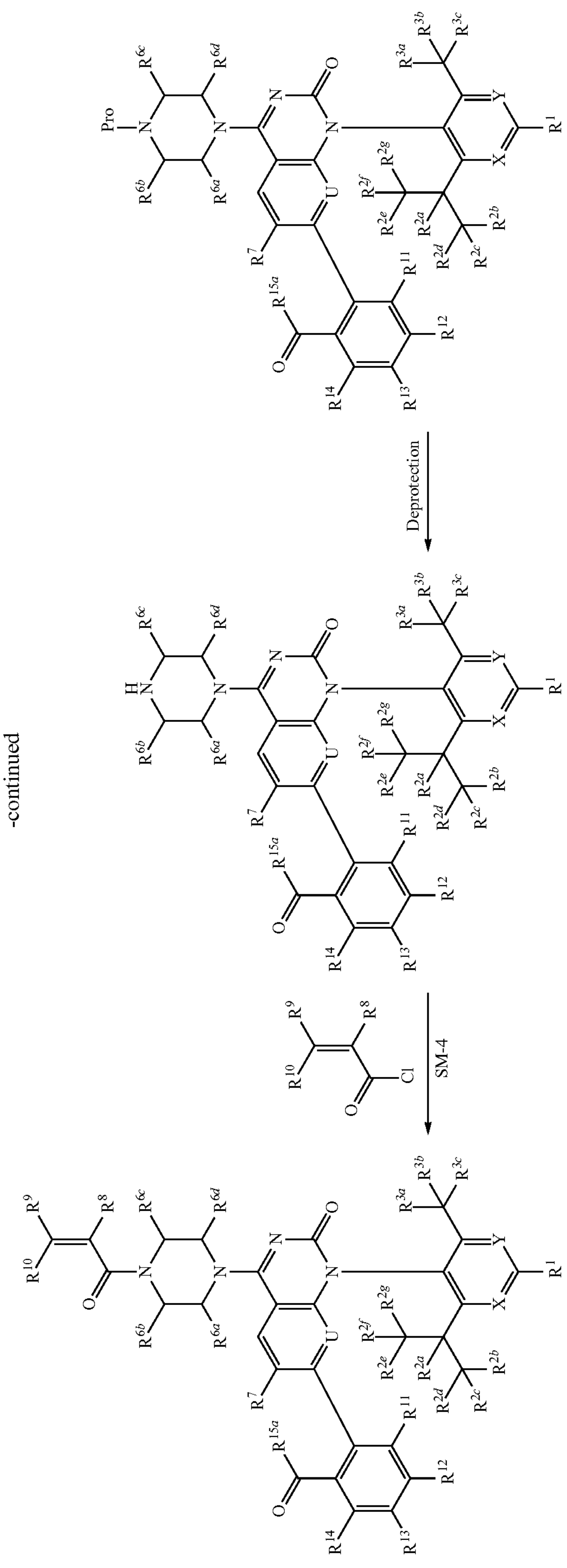
M-2
M-3
II

Firstly, SM-1 was used as a starting material to undergo a nucleophilic substitution reaction with SM2 to obtain M1, then reacted with SM-3 to obtain M2, then a protective group was removed to obtain M3, and then M3 was further reacted to obtain a compound II.

The compounds of the present invention and the corresponding preparation methods are further explained and listed in the following examples and preparations. It should be understood that although typical or preferred reaction conditions are given in the specific examples, those skilled in the art can also use other reaction conditions. The optimum reaction conditions may vary with the specific reaction substrate or solvent used, but the conditions can be determined by those skilled in the art through routine optimization.

PREPARATION OF INTERMEDIATES

Intermediate 1

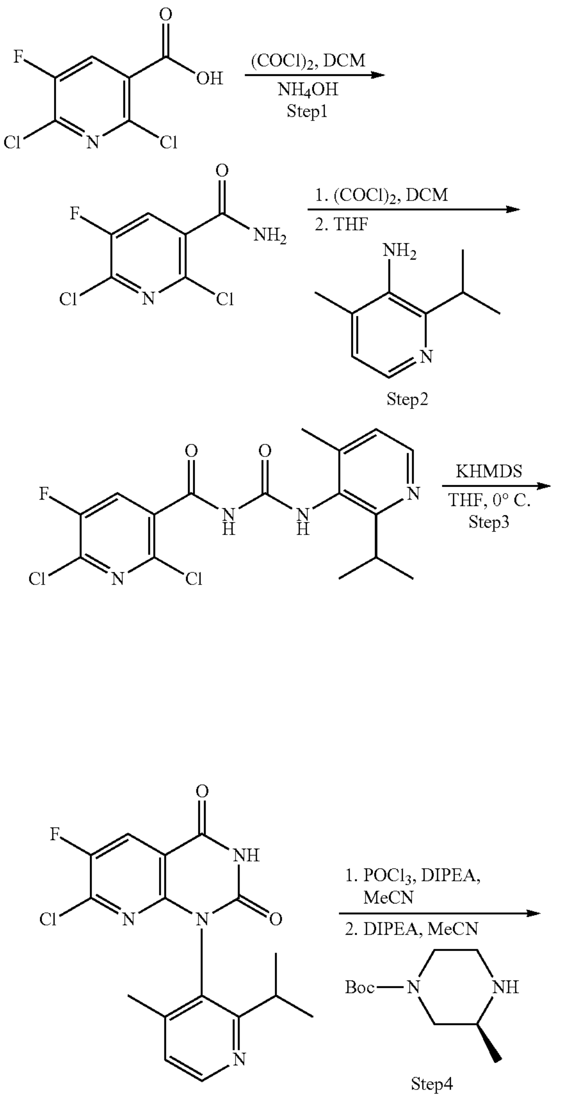

-continued

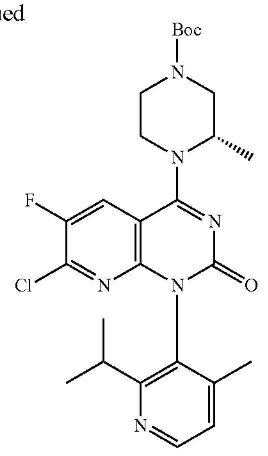

Intermediate 1

Step 1

2,4-dichloro-5-fluoronicotinic acid (61.0 g), dichloromethane (600 ml) and N,N-dimethylformamide (1 ml) were added into a 2000 ml single-necked flask, cooled to 0° C., dropwise added with a dichloromethane solution (30 ml) containing oxalyl chloride (36.9 ml), and then gradually heated to room temperature for stirring after the dropwise addition. The reaction solution was concentrated to dryness under reduced pressure, cooled to 0° C., added with 1,4-dioxane (600 ml), then dropwise added with aqueous ammonia (120 ml), and continuously stirred at 0° C. after the dropwise addition. The reaction solution was concentrated to dryness under reduced pressure, and the concentrate was pulped with ethyl acetate and n-hexane, was allowed to settle and filtered, and the filter cake was washed with n-hexane, and dried. The filtrate was concentrated and purified by silica gel column chromatography to yield a total of 38 g of white solid.

Step 2

The product of the previous step was added to a 1000 ml three-necked flask, a dichloromethane solution (20 ml) containing oxalyl chloride (18.5 ml) was dropwise added at 0° C., and then heated to 75° C. for stirring after the dropwise addition. The reaction solution was concentrated to dryness under reduced pressure, cooled to 0° C., added with tetrahydrofuran (300 ml), and then dropwise added with a tetrahydrofuran solution (150 ml) containing 2-isopropyl-4-methylpyridine-3-amine (28.7 g), kept at 0° C. and continuously stirred. The reaction solution was poured into a saturated aqueous solution of ammonium chloride and extracted with ethyl acetate; organic layers were combined, washed with saturated brine, dried with anhydrous sodium sulfate, filtered, concentrated under reduced pressure until a solid was precipitated, cooled to 0° C. and kept for 15 minutes, and then filtered; and the filter cake was washed with ethyl acetate and petroleum ether and dried. The filtrate was purified by silica gel column chromatography to yield a total of 51 g of white solid.

Step 3

2,6-dichloro-5-fluoro-N-((2-isopropyl-4-methylpyridine-3-yl)carbamoyl)nicotinamide (51.0 g) and tetrahydrofuran (500 ml) were added into a 1000 ml single-necked flask, cooled to 0° C., dropwise added with potassium bis(trimethylsilyl)amide (278 ml), and gradually heated to room temperature and stirred after the dropwise addition. The reaction solution was poured into a saturated aqueous solution of ammonium chloride and extracted with ethyl acetate; organic layers were combined, washed with saturated brine, dried with anhydrous sodium sulfate, filtered, concentrated under reduced pressure until a solid was precipitated, cooled to 0° C. and kept for 30 minutes, and then filtered; and the filter cake was washed with ethyl acetate and petroleum ether and dried. The filtrate was concentrated and purified by silica gel column chromatography to yield a total of 38 g of light yellow solid.

Step 4

The product of the previous step (24.0 g), acetonitrile (240 ml) and N,N-diisopropylethylamine (68.2 ml) were added into a 500 ml single-necked flask, cooled to 0° C., dropwise added with phosphorus oxychloride (38.5 ml), and then heated to 80° C. and stirred after the dropwise addition. The reaction solution was concentrated to dryness under reduced pressure and azeotroped with toluene twice; then acetonitrile (240 ml) was added into the residues, cooled to 0° C., added with N,N-diisopropylethylamine (68.2 ml), and then added with (S)-4-N-t-Boc-2-methylpiperazine (20.7 g) in batches, and stirred at room temperature after the addition. The reaction solution was poured into a saturated aqueous sodium bicarbonate solution to quench a reaction and extracted with ethyl acetate; organic layers were combined, washed with saturated brine, dried with anhydrous sodium sulfate, filtered, concentrated under reduced pressure until a solid was precipitated, cooled to 0° C., and then filtered; and the filter cake was washed with ethyl acetate and petroleum ether and dried. The filtrate was concentrated and purified by silica gel column chromatography to yield a total of 18 g of yellow solid. $^1$H NMR (400 MHz, DMSO-$d_6$): δ 8.50 (d, J=4.9 Hz, 1H), 8.38 (d, J=8.5 Hz, 1H), 7.30 (d, J=4.8 Hz, 1H), 4.84 (s, 1H), 4.27-4.10 (m, 1H), 4.03-3.88 (m, 1H), 3.88-3.76 (m, 1H), 3.75-3.58 (m, 2H), 3.38-3.24 (m, 1H), 2.70-2.56 (m, 1H), 1.96 (s, 3H), 1.45 (s, 9H), 1.36-1.29 (m, 3H), 1.07 (d, J=6.7 Hz, 3H), 1.04-0.97 (m, 3H); MS: m/z 531.2, $[M+H]^+$.

Intermediate 2

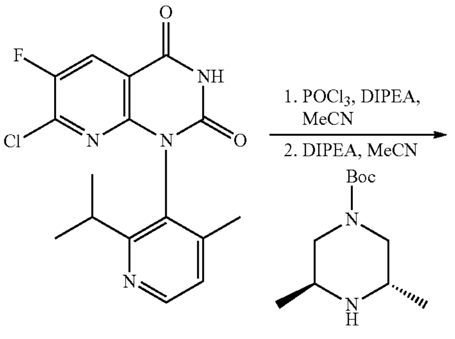

-continued

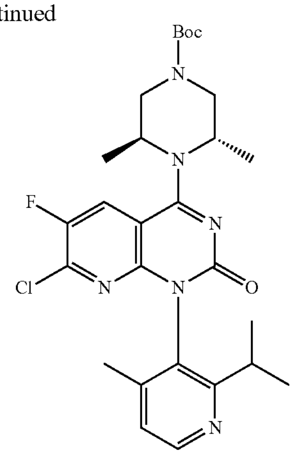

Intermediate 2

7-chloro-6-fluoro-1-(2-isopropyl-4-methylpyridin-3-yl) pyrido[2,3-d]pyrimidine-2,4 (1H,3H)-dione (2.0 g), acetonitrile (20 ml) and N,N-diisopropylethylamine (5.8 ml) were added into a 50 ml single-necked flask, cooled to 0° C., dropwise added with phosphorus oxychloride (3.2 ml), and then heated to 80° C. and stirred after the dropwise addition. The reaction solution was concentrated to dryness under reduced pressure and azeotroped with toluene twice; then acetonitrile (20 ml) was added into the residues, cooled to 0° C., added with N,N-diisopropylethylamine (5.8 ml), and then added with (3S,5S)-tert-butyl 3,5-dimethylpiperazine-1-carboxylate (1.3 g) in batches, gradually heated to room temperature and stirred after the addition. The reaction solution was poured into a saturated aqueous solution of sodium bicarbonate to quench the reaction and extracted with ethyl acetate; organic layers were combined, washed with saturated salt solution, dried with anhydrous sodium sulfate, filtered, concentrated under reduced pressure, and purified by silica gel column chromatography to yield 2 g of yellow solid. $^1$H NMR (400 MHz, DMSO-$d_6$): δ 8.50 (dd, J=4.8, 1.7 Hz, 1H), 8.45 (dd, J=8.6, 6.4 Hz, 1H), 7.28 (d, J=4.8 Hz, 1H), 4.43-4.27 (m, 2H), 3.74 (br s, 2H), 3.48 (br s, 2H), 2.70-2.55 (m, 1H), 1.94 (d, J=4.4 Hz, 3H), 1.45 (s, 9H), 1.30-1.21 (m, 6H), 1.08-1.04 (m, 3H), 1.02 (t, J=6.4 Hz, 3H); MS: m/z 545.3, $[M+H]^+$.

Intermediate 3

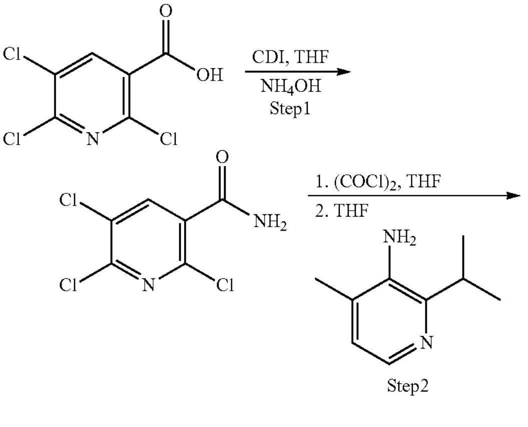

-continued

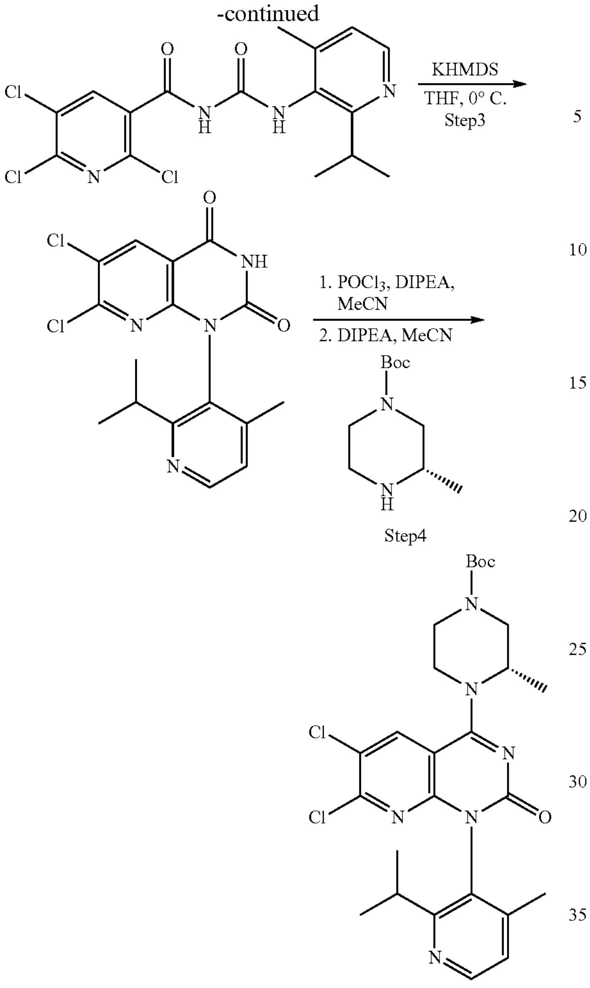

Intermediate 3

Step 1

2,5,6-trichloronicotinic acid (50.0 g) and tetrahydrofuran (500 ml) were added into a 2000 ml single-necked flask, added with N,N'-carbonyldiimidazole (39.4 g) in batches, gradually heated to 50° C. and stirred after the addition. The reaction solution was cooled to room temperature, added with toluene (100 ml), subjected to distillation under reduced pressure to remove a half of the solvent, then cooled to 0° C., dropwise added with aqueous ammonia (60 ml), kept at 0° C. and continuously stirred after the dropwise addition. The reaction solution was added with water for liquid separation, aqueous phases were extracted with ethyl acetate, and organic layers were combined, washed with saturated salt solution, dried with anhydrous sodium sulfate, filtered, concentrated under reduced pressure, and purified by silica gel column chromatography to yield 36 g of white solid. $^1$H NMR (400 MHz, $CDCl_3$): δ 8.36 (s, 1H), 6.76 (br s, 1H), 6.47 (br s, 1H).

Step 2

2,5,6-trichloronicotinamide (15.4 g) and tetrahydrofuran (150 ml) were added into a 500 ml single-necked flask, cooled to 0° C., dropwise added with a dichloromethane solution (7 ml) containing oxalyl chloride (7.0 ml), and then heated to 75° C. and stirred after the dropwise addition. The reaction solution was concentrated to dryness under reduced pressure, cooled to 0° C., added with tetrahydrofuran (150 ml), and then dropwise added with a tetrahydrofuran solution (70 ml) containing 2-isopropyl-4-methylpyridine-3-amine (10.8 g), kept at 0° C. and continuously stirred after the dropwise addition. The reaction solution was poured into a saturated aqueous solution of ammonium chloride and extracted with ethyl acetate; organic layers were combined, washed with saturated salt solution, dried with anhydrous sodium sulfate, filtered, concentrated under reduced pressure, and purified by silica gel column chromatography to yield 12 g of white solid. $^1$H NMR (400 MHz, DMSO-$d_6$): δ 11.34 (s, 1H), 9.58 (br s, 1H), 8.68 (s, 1H), 8.34 (d, J=4.8 Hz, 1H), 7.16 (d, J=4.8 Hz, 1H), 3.33-3.23 (m, 1H), 2.22 (s, 3H), 1.17 (d, J=6.6 Hz, 6H).

Step 3

The product of the previous step (12.0 g) and tetrahydrofuran (150 ml) were added into a 500 ml single-necked flask, cooled to 0° C., dropwise added with potassium bis(trimethylsilyl)amide (74.8 ml), and stirred at room temperature after the dropwise addition. The reaction solution was poured into a saturated aqueous solution of ammonium chloride and extracted with ethyl acetate; organic layers were combined, washed with saturated salt solution, dried with anhydrous sodium sulfate, filtered, concentrated under reduced pressure, and purified by silica gel column chromatography to yield 9.6 g of light yellow solid.

Step 4

The product of the previous step (26.0 g), acetonitrile (250 ml) and N,N-diisopropylethylamine (16.4 g) were added into a 500 ml single-necked flask, cooled to 0° C., dropwise added with phosphorus oxychloride (11.9 ml), and then heated to 80° C. and stirred after the dropwise addition. The reaction solution was concentrated to dryness under reduced pressure and azeotroped with toluene twice; then acetonitrile (250 ml) was added into the residues, cooled to 0° C., added with N,N-diisopropylethylamine (16.4 g), and then added with (S)-4-N-t-Boc-2-methylpiperazine (15.0 g) in batches, and stirred at room temperature for 1 hour after the addition. The reaction solution was poured into a saturated aqueous solution of sodium bicarbonate to quench the reaction and extracted with ethyl acetate; organic layers were combined, washed with saturated salt solution, dried with anhydrous sodium sulfate, filtered, concentrated under reduced pressure, and purified by silica gel column chromatography to yield 23.5 g of yellow solid. $^1$H NMR (400 MHz, DMSO-$d_6$): δ 8.55-8.43 (m, 2H), 7.26 (d, J=4.9 Hz, 1H), 4.88 (br s, 1H), 4.26-4.09 (m, 1H), 4.02-3.88 (m, 1H), 3.88-3.77 (m, 1H), 3.77-3.61 (m, 1H), 3.33-2.92 (m, 2H), 2.72-2.55 (m, 1H), 1.98-1.90 (m, 3H), 1.45 (s, 9H), 1.36-1.28 (m, 3H), 1.06 (d, J=6.7 Hz, 3H), 1.01 (d, J=6.6 Hz, 3H); MS: m/z 547.2, $[M+H]^+$.

Intermediate 4

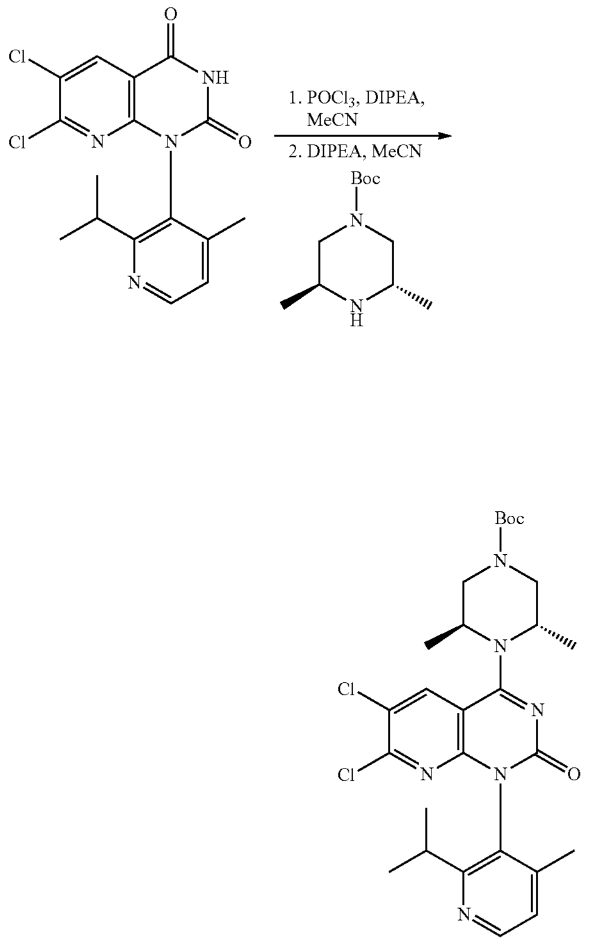

Intermediate 4

6,7-dichloro-1-(2-isopropyl-4-methylpyridin-3-yl)pyrido[2,3-d]pyrimidine-2,4(1H,3H)-dione (3.0 g), acetonitrile (30 ml) and N,N-diisopropylethylamine (8.1 ml) were added into a 100 ml single-necked flask, cooled to 0° C., dropwise added with phosphorus oxychloride (4.6 ml), and then heated to 80° C. and stirred after the dropwise addition. The reaction solution was concentrated to dryness under reduced pressure and azeotroped with toluene twice; then acetonitrile (30 ml) was added into the residues, cooled to 0° C., added with N,N-diisopropylethylamine (5.8 ml), and then added with (3S,5S)-tert-butyl 3,5-dimethylpiperazine-1-carboxylate (1.8 g) in batches, and stirred at room temperature for 1 hour after the addition. The reaction solution was poured into a saturated aqueous solution of sodium bicarbonate to quench the reaction and extracted with ethyl acetate; organic layers were combined, washed with saturated salt solution, dried with anhydrous sodium sulfate, filtered, concentrated under reduced pressure, and purified by silica gel column chromatography to yield 2.2 g of yellow solid. $^1H$ NMR (400 MHz, DMSO-$d_6$): δ 8.53 (d, J=7.2 Hz, 1H), 8.50 (dd, J=4.8, 1.6 Hz, 1H), 7.28 (d, J=4.8 Hz, 1H), 4.47-4.31 (m, 2H), 3.73 (br s, 2H), 3.52 (br s, 2H), 2.71-2.54 (m, 1H), 1.95 (d, J=7.3 Hz, 3H), 1.45 (s, 9H), 1.31-1.24 (m, 6H), 1.08-0.99 (m, 6H); MS: m/z 561.2, $[M+H]^+$.

Intermediate 5

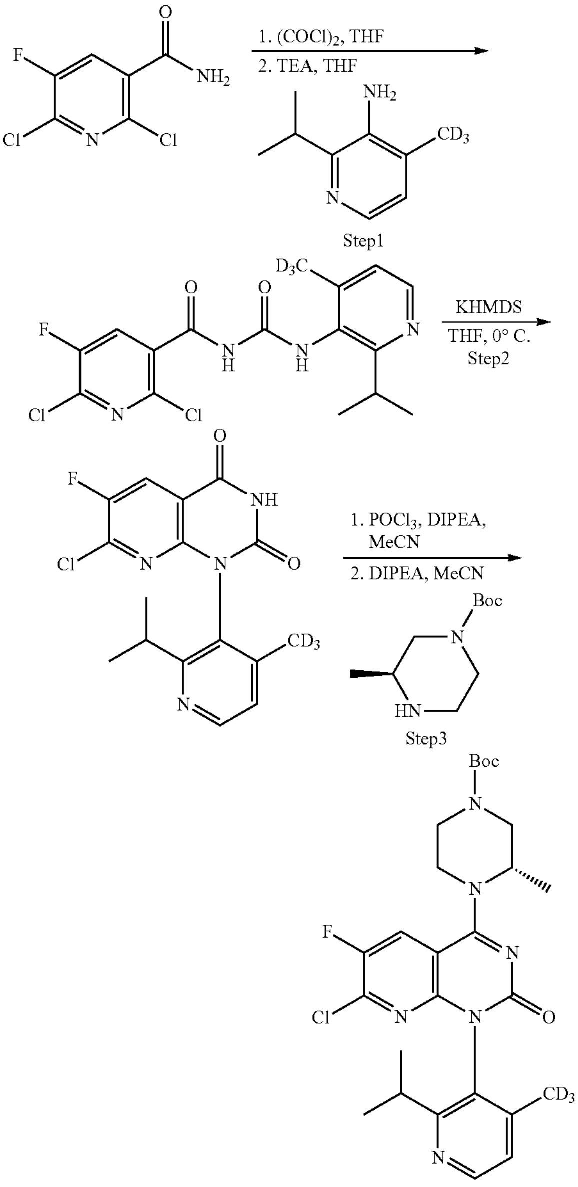

Intermediate 5

Step 1

2,6-dichloro-5-fluoronicotinamide (1.2 g) and tetrahydrofuran (40 ml) were added into a 250 ml single-necked flask, cooled to 0° C., dropwise added with oxalyl chloride (860 mg), and then heated to 70° C. and stirred after the dropwise addition. The reaction solution was concentrated to dryness under reduced pressure, cooled to 0° C., added with tetrahydrofuran (40 ml), then dropwise added with a tetrahydrofuran solution (10 ml) containing 2-isopropyl-4-(methyl-d3)pyridin-3-amine (783 mg), dropwise added with triethylamine (580 mg) after 5 minutes, and then continuously stirred after the addition. The reaction solution was poured into a saturated aqueous solution of ammonium chloride and extracted with ethyl acetate; organic layers were combined, washed with saturated salt solution, dried with anhydrous sodium sulfate, filtered, concentrated under reduced pressure, and purified by silica gel column chromatography to yield 1.45 g of off-white solid. $^1$H NMR (400 MHz, $CDCl_3$): δ 10.38 (s, 1H), 9.79 (s, 1H), 8.45 (d, J=4.9 Hz, 1H), 7.85 (d, J=7.0 Hz, 1H), 7.07 (d, J=4.9 Hz, 1H), 3.33-3.19 (m, 1H), 1.25 (d, J=6.8 Hz, 6H), MS: m/z 388.1, $[M+H]^+$.

Step 2

The product of the previous step (1.45 g) and tetrahydrofuran (20 ml) were added into a 250 ml single-necked flask, cooled to 0° C., dropwise added with potassium bis(trimethylsilyl)amide (8.3 ml), gradually heated to room temperature and stirred for 1 hour after the dropwise addition. The reaction solution was poured into a saturated aqueous solution of ammonium chloride and extracted with ethyl acetate; organic layers were combined, washed with saturated salt solution, dried with anhydrous sodium sulfate, filtered, concentrated under reduced pressure, and purified by silica gel column chromatography to yield 1.15 g of off-white solid. $^1$H NMR (400 MHz, $CDCl_3$): δ 8.64 (d, J=4.9 Hz, 1H), 8.28 (d, J=6.6 Hz, 1H), 7.19 (d, J=4.9 Hz, 1H), 6.64 (br s, 1H), 2.80-2.65 (m, 1H), 1.24 (d, J=6.7 Hz, 3H), 1.15 (d, J=6.7 Hz, 3H); MS: m/z 352.1, $[M+H]^+$.

Step 3

The product of the previous step (1.1 g), acetonitrile (20 ml) and N,N-diisopropylethylamine (1.0 g) were added into a 250 ml single-necked flask, cooled to 0° C., dropwise added with phosphorus oxychloride ((970 mg), then dropwise added with 2 drops of N-methylmorpholine, and stirred at room temperature. The reaction solution was concentrated to dryness under reduced pressure and azeotroped with toluene twice; then acetonitrile (20 ml) was added into the residues, cooled to 0° C., added with N,N-diisopropylethylamine (1.0 g), and then added with (S)-4-N-t-Boc-2-methylpiperazine (632 mg), and stirred at room temperature for 1 hour after the addition. The reaction solution was poured into a saturated aqueous solution of sodium bicarbonate to quench the reaction and extracted with ethyl acetate; organic layers were combined, washed with saturated salt solution, dried with anhydrous sodium sulfate, filtered, concentrated under reduced pressure, and purified by silica gel column chromatography to yield 1.2 g of yellow solid. MS: m/z 534.2, $[M+H]^+$.

Intermediate 6

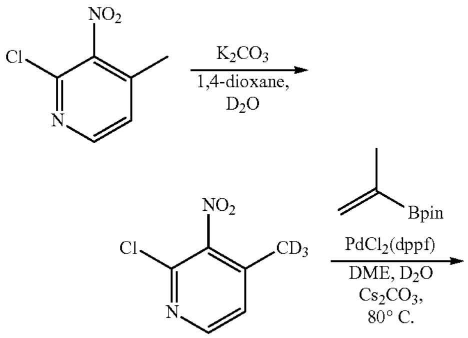

-continued

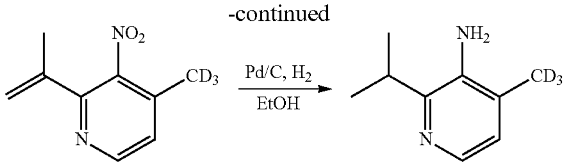

Step 1

2-chloro-4-methyl-3-nitropyridine (19 g), potassium carbonate (14 g), 1,4-dioxane (100 ml) and deuteroxide (60 ml) were added in a reaction flask, and refluxed at 100° C. after the addition. The reaction solution was cooled to room temperature, diluted with water, and extracted with ethyl acetate; organic layers were combined, washed with water once, dried with anhydrous sodium sulfate, filtered, and then concentrated to dryness under reduced pressure. The operation was repeated for three times according to the above method to obtain the product. $^1$H NMR (400 MHz, $CDCl_3$): δ 8.40 (d, J=5.0 Hz, 1H), 7.27 (d, J=5.0 Hz, 1H). MS: m/z 176.0, $[M+H]^+$.

Step 2

The product of the previous step (15 g), caesium carbonate (85.3 g), 1,2-dimethoxyethane (240 ml), deuteroxide (60 ml), isopropenylboronic acid pinacol ester (17.6 g) and [1,1'-bis(diphenylphosphino)ferrocene]dichloropalladium (6.2 g) were added in a 500 ml single-necked flask, subjected to nitrogen displacement, and then heated to 80° C. for reflux reaction. The reaction solution was cooled and then poured into a saturated sodium bicarbonate solution and extracted with ethyl acetate; organic layers were combined, dried with anhydrous sodium sulfate, filtered, concentrated under reduced pressure, and purified by silica gel column chromatography to yield 14 g of pale yellow oily matter. $^1$H NMR (400 MHz, $CDCl_3$): δ 8.54 (d, J=5.0 Hz, 1H), 7.18 (d, J=5.0 Hz, 1H), 5.37-5.31 (m, 1H), 5.20 (s, 1H), 2.20 (t, J=1.2 Hz, 3H).

Step 3

The product of the previous step (14 g), absolute ethyl alcohol (200 ml) and 5% palladium on carbon (7 g) were added into a 500 ml single-necked flask, subjected to hydrogen displacement, and reacted at room temperature overnight under the pressure of a hydrogen bag. The reaction solution was filled with diatomite to remove palladium on carbon, then the filtrate was concentrated under reduced pressure and purified by silica gel column chromatography to obtain 8 g of pale yellow oily matter. $^1$H NMR (400 MHz, $CDCl_3$): δ 7.96 (d, J=4.8 Hz, 1H), 6.85 (d, J=4.8 Hz, 1H), 3.63 (br s, 2H), 3.12-2.97 (m, 1H), 1.31 (d, J=6.8 Hz, 6H).

Intermediate 7

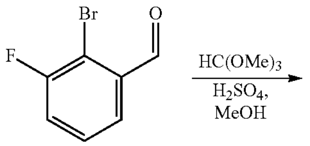

-continued

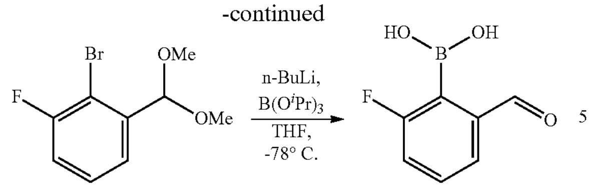

Step 1

2-bromo-3-fluorobenzaldehyde (20.0 g), methanol (40 ml) and concentrated sulfuric acid (0.5 ml) were added into a 100 ml single-necked flask, then dropwise added with trimethyl orthoformate (13.6 g), and then heated to 70° C. and stirred after the dropwise addition. After the reaction was completed, the reaction solution was cooled to 0° C., and slowly added with sodium methylate to adjust the pH to be 8-9, then diluted with water, and extracted with ethyl acetate; organic layers were combined, washed with saturated salt solution once, dried with anhydrous sodium sulfate, filtered, and concentrated under reduced pressure to yield 21 g of white solid. $^1$H NMR (400 MHz, $CDCl_3$): δ 7.42 (d, J=7.8 Hz, 1H), 7.36-7.27 (m, 1H), 7.12 (td, J=8.2, 1.3 Hz, 1H), 5.58 (s, 1H), 3.40 (s, 6H).

Step 2

The product of the previous step (10.0 g) and tetrahydrofuran (100 ml) were added into a 500 ml three-necked flask, cooled to −78° C., dropwise added with a n-hexane solution (2.5 M, 24 ml) containing n-butyl lithium, continuously stirred for 1 hour after the dropwise addition, then dropwise added with triisopropyl borate (9.8 g), and continuously stirred for 2 hours after the dropwise addition. After the reaction was completed, the reaction solution was slowly added with 3N dilute hydrochloric acid to adjust the pH to be 2-3, and then extracted with ethyl acetate; organic layers were combined, washed with saturated salt solution once, dried with anhydrous sodium sulfate, filtered, concentrated under reduced pressure, and purified by silica gel column chromatography to yield 5.3 g of white solid. $^1$H NMR (400 MHz, Acetone-$d_6$): δ 10.06 (d, J=2.4 Hz, 1H), 7.77 (d, J=7.5 Hz, 1H), 7.65-7.57 (m, 1H), 7.44 (s, 2H), 7.38 (td, J=8.2, 0.7 Hz, 1H).

Intermediate 9

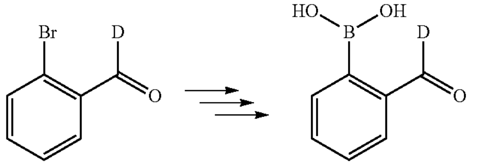

191-4 AL-BD 191-4 was used as a starting material and was transformed through a chemical reaction to obtain AL-BD. (With reference to literatures Organic Letters (2018), 20(7), 1712-1715; Synlett (2020), 31(7), 699-702; Organic Letters (2019), 21(7), 2231-2235; Organometallics (2019), 38(1), 119-128; Journal of the American Chemical Society (2021), 143(1), 53-59). The specific preparation method was as follows:

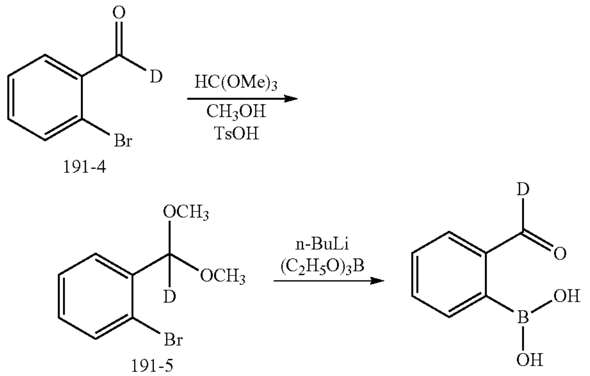

191-4 191-5 AL-BD

Step 1

191-4 (4.75 kg), trimethyl orthoformate (5.5 kg), p-toluenesulfonic acid (0.45 kg) and methanol (19 L) were added into a 50 L double-glass reactor, and slowly heated to 50° C. for reaction; cooled to be 40° C. or lower, then the temperature was controlled at 40° C. for concentrating to a small volume. The temperature was cooled to be 20° C. or lower, and triethylamine (0.34 kg) was added to adjust the pH to be 7-8. The reaction solution was added with 10% aqueous solution of sodium bicarbonate (6 L) and 6 L of methyl tert-butyl ether, then was allowed to settle, subjected to liquid separation, and aqueous phases were extracted twice with methyl tert-butyl ether (4 Lx2), organic phases were combined, respectively washed twice with saturated salt solution, and then dried with anhydrous sodium sulfate. The temperature was controlled at 45° C. for concentrating to dryness to yield 5.6 kg of 191-5 product.

Step 2

191-5 (3.75 kg) and tetrahydrofuran (37.5 L) were added into a 50 L round-glass reactor, subjected to nitrogen displacement, and then cooled to be −90° C.; 2.5 M butyllithium (6.5 L) was dropwise added slowly, and then the temperature was controlled at −90° C. and stirred for reaction after the dropwise addition. Triethyl borate (2.6 kg) was continuously dropwise added slowly, and then the temperature was controlled at −80° C. and stirred for reaction after the dropwise addition. The materials were completely reacted. The reaction solution was added to a saturated ammonium chloride solution for quenching, extracted with ethyl acetate, and then organic phases were combined. The organic phases were cooled, 0.5 M aqueous solution of hydrochloric acid (8 L) was slowly added first, and then 1.0 M aqueous solution of hydrochloric acid (2 L) was added, and the mixture was stirred while keeping the temperature. Liquids were separated, washed with saturated salt solution for four times, and dried with anhydrous sodium sulfate for 30 minutes; concentrated to dryness, added with petroleum ether (3.75 L), cooled, stirred and filtered, then the filter cake was rinsed with petroleum ether, and placed at 40° C. for forced air drying to yield 1.9 kg of the product. $^1$HNMR (400 MHz, $CDCl_3$): δ 8.35-8.33 (m, 1H), 7.96-7.93 (m, 1H), 7.75-7.73 (m, 4H); $^{13}$C NMR (100 MHz, DMSO-$d_6$) δ198.3, 139.7, 138.7, 138.4, 134.4, 131.1.

A specific preparation method of another boron-containing similar intermediate (aromatic potassium fluoroborate) was as follows:

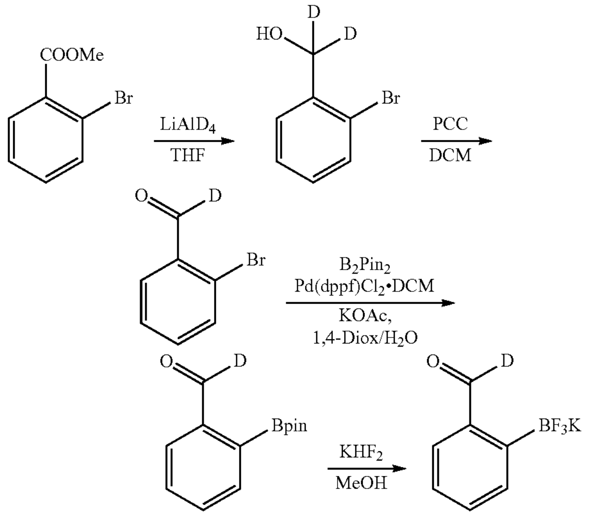

Step 1

Methyl 2-bromobenzoate (8.5 g) and tetrahydrofuran (50 ml) were added in a 250 ml three-necked flask, subjected to nitrogen displacement, slowly added with deuterated lithium aluminum hydride (3.3 g) in an ice bath, and stirred at room temperature for 2 hours. After the reaction was completed, deuteroxide (3.3 ml), 15% aqueous solution of sodium hydroxide (3.3 ml), tap water (10 ml) and anhydrous sodium sulfate (5 g) were slowly added in an ice bath, stirred for 20 minutes and then filtered. The filtrate was concentrated to yield 7.45 g of white solid. $^1$HNMR (400 MHz, $CDCl_3$): δ 7.57 (dd, J=8.0, 1.2 Hz, 1H), 7.50 (dd, J=7.6, 1.7 Hz, 1H), 7.36 (td, J=7.5, 1.3 Hz, 1H), 7.19 (td, J=7.7, 1.8 Hz, 1H).

Step 2

The product of the previous step (7.4 g), dichloromethane (50 ml) and silica gel (15 g) were added in a 100 ml single-necked flask, subjected to nitrogen displacement, slowly added with PCC (10.1 g) in an ice bath, and stirred at room temperature for 2 hours. After the reaction was completed, the reaction solution was concentrated and purified by silica gel column chromatography to yield 6.2 g of light yellow oily matter.

Step 3

The product of the previous step (6.1 g), dioxane (50 ml), potassium acetate (9.5 g), bis(pinacolato)diboron (9.8 g) and a complex of [1,1'-bis(diphenylphosphino)ferrocene]dichloropalladium and dichloromethane (790.8 mg) were added in a 100 ml single-necked flask, subjected to nitrogen displacement, heated to 80° C., and stirred for 3 hours. After the reaction was completed, the reaction solution was cooled to room temperature and filtered. The filtrate was concentrated and purified by silica gel column chromatography to yield 6.1 g of light yellow oily matter. $^1$HNMR (400 MHz, DMSO-$d_6$): δ 7.94-7.90 (m, 1H), 7.76-7.73 (m, 1H), 7.72-7.63 (m, 2H), 1.35 (s, 12H).

Step 4

The product of the previous step (2 g), methanol (20 ml) and potassium bifluoride (3.4 g) were added into a 100 ml single-necked flask, subjected to nitrogen displacement, heated to 70° C., and stirred for 2 hours. After the reaction was completed, the reaction solution was filtered, and the filtrate was concentrated to dryness, added with acetone (6 ml) for dissolution, slowly dropwise added with n-hexane (20 ml) in an ice water bath, stirred for 1 hour, and filtered. The filter cake was dried to yield 1.3 g of off-white solid. $^1$HNMR (400 MHz, DMSO-$d_6$): δ 7.69 (d, J=6.9 Hz, 1H), 7.62 (d, J=5.2 Hz, 1H), 7.41 (br s, 1H), 7.24 (br s, 1H).

Intermediate 10

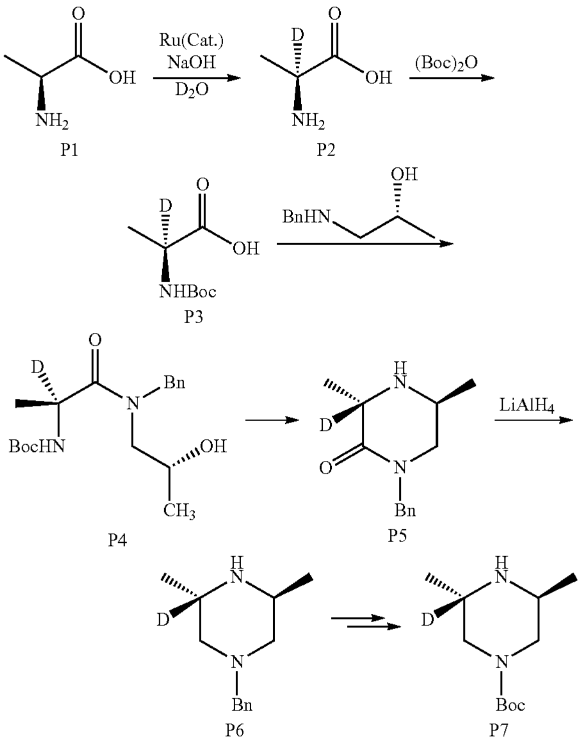

P1 was used as a raw material to carry out deuteration substitution to obtain P2, and finally P7 was prepared. (With reference to Organic Process Research & Development (2017), 21(11), 1741-1744; CN103265498).

Intermediate 11 (X2)

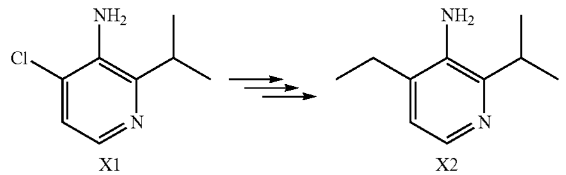

X1 X2

X1 was used as a raw material to obtain X2 by chemical reaction (with reference to literature US20190374542).

Alternatively, another preparation method was adopted, wherein the specific preparation method was as follows:

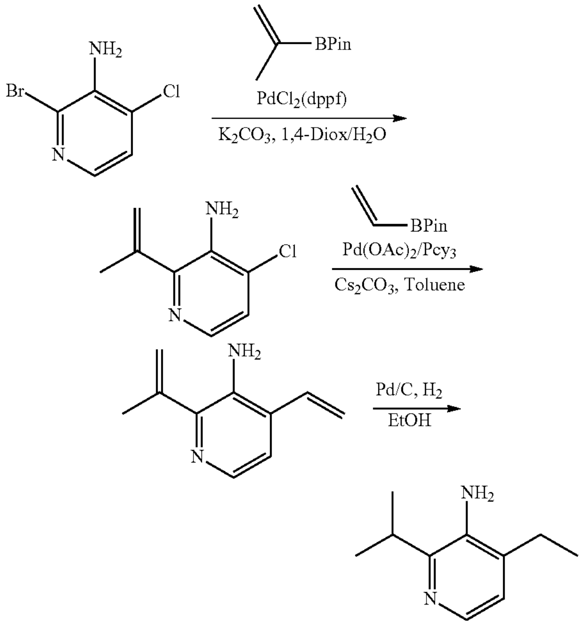

Intermediate 11

Step 1

2-bromo-4-chloropyridin-3-amine (9.2 g), isopropenylboronic acid pinacol ester (11.9 g), potassium carbonate (7.6 g), $PdCl_2$(dppf) (5.5 g), 1,4-dioxane (85 ml) and water (17 ml) were added into a 250 ml flask, subjected to nitrogen displacement, heated to 105° C., and stirred for 3 hours. After the reaction was completed, the reaction solution was cooled to room temperature, and filtered. The filtrate was added with water, and then extracted with ethyl acetate; organic layers were combined, washed with saturated salt solution twice, dried with anhydrous sodium sulfate, and filtered. The filtrate was concentrated and purified by silica gel column chromatography to yield 9.3 g of orange yellow solid. $^1$H NMR (400 MHz, $CDCl_3$): δ 7.92 (d, J=5.2 Hz, 1H), 7.11 (d, J=5.1 Hz, 1H), 5.54-5.51 (m, 1H), 5.36-5.34 (m, 1H), 4.37 (s, 2H), 2.18 (t, J=1.3 Hz, 3H).

Step 2

The product of the previous step (10.0 g), vinylboronic acid pinacol cyclic ester (13.8 g), Pcy3 (1.0 g), palladium acetate (0.5 g), caesium carbonate (38.8 g) and toluene (200 ml) were added into a 500 ml flask, subjected to nitrogen displacement, heated to 120° C., and stirred for reaction for 12 hours. After the reaction was completed, the reaction solution was cooled to room temperature, added with water, and then extracted with ethyl acetate; organic layers were combined, washed with saturated salt solution twice, dried with anhydrous sodium sulfate, and filtered. The filtrate was concentrated and purified by silica gel column chromatography to yield 7.1 g of brown oily matter. $^1$H NMR (400 MHz, $CDCl_3$): δ 8.01 (d, J=4.9 Hz, 1H), 7.06 (d, J=4.9 Hz, 1H), 6.76 (dd, J=17.4, 11.1 Hz, 1H), 5.80 (dd, J=17.4, 1.2 Hz, 1H), 5.54-5.48 (m, 2H), 5.30-5.28 (m, 1H), 4.05 (s, 2H), 2.18 (t, J=1.2 Hz, 3H). MS: m/z 161.1, $[M+H]^+$.

Step 3

The product of the previous step (7.1 g), ethanol (150 ml) and palladium on carbon (0.7 g) were added into a 250 ml single-necked flask, subjected to hydrogen displacement, and stirred overnight at room temperature. After the reaction was completed, the reaction solution was filtered, then the filtrate was concentrated and purified by silica gel column chromatography to yield 5.5 g of purple oily matter. $^1$H NMR (400 MHz, $CDCl_3$): δ 8.02 (d, J=4.9 Hz, 1H), 6.88 (d, J=4.9 Hz, 1H), 3.66 (s, 2H), 3.12-3.01 (m, 1H), 2.52 (q, J=7.6 Hz, 2H), 1.32 (d, J=6.7 Hz, 6H), 1.28 (t, J=7.5 Hz, 3H). MS: m/z 165.1, $[M+H]^+$.

Then, referring to the preparation solutions of intermediate 1, intermediate 2, intermediate 3 and intermediate 4, the following intermediates can be prepared:

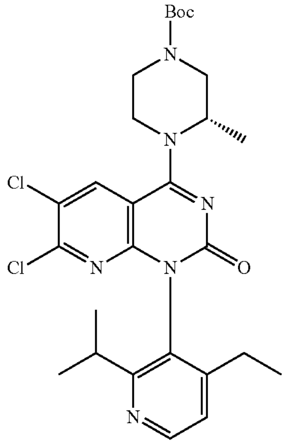

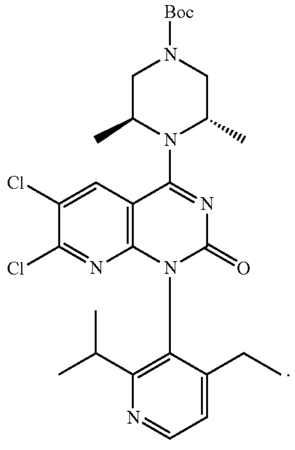

The specific preparation method was as follows:

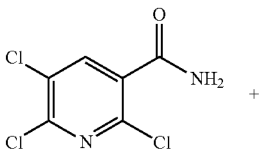

-continued

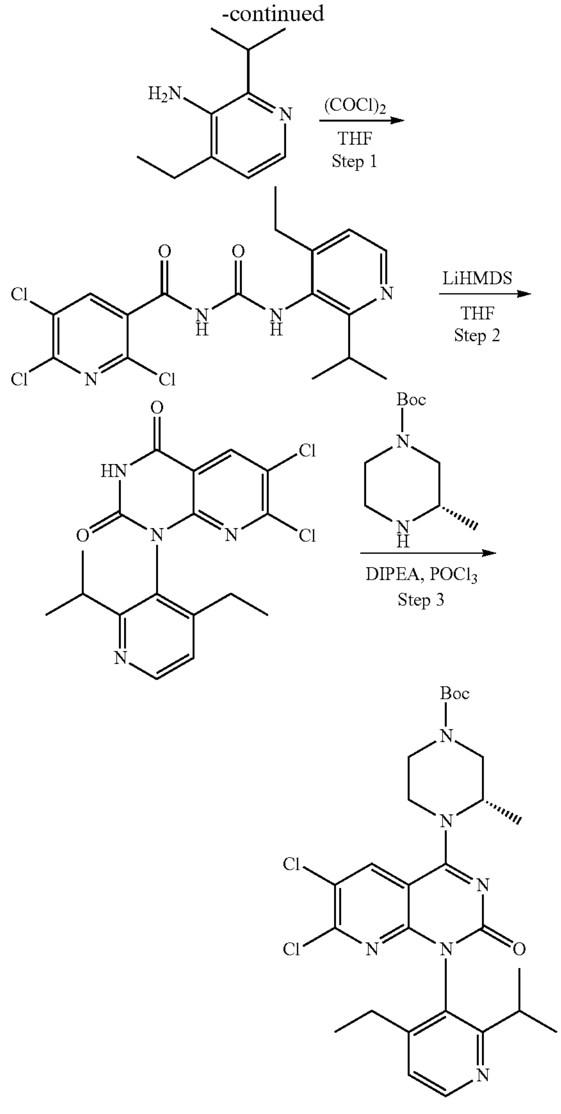

Step 1

Tetrahydrofuran (50 ml) was added into a 250 ml three-necked flask, the system was subjected to nitrogen displacement, cooled to −5° C., dropwise added with oxalyl chloride (2.9 g) slowly, stirred for 10 minutes, added with 2,5,6-trichloronicotinamide (4.4 g) in batches, heated to 45° C., and stirred for 1 hour. After the reaction was completed, the reaction solution was concentrated to dryness, and added with tetrahydrofuran (25 ml), subjected to nitrogen displacement, cooled to −5° C., slowly dropwise added with a tetrahydrofuran solution (18 ml) containing 2-isopropyl-4-ethylpyridine-3-amine (2.1 g), and stirred for 1 hour at room temperature. After the reaction was completed, the reaction solution was concentrated to dryness, added with water and a proper amount of saturated aqueous solution of sodium carbonate to adjust the pH to be 7-8, and then extracted with dichloromethane; organic layers were combined, washed with saturated salt solution once, dried with anhydrous sodium sulfate, and filtered. The filtrate was concentrated to yield a crude product of pink solid. A mixed solvent (110 ml) of petroleum ether and ethyl acetate (petroleum ether:ethyl acetate=10:1) was added, stirred for 1 hour at room temperature, and then filtered. The filter cake was dried to yield 6.3 g of off-white solid. MS: m/z 415.1, $[M+H]^+$.

Step 2

The product of the previous step (6.3 g) and tetrahydrofuran (160 ml) were added into a 500 ml three-necked flask, subjected to nitrogen displacement, cooled to 10-15° C., dropwise added with LiHMDS (1 M in THF, 33.5 ml), and stirred at room temperature for 2 hours. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated until a large number of solids were precipitated, added with MTBE (10 ml), and then filtered. The filter cake was dried to yield 3.8 g of white solid. MS: m/z 379.1, $[M+H]^+$.

Step 3

The product of the previous step (3.8 g), tetrahydrofuran (95 ml), DIPEA (7.8 g) and (S)-4-N-t-Boc-2-methylpiperazine (2.0 g) were added into a 250 ml three-necked flask, subjected to nitrogen displacement, dropwise added with phosphorus oxychloride (3.1 g) slowly in an ice bath, heated to 30° C., stirred for 15 minutes, added with (S)-4-N-t-Boc-2-methylpiperazine (1.0 g), and stirred for reaction for 30 minutes. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated to yield 5.7 g of brown solid. MS: m/z 561.2, $[M+H]^+$.

Referring to the separation method of the supercritical fluid chromatography (SFC) recorded in patent WO2019051291, the following intermediates could be prepared and separated.

Intermediate 5M

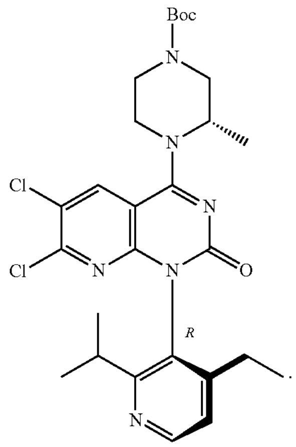

Intermediate 8

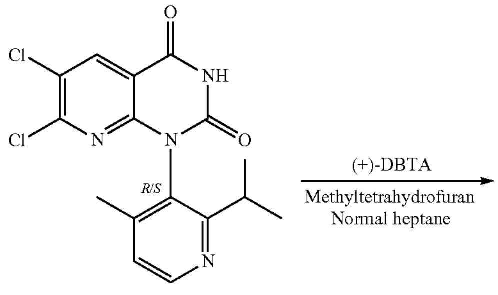

A

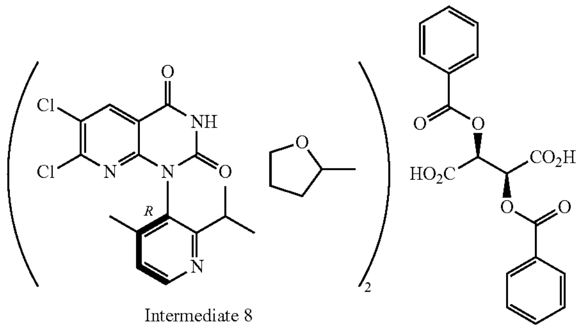

Intermediate 8

5.00 g of compound A (prepared according to WO2020050890 and WO2019051291) was weighed and placed in a 250 mL round-bottom flask, added with 50 mL of methyltetrahydrofuran, and stirred for 30 minutes under nitrogen protection while keeping the temperature at 75° C.; after the mixture was completely resolved into a clear solution, 20 mL of methyltetrahydrofuran resolved with 10 g of (+) -DBTA was added; after the above two methyltetrahydrofuran solutions were mixed, 50 mL of normal heptane was dropwise added at 75° C. continuously, then the above mixture was continuously stirred for 8 hours at 25° C., and then filtered to obtain solids. The solids were subjected to forced air drying for 5 hours at 50° C. to yield 4 g of the target complex (>99% ee). $^{1}$H NMR (400 MHz, DMSO-d6) δ12.31 (br.s, 1H), 8.60 (s, 1H), 8.53-8.52 (m, 1H), 7.99-7-96 (m, 2H), 7.71-7-67 (m, 1H), 7.57-7.53 (m, 2H), 7.29-7.28 (m, 1H), 5.77 (s, 1H), 3.86-3.72 (m, 2H), 3.58-3.52 (m, 1H), 2.94-2.84 (m, 1H), 2.05 (s, 3H), 1.97-1.90 (m, 1H), 1.85-1.74 (m, 1H), 1.36-1.24 (m, 1H), 1.13-1.12 (m, 3H), 1.09-1.07 (m, 3H), 1.02-1.00 (m, 3H); $^{13}$C NMR (100 MHz, DMSO-$d_6$) 3168.0, 165.2, 164.6, 160.5, 151.7, 150.1, 149.9, 149.7, 146.3, 139.7, 134.1, 129.8, 129.6, 129.3, 128.7, 124.4, 124.1, 112.8, 74.8, 72.0, 67.2, 33.2, 30.0, 25.9, 22.7, 22.3, 21.4, 17.5.

According to the preparation solution of intermediate 3, the following intermediate 3M was prepared (see FIG. 1 of the specification for the single crystal structure thereof):

Intermediate 3M

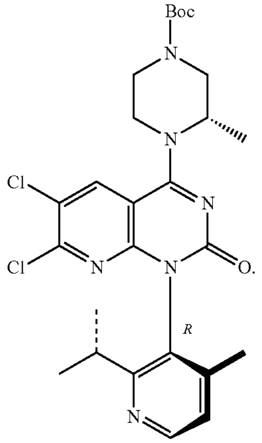

Referring to the preparation solution of intermediate 8, (−)-DBTA was used as a resolution reagent to prepare the following intermediate 20:

Intermediate 20

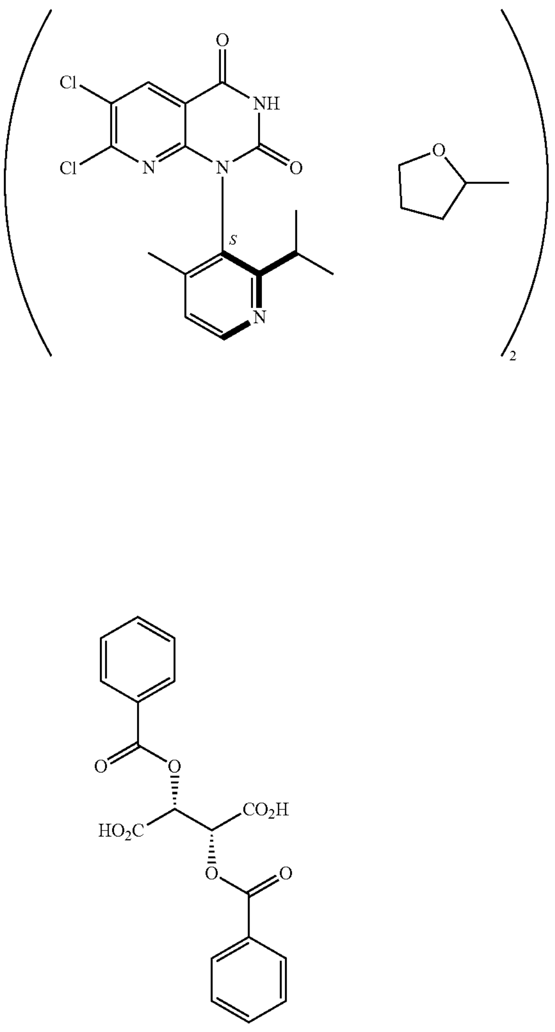

The following intermediate 3P can be prepared:

Intermediate 3P

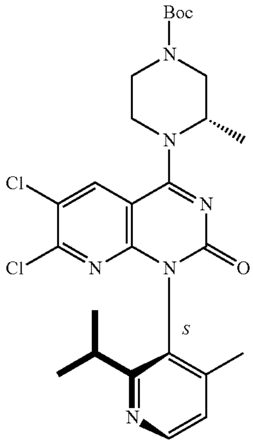

The following intermediates can be prepared using intermediate 8 and intermediate 20 with reference to the preparation solution of intermediate 4:

Intermediate 4M

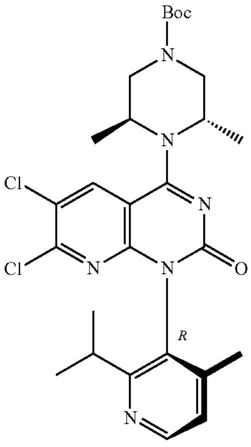

Intermediate 4P

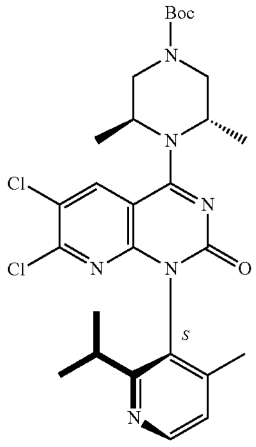

Intermediate 22

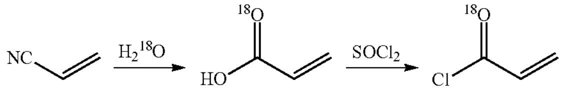

Intermediate 22

Vinyl cyanide was used as a starting material and a deuteroxide was used as a isotope source to prepare the intermediate 22 with reference to the method in the literature. (Referring to literatures Journal of Biosciences (Bangalore, India) (2009), 34(1), 21-26; JP61282089; US20030148480, or the like).

The specific preparation method was as follows:

25 ml of $H_2{}^{18}O$ with a pH of 7.2, about 2 ml of acrylonitrile and 10 mg of nitrilase were added into a reaction flask, and reacted overnight at 28° C. after the addition. A dioxane solution of HCl was slowly added to adjust the pH to be 2-3, and then added with dichloromethane for extraction twice. Organic phases were dried with anhydrous sodium sulfate, filtered, and concentrated to dryness under reduced pressure to yield light yellow oily matter. Then the oily matter was dissolved in a dichloromethane solution, added with thionyl chloride, and refluxed for 2 hours. The reaction solution was concentrated under reduced pressure to yield an acyl chloride product, which was directly used for reaction.

Intermediate 23

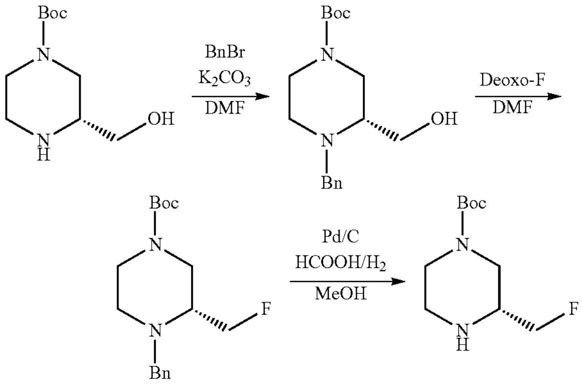

Step 1 tert-butyl (R)-3-(hydroxymethyl)piperazine-1-carboxylate (12 g), N,N-dimethylformamide (120 ml) and potassium carbonate (23 g) were added into a 250 ml three-necked flask, subjected to nitrogen displacement, dropwise added with benzyl bromide (14.2 g) slowly in an ice bath, and stirred for 2 hours at 0° C. After the reaction was completed, suction filtration was performed, and the filtrate was added with a saturated salt solution and extracted with methyl tertbutyl ether; organic phases were combined, washed with saturated salt solution, dried with anhydrous sodium sulfate, and then concentrated to dryness. A proper amount of normal hexane was added to crystallize, stirred at room temperature for 20 minutes, filtered and dried to yield 13.8 g of white solid. $^1$HNMR (400 MHz, $CDCl_3$): δ 7.37-7.26 (m, 5H), 4.05 (d, J=13.3 Hz, 1H), 3.88 (dd, J=11.4, 5.4 Hz, 1H), 3.76-3.50 (m, 3H), 3.49-3.05 (m, 3H), 2.86-2.42 (m, 3H), 2.33-2.24 (m, 1H), 1.47 (s, 9H). MS: m/z 307.2, $[M+H]^+$.

Step 2

The product of the previous step (6.2 g) and dichloromethane (150 ml) were added into a 250 ml three-necked flask, subjected to nitrogen displacement, cooled to −20° C., dropwise added with a dichloromethane solution (81 ml) containing Deoxo-F (9.0 g) slowly, stirred for 2 hours while keeping the temperature at −20° C., then heated to room temperature, and stirred at room temperature for 2 hours. After the reaction was completed, the reaction solution was added with a saturated aqueous solution of sodium bicarbonate to adjust the pH of the aqueous phase to be 7-8, and extracted with dichloromethane; organic phases were combined, dried with anhydrous sodium sulfate, and then filtered. The filtrate was concentrated and purified by silica gel column chromatography to yield 5.9 g of colorless oily liquid. MS: m/z 309.2, $[M+H]^+$.

Step 3

The product of the previous step (2.8 g), methanol (40 ml), formic acid (3 g) and 5% Pd/C (3.5 g) were added into a 100 ml single-necked flask, subjected to hydrogen displacement, stirred at room temperature for 10 hours. After the reaction was completed, the reaction solution was filled with diatomite for filtering, and the filtrate was added with an aqueous solution of sodium bicarbonate to adjust the pH of the aqueous phase to be 7-8, and then extracted with dichloromethane. Organic phases were combined, dried with anhydrous sodium sulfate, and then filtered. The filtrate was concentrated and purified by silica gel column chromatography to yield 1.1 g of colorless oily liquid. $^1$HNMR (400 MHz, $CDCl_3$): δ 4.52-4.24 (m, 2H), 4.05-3.76 (m, 2H), 3.07-2.83 (m, 3H), 2.82-2.48 (m, 2H), 2.03 (s, 1H), 1.47 (s, 9H). MS: m/z 219.2, $[M+H]^+$.

PREPARATION OF COMPOUNDS

Example 1

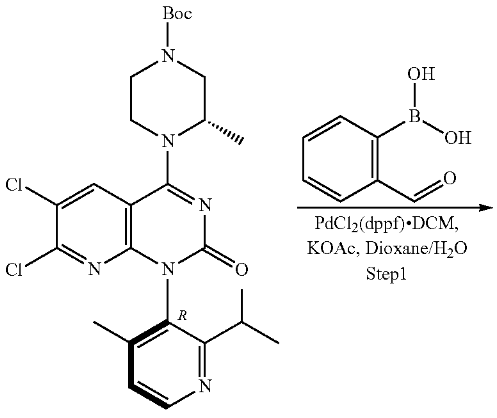

Intermediate 3M

-continued

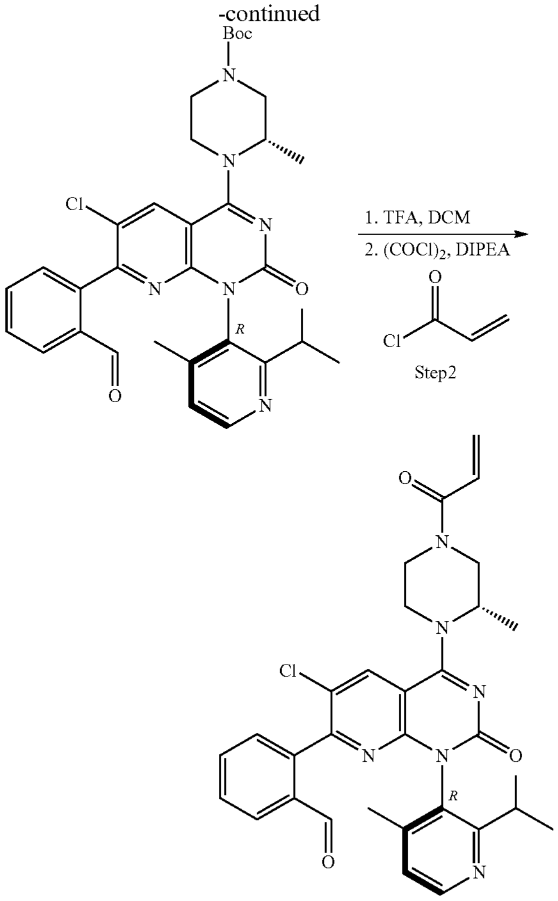

3-2M

Step 1

Starting materials tert-butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (intermediate 3M) (100.0 g), 2-formylphenylboronic acid (29.6 g), potassium acetate (53.8 g), 1,4-dioxane (1000 ml), water (100 ml) and a complex of [1,1'-bis(diphenylphosphino)ferrocene]dichloropalladium and dichloromethane (7.5 g) were added into a 2000 ml three-necked flask, subjected to nitrogen displacement for three times, and then gradually heated to 80° C., and stirred. After the reaction was completed, the reaction solution was cooled to room temperature, and filtered with diatomite. The filtrate was concentrated to remove most 1,4-dioxane, diluted with ethyl acetate, and then added with a saturated aqueous solution of potassium carbonate, and subjected to liquid separation; aqueous phases were extracted three times with ethyl acetate, and organic layers were combined, washed with saturated salt solution once, dried with anhydrous sodium sulfate, filtered, concentrated under reduced pressure, and purified by silica gel column chromatography to yield 101.5 g of yellow solid. $^1$H NMR (400 MHz, DMSO-$d_6$): δ 9.78 (s, 1H), 8.41 (s, 1H), 8.35 (d, J=4.8 Hz, 1H), 7.95 (dd, J=7.6, 1.1 Hz, 1H), 7.75 (td, J=7.5, 1.4 Hz, 1H), 7.68 (td, J=7.5, 1.1 Hz, 1H), 7.31 (dd, J=7.6, 1.0 Hz, 1H), 7.15 (d, J=4.9 Hz, 1H), 4.89 (s, 1H), 4.27 (d, J=13.5 Hz, 1H), 4.09-3.92 (m, 1H), 3.86 (d, J=13.0 Hz, 1H), 3.73 (t, J=11.1 Hz, 1H), 3.35-3.03 (m, 2H), 2.77-2.65 (m, 1H), 1.91 (s, 3H), 1.46 (s, 9H), 1.38 (d, J=6.6 Hz, 3H), 1.06 (d, J=6.7 Hz, 3H), 0.88 (d, J=6.7 Hz, 3H).

Step 2

The product of the previous step (3.0 g) and dichloromethane (30 ml) were added to a 100 ml single-necked flask, cooled to 0° C., slowly added with trifluoroacetic acid (12 ml), and continuously stirred at room temperature after the addition. After the reaction was completed, the reaction solution was slowly added to ice water and extracted once with ethyl acetate. Organic phases were discarded, and aqueous phases were adjusted with a saturated aqueous solution of sodium bicarbonate till the pH was 7-8, and then extracted three times with ethyl acetate. Organic phases were combined, washed with a saturated aqueous solution of sodium chloride once, dried with anhydrous sodium sulfate, filtered, and concentrated under reduced pressure to yield 1.6 g of yellow solid. The product was dissolved in dichloromethane (15 ml), added with N,N-diisopropylethylamine (598 mg), cooled to 0° C. under nitrogen protection, then dropwise added with a dichloromethane solution (1 ml) containing acryloyl chloride (336 mg) slowly, and stirred at room temperature for 30 minutes after the dropwise addition. After the reaction was completed, the reaction solution was poured into a saturated aqueous solution of ammonium chloride and extracted three times with ethyl acetate; organic layers were combined, washed with saturated salt solution once, dried with anhydrous sodium sulfate and filtered. The filtrate was concentrated and purified by silica gel column chromatography to yield 1.2 g of light yellow solid. $^1$H NMR (400 MHz, DMSO-$d_6$): δ 9.79 (s, 1H), 8.45 (d, J=7.7 Hz, 1H), 8.35 (d, J=4.8 Hz, 1H), 7.95 (dd, J=7.6, 0.8 Hz, 1H), 7.75 (td, J=7.5, 1.2 Hz, 1H), 7.67 (td, J=7.5, 0.8 Hz, 1H), 7.32 (d, J=7.4 Hz, 1H), 7.15 (d, J=4.9 Hz, 1H), 6.97-6.79 (m, 1H), 6.22 (dd, J=16.6, 4.8 Hz, 1H), 5.78 (dd, J=10.3, 2.2 Hz, 1H), 4.95 (s, 1H), 4.49-4.03 (m, 3H), 3.88-3.44 (m, 2H), 3.33-3.07 (m, 1H), 2.80-2.64 (m, 1H), 1.92 (s, 3H), 1.36 (d, J=6.7 Hz, 3H), 1.06 (d, J=6.7 Hz, 3H), 0.89 (d, J=6.6 Hz, 3H); MS: m/z 571.2229, [M+H]$^+$.

Example 1-1

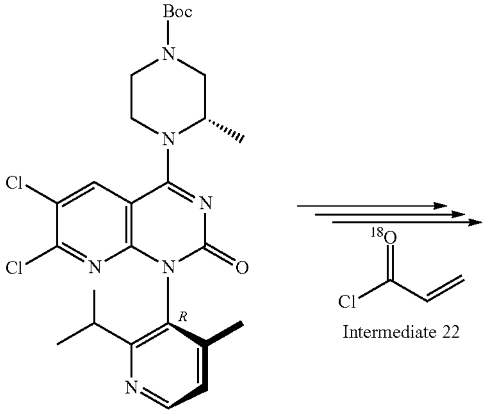

Intermediate 3M

-continued

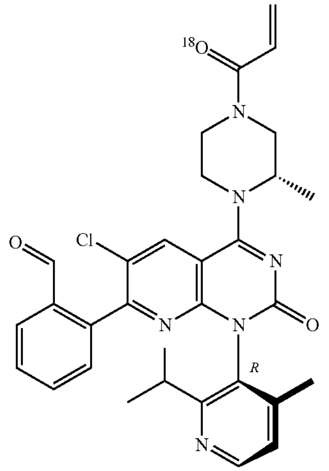

3-1MIS

Referring to the method of Example 1, a compound 3-1MIS was prepared using intermediate 3M and intermediate 22 as starting materials. $R_f$: 0.52 (DCM:MeOH=10:1). The specific preparation method was as follows:

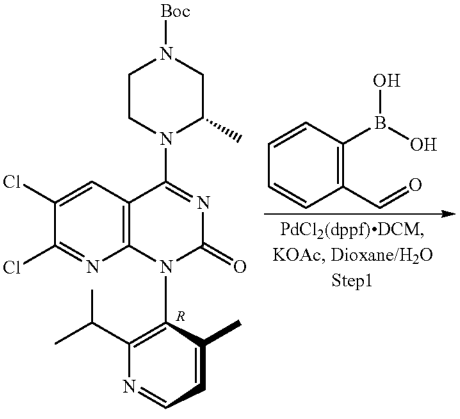

Intermediate 3M

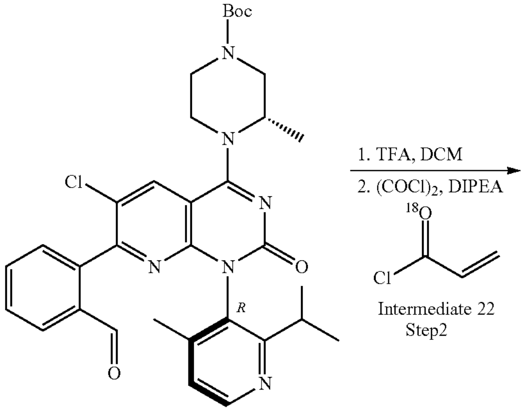

-continued

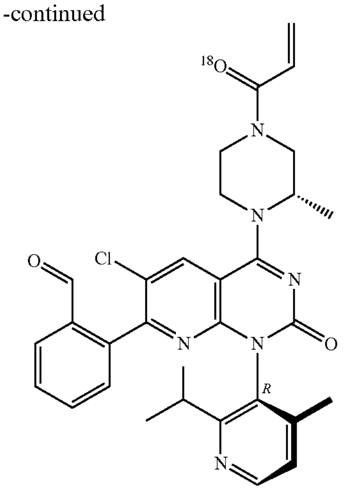

3-1MIS

Step 1

The starting material intermediate 3M, 2-formylphenylboronic acid, potassium acetate, 1,4-dioxane, water and palladium catalyst were added into a three-necked flask, subjected to nitrogen displacement, and then heated and stirred. After the reaction was completed, the reaction solution was filtered with diatomite, and the filtrate was concentrated, diluted with ethyl acetate, added with a saturated aqueous solution of potassium carbonate, and then subjected to liquid separation. Aqueous phases were extracted with ethyl acetate, organic layers were combined, washed with saturated salt solution, dried with anhydrous sodium sulfate, filtered, concentrated under reduced pressure and purified by silica gel column chromatography to yield yellow solid for the next reaction.

Step 2

The product of the previous step and dichloromethane were added into a single-necked flask, cooled to ice point, slowly added with trifluoroacetic acid, and continuously stirred at room temperature after the addition. After the reaction was completed, the reaction solution was slowly added to ice water and extracted once with ethyl acetate. Organic phases were discarded, and aqueous phases were adjusted with a saturated aqueous solution of sodium bicarbonate till the pH was 7-8, and then extracted with ethyl acetate. Organic phases were combined, washed with a saturated aqueous solution of sodium chloride once, dried with anhydrous sodium sulfate, filtered, and concentrated under reduced pressure to yield yellow solid for the next reaction. The above product was dissolved in dichloromethane, added with N,N-diisopropylethylamine, cooled under nitrogen protection, then dropwise added with a dichloromethane solution containing $^{18}$O-acryloyl chloride slowly, stirred at room temperature after the dropwise addition. After the reaction was completed, an aqueous solution of ammonium chloride was poured into the reaction solution, and extracted with ethyl acetate. Organic layers were combined, washed with saturated salt solution, dried with anhydrous sodium sulfate, filtered, concentrated, and purified by silica gel column chromatography to yield the target compound.

Example 1-2

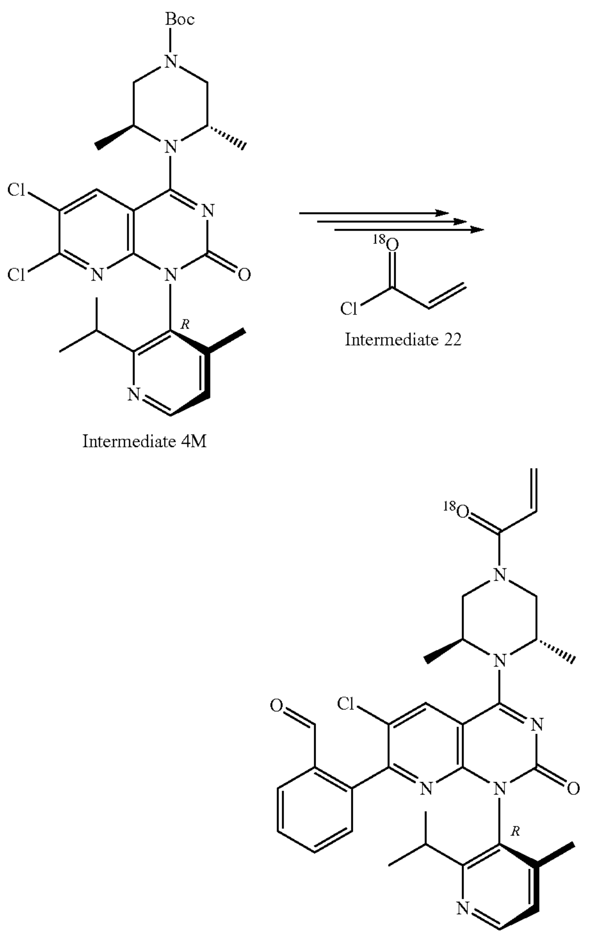

Intermediate 4M

Intermediate 22

3-4MIS

Referring to the method of Example 1, a compound 3-4MIS was prepared using intermediate 4M and intermediate 22 as starting materials. $R_f$: 0.53 (DCM:MeOH=10:1). The specific preparation method was as follows:

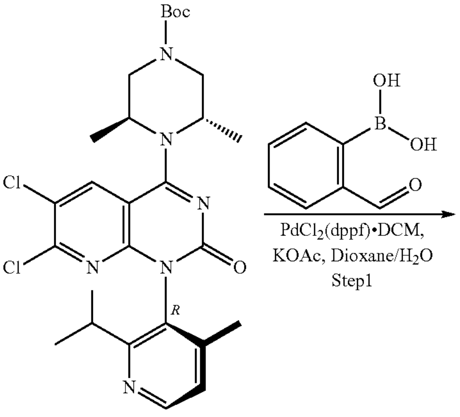

Intermediate 4M

-continued

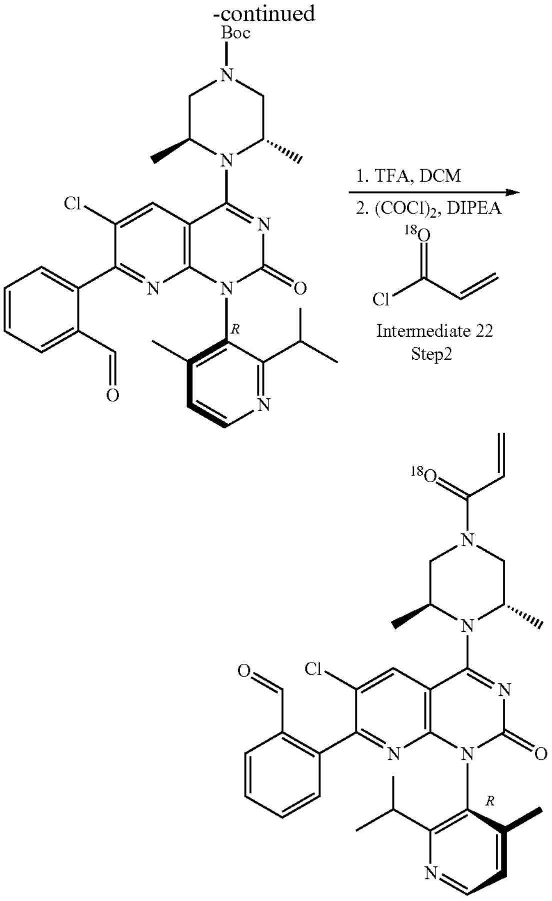

3-4MIS

Step 1

The starting materials intermediate 4M, 2-formylphenylboronic acid, potassium acetate, 1,4-dioxane, water and palladium catalyst were added into a three-necked flask, subjected to nitrogen displacement, and then gradually heated. After the reaction was completed, the reaction solution was cooled to room temperature, and filtered with diatomite. The filtrate was concentrated, diluted with ethyl acetate, added with a saturated aqueous solution of potassium carbonate, and then subjected to liquid separation. Aqueous phases were extracted with ethyl acetate, organic layers were combined, washed once with saturated salt solution, dried with anhydrous sodium sulfate, filtered, concentrated under reduced pressure and purified by silica gel column chromatography to yield yellow solid which was directly used for the next reaction.

Step 2

The product of the previous step and dichloromethane were added into a single-necked flask, cooled to a low temperature, slowly added with trifluoroacetic acid, and continuously stirred at room temperature. After the reaction was completed, the reaction solution was slowly added into ice water, and extracted once with ethyl acetate. Organic phases were discarded, and aqueous phases were adjusted with a saturated aqueous solution of sodium bicarbonate till the pH was 7-8, and then extracted with ethyl acetate. Organic phases were combined, washed once with a saturated aqueous solution of sodium chloride, dried with anhydrous sodium sulfate, filtered and concentrated to dryness under reduced pressure to yield yellow solid. The product was dissolved in dichloromethane, added with N,N-diisopropylethylamine, cooled to a low temperature under nitrogen protection, then dropwise added with a dichloromethane solution containing acryloyl chloride slowly, and stirred at room temperature after the dropwise addition. After the reaction was completed, the reaction solution was poured into an aqueous solution of ammonium chloride and extracted with ethyl acetate; organic layers were combined, washed with saturated salt solution, dried with anhydrous sodium sulfate, filtered, concentrated, and purified by silica gel column chromatography to yield the target product molecule.

Example 1-3

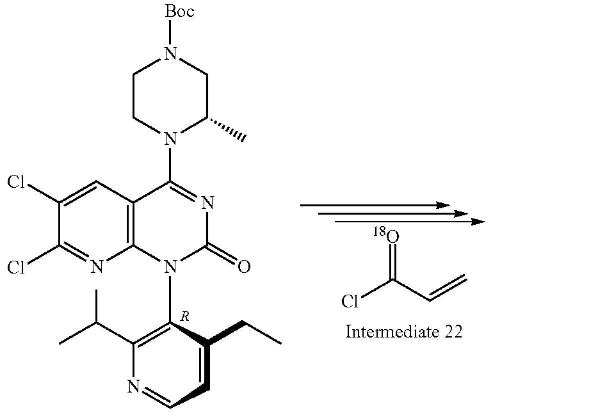

Intermediate 5M

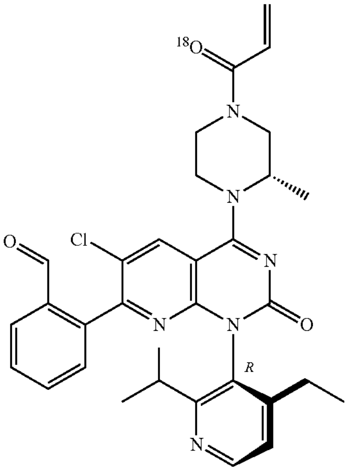

3-2MIS

Referring to the method of Example 1, a compound 3-2MIS was prepared using intermediate 5M and intermediate 22 as starting materials. $R_f$: 0.51 (DCM:MeOH=10:1). The specific preparation method was as follows:

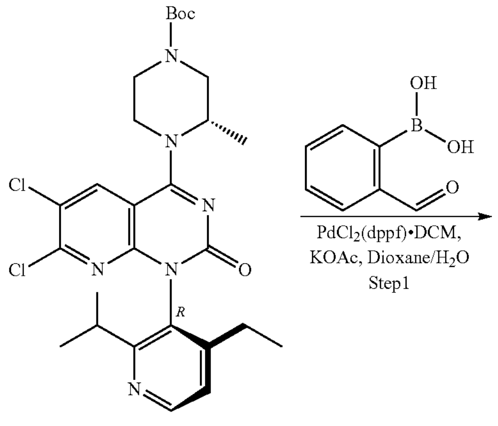

Intermediate 5M

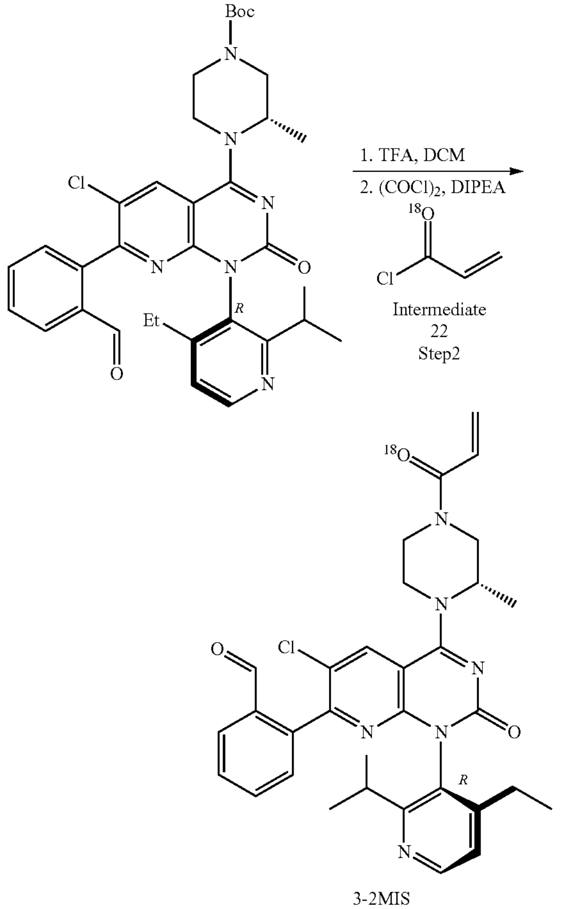

3-2MIS

Step 1

The starting material intermediates, 2-formylphenylboronic acid, potassium acetate, 1,4-dioxane, water and palladium catalyst were added into a three-necked flask, subjected to nitrogen displacement for three times, and then gradually heated and stirred. After the reaction was completed, the reaction solution was cooled to room temperature, and filtered with diatomite. The filtrate was concentrated to remove most 1,4-dioxane, diluted with ethyl acetate, and then added with a saturated aqueous solution of potassium carbonate, and subjected to liquid separation;

aqueous phases were extracted with ethyl acetate, and organic layers were combined, washed with saturated salt solution once, dried with anhydrous sodium sulfate, filtered, concentrated under reduced pressure, and purified by silica gel column chromatography to yield the product for the next reaction.

Step 2

The product of the previous step and dichloromethane were added into a single-necked flask, cooled to a low temperature, slowly added with trifluoroacetic acid, and continuously stirred at room temperature after the addition. After the reaction was completed, the reaction solution was slowly added to ice water and extracted once with ethyl acetate. Organic phases were discarded, and aqueous phases were adjusted with a saturated aqueous solution of sodium bicarbonate till the pH was 7-8, and then extracted with ethyl acetate. Organic phases were combined, washed with a saturated aqueous solution of sodium chloride once, dried with anhydrous sodium sulfate, filtered, and concentrated under reduced pressure to yield yellow solid. The product was dissolved in dichloromethane, added with N,N-diisopropylethylamine, cooled under nitrogen protection, then dropwise added with a dichloromethane solution containing $^{18}$O-acryloyl chloride slowly, stirred at room temperature after the dropwise addition. After the reaction was completed, the reaction solution was poured in a saturated aqueous solution of ammonium chloride, and extracted and combined with ethyl acetate, washed with saturated salt solution, dried with anhydrous sodium sulfate, and filtered. The filtrate was concentrated and purified by silica gel column chromatography to yield the product.

Example 1P

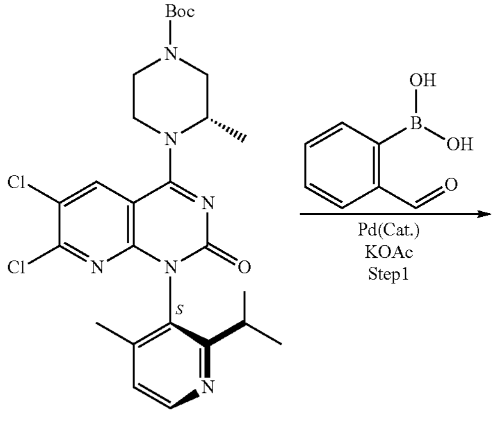

Intermediate 3P

-continued

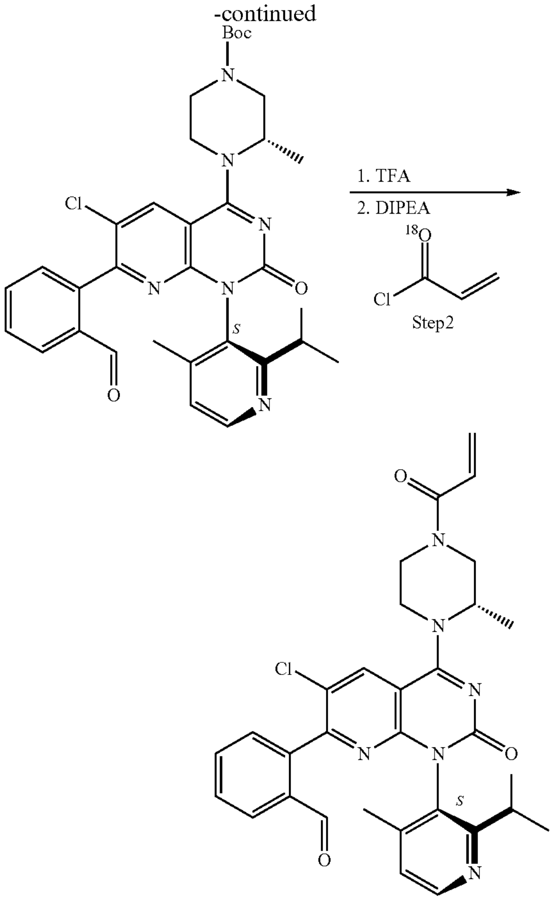

3-2P

Referring to the preparation solution of Example 1, a compound 3-2P was prepared using intermediate 3P as starting material. Rf: 0.51 ($CH_2Cl_2$: MeGH=10:1). The specific preparation method was as follows:

Step 1

The starting material intermediate 3P, 2-formylphenylboronic acid, potassium acetate, 1,4-dioxane, water and palladium catalyst were added into a three-necked flask, and then gradually heated and stirred under nitrogen protection. After the reaction was completed, the reaction solution was cooled to room temperature, and filtered with diatomite. The filtrate was concentrated to remove most 1,4-dioxane, diluted with ethyl acetate, and then added with a saturated aqueous solution of potassium carbonate, and subjected to liquid separation; aqueous phases were extracted with ethyl acetate, and organic layers were combined, washed with saturated salt solution once, dried with anhydrous sodium sulfate, filtered, concentrated under reduced pressure, and purified by silica gel column chromatography to yield yellow solid for the next reaction.

Step 2

The product of the previous step and dichloromethane were added into a single-necked flask, cooled, slowly added with trifluoroacetic acid, and continuously stirred at room temperature after the addition. After the reaction was completed, the reaction solution was slowly added to ice water and extracted once with ethyl acetate. Organic phases were discarded, and aqueous phases were adjusted with a saturated aqueous solution of sodium bicarbonate till the pH was 7-8, and then extracted three times with ethyl acetate. Organic phases were combined, washed with a saturated aqueous solution of sodium chloride once, dried with anhydrous sodium sulfate, filtered, and concentrated under reduced pressure to dryness to yield yellow solid. The product was dissolved in dichloromethane, added with N,N-diisopropylethylamine, cooled under nitrogen protection, then dropwise added with a dichloromethane solution containing $^{18}$O-acryloyl chloride slowly, stirred at room temperature after the dropwise addition. The reaction solution was poured in a saturated aqueous solution of ammonium chloride, and extracted with ethyl acetate. Organic layers were combined, washed with saturated salt solution, dried with anhydrous sodium sulfate, filtered, concentrated, and purified by silica gel column chromatography to yield light yellow solid.

Example 2

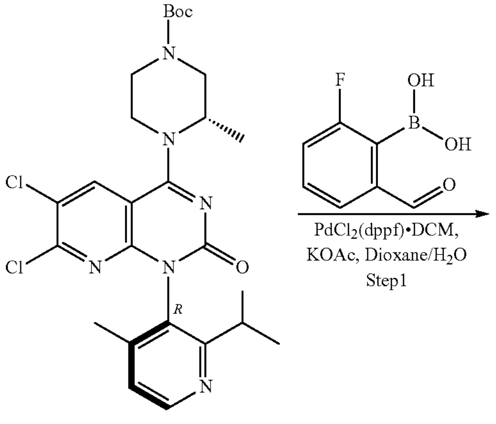

Intermediate 3M

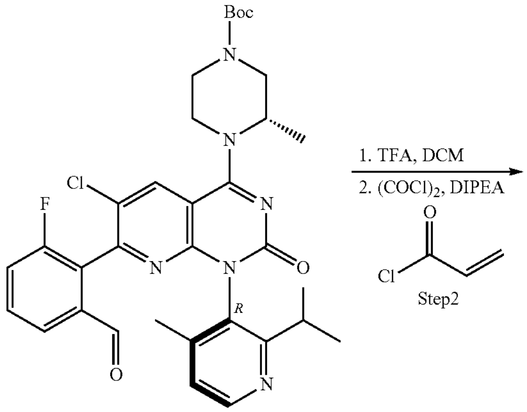

-continued

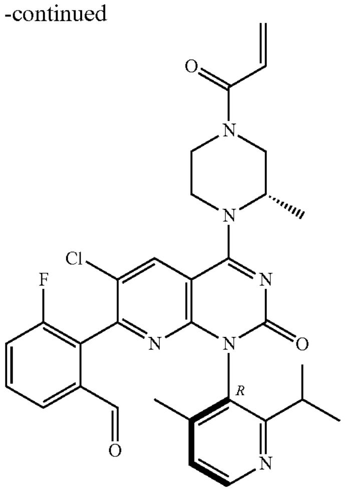

3-6M

Step 1

Tert butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (intermediate 3M) (4.0 g), 2-fluoro-6-formylphenylboronic acid (1.8 g), potassium acetate (2.2 g), 1,4-dioxane (40 ml), water (4 ml) and a complex of [1,1'-bis(diphenylphosphino) ferrocene]dichloropalladium and dichloromethane (596 mg) were added into a 50 ml single-necked flask, subjected to nitrogen displacement, and then gradually heated to 90° C., and stirred. After the reaction was completed, the reaction solution was diluted with water, and extracted with ethyl acetate. Organic layers were combined, washed with saturated salt solution once, dried with anhydrous sodium sulfate, filtered, concentrated, and purified by silica gel column chromatography to yield 3.4 g of yellow solid.

Step 2

The product of the previous step (700 mg) and dichloromethane (7 ml) were added to a 100 ml single-necked flask, cooled to 0° C., slowly added with trifluoroacetic acid (3 ml), and continuously stirred at room temperature after the addition. After the reaction was completed, the reaction solution was concentrated to dryness. Dichloromethane (7 ml) and N,N-diisopropylethylamine (882 mg) were added into the residue, cooled to 0° C. under nitrogen protection, and then dropwise added with a dichloromethane solution (0.5 ml) containing acryloyl chloride (124 mg) slowly, and stirred at room temperature after the dropwise addition. After the reaction was completed, the reaction solution was poured into a saturated aqueous solution of ammonium chloride, and extracted three times with ethyl acetate. Organic layers were combined, washed once with saturated salt solution, dried with anhydrous sodium sulfate, and filtered. The filtrate was concentrated and purified by silica gel column chromatography to yield 600 mg of light yellow solid. $^1$H NMR (400 MHz, DMSO-$d_6$): δ (9.79, 9.76 (s, 1H)), 8.50 (s, 1H), 8.34 (d, J=4.7 Hz, 1H), 7.91-7.80 (m, 1H), 7.80-7.71 (m, 1H), 7.71-7.62 (m, 1H), 7.20-7.07 (m, 1H), 6.97-6.78 (m, 1H), 6.23 (d, J=16.6 Hz, 1H), 5.78 (dd, J=10.4, 1.8 Hz, 1H), 4.94 (s, 1H), 4.49-4.03 (m, 3H), 3.90-3.46 (m, 2H), 3.33-3.10 (m, 1H), 2.82-2.62 (m, 1H), (1.89, 1.88 (s, 3H)), 1.43-1.32 (m, 3H), 1.12-1.01 (m, 3H), 0.93-0.78 (m, 3H); MS: m/z 589.2127, [M+H]$^+$.

Example 2-1

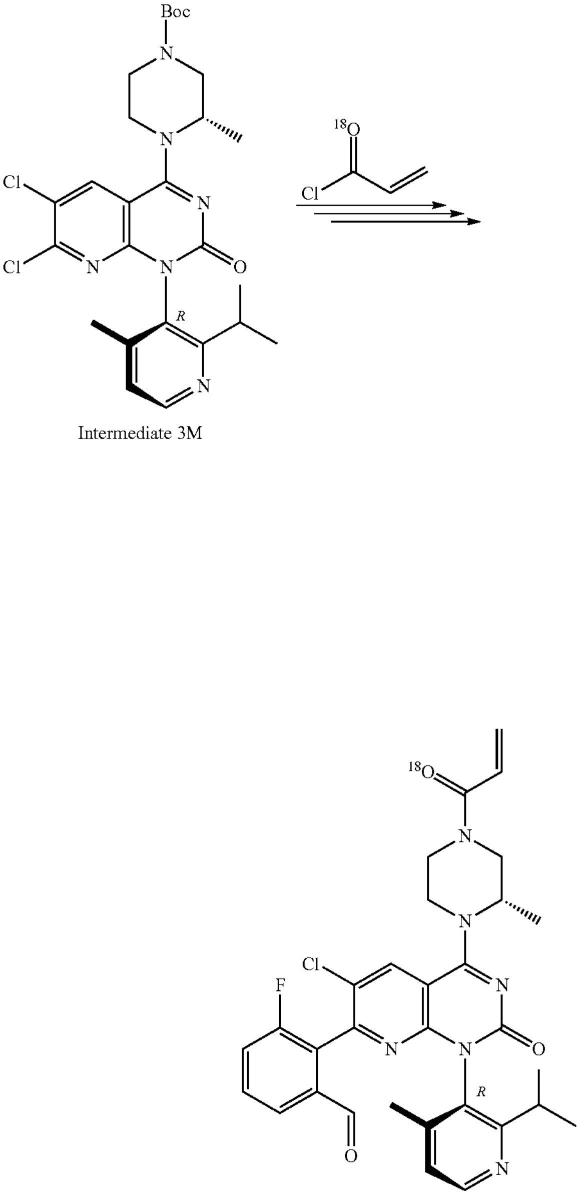

Intermediate 3M 3-3MIS

Referring to the preparation solution of Example 2, a compound 3-3MIS was prepared using intermediate 3M as starting material. Rf: 0.53 ($CH_2Cl_2$:MeOH=10:1). The specific preparation method was as follows:

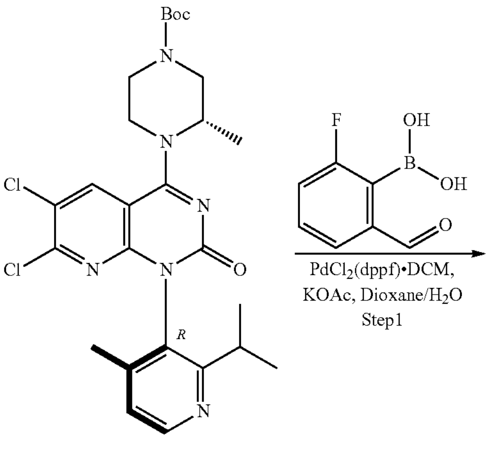

Intermediate 3M

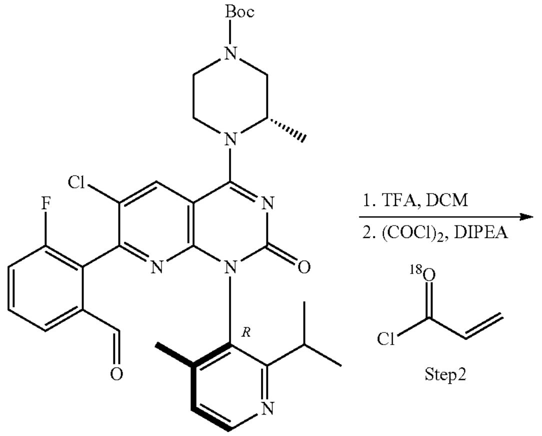

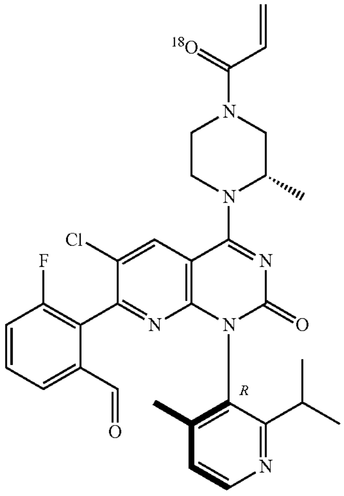

3-3MIS

Step 1

The starting material, 2-fluoro-6-formylphenylboronic acid, potassium acetate, 1,4-dioxane, water and palladium catalyst were added into a single-necked flask, subjected to nitrogen displacement, and then heated and stirred. After the reaction was completed, the reaction solution was diluted with water, and extracted with ethyl acetate. Organic layers were combined, washed with saturated salt solution once, dried with anhydrous sodium sulfate, filtered, concentrated under reduced pressure, and purified by silica gel column chromatography to yield yellow solid.

Step 2

The product of the previous step and dichloromethane were added into a single-necked flask, cooled, slowly added with trifluoroacetic acid, and continuously stirred at room temperature after the addition. After the reaction was completed, the reaction solution was concentrated to dryness. Dichloromethane and N,N-diisopropylethylamine were added into the residue, cooled under nitrogen protection, and then dropwise added with a dichloromethane solution containing $^{18}$O-acryloyl chloride slowly, and stirred at room temperature after the dropwise addition. After the reaction was completed, the reaction solution was poured into an aqueous solution of ammonium chloride, and extracted with ethyl acetate. Organic layers were combined, washed with saturated salt solution, dried with anhydrous sodium sulfate, and filtered. The filtrate was concentrated and purified by silica gel column chromatography to yield light yellow solid.

Example 2-2

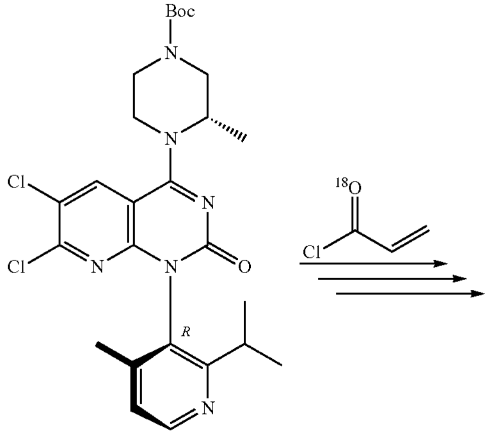

Intermediate 3M

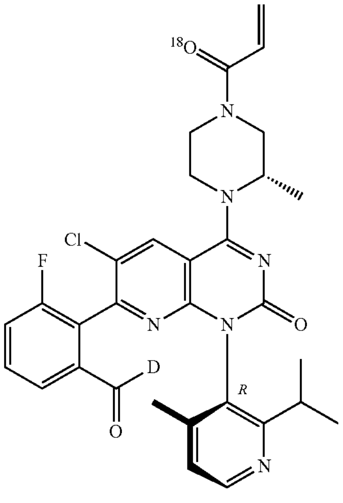

3-7MIS

Referring to the preparation solution of Example 2, a compound 3-7MIS was prepared using intermediate 3M as starting material. Rf: 0.50 ($CH_2Cl_2$:MeOH=10:1). The specific preparation method was as follows:

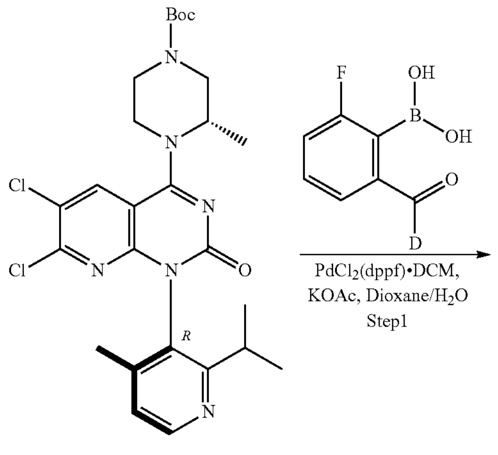

Intermediate 3M

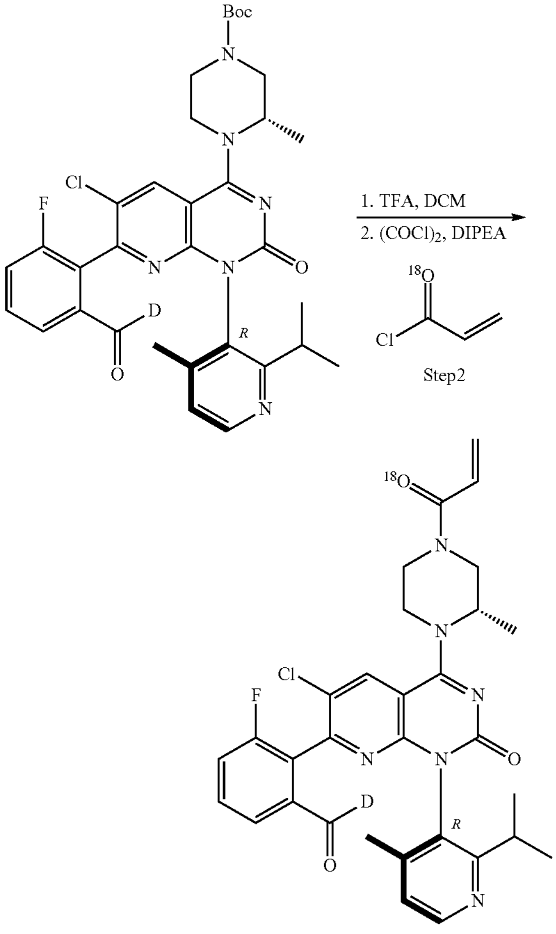

3-7MIS

Step 1

The starting material, 2-fluoro-6-formylphenylboronic acid, potassium acetate, 1,4-dioxane, water and palladium catalyst were added into a single-necked flask, subjected to nitrogen displacement, and then heated and stirred. After the reaction was completed, the reaction solution was diluted with water, and extracted with ethyl acetate. Organic layers were combined, washed with saturated salt solution once, dried with anhydrous sodium sulfate, filtered, concentrated under reduced pressure, and purified by silica gel column chromatography to yield yellow solid.

Step 2

The product of the previous step and dichloromethane were added into a single-necked flask, cooled, slowly added with trifluoroacetic acid, and continuously stirred at room temperature after the addition. After the reaction was completed, the reaction solution was concentrated to dryness. Dichloromethane and N,N-diisopropylethylamine were added into the residue, cooled under nitrogen protection, and then dropwise added with a dichloromethane solution containing $^{18}$O-acryloyl chloride slowly, and stirred at room temperature after the dropwise addition. After the reaction was completed, the reaction solution was poured into an aqueous solution of ammonium chloride, and extracted with ethyl acetate. Organic layers were combined, washed with saturated salt solution, dried with anhydrous sodium sulfate, and filtered. The filtrate was concentrated and purified by silica gel column chromatography to yield light yellow solid.

Example 2P

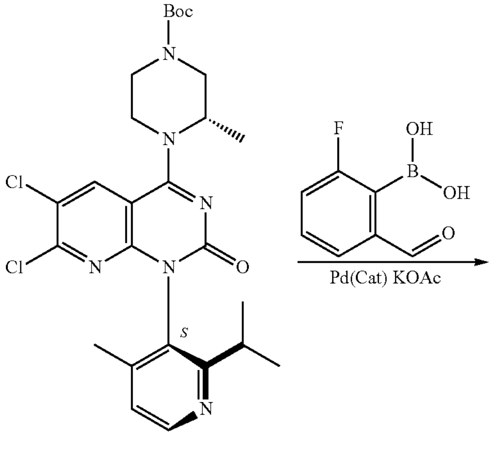

Intermediate 3P

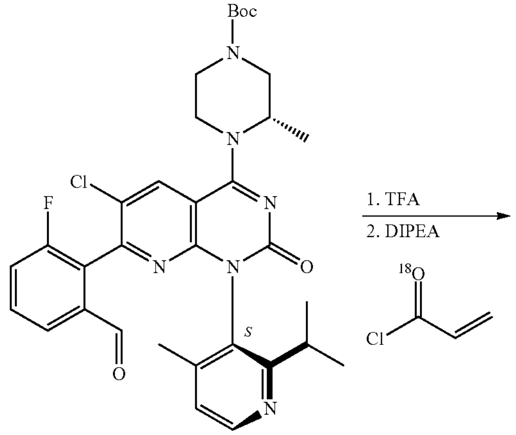

-continued

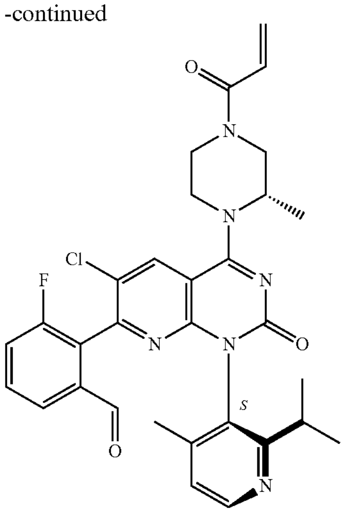

3-6P

Referring to the preparation solution of Example 1, a compound 3-6P was prepared using intermediate 3P as starting material. Rf: 0.52 ($CH_2Cl_2$:MeOH=10:1). The specific preparation method was as follows:

Step 1

The starting material, 2-fluoro-6-formylphenylboronic acid, potassium acetate, 1,4-dioxane, water and palladium catalyst were added into a single-necked flask, subjected to nitrogen displacement, and then heated and stirred. After the reaction was completed, the reaction solution was diluted with water, and extracted with ethyl acetate. Organic layers were combined, washed with saturated salt solution once, dried with anhydrous sodium sulfate, filtered, concentrated under reduced pressure, and purified by silica gel column chromatography to yield yellow solid.

Step 2

The product of the previous step and dichloromethane were added into a single-necked flask, cooled, slowly added with trifluoroacetic acid, and continuously stirred at room temperature after the addition. After the reaction was completed, the reaction solution was concentrated to dryness. Dichloromethane and N,N-diisopropylethylamine were added into the residue, cooled under nitrogen protection, and then dropwise added with a dichloromethane solution containing acryloyl chloride slowly, and stirred at room temperature after the dropwise addition. After the reaction was completed, the reaction solution was poured into an aqueous solution of ammonium chloride, and extracted with ethyl acetate. Organic layers were combined, washed with saturated salt solution, dried, and filtered. The filtrate was concentrated and purified by silica gel column chromatography to yield yellow solid.

Example 3

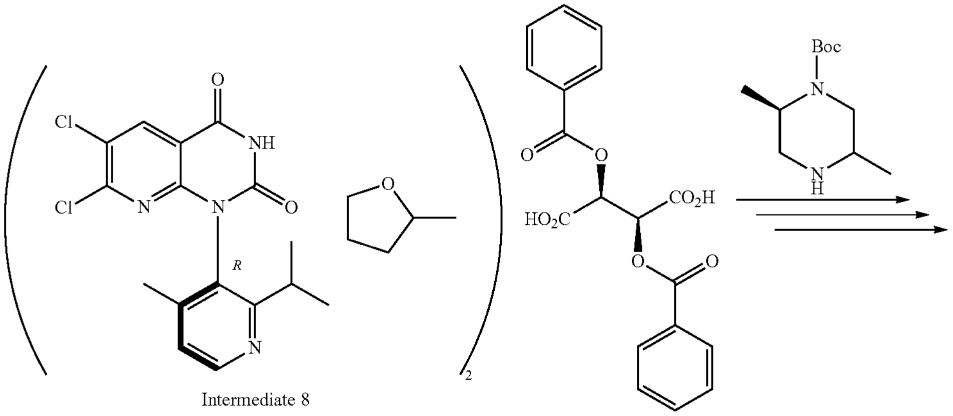

Intermediate 8

-continued

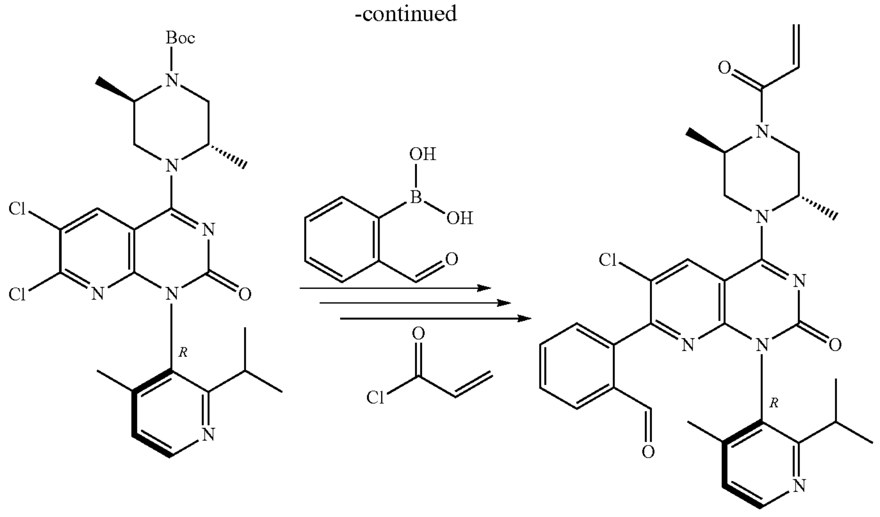

3-17M

Referring to the preparation solution of Example 1, a compound 3-17M was prepared using intermediate 8 as starting material. Rf: 0.50 ($CH_2Cl_2$:MeOH=10:1). The specific preparation method was as follows:

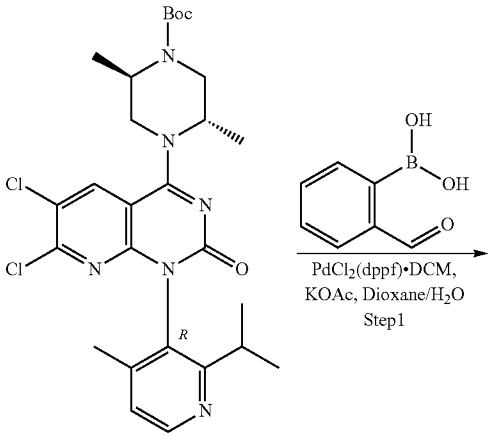

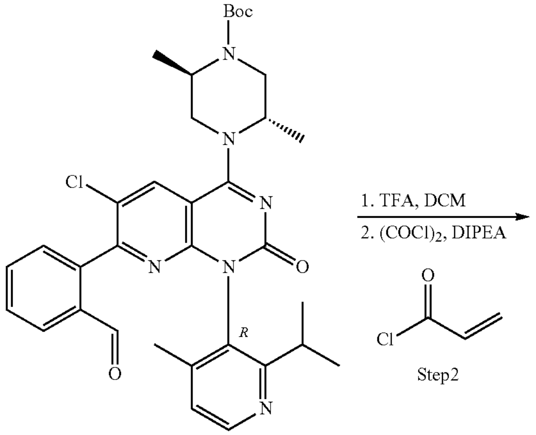

-continued

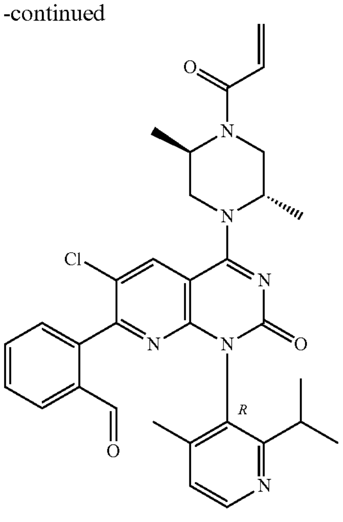

3-17M

Step 1

The starting material, 2-formylphenylboronic acid, potassium acetate, 1,4-dioxane, water and a complex of [1,1'-bis(diphenylphosphino)ferrocene]dichloropalladium and dichloromethane were added into a three-necked flask, subjected to nitrogen displacement, and then gradually heated and stirred. After the reaction was completed, the reaction solution was cooled to room temperature, and filtered with diatomite. The filtrate was concentrated to remove most 1,4-dioxane, diluted with ethyl acetate, and then added with a saturated aqueous solution of potassium carbonate, and subjected to liquid separation; aqueous phases were extracted with ethyl acetate, and organic layers were combined, washed with saturated salt solution once, dried, filtered, concentrated under reduced pressure, and purified by silica gel column chromatography to yield yellow solid.

Step 2

The product of the previous step and dichloromethane were added into a single-necked flask, cooled, slowly added with trifluoroacetic acid, and continuously stirred at room temperature after the addition. After the reaction was completed, the reaction solution was slowly added to ice water and extracted once with ethyl acetate. Organic phases were discarded, and aqueous phases were adjusted with a saturated aqueous solution of sodium bicarbonate till the pH was 7-8, and then extracted with ethyl acetate. Organic phases were combined, washed with a saturated aqueous solution of sodium chloride, dried with anhydrous sodium sulfate, filtered, and concentrated under reduced pressure to yield yellow solid. The product was dissolved in dichloromethane, added with N,N-diisopropylethylamine, cooled to 0° C. under nitrogen protection, then dropwise added with a dichloromethane solution containing acryloyl chloride slowly, and stirred at room temperature after the dropwise addition. After the reaction was completed, the reaction solution was poured into a saturated aqueous solution of ammonium chloride and extracted with ethyl acetate; organic layers were combined, washed with saturated salt solution, dried with anhydrous sodium sulfate, filtered, concentrated, and purified by silica gel column chromatography to yield light yellow solid.

Example 4

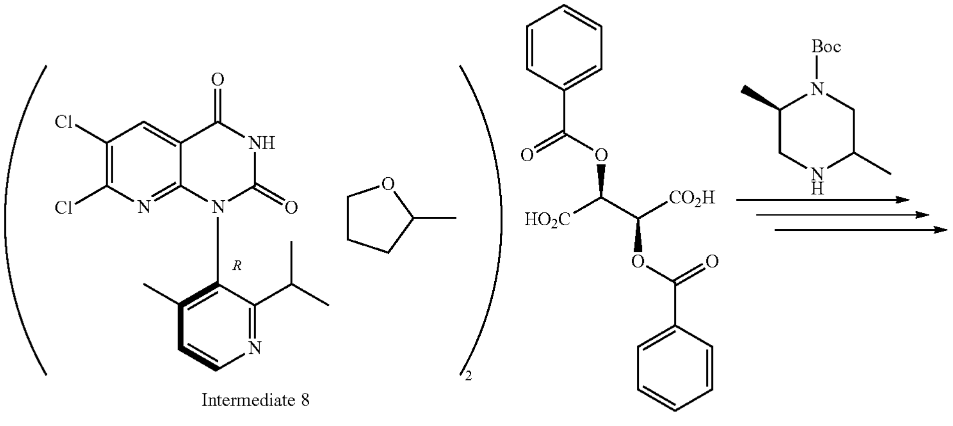

Intermediate 8

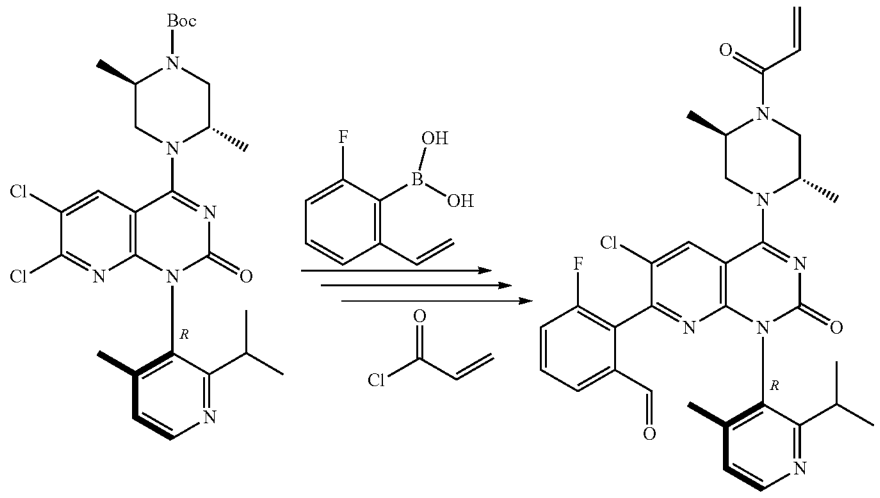

3-19M

Referring to the preparation solution of Example 1, a compound 3-19M was prepared using intermediate 8 as starting material. Rf: 0.49 ($CH_2Cl_2$:MeOH=10:1). The specific preparation method was as follows:

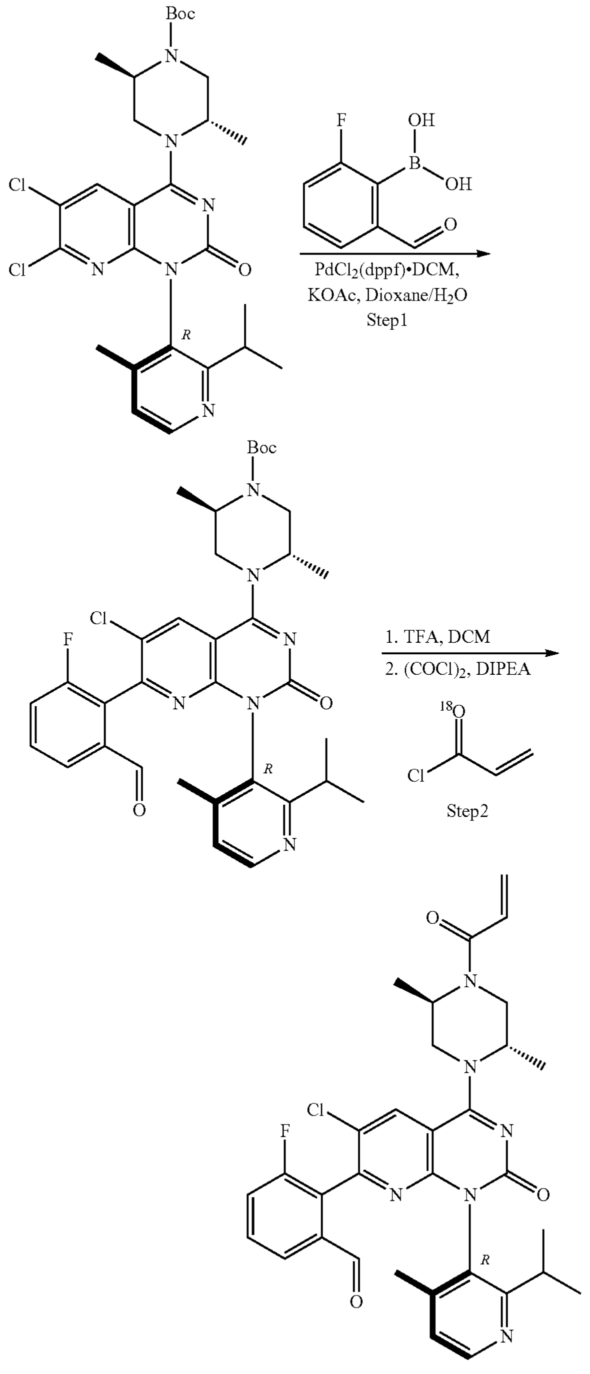

3-19M

Step 1

The starting material, 2-formylphenylboronic acid, potassium acetate, 1,4-dioxane, water and a complex of [1,1'-bis (diphenylphosphino)ferrocene]dichloropalladium and dichloromethane were added into a three-necked flask, subjected to nitrogen displacement, and then gradually heated and stirred. After the reaction was completed, the reaction solution was cooled to room temperature, and filtered with diatomite. The filtrate was concentrated to remove most 1,4-dioxane, diluted with ethyl acetate, and then added with a saturated aqueous solution of potassium carbonate, and subjected to liquid separation; aqueous phases were extracted with ethyl acetate, and organic layers were combined, washed with saturated salt solution once, dried with anhydrous sodium sulfate, filtered, concentrated under reduced pressure, and purified by silica gel column chromatography to yield yellow solid.

Step 2

The product of the previous step and dichloromethane were added into a single-necked flask, cooled, slowly added with trifluoroacetic acid, and continuously stirred at room temperature after the addition. After the reaction was completed, the reaction solution was slowly added to ice water and extracted once with ethyl acetate. Organic phases were discarded, and aqueous phases were adjusted with a saturated aqueous solution of sodium bicarbonate till the pH was 7-8, and then extracted with ethyl acetate. Organic phases were combined, washed with a saturated aqueous solution of sodium chloride once, dried with anhydrous sodium sulfate, filtered, and concentrated under reduced pressure to yield yellow solid. The product was dissolved in dichloromethane, added with N,N-diisopropylethylamine, cooled to 0° C. under nitrogen protection, then dropwise added with a dichloromethane solution containing acryloyl chloride slowly, and stirred at room temperature after the dropwise addition. After the reaction was completed, the reaction solution was poured into a saturated aqueous solution of ammonium chloride and extracted with ethyl acetate; organic layers were combined, washed with saturated salt solution, dried, filtered, concentrated, and purified by silica gel column chromatography to yield the solid product.

Example 5

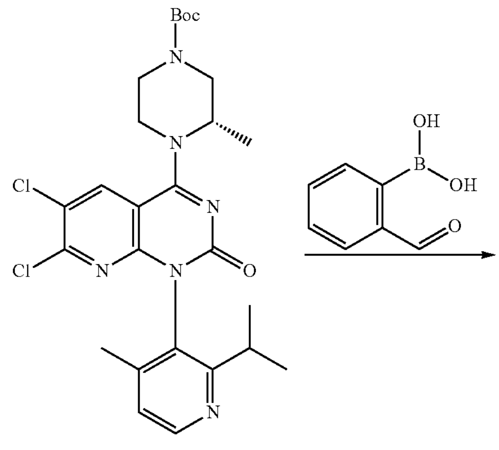

Intermediate 3

-continued

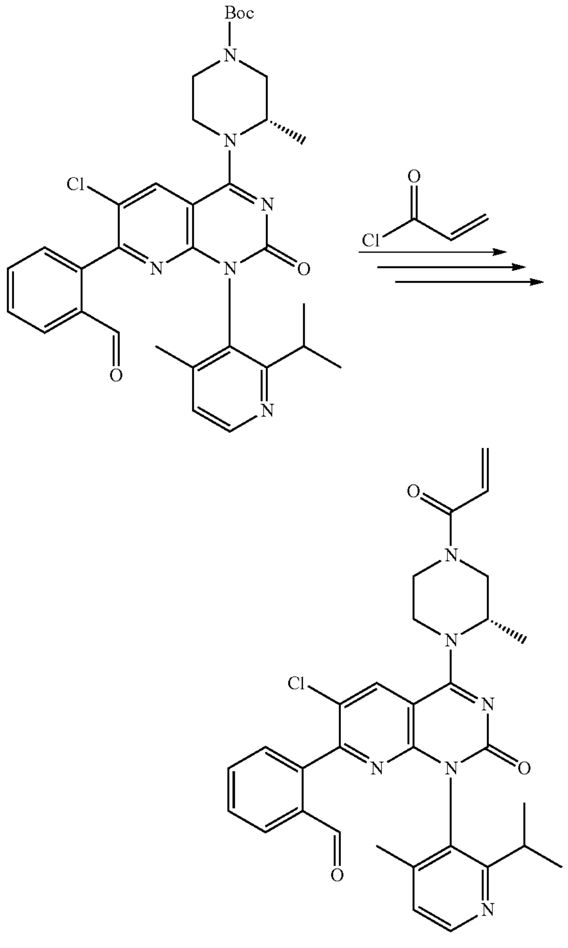

3-2

Referring to the preparation solution of Example 1, a compound 3-2 was prepared using intermediate 3 as starting material. Rf: 0.48 ($CH_2Cl_2$:MeOH=10:1). The specific preparation method was as follows:

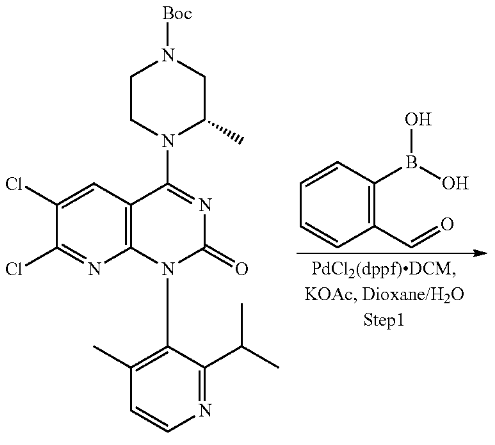

Intermediate 3M

-continued

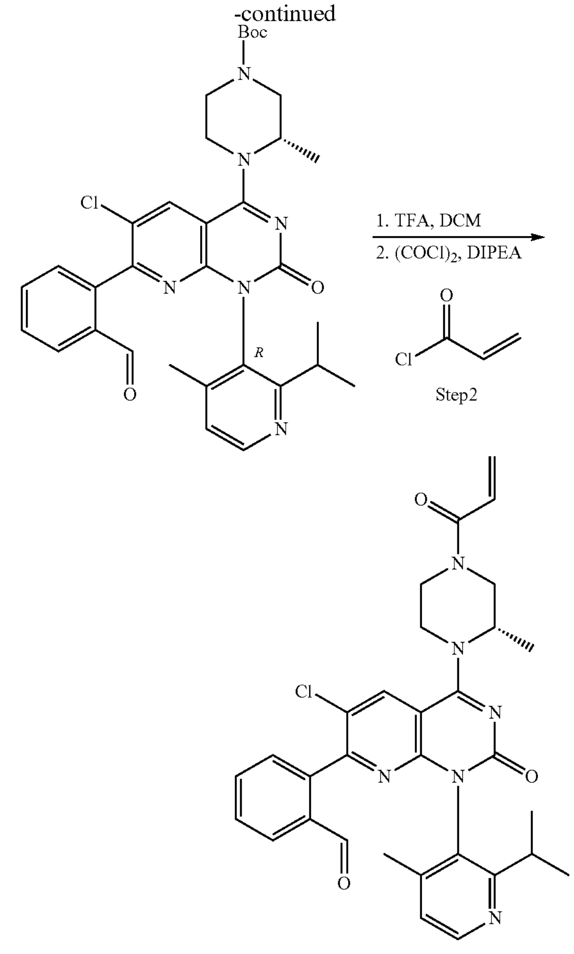

3-2

Step 1

The starting material, 2-formylphenylboronic acid, potassium acetate, 1,4-dioxane, water and palladium catalyst were added into a three-necked flask, subjected to nitrogen displacement, and then gradually heated and stirred. After the reaction was completed, the reaction solution was cooled to room temperature, and filtered with diatomite. The filtrate was concentrated to remove most 1,4-dioxane, diluted with ethyl acetate, and then added with a saturated aqueous solution of potassium carbonate, and subjected to liquid separation; aqueous phases were extracted with ethyl acetate, and organic layers were combined, washed with saturated salt solution, dried with anhydrous sodium sulfate, filtered, concentrated under reduced pressure, and purified by silica gel column chromatography to yield yellow solid.

Step 2

The product of the previous step and dichloromethane were added into a single-necked flask, cooled to 0° C., slowly added with trifluoroacetic acid, and continuously stirred at room temperature after the addition. After the reaction was completed, the reaction solution was slowly added to ice water and extracted with ethyl acetate. Organic phases were discarded, and aqueous phases were adjusted with a saturated aqueous solution of sodium bicarbonate till the pH was 7-8, and then extracted with ethyl acetate. Organic phases were combined, washed with a saturated aqueous solution of sodium chloride, dried with anhydrous sodium sulfate, filtered, and concentrated under reduced pressure to dryness to yield yellow solid. The product was dissolved in dichloromethane, added with N,N-diisopropylethylamine, cooled under nitrogen protection, then dropwise added with a dichloromethane solution containing acryloyl chloride slowly, and stirred at room temperature after the dropwise addition. After the reaction was completed, the reaction solution was poured into a saturated aqueous solution of ammonium chloride and extracted with ethyl acetate, combined, washed with saturated salt solution, dried with anhydrous sodium sulfate, filtered, concentrated, and purified by silica gel column chromatography to yield light yellow solid.

Example 6

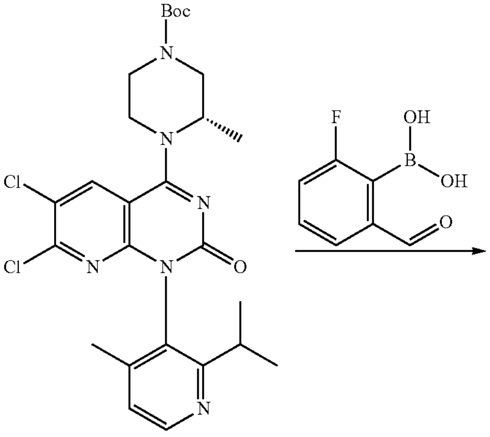

Intermediate 3

-continued

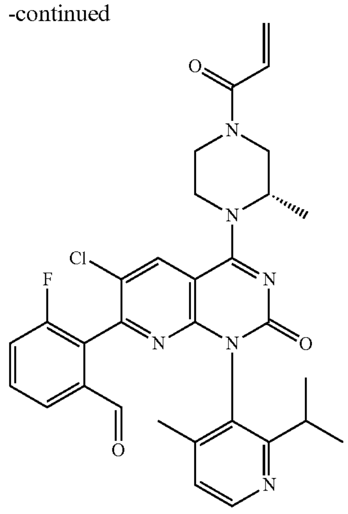

3-6

Referring to the preparation solution of Example 1, a compound 3-6 was prepared using intermediate 3 as starting material. Rf: 0.51 ($CH_2Cl_2$:MeOH=10:1). The specific preparation method was as follows:

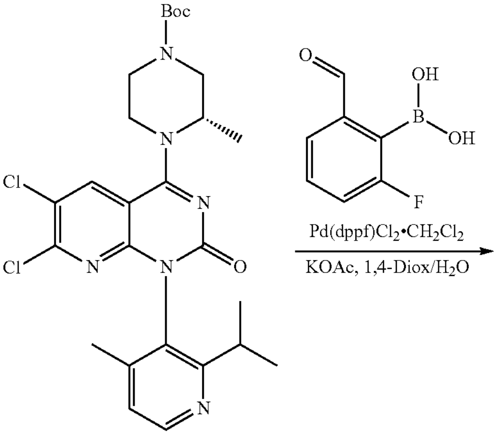

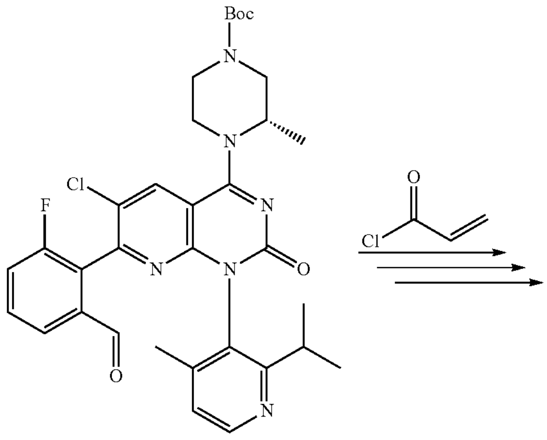

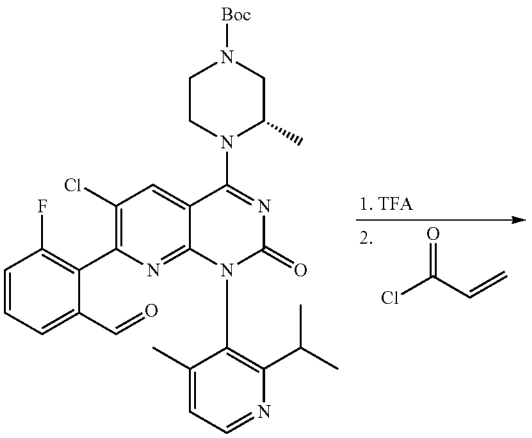

-continued

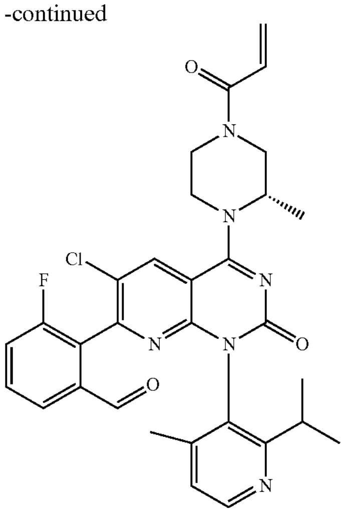

3-6

Step 1

The starting material, (2-fluoro-6-formylphenyl)boronic acid, potassium acetate, 1,4-dioxane, water and palladium catalyst were added into a 50 ml three-necked flask, subjected to nitrogen displacement, heated to 80° C., and stirred. After the reaction was completed, the reaction solution was cooled to room temperature and filtered. The filtrate was concentrated and purified by silica gel column chromatography to yield light yellow solid.

Step 2

The product of the previous step and dichloromethane were added into a single-necked flask, subjected to nitrogen displacement, slowly added with trifluoroacetic acid in an ice bath, and stirred at room temperature. After the reaction was completed, the reaction solution was concentrated to dryness, added with dichloromethane, subjected to nitrogen protection, dropwise added with DIPEA and acryloyl chloride, and then stirred at room temperature. After the reaction was completed, the reaction solution was quenched with a saturated aqueous solution of ammonium chloride and extracted with dichloromethane, combined, washed with salt solution, dried with anhydrous sodium sulfate, filtered, concentrated, and purified by silica gel column to yield yellow solid.

Embodiment 7

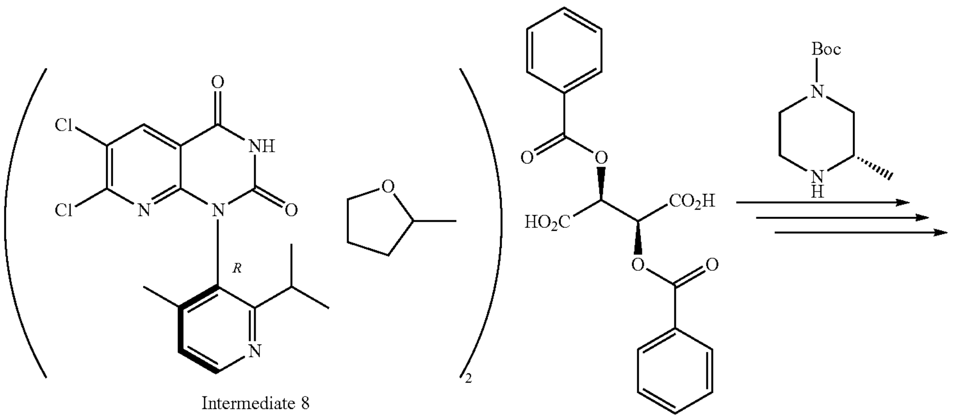

Intermediate 8

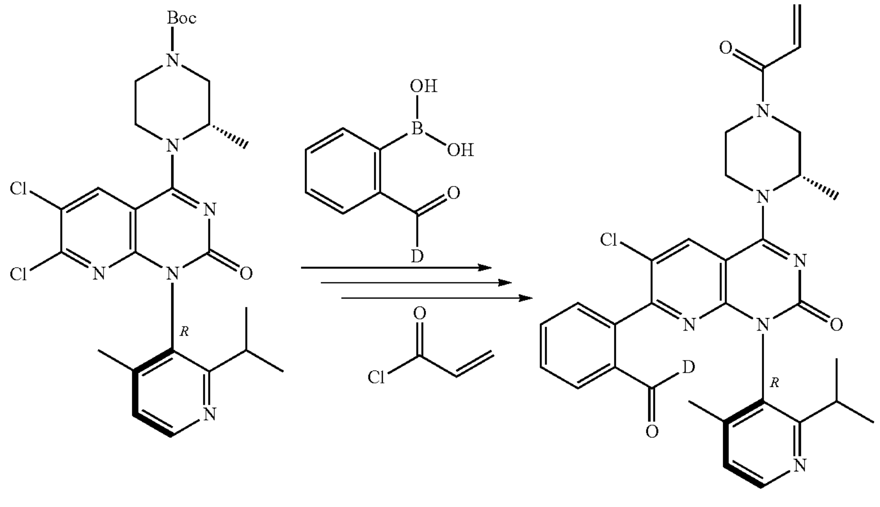

3-17M

Referring to the preparation solution of Example 1, a compound 3-16M was prepared. Rf: 0.43 ($CH_2Cl_2$: MeOH=10:1). The specific preparation method was as follows:

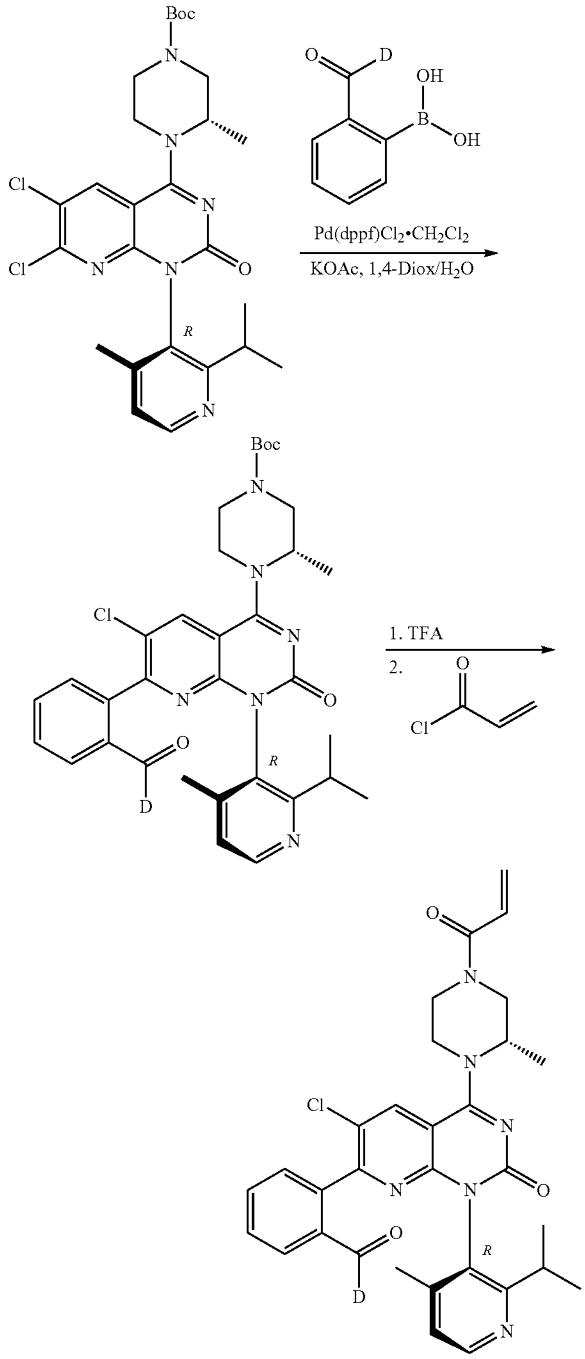

3-16M

Step 1

Tert-butyl (R)—(S)-4-(6,7-dichloro-1-(2-isopropyl-4-methylpyridine-3-yl)-2-oxo-1,2-ihydropyrido[2,3-d]pyrimidine-4-yl)-3-methylpiperazine-1-carboxylate (550 mg), 2-(deuterated aldehyde)phenylboronic acid (240 mg), potassium acetate (296 mg), 1,4-dioxane (5.5 ml), water (0.55 ml) and a complex of [1,1'-bis(diphenylphosphino) ferrocene] dichloropalladium and dichloromethane (41 mg) were added into a 50 ml three-necked flask, subjected to nitrogen displacement, heated to 80° C., and stirred for 2 hours. After the reaction was completed, the reaction solution was cooled to room temperature and filtered. The filtrate was concentrated and purified by silica gel column chromatography to yield 235 mg of light yellow solid. $^1$H NMR (400 MHz, DMSO-$d_6$): δ 8.41 (s, 1H), 8.35 (d, J=4.8 Hz, 1H), 7.95 (dd, J=7.6, 1.4 Hz, 1H), 7.75 (td, J=7.5, 1.4 Hz, 1H), 7.68 (td, J=7.6, 1.4 Hz, 1H), 7.31 (dd, J=7.6, 1.2 Hz, 1H), 7.15 (d, J=4.9 Hz, 1H), 4.89 (s, 1H), 4.27 (d, J=13.5 Hz, 1H), 4.04-3.92 (m, 1H), 3.86 (d, J=13.5 Hz, 1H), 3.73 (t, J=12.2 Hz, 1H), 3.31-3.08 (m, 2H), 2.76-2.67 (m, 1H), 1.91 (s, 3H), 1.46 (s, 9H), 1.38 (d, J=6.7 Hz, 3H), 1.06 (d, J=6.7 Hz, 3H), 0.88 (d, J=6.7 Hz, 3H). MS: m/z 618.3, $[M+H]^+$.

Step 2

The product of the previous step (220 mg) and dichloromethane (2.2 ml) were added into a 50 ml single-necked flask, subjected to nitrogen displacement, dropwise added with trifluoroacetic acid (1.2 g) slowly in an ice bath, and stirred at room temperature for 1 hour. After the reaction was completed, the reaction solution was concentrated to dryness, added with dichloromethane (2.2 ml), subjected to nitrogen displacement, dropwise added with DIPEA (276 mg) and acryloyl chloride (49 mg) slowly in an ice bath, and stirred at room temperature for 0.5 hour. After the reaction was completed, the reaction solution was added with a saturated aqueous solution of ammonium chloride for quenching and extracted with dichloromethane; organic layers were combined, washed with saturated salt solution once, dried with anhydrous sodium sulfate and filtered. The filtrate was concentrated and purified by silica gel column chromatography to yield 165 mg of light yellow solid. $^1$H NMR (400 MHz, DMSO-$d_6$): δ 8.44 (d, J=7.8 Hz, 1H), 8.35 (d, J=4.9 Hz, 1H), 7.95 (dd, J=7.6, 1.4 Hz, 1H), 7.75 (td, J=7.6, 1.5 Hz, 1H), 7.68 (td, J=7.6, 1.3 Hz, 1H), 7.32 (d, J=7.4 Hz, 1H), 7.15 (d, J=4.9 Hz, 1H), 6.95-6.82 (m, 1H), 6.27-6.17 (m, 1H), 5.78 (dd, J=10.4, 2.4 Hz, 1H), 4.94 (s, 1H), 4.48-4.02 (m, 3H), 3.85-3.45 (m, 2H), 3.32-3.10 (m, 1H), 2.76-2.66 (m, 1H), 1.92 (s, 3H), 1.36 (d, J=6.8 Hz, 3H), 1.06 (d, J=6.7 Hz, 3H), 0.88 (d, J=6.7 Hz, 3H). MS: m/z 572.2310, $[M+H]^+$.

Example 7-1

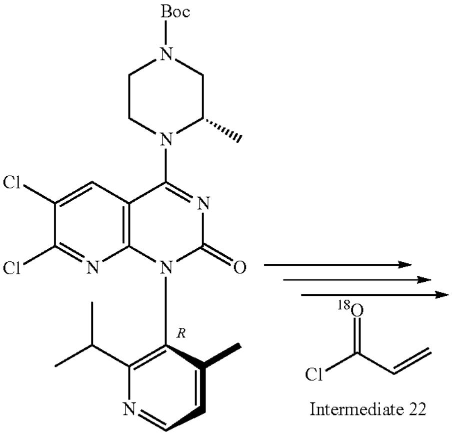

Intermediate 22

Intermediate 3M

-continued

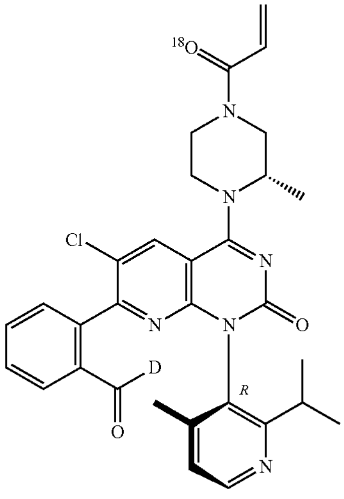

3-5MIS

-continued

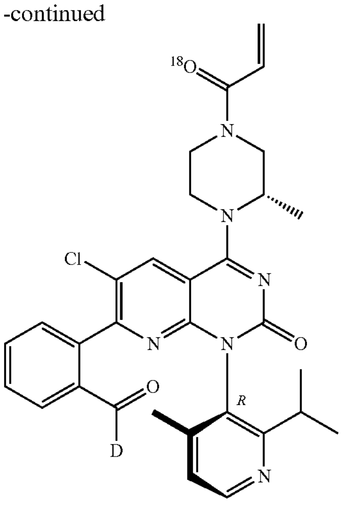

3-5MIS

Referring to the method of Example 1, a compound 3-5MIS was prepared using intermediate 3M and intermediate 22 as starting materials. $R_f$: 0.51 (DCM:MeOH=10:1). The specific preparation method was as follows:

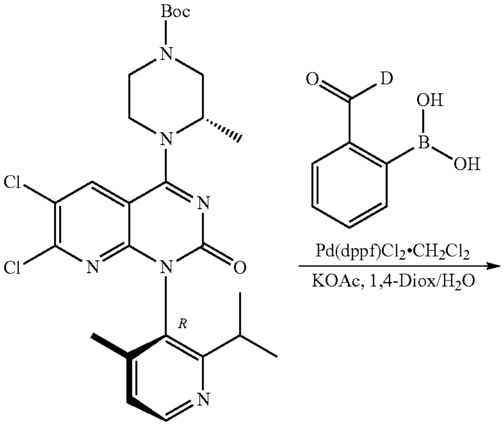

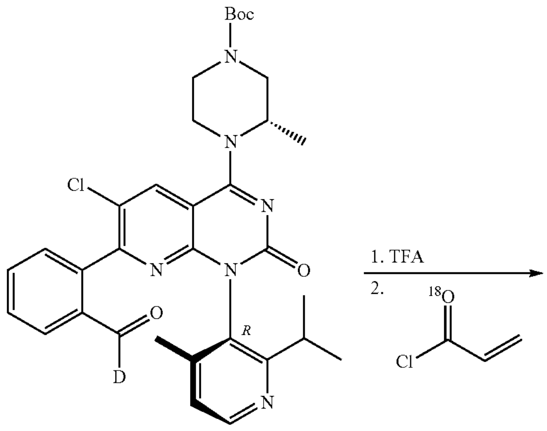

Step 1

The starting materials, 2-(deuterated aldehyde)phenylboronic acid, potassium acetate, 1,4-dioxane, water and a complex of [1,1'-bis(diphenylphosphino) ferrocene]dichloropalladium and dichloromethane were added into a three-necked flask, subjected to nitrogen displacement, heated to 80° C., and stirred for 2 hours. After the reaction was completed, the reaction solution was cooled to room temperature and filtered. The filtrate was concentrated and purified by silica gel column chromatography to yield light yellow solid.

Step 2

The product of the previous step and dichloromethane were added into a single-necked flask, subjected to nitrogen displacement, dropwise added with trifluoroacetic acid slowly in an ice bath, and stirred at room temperature. After the reaction was completed, the reaction solution was concentrated to dryness, added with dichloromethane, subjected to nitrogen displacement, dropwise added with DIPEA and $^{18}$O-acryloyl chloride slowly in an ice bath, and stirred at room temperature. After the reaction was completed, the reaction solution was added with a saturated aqueous solution of ammonium chloride for quenching and extracted with dichloromethane; organic layers were combined, washed with saturated salt solution, dried with anhydrous sodium sulfate and filtered. The filtrate was concentrated and purified by silica gel column chromatography to yield light yellow solid.

Example 7-2

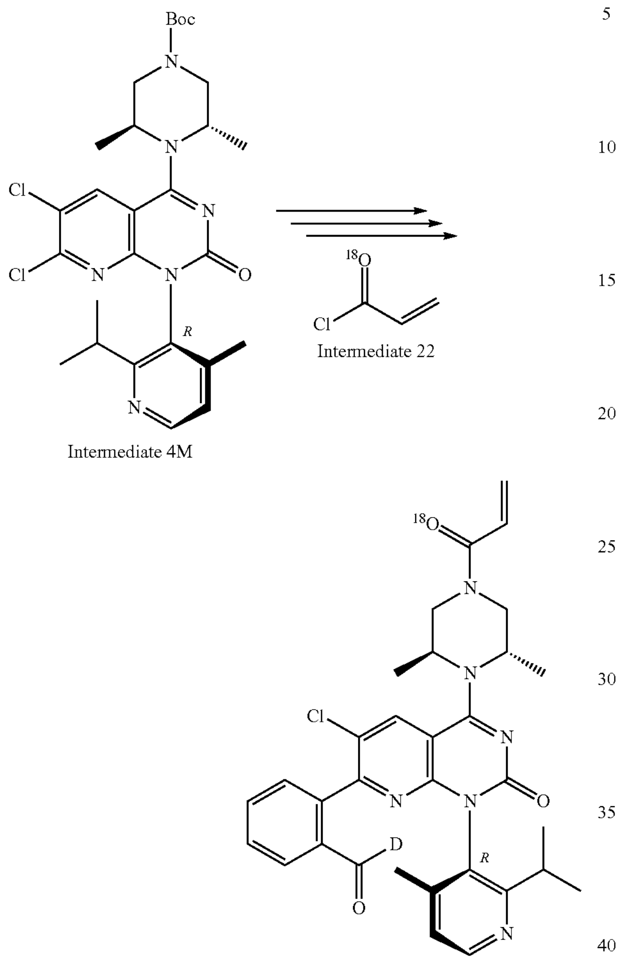

Intermediate 4M

Intermediate 22

3-8MIS

Referring to the method of Example 1, a compound 3-8MIS was prepared using intermediate 4M and intermediate 22 as starting materials. $R_f$ 0.50 (DCM:MeOH=10:1). The specific preparation method was as follows:

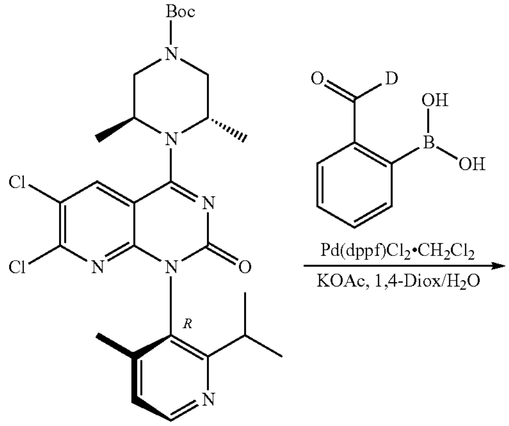

-continued

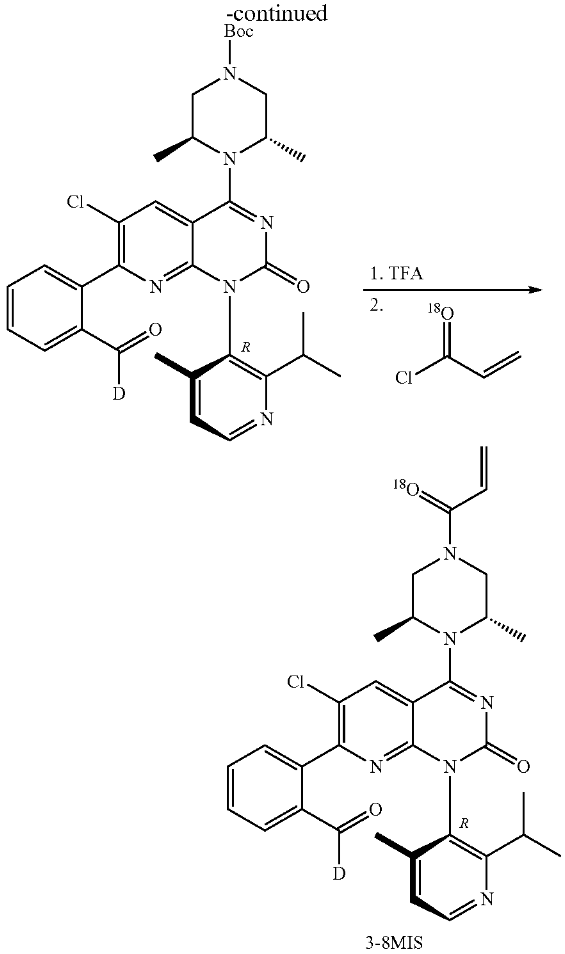

3-8MIS

Step 1

The starting materials, 2-(deuterated aldehyde)phenylboronic acid, potassium acetate, 1,4-dioxane, water and palladium catalyst were added into a three-necked flask, subjected to nitrogen displacement, heated to 80° C., and stirred. After the reaction was completed, the reaction solution was cooled to room temperature and filtered. The filtrate was concentrated and purified by silica gel column chromatography to yield light yellow solid.

Step 2

The product of the previous step and dichloromethane were added into a single-necked flask, subjected to nitrogen displacement, dropwise added with trifluoroacetic acid slowly in an ice bath, and stirred at room temperature. After the reaction was completed, the reaction solution was concentrated, added with dichloromethane, subjected to nitrogen displacement, dropwise added with DIPEA and $^{18}$O-acryloyl chloride slowly, and then stirred. After the reaction was completed, the reaction solution was quenched with a saturated aqueous solution of ammonium chloride and extracted with dichloromethane, combined, washed with saturated salt solution, dried with anhydrous sodium sulfate, filtered, concentrated and purified by silica gel column chromatography to yield light yellow solid.

Example 7-3

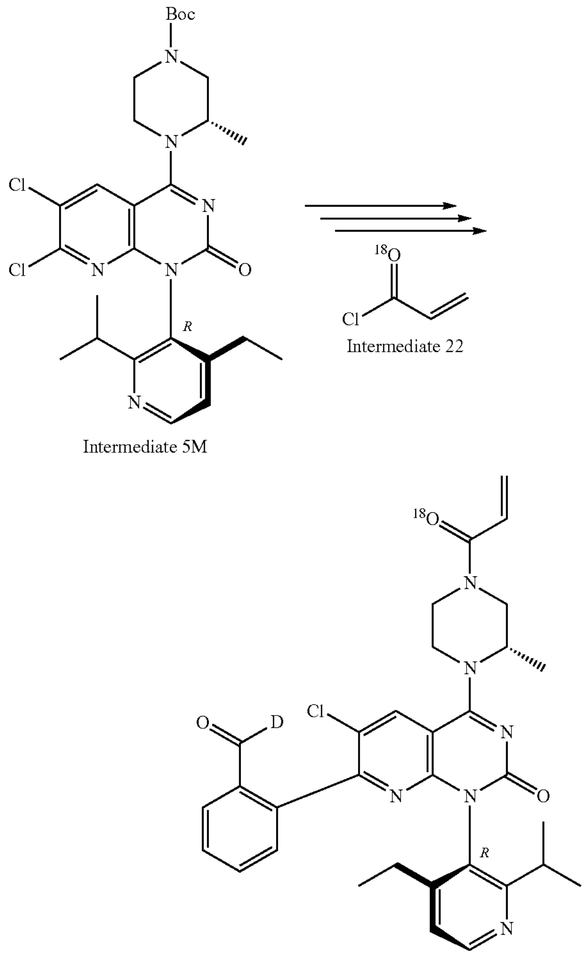

Intermediate 5M

Intermediate 22

3-6MIS

Referring to the method of Example 1, a compound 3-6MIS was prepared using intermediate 5M and intermediate 22 as starting materials. $R_f$: 0.49 (DCM:MeH=10:1). The specific preparation method was as follows:

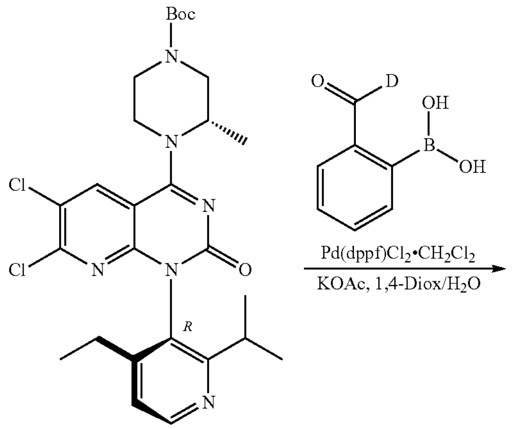

-continued

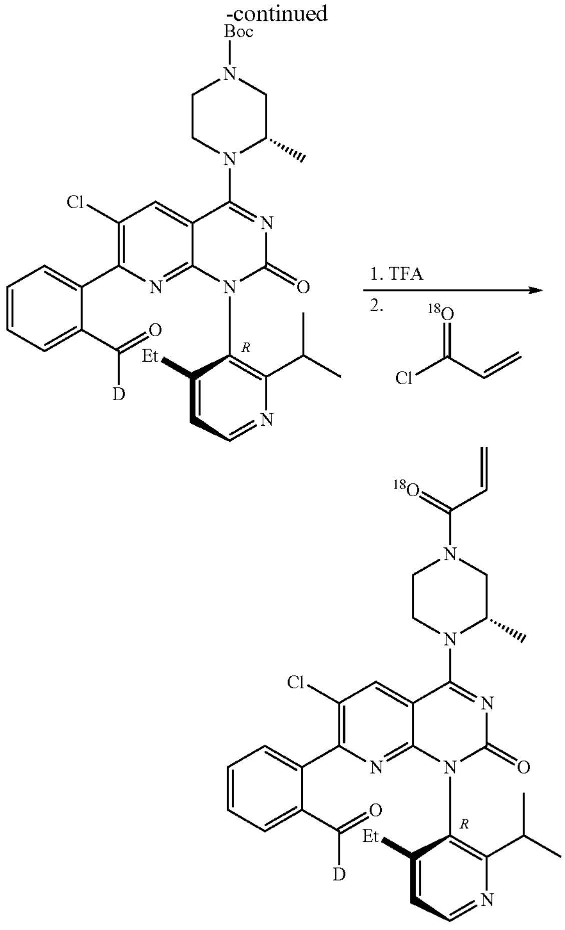

3-6MIS

Step 1

The intermediates, 2-(deuterated aldehyde)phenylboronic acid, potassium acetate, 1,4-dioxane, water and palladium catalyst were added into a three-necked flask, subjected to nitrogen displacement, and then heated and stirred. After the reaction was completed, the reaction solution was cooled to room temperature and filtered. The filtrate was concentrated and purified by silica gel column chromatography to yield a solid product.

Step 2

The product of the previous step and dichloromethane were added into a single-necked flask, subjected to nitrogen displacement, dropwise added with trifluoroacetic acid slowly in an ice bath, and stirred at room temperature. After the reaction was completed, the reaction solution was concentrated to dryness, added with dichloromethane, subjected to nitrogen displacement, dropwise added with N,N-diisopropylethylamine and $^{18}$O-acryloyl chloride slowly in an ice bath, and stirred at room temperature. After the reaction was completed, the reaction solution was added with a saturated aqueous solution of ammonium chloride for quenching and extracted with dichloromethane; organic layers were combined, washed with saturated salt solution, dried with anhydrous sodium sulfate and filtered. The filtrate was concentrated and purified by silica gel column chromatography to yield the target product.

Example 8
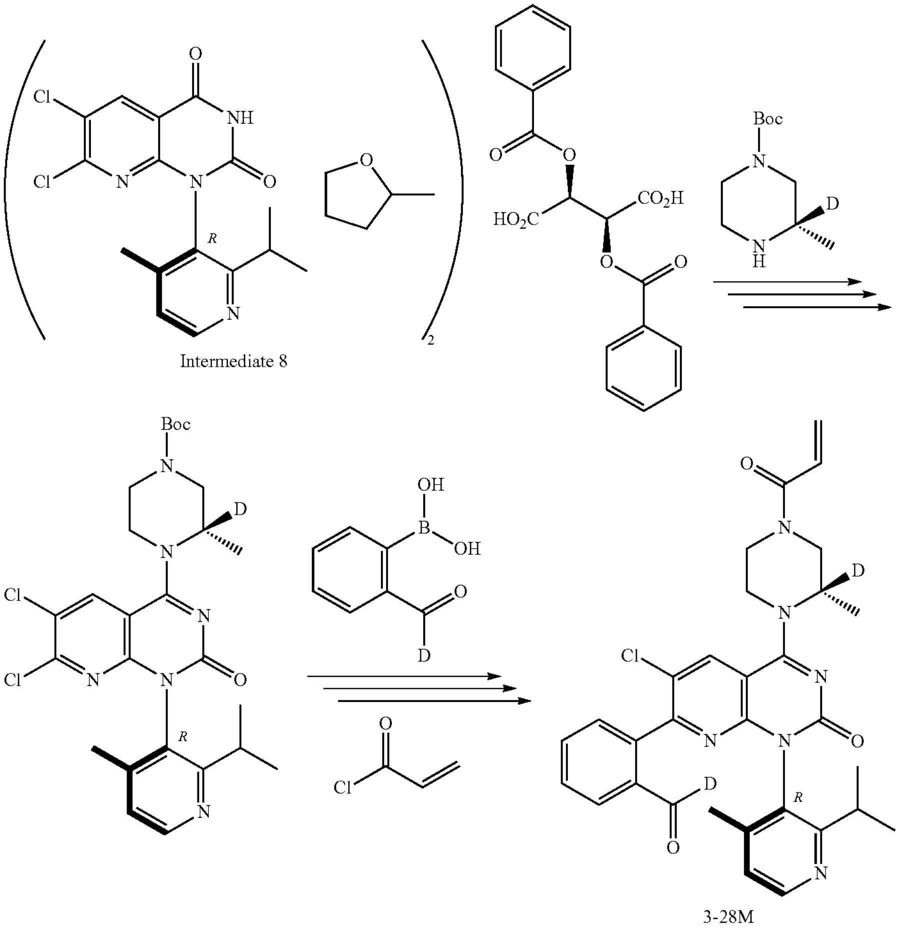
Intermediate 8
3-28M
Referring to the preparation solution of Example 1, a compound 3-28M was prepared. Rf: 0.42 ($CH_2Cl_2$:MeOH=10:1). The specific preparation method was as follows:
-continued
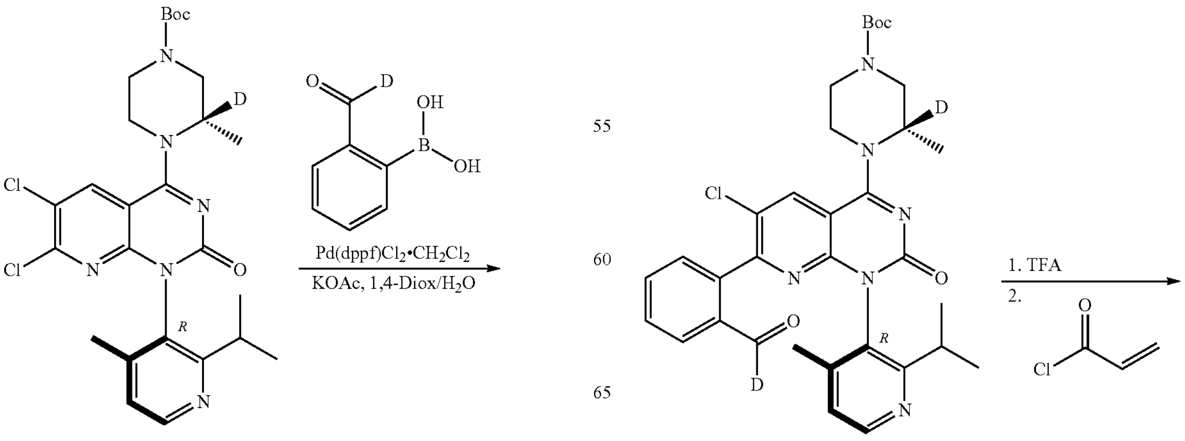

-continued

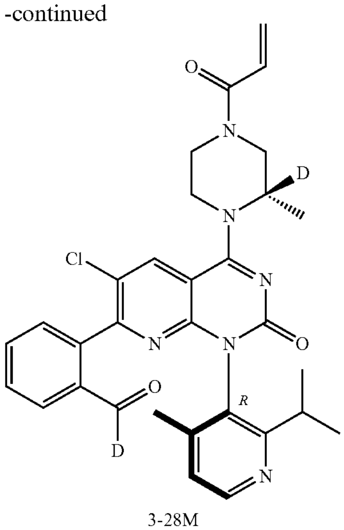

3-28M

Step 1

The starting material, 2-(deuterated aldehyde)phenylboronic acid, potassium acetate, 1,4-dioxane, water and palladium catalyst were added into a three-necked flask, subjected to nitrogen displacement, heated to 80° C., and stirred. After the reaction was completed, the reaction solution was cooled to room temperature and filtered. The filtrate was concentrated and purified by silica gel column chromatography to yield solid for the next reaction.

Step 2

The product of the previous step and dichloromethane were added into a single-necked flask, subjected to nitrogen displacement, dropwise added with trifluoroacetic acid slowly in an ice bath, and stirred at room temperature. After the reaction was completed, the reaction solution was concentrated to dryness, added with dichloromethane, subjected to nitrogen displacement, dropwise added with DIPEA and acryloyl chloride slowly in an ice bath, and continuously stirred at room temperature. After the reaction was completed, the reaction solution was quenched with an aqueous solution of ammonium chloride, and extracted with dichloromethane. Organic layers were combined, washed with saturated salt solution, dried with anhydrous sodium sulfate, filtered, concentrated, and purified by silica gel column chromatography to yield the product.

Example 9

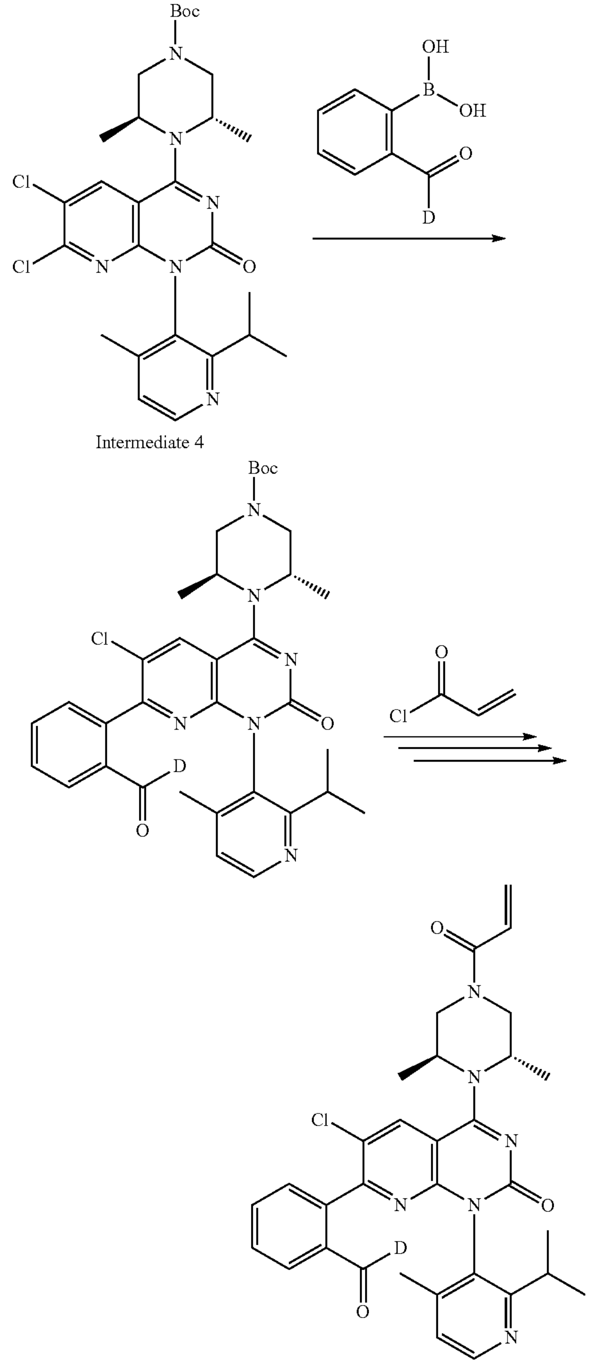

Intermediate 4

3-14

Referring to the preparation solution of Example 1, a compound 3-14 was prepared using intermediate 4 as starting material. Rf: 0.43 ($CH_2Cl_2$:MeOH=10:1). The specific preparation method was as follows:

Step 1

The starting material, 2-(deuterated aldehyde)phenylboronic acid, potassium acetate, 1,4-dioxane, water and palladium catalyst were added into a 50 ml three-necked flask, subjected to nitrogen displacement, heated to 80° C., and stirred. After the reaction was completed, the reaction solution was cooled to room temperature and filtered. The filtrate was concentrated and purified by silica gel column chromatography to yield light yellow solid for the next reaction.

Step 2

The product of the previous step and dichloromethane were added into a single-necked flask, subjected to nitrogen displacement, dropwise added with trifluoroacetic acid slowly, and stirred at room temperature. After the reaction was completed, the reaction solution was concentrated to dryness, added with dichloromethane, subjected to nitrogen displacement, dropwise added with DIPEA and acryloyl chloride slowly in an ice bath, and stirred at room temperature. After the reaction was completed, the reaction solution was quenched with an aqueous solution of ammonium chloride and extracted with dichloromethane, combined, washed with saturated salt solution, dried with anhydrous sodium sulfate, filtered, concentrated and purified by column chromatography to yield the target product.

Example 10

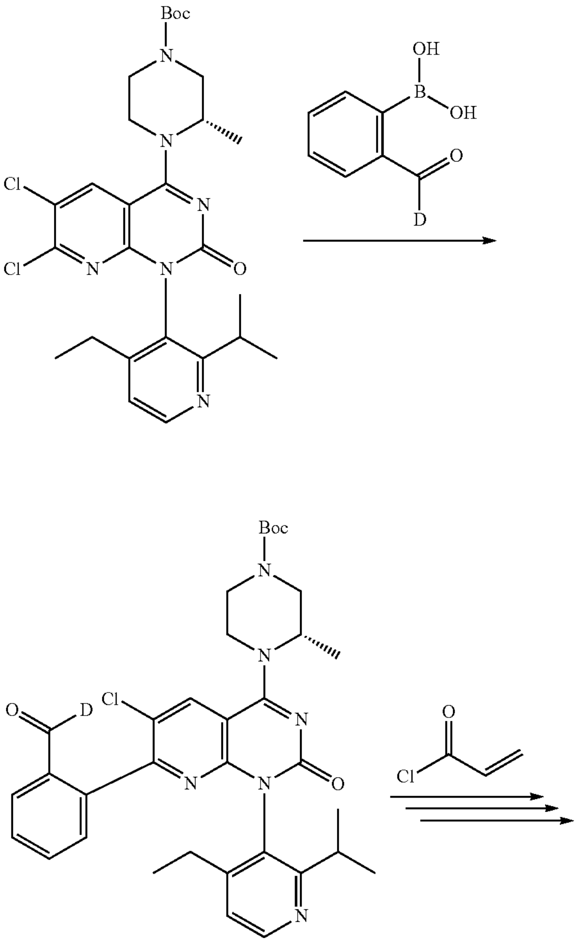

-continued

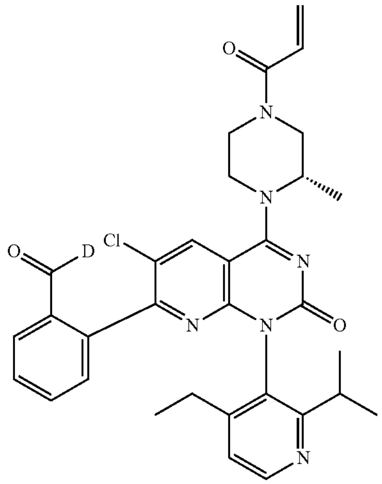

3-6B

Referring to the preparation solution of Example 1, a compound 3-6B was prepared. Rf: 0.42 ($CH_2Cl_2$: MeOH=10:1). The specific preparation method was as follows:

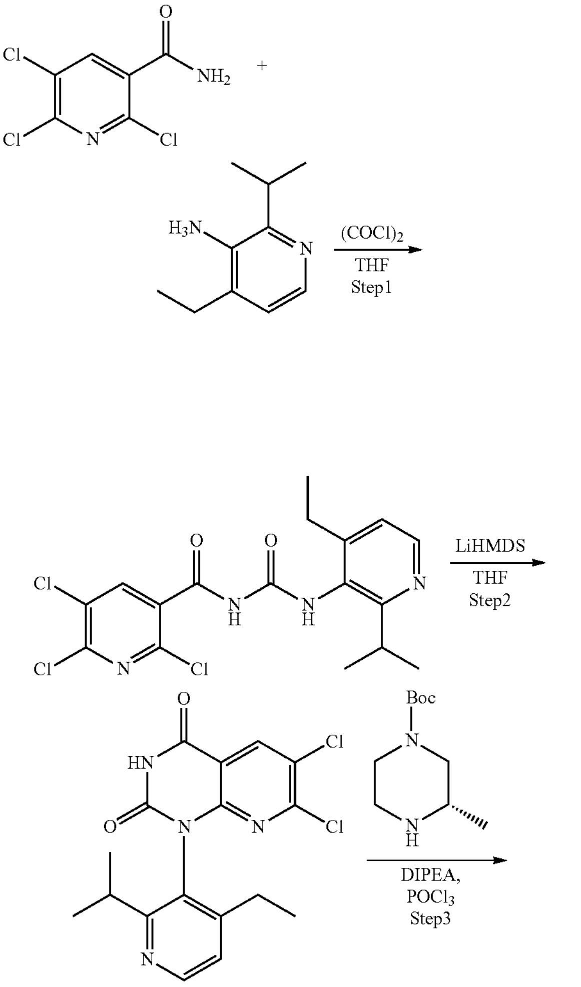

-continued

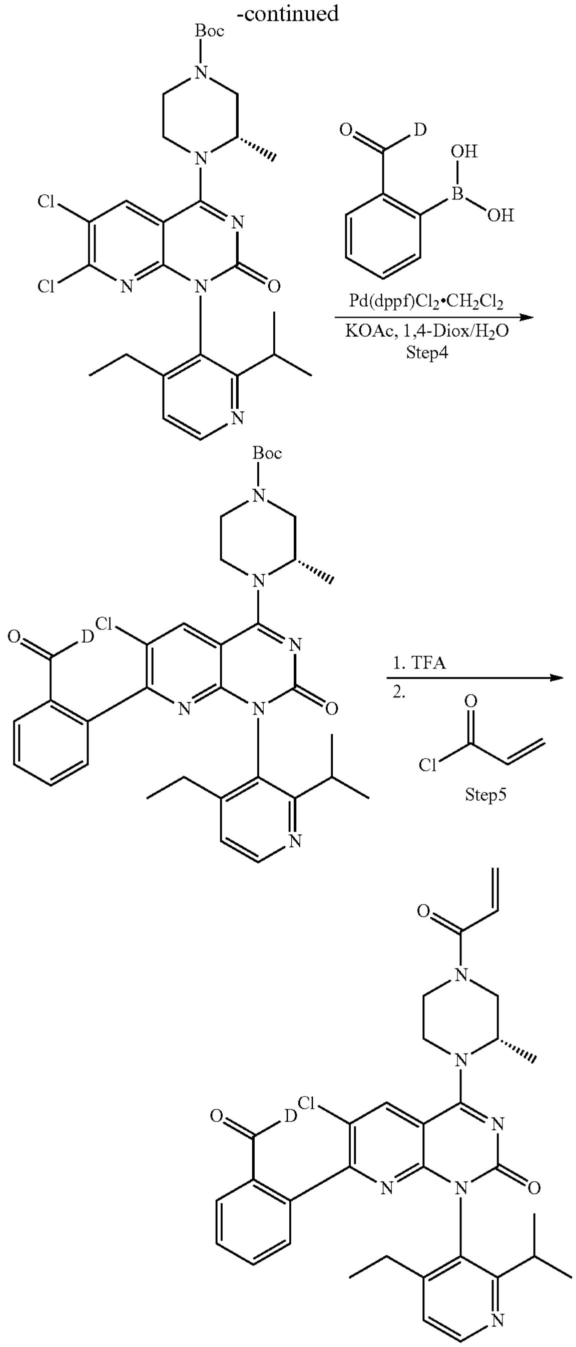

3-6B

Step 1

Tetrahydrofuran (50 ml) was added into a 250 ml three-necked flask, subjected to nitrogen displacement, cooled to −5° C., dropwise added with oxalyl chloride (2.9 g) slowly, stirred for 10 minutes, added with 2,5,6-trichloronicotinamide (4.4 g) in batches, heated to 45° C., and stirred for 1 hour. After the reaction was completed, the reaction solution was concentrated to dryness, added with tetrahydrofuran (25 ml), subjected to nitrogen displacement, cooled to −5° C., dropwise added with a tetrahydrofuran solution (18 ml) containing 2-isopropyl-4-ethylpyridine-3-amine (2.1 g) slowly, and stirred at room temperature for 1 hour. After the reaction was completed, the reaction solution was concentrated to dryness, added with water and a proper amount of saturated aqueous solution of sodium carbonate to adjust the pH to be 7-8, and then extracted with dichloromethane; organic layers were combined, washed with saturated salt solution once, dried with anhydrous sodium sulfate, and filtered. The filtrate was concentrated to yield a crude product of pink solid. The crude product was mixed with a solvent (110 ml), stirred at room temperature for 1 hour, and then filtered. The filter cake was dried to yield 6.3 g of off-white solid. MS: m/z 415.1, $[M+H]^+$.

Step 2

The product of the previous step (6.3 g) and tetrahydrofuran (160 ml) were added into a 500 ml three-necked flask, subjected to nitrogen displacement, cooled to 10-15° C., dropwise added with LiHMDS (1 M in THF, 33.5 ml), and stirred at room temperature for 2 hours. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated until a large number of solids were precipitated, added with MTBE (10 ml), and then filtered. The filter cake was dried to yield 3.8 g of white solid. MS: m/z 379.1, $[M+H]^+$.

Step 3

The product of the previous step (3.8 g), tetrahydrofuran (95 ml), DIPEA (7.8 g) and (S)-4-N-t-Boc-2-methylpiperazine (2.0 g) were added into a 250 ml three-necked flask, subjected to nitrogen displacement, dropwise added with phosphorus oxychloride (3.1 g) slowly in an ice bath, heated to 30° C., stirred for 15 minutes, added with (S)-4-N-t-Boc-2-methylpiperazine (1.0 g), and stirred for reaction for 30 minutes. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated to yield 5.7 g of brown solid. MS: m/z 561.2, $[M+H]^+$.

Step 4

The product of the previous step (1.0 g), deuterated 2-formylphenylboronic acid (0.3 g), potassium acetate (0.5 g), $PdCl_2(dppf)CH_2Cl_2$ (0.1 g), dioxane (10 ml) and water (1 ml) were added into a 50 ml single-necked flask, subjected to nitrogen displacement, heated to 80° C., and stirred for 1 hour. After the reaction was completed, the reaction solution was filtered. The filtrate was concentrated and purified by silica gel column chromatography to yield 876 mg of brown solid. MS: m/z 632.3, $[M+H]^+$.

Step 5

The product of the previous step (876 mg) and dichloromethane (10 ml) were added into a 50 ml single-necked flask, subjected to nitrogen displacement, dropwise added with trifluoroacetic acid (4.7 g) slowly in ice bath, heated to 30° C., and stirred for 30 minutes. After the reaction was completed, the reaction solution was concentrated until the flow was cut out, added with dichloromethane (10 mL), dropwise added with DIPEA (1.1 g) and acryloyl chloride (188 mg) slowly in an ice bath, heated to 30° C., and stirred for 20 minutes. After the reaction was completed, the reaction solution was quenched with a saturated aqueous solution of ammonium chloride, and extracted with dichloromethane. Organic layers were combined, washed once with saturated salt solution, dried with anhydrous sodium sulfate and filtered. The filtrate was concentrated and purified by silica gel column chromatography to yield 535 mg of brown solid. $^1$H NMR (400 MHz, DMSO-$d_6$): δ 8.49-8.43 (m, 1H), 8.41 (d, J=5.0 Hz, 1H), 7.95 (d, J=7.6 Hz, 1H), 7.75 (td, J=7.5, 1.4 Hz, 1H), 7.67 (td, J=7.5, 1.2 Hz, 1H), 7.29 (d, J=8.1 Hz, 1H), 7.18 (d, J=5.0 Hz, 1H), 6.95-6.82 (m, 1H), 6.28-6.17 (m, 1H), 5.78 (dd, J=10.4, 2.3 Hz, 1H), 4.97 (s, 1H), 4.48-4.04 (m, 3H), 3.90-3.44 (m, 2H), 3.33-3.08 (m, 1H), 2.75-2.61 (m, 1H), 2.31-2.15 (m, 2H), 1.35 (d, J=6.7 Hz, 3H), 1.06 (d, J=5.0 Hz, 3H), 0.98 (t, J=7.6, 3H), 0.88 (d, J=6.4 Hz, 3H). MS: m/z 586.2, [M+H]$^+$.

Example 11

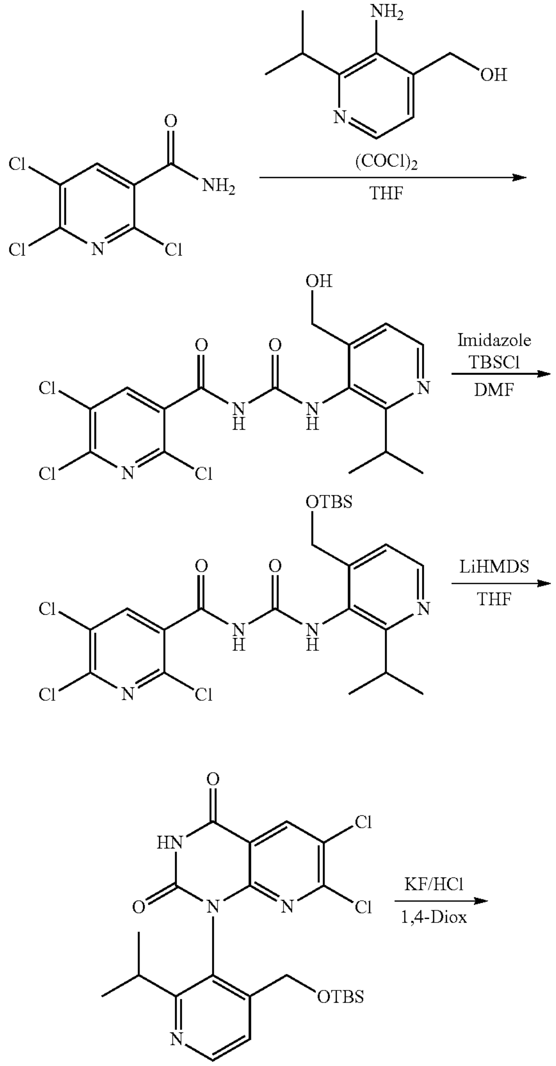

-continued

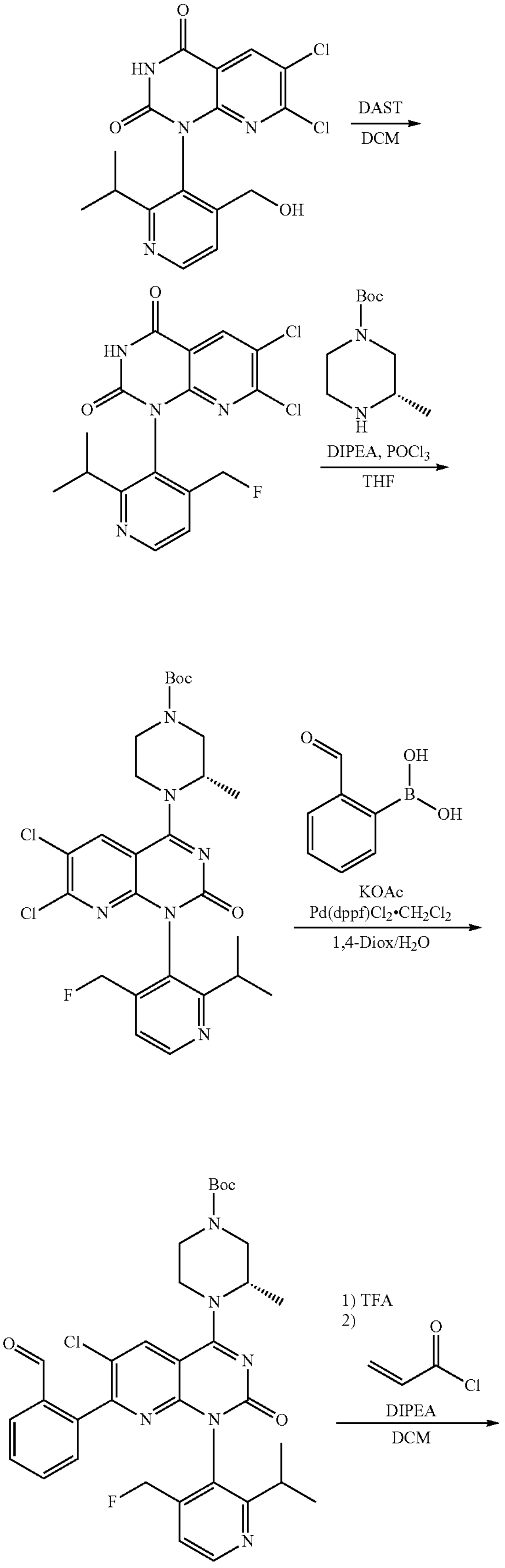

-continued

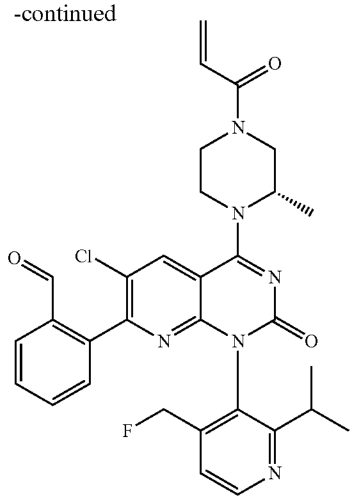

3-29

Step 1

Tetrahydrofuran (50 ml) was added into a 250 ml three-necked flask, subjected to nitrogen displacement, cooled to −5° C., dropwise added with oxalyl chloride (1.6 g) slowly, stirred for 10 minutes, added with 2,5,6-trichloronicotinamide (2.4 g) in batches, heated to 45° C., and stirred for 1 hour. After the reaction was completed, the reaction solution was concentrated until the flow was cut out, added with tetrahydrofuran (50 ml), subjected to nitrogen displacement, cooled to −5° C., dropwise added with a tetrahydrofuran solution (10 ml) containing (3-amino-2-isopropylpyridin-4-yl)methanol (1.5 g) slowly, and stirred at room temperature for 1 hour. After the reaction was completed, the reaction solution was concentrated to dryness, added with water and a proper amount of saturated aqueous solution of sodium carbonate to adjust the pH of aqueous phases to be 7-8, stirred for 10 minutes, and then filtered. The filter cake was dried to yield 1.6 g of off-white solid. MS: m/z 417.0, $[M+H]^+$.

Step 2

The product of the previous step (1.1 g), imidazole (4.5 g), TBSCl (5.0 g) and DMF (30 ml) were added into a 250 ml three-necked flask, and stirred at room temperature for 10 minutes. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and filtered. The filtrate was concentrated and purified by silica gel column chromatography to yield 1.2 g of white solid.

Step 3

The product of the previous step (1.2 g) and tetrahydrofuran (50 ml) were added into a 100 ml three-necked flask, subjected to nitrogen displacement, cooled to 10-15° C., dropwise added with LiHMDS (1 M THF, 4.5 ml) slowly, and stirred at room temperature for 1 hour. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated and purified by silica gel column chromatography to yield 950 mg of white solid.

Step 4

The product of the previous step (950 mg), dioxane (20 ml), potassium fluoride (5.0 g) and hydrochloric acid (1.5 ml) were added into a 100 ml single-necked flask, and stirred at room temperature for 2 hours. After the reaction was completed, the reaction solution was added with water for quenching and extracted with ethyl acetate; organic layers were combined, washed with saturated salt solution once, dried with anhydrous sodium sulfate, and then filtered. The filtrate was concentrated to dryness to yield 790 mg of white solid.

Step 5

The product of the previous step (790 mg) and dichloromethane (20 ml) were added into a 100 ml three-necked flask, subjected to nitrogen displacement, dropwise added with DAST (617 mg) slowly in an ice bath, and stirred at 0° C. for 30 minutes. After the reaction was completed, the reaction solution was added with a saturated aqueous solution of ammonium chloride for quenching and extracted with dichloromethane; organic layers were combined, washed with saturated salt solution once, dried with anhydrous sodium sulfate, and then filtered. The filtrate was concentrated to dryness to yield 680 mg of white solid.

Step 6

The product of the previous step (680 mg), DIPEA (1.4 g), (S)-4-N-t-Boc-2-methylpiperazine (355 mg) and tetrahydrofuran (20 ml) were added into a 100 ml three-necked flask, subjected to nitrogen displacement, dropwise added with phosphorus oxychloride (544 mg) slowly in an ice bath, stirred for 30 minutes at normal temperature, added with (S)-4-N-t-Boc-2-methylpiperazine (177 mg), and continuously stirred for 30 minutes at normal temperature. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated and purified by silica gel column chromatography to yield 600 mg of white solid. MS: m/z 565.1, $[M+H]^+$.

Step 7

The product of the previous step (600 mg), 2-formylphenylboronic acid (181 mg), potassium acetate (323 mg), $Pd(dppf)Cl_2{\cdot}CH_2Cl_2$ (44 mg), dioxane (15 ml) and water (1.5 ml) were added into a 50 ml single-necked flask, subjected to nitrogen displacement, heated to 80° C., and stirred for 1 hour. After the reaction was completed, the reaction solution was filtered. The filtrate was concentrated and purified by silica gel column chromatography to yield 520 mg of yellow solid.

Step 8

The product of the previous step (520 mg) and dichloromethane (10 ml) were added into a 50 ml single-necked flask, subjected to nitrogen displacement, dropwise added with trifluoroacetic acid (2 ml) slowly in an ice bath, heated to 30° C., and stirred for 30 minutes. After the reaction was completed, the reaction solution was concentrated to dryness, added with dichloromethane (10 ml) for dissolution, dropwise added with DIPEA (2 ml) and acryloyl chloride (111 mg) slowly in an ice bath, heated to 30° C., and stirred for 20 minutes. After the reaction was completed, the reaction solution was added with a saturated aqueous solution of ammonium chloride for quenching and extracted with dichloromethane; organic layers were combined, washed with saturated salt solution once, dried with anhydrous sodium sulfate, and then filtered. The filtrate was concentrated and purified by silica gel column chromatography to yield 350 mg of brown solid. $^1H$ NMR (400 MHz, $CDCl_3$): δ 9.82 (s, 1H), 8.65 (d, J=4.9 Hz, 1H), 8.10 (s, 1H), 7.91-7.84 (m, 1H), 7.68-7.59 (m, 2H), 7.32-7.29 (m, 1H), 7.24-7.17 (m, 1H), 6.74-6.56 (m, 1H), 6.44 (dd, J=16.8, 1.9 Hz, 1H), 5.84 (dd, J=10.4, 1.8 Hz, 1H), 5.43-4.28 (m, 5H), 4.08-3.56 (m, 3H), 3.38-3.02 (m, 1H), 2.88-2.64 (m, 1H), 1.64-1.44 (m, 3H), 1.22 (d, J=6.8 Hz, 3H), 1.01 (d, J=6.6 Hz, 3H). MS: m/z 589.2, $[M+H]^+$.

Example 12

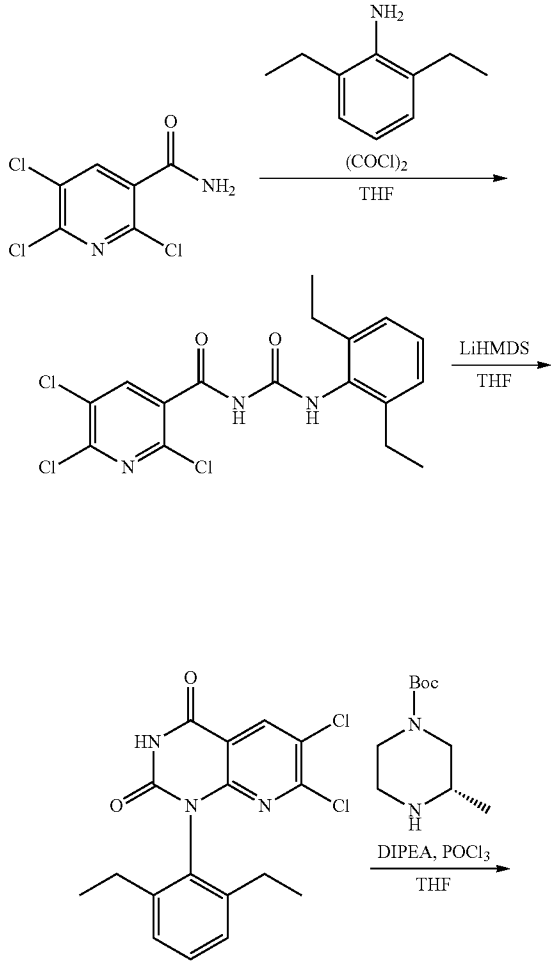

-continued

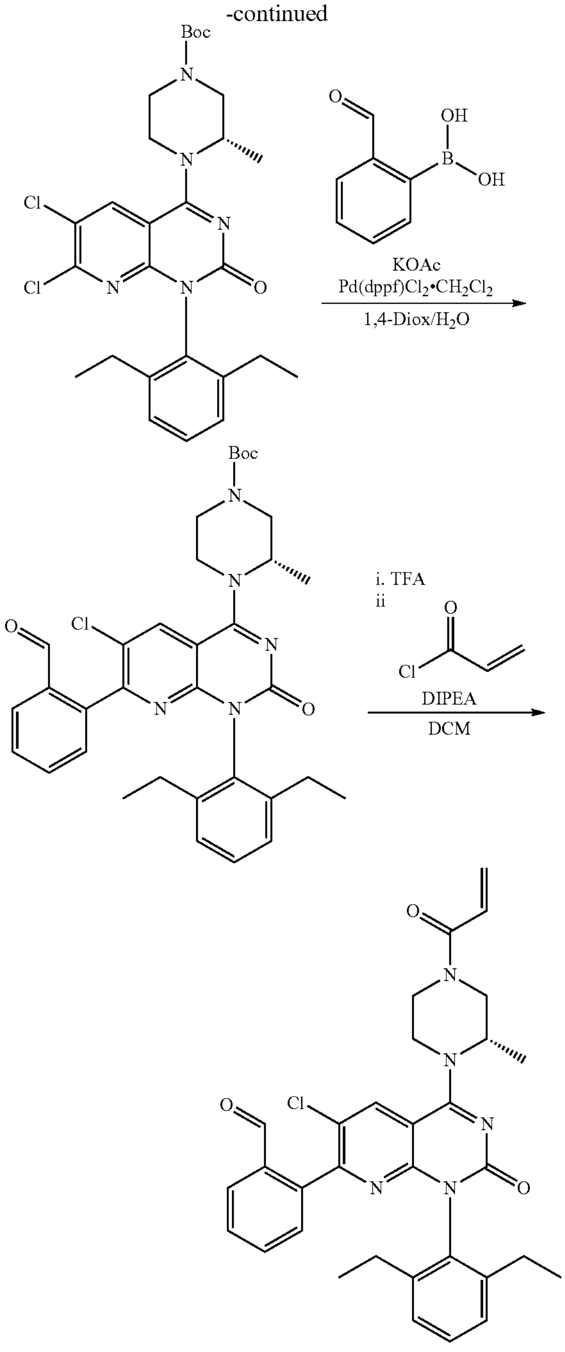

3-28

Step 1

Tetrahydrofuran (50 ml) was added into a 250 ml three-necked flask, subjected to nitrogen displacement, cooled to −5° C., dropwise added with oxalyl chloride (2.5 g) slowly, stirred for 10 minutes, added with 2,5,6-trichloronicotinamide (4.0 g) in batches, heated to 45° C., and stirred for 1 hour. After the reaction was completed, the reaction solution was concentrated until the flow was cut out, added with tetrahydrofuran (50 ml), subjected to nitrogen displacement, cooled to −5° C., dropwise added with a tetrahydrofuran solution (10 ml) containing 2,6-diethylaniline (2.3 g) slowly, and stirred at room temperature for 3 hours. After the reaction was completed, the reaction solution was concentrated to dryness, added with water and a proper amount of saturated aqueous solution of sodium carbonate to adjust the pH of the aqueous phases to be 7-8, stirred for 10 minutes, and filtered. The filter cake was dried to yield 3.3 g of off-white solid.

Step 2

The product of the previous step (3.3 g) and tetrahydrofuran (100 ml) were added into a 250 ml three-necked flask, subjected to nitrogen displacement, cooled to 10-15° C., dropwise added with LiHMDS (1 M THF, 18.1 ml), and stirred at room temperature for 3 hours. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated to dryness to yield 3.3 g of brown solid. MS: m/z 364.0, $[M+H]^+$.

Step 3

The product of the previous step (3.3 g), DIPEA (9.3 g), (S)-4-N-t-Boc-2-methylpiperazine (1.8 g) and tetrahydrofuran (20 ml) were added into a 100 ml three-necked flask, subjected to nitrogen displacement, dropwise added with phosphorus oxychloride (5.5 g) slowly in an ice bath, stirred for 30 minutes at normal temperature, added with (S)-4-N-t-Boc-2-methylpiperazine (900 mg), and continuously stirred for 30 minutes at normal temperature. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated and purified by silica gel column chromatography to yield 1.3 g of brown solid. MS: m/z 546.2, $[M+H]^+$.

Step 4

The product of the previous step (1.3 g), 2-formylphenylboronic acid (392 mg), potassium acetate (700 mg), $Pd(dppf)Cl_2 \cdot CH_2Cl_2$ (97 mg), dioxane (30 ml) and water (3 ml) were added into a 50 ml single-necked flask, subjected to nitrogen displacement, heated to 80° C., and stirred for 1 hour. After the reaction was completed, the reaction solution was filtered. The filtrate was concentrated and purified by silica gel column chromatography to yield 860 mg of yellow solid.

Step 5

The product of the previous step (860 mg) and dichloromethane (10 ml) were added into a 50 ml single-necked flask, subjected to nitrogen displacement, dropwise added with trifluoroacetic acid (2 ml) slowly in an ice bath, heated to 30° C., and stirred for 30 minutes. After the reaction was completed, the reaction solution was concentrated to dryness, added with dichloromethane (10 ml) for dissolution, added with water and a proper amount of saturated aqueous solution of sodium carbonate to adjust the PH of the aqueous phases to be 7-8, and extracted with dichloromethane. Organic layers were combined, washed with saturated salt solution once, dried with anhydrous sodium sulfate and filtered. The filtrate was concentrated to dryness to yield 707 mg of brown solid. The reaction solution was added with dichloromethane (10 ml) for dissolution, subjected to nitrogen displacement, dropwise added with DIPEA (267 mg) and acryloyl chloride (144 mg) slowly in an ice bath, heated to 30° C., and stirred for 20 minutes. After the reaction was completed, the reaction solution was added with water for quenching and extracted with dichloromethane; organic layers were combined, washed with saturated salt solution once, dried with anhydrous sodium sulfate, and then filtered. The filtrate was concentrated and purified by silica gel column chromatography to yield 416 mg of brown solid. $^1H$ NMR (400 MHz, DMSO): δ 9.76 (s, 1H), 8.44 (d, J=7.6 Hz, 1H), 7.92 (dd, J=7.7, 1.4 Hz, 1H), 7.78-7.71 (m, 1H), 7.70-7.63 (m, 1H), 7.36-7.31 (m, 1H), 7.24 (t, J=7.6 Hz, 1H), 7.13 (d, J=7.6 Hz, 2H), 6.96-6.81 (m, 1H), 6.27-6.17 (m, 1H), 5.78 (dd, J=10.4, 2.4 Hz, 1H), 4.99-4.86 (m, 1H), 4.48-4.00 (m, 3H), 3.84-3.43 (m, 2H), 3.32-3.04 (m, 1H), 2.29-2.11 (m, 4H), 1.34 (d, J=6.7 Hz, 3H), 0.97 (td, J=7.6, 3.2 Hz, 6H). MS: m/z 570.2, $[M+H]^+$.

Example 13

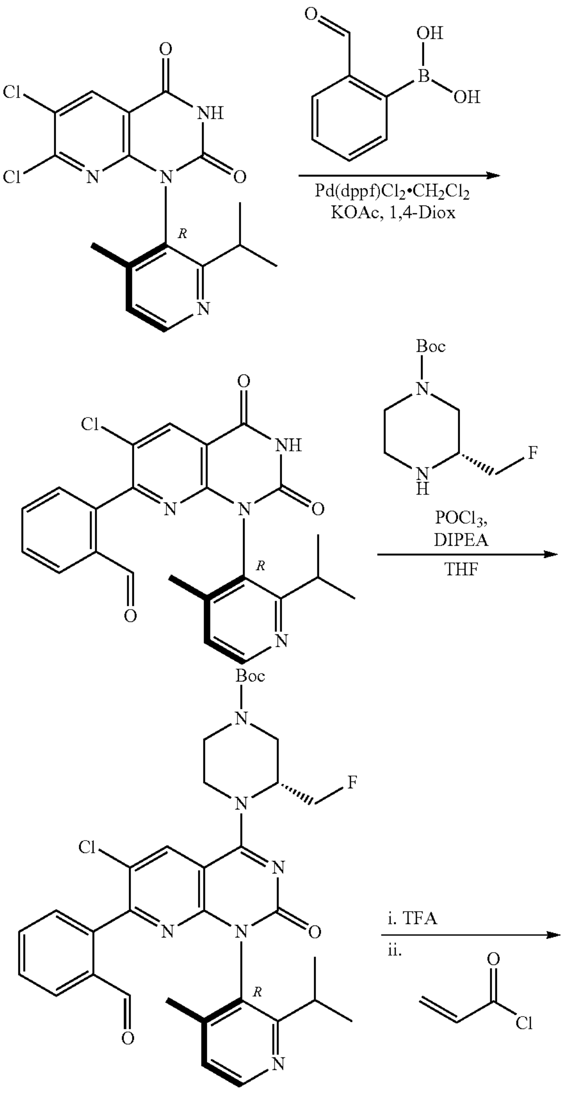

-continued

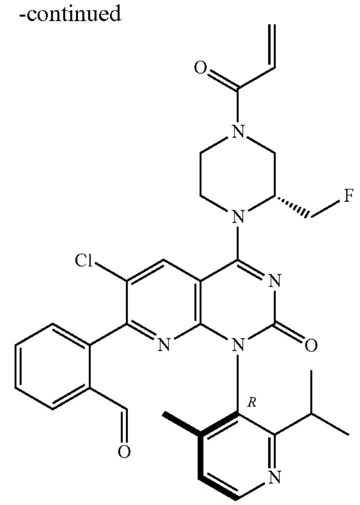

3-30M

Step 1

(R)-6,7-dichloro-1-(2-isopropyl-4-methylpyridin-3-yl) pyridine[2,3-d]pyrimidine-2, 4(1H,3H)-dione (3 g), 2-formylphenylboronic acid (1.9 g), potassium acetate (2.4 g), $Pd(dppf)Cl_2 \cdot CH_2Cl_2$ (709 mg) and dioxane (30 ml) were added into a 100 ml single-necked flask, subjected to nitrogen displacement, heated to 85° C., and stirred for 4 hours. After the reaction was completed, the reaction solution was filtered, and the filtrate was added with a saturated salt solution and extracted with ethyl acetate; organic layers were combined, washed with saturated salt solution once, dried with anhydrous sodium sulfate, and filtered. The filtrate was concentrated and purified by silica gel column chromatography to yield 3.6 g of white solid. $^1$HNMR (400 MHz, $CDCl_3$): δ 9.81 (s, 1H), 9.04 (s, 1H), 8.60 (s, 1H), 8.51 (d, J=4.9 Hz, 1H), 7.87-7.91 (m, 1H), 7.68-7.60 (m, 2H), 7.24-7.19 (m, 1H), 7.09 (d, J=5.0 Hz, 1H), 2.89-2.76 (m, 1H), 2.11 (s, 3H), 1.24 (d, J=6.8 Hz, 3H), 1.04 (d, J=6.7 Hz, 3H). MS: m/z 435.1, $[M+H]^+$.

Step 2

The product of the previous step (1.0 g), N,N-diisopropylethylamine (2.4 g), tert-butyl (R)-3-(fluoromethyl)piperazing-1-carboxylate (753 mg) and tetrahydrofuran (40 ml) were added into a 100 ml three-necked flask, subjected to nitrogen displacement, dropwise added with phosphorus oxychloride (705 mg) slowly in an ice bath, heated to room temperature, and stirred for 1 hour. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated and purified by silica gel column chromatography to yield 340 mg of white solid. $^1$HNMR (400 MHz, $CDCl_3$): δ 9.82 (s, 1H), 8.47 (d, J=4.9 Hz, 1H), 8.25 (br s, 1H), 7.93-7.84 (m, 1H), 7.68-7.59 (m, 2H), 7.25-7.19 (m, 1H), 7.07 (d, J=5.0 Hz, 1H), 5.25-4.65 (m, 3H), 4.45-4.18 (m, 3H), 3.91-3.67 (m, 1H), 3.52-3.12 (m, 2H), 2.78-2.64 (m, 1H), 2.05 (s, 3H), 1.53 (s, 9H), 1.24 (d, J=6.7 Hz, 3H), 1.03 (d, J=6.7 Hz, 3H). MS: m/z 635.3, $[M+H]^+$.

Step 3

The product of the previous step (340 mg) and dichloromethane (5 ml) were added into a 50 ml single-necked flask, subjected to nitrogen displacement, dropwise added with trifluoroacetic acid (1.2 ml) slowly in an ice bath, and stirred at room temperature for 1 hour. After the reaction was completed, the reaction solution was concentrated to dryness, added with dichloromethane (20 ml), subjected to nitrogen displacement, dropwise added with a proper amount of DIPEA to adjust the pH to be 7-8, and acryloyl chloride (54 mg) slowly in an ice bath, and stirred at 0° C. for 1 hour. After the reaction was completed, the reaction solution was added with an aqueous solution of saturated ammonium chloride for quenching and extracted with dichloromethane; organic layers were combined, washed with saturated salt solution once, dried with anhydrous sodium sulfate, and then filtered. The filtrate was concentrated and purified by silica gel column chromatography to yield 291 mg of white solid. MS: m/z 589.2, $[M+H]^+$.

Example 14

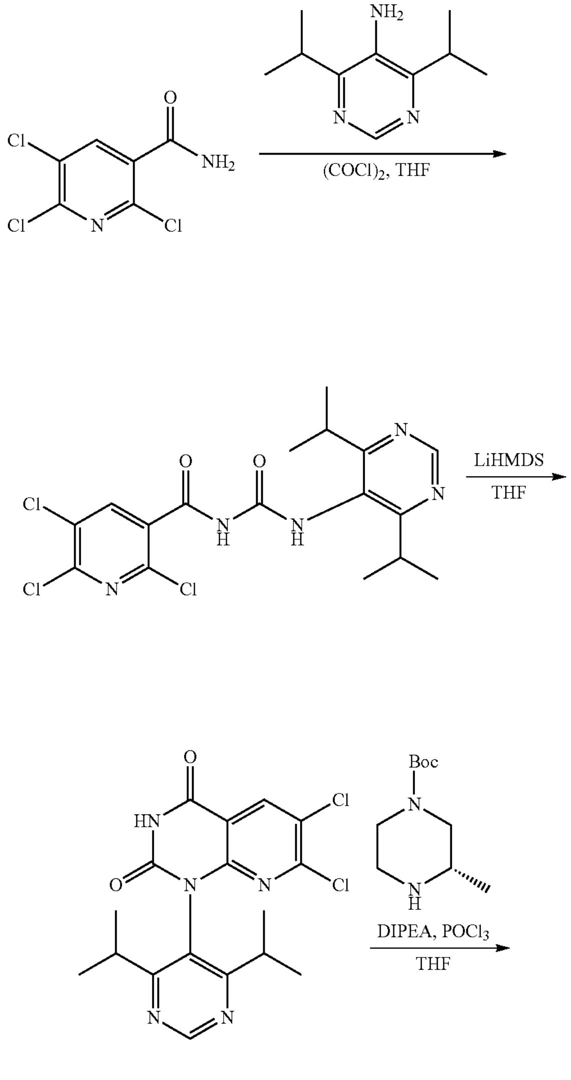

-continued

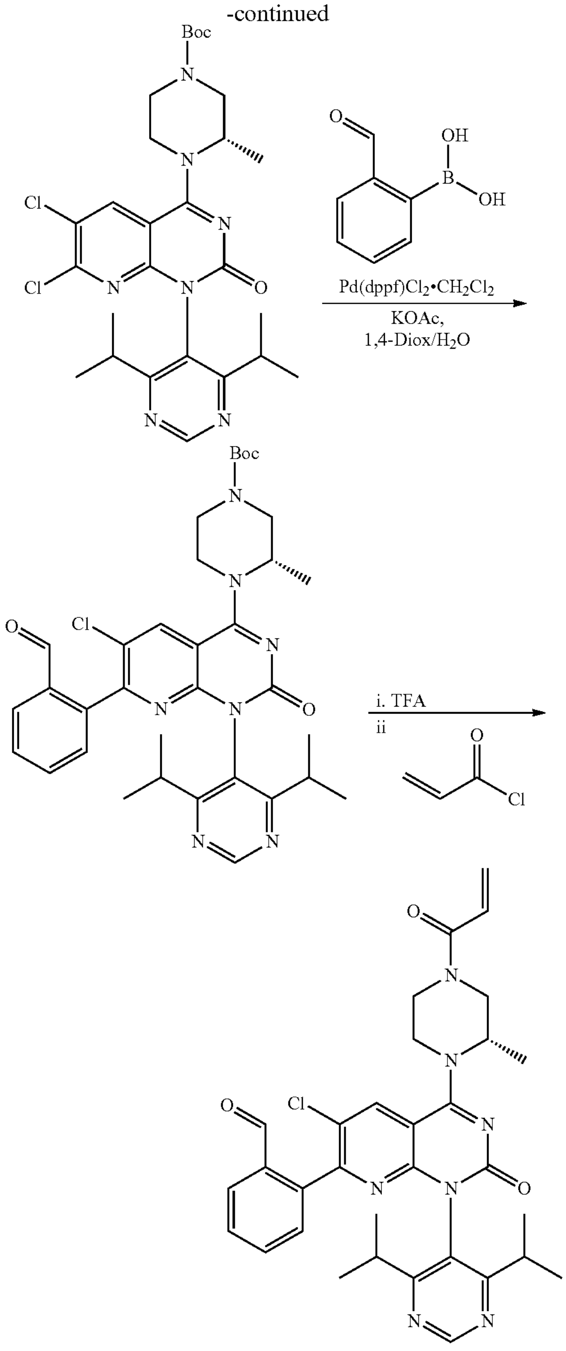

3-31

Step 1

Tetrahydrofuran (20 ml) was added into a 50 ml three-necked flask, subjected to nitrogen displacement, cooled to −5° C., dropwise added with oxalyl chloride (1.3 g) slowly, stirred for 10 minutes, added with 2,5,6-trichloronicotinamide (2.0 g) in batches, heated to 45° C., and stirred for 1 hour. After the reaction was completed, the reaction solution was concentrated until the flow was cut out, added with tetrahydrofuran (15 ml), subjected to nitrogen displacement, cooled to −5° C., dropwise added with a tetrahydrofuran solution (10 ml) containing 4,6-diisopropylpyridin-5-amine (1.1 g) slowly, and stirred at room temperature for 1 hour. After the reaction was completed, the reaction solution was quenched with water, concentrated to remove tetrahydrofuran, added with a saturated aqueous solution of sodium carbonate to adjust the pH of aqueous phases to be 7-8, stirred at normal temperature for 10 minutes, and then filtered. The filter cake was dried to yield 2.6 g of off-white solid. MS: m/z 430.1, $[M+H]^+$.

Step 2

The product of the previous step (2.6 g) and tetrahydrofuran (100 ml) were added into a 250 ml three-necked flask, subjected to nitrogen displacement, cooled to 10-15° C., dropwise added with LiHMDS (1 M THF, 13.6 ml) slowly, and stirred at room temperature for 3 hours. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and then filtered. The filtrate was concentrated until a large number of solids were precipitated, added with methyl tertbutyl ether (3 ml), stirred at normal temperature for 10 minutes, and then filtered. The filter cake was dried to yield 1.7 g of white solid. MS: m/z 394.1, $[M+H]^+$.

Step 3

The product of the previous step (1.7 g), tetrahydrofuran (45 ml), DIPEA (3.3 g) and (S)-4-N-t-Boc-2-methylpiperazine (861 mg) were added into a 100 ml three-necked flask, subjected to nitrogen displacement, dropwise added with phosphorus oxychloride (1.3 g) slowly in an ice bath, stirred at normal temperature for 30 minutes, added with (S)-4-N-t-Boc-2-methylpiperazine (430 mg), stirred for 30 minutes, then added with a saturated aqueous solution of ammonium chloride for quenching, and extracted with ethyl acetate; organic layers were combined, washed with saturated salt solution once, dried with anhydrous sodium sulfate, and then filtered. The filtrate was concentrated to yield 2.5 g of brown solid. MS: m/z 576.2, $[M+H]^+$.

Step 4

The product of the previous step (1.5 g), 2-formylphenylboronic acid (435 mg), potassium acetate (765 mg), $Pd(dppf)Cl_2 \cdot CH_2Cl_2$ (245 mg), 1,4-dioxane (15 ml) and water (1.5 ml) were added into a 50 ml single-necked flask, subjected to nitrogen displacement, heated to 80° C., and stirred for 1 hour. After the reaction was completed, the reaction solution was filtered. The filtrate was concentrated and purified by silica gel column chromatography to yield 1.3 g of brown solid. MS: m/z 646.3, $[M+H]^+$.

Step 5

The product of the previous step (800 mg) and dichloromethane (10 ml) were added into a 50 ml single-necked flask, subjected to nitrogen displacement, dropwise added with trifluoroacetic acid (4.1 g) slowly in an ice bath, heated to 30° C., and stirred for 30 minutes. After the reaction was completed, the reaction solution was concentrated to dryness, added with a saturated aqueous solution of $NaHCO_3$ for adjusting the pH of the aqueous phases to be 7-8, and then extracted with ethyl acetate; organic layers were combined, washed with saturated salt solution once, dried with anhydrous sodium sulfate, and then filtered. The filtrate was concentrated until a large number of solids were precipitated, added with MTBE (5 ml), stirred at normal temperature for 10 minutes, and then filtered. The filter cake was dried. The dried filter cake and dichloromethane (10 ml) were added into a 50 ml single-necked flask, dropwise added with DIPEA (930 mg) and acryloyl chloride (163 mg) slowly in an ice bath, heated to 30° C., and stirred for 20 minutes. After the reaction was completed, the reaction solution was added with a saturated aqueous solution of ammonium chloride for quenching and extracted with dichloromethane; organic layers were combined, washed with saturated salt solution once, dried with anhydrous sodium sulfate, and then filtered. The filtrate was concentrated and purified by silica gel column chromatography to yield 470 mg of brown solid. $^1$H NMR (400 MHz, DMSO-$d_6$): δ 9.78 (s, 1H), 9.01 (s, 1H), 8.48 (d, J=7.9 Hz, 1H), 7.97 (dd, J=7.6, 1.0 Hz, 1H), 7.77 (td, J=7.5, 1.2 Hz, 1H), 7.69 (td, J=7.5, 0.9 Hz, 1H), 7.25 (d, J=7.2, 1H), 6.96-6.81 (m, 1H), 6.27-6.17 (m, 1H), 5.78 (dd, J=10.4, 2.2 Hz, 1H), 5.00 (s, 1H), 4.46-4.07 (m, 3H), 3.92-3.46 (m, 2H), 3.33-3.10 (m, 1H), 2.81-2.65 (m, 2H), 1.36 (d, J=6.7 Hz, 3H), 1.08 (d, J=6.7 Hz, 6H), 0.92-0.86 (m, 6H). MS: m/z 600.3, [M+H]$^+$.

Example 15

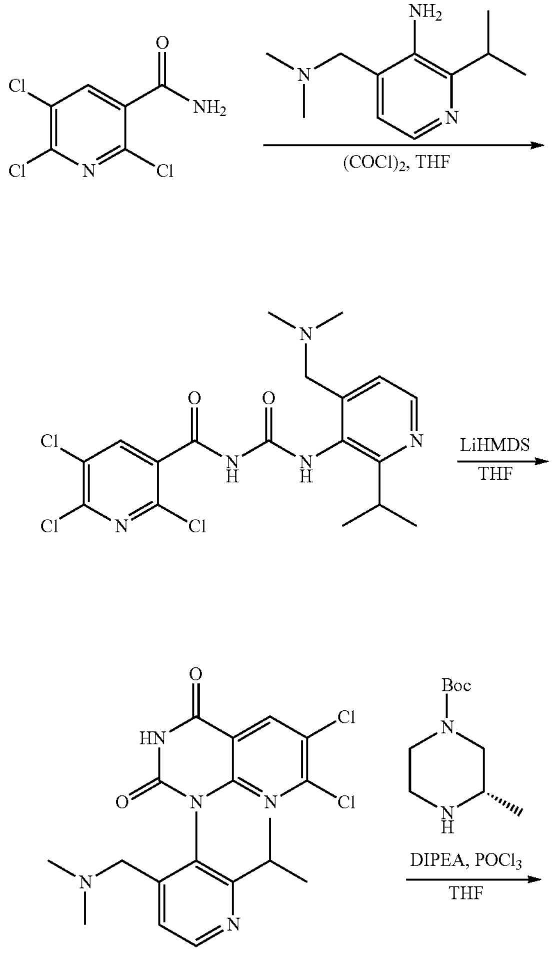

-continued

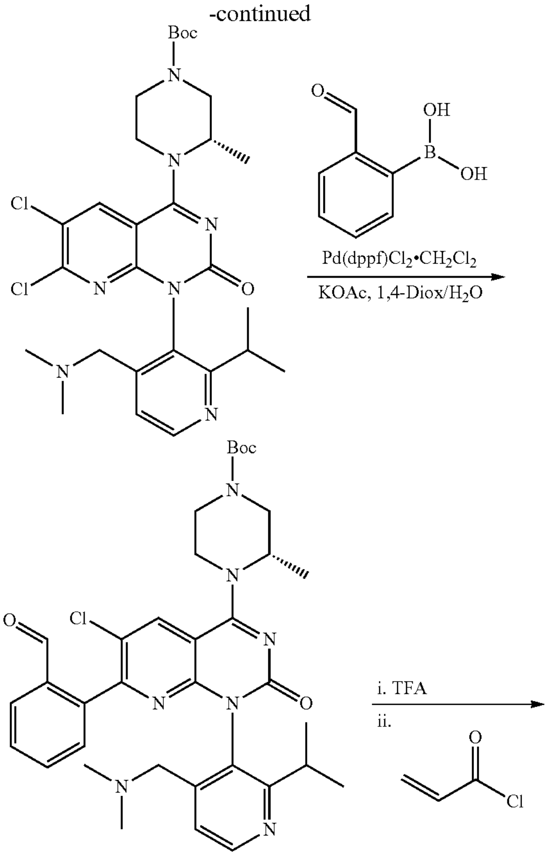

3-32

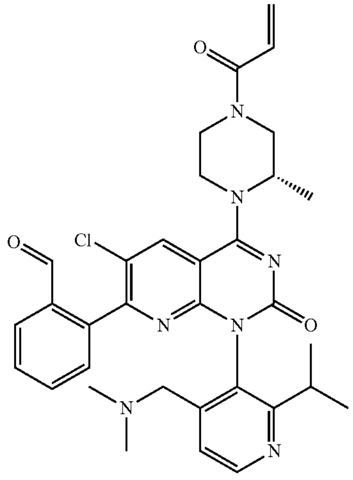

Step 1

Tetrahydrofuran (20 ml) was added into a 50 ml three-necked flask, subjected to nitrogen displacement, cooled to −5° C., dropwise added with oxalyl chloride (1.3 g) slowly, stirred for 10 minutes, added with 2,5,6-trichloronicotinamide (2.0 g) in batches, heated to 55° C., and stirred for 1 hour. After the reaction was completed, the reaction solution was concentrated until the flow was cut out, added with tetrahydrofuran (15 ml), subjected to nitrogen displacement, cooled to −5° C., dropwise added with a tetrahydrofuran solution (8 ml) containing 4-((dimethylamino(methyl)-2-isopropylpyridin-3-amine (1.5 g) slowly, and stirred at room temperature for 1 hour. After the reaction was completed, the reaction solution was added with a saturated aqueous solution of ammonium chloride for quenching and extracted with ethyl acetate; organic layers were combined, washed with saturated salt solution once, and dried with anhydrous sodium sulfate. The filtrate was concentrated and purified by silica gel column chromatography to yield 2.2 g of white solid. MS: m/z 444.1, $[M+H]^+$.

Step 2

The product of the previous step (1.8 g) and tetrahydrofuran (50 ml) were added into a 100 ml three-necked flask, subjected to nitrogen displacement, cooled to 10° C., dropwise added with LiHMDS (1 M in THF), and stirred at room temperature for 2 hours. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and filtered. The filtrate was concentrated and purified by silica gel column chromatography to yield 1.2 g of off-white solid. MS: m/z 408.1, $[M+H]^+$.

Step 3

The product of the previous step (1.2 g), tetrahydrofuran (30 ml), DIPEA (2.3 g) and (S)-4-N-t-Boc-2-methylpiperazine (588 mg) were added into a 100 ml three-necked flask, subjected to nitrogen displacement, dropwise added with phosphorus oxychloride (901 mg) slowly in an ice bath, stirred at room temperature for 30 minutes, added with (S)-4-N-t-Boc-2-methylpiperazine (294 mg), and stirred for 30 minutes. After the reaction was completed, the reaction solution was added with a saturated aqueous solution of ammonium chloride for quenching and extracted with ethyl acetate; organic layers were combined, washed with saturated salt solution once, dried with anhydrous sodium sulfate, and filtered. The filtrate was concentrated and purified by silica gel column chromatography to yield 1.7 g of off-white solid. MS: m/z 590.2, $[M+H]^+$.

Step 4

The product of the previous (1.6 g), 2-formylphenylboronic acid (455 mg), potassium acetate (813 mg), $Pd(dppf)Cl_2 \cdot CH_2Cl_2$ (112 mg), 1,4-dioxane (20 ml) and water (2 ml) were added into a 50 ml single-necked flask, subjected to nitrogen displacement, heated to 80° C., and stirred for 1 hour. After the reaction was completed, the reaction solution was filtered. The filtrate was concentrated and purified by silica gel column chromatography to yield 1.1 g of brown solid. MS: m/z 660.3, $[M+H]^+$.

Step 5

The product of the previous step (1.1 g) and dichloromethane (20 ml) were added into a 50 ml single-necked flask, subjected to nitrogen displacement, dropwise added with trifluoroacetic acid (5.7 g) slowly in an ice bath, heated to 30° C., and stirred for 20 minutes. After the reaction was completed, the reaction solution was concentrated to dryness, added with a saturated aqueous solution of sodium carbonate to adjust the pH of the aqueous phases to be 7-8, and extracted with ethyl acetate. Organic layers were combined, washed with saturated salt solution once, dried with anhydrous sodium sulfate and filtered. The filtrate was concentrated and purified by silica gel column chromatography to yield 800 mg of off-white solid. The off-white solid was dissolved in dichloromethane (10 ml), dropwise added with DIPEA (1.1 g) and acryloyl chloride (190 mg) slowly in an ice bath, heated to 30° C., and stirred for 20 minutes. After the reaction was completed, the reaction solution was added with a saturated aqueous solution of ammonium chloride for quenching and extracted with dichloromethane; organic layers were combined, washed with saturated salt solution once, dried with anhydrous sodium sulfate, and then filtered. The filtrate was concentrated and purified by silica gel column chromatography to yield 465 mg of brown solid. $^1H$ NMR (400 MHz, $CDCl_3$): δ 9.83 (s, 1H), 8.56 (d, J=4.9 Hz, 1H), 8.09 (s, 1H), 7.91-7.85 (m, 1H), 7.66-7.60 (m, 2H), 7.44-7.31 (m, 1H), 7.19-7.13 (m, 1H), 6.74-6.55 (m, 1H), 6.44 (dd, J=16.6, 1.0 Hz, 1H), 5.84 (dd, J=10.4, 1.4 Hz, 1H), 5.22-4.28 (m, 3H), 4.12-3.55 (m, 3H), 3.35-3.06 (m, 3H), 2.82-2.64 (m, 1H), 2.17-1.96 (m, 6H), 1.61-1.46 (m, 3H), 1.22 (d, J=6.7 Hz, 3H), 1.04 (d, J=6.4 Hz, 3H). MS: m/z 614.3, $[M+H]^+$.

Preparation of Contrast Compound TM-1

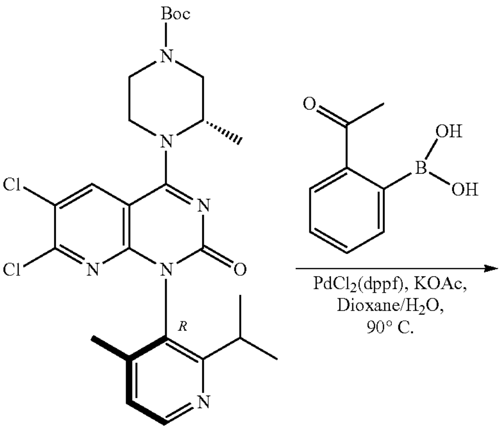

Intermediate 3M

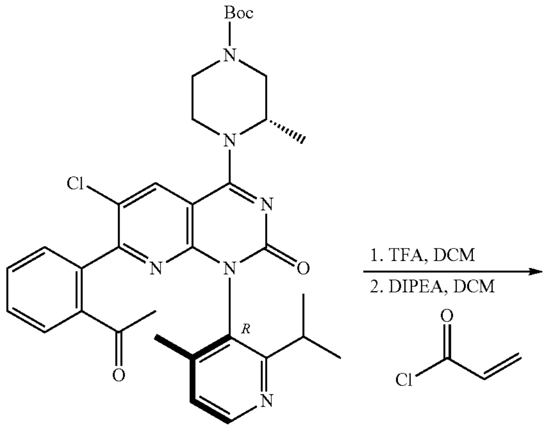

-continued

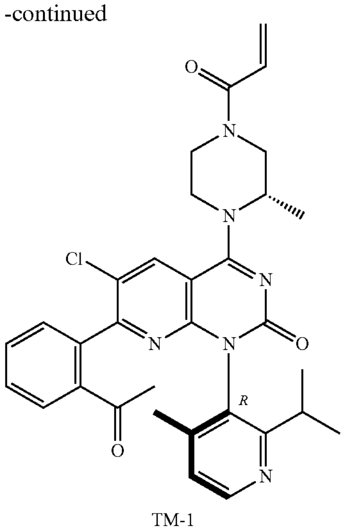

TM-1

TM-2

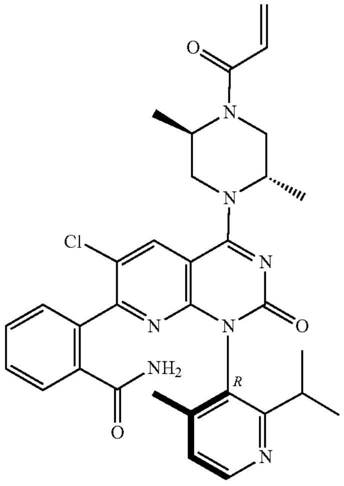

TM-3

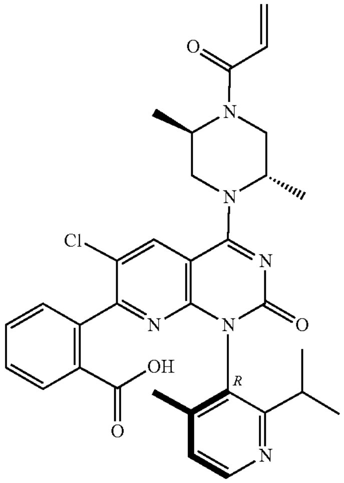

Step 1

The intermediate 3M (2.23 g), 2-acetonophenylboronic acid (1.2 g), potassium acetate (2.3 g), 1,4-dioxane (50 ml), water (2.5 ml) and [1,1'-bis(diphenylphosphino) ferrocene] dichloropalladium (307 mg) were added into a 100 ml single-necked flask, subjected to nitrogen displacement, heated to 90° C., and stirred. After the reaction was completed, the reaction solution was diluted with water and extracted with ethyl acetate; organic layers were combined, washed with saturated salt solution once, dried with anhydrous sodium sulfate, filtered, concentrated under reduced pressure, and purified by silica gel column chromatography to yield 830 mg of light solid. MS: m/z 631.3, $[M+H]^+$.

Step 2

The product of the previous step (830 mg), dichloromethane (20 ml) and trifluoroacetic acid (5 ml) were added into a 50 ml single-necked flask, and stirred at room temperature after the dropwise addition. After the reaction was completed, the reaction solution was cooled to 0° C., slowly added with a saturated aqueous solution of sodium bicarbonate to adjust the pH to alkalescence, and extracted with dichloromethane; organic layers were combined, dried with anhydrous sodium sulfate, filtered and concentrated to dryness under reduced pressure. Dichloromethane (30 ml) and N,N-diisopropylethylamine (476 mg) were added into the concentrate, cooled to 0° C. under nitrogen protection, dropwise added with a dichloromethane solution (5 ml) containing acryloyl chloride (121 mg) slowly, and stirred for 30 minutes after the dropwise addition. After the reaction was completed, the reaction solution was diluted with water and extracted with dichloromethane; organic layers were combined, washed with saturated salt solution once, dried with anhydrous sodium sulfate, filtered, concentrated under reduced pressure and purified by silica gel column chromatography to yield 420 mg of light yellow solid TM-1. MS: m/z 585.4, $[M+H]^+$.

The following compounds were prepared according to literatures US20190374542 and WO2020050890:

Compared with AMG510, the advantages of the compounds of the present invention in synthesis and preparation are summarized as follows:

On page 65 of patent literature WO2020102730A1, the industrial production method of AMG510 is described, wherein the key "carbon-carbon bond construction" reaction is carried out in the following way.

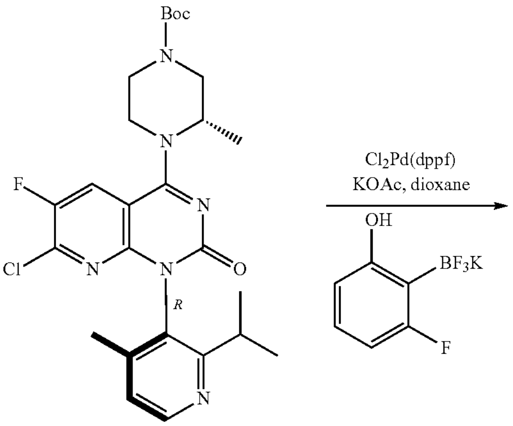

-continued

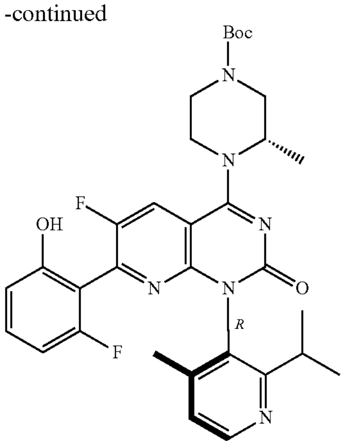

The Suzuki reaction of the "carbon-carbon bond construction" is the core step of AMG510 manufacturing, and the reaction efficiency and specificity thereof are related to the generation and control strategy of AMG510 impurities. There are three key technical points in the Suzuki reaction: (1) the Suzuki reaction uses catalyst; (2) temperature of the Suzuki reaction; and (3) starting materials used in the Suzuki reaction.

For the preparation of the compounds of the present invention (for example, compound 3-2M), the starting material of the Suzuki reaction used is an aromatic boric acid starting material (i.e., compound BOH), while the starting material of AMG510 used is an aromatic potassium fluoroborate starting material (i.e., compound BFK).

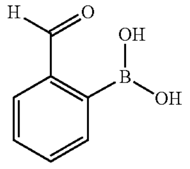

BOH

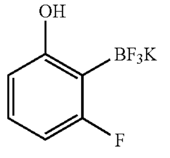

BFK

Wherein, compound BFK needs to be prepared in advance using the following method (recorded on Page 72 of WO2020102730A1):

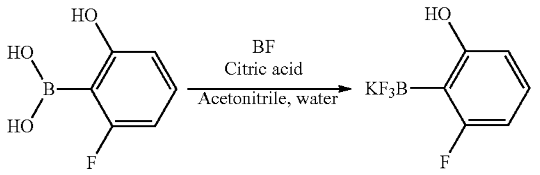

BFK

In the process of preparing AMG510 and using BFK for Suzuki reaction, hydrogen fluoride may be produced, which is corrosive and toxic, and can corrode glass and carbon steel equipment, causing a great impact on the surrounding environment. On one hand, the production cost is increased; on the other hand, unpredictable risks are brought to the quality control of AMG510 bulk drug products due to impurities such as heavy metals produced by corroding equipment.

However, the Suzuki reaction, the key step in the preparation of the compounds of the present invention, uses BOH as the raw material, and does not need to convert "boric acid intermediate" into "potassium fluoborate" intermediate, which can avoid the cost increase caused by equipment corrosion and the quality control risk caused by impurities such as heavy metals. Therefore, compared with similar preparation steps of AMG510, the Suzuki reaction step in the synthesis of the compounds of the present invention has more advantages in industrial application.

Biological Test

1. Cell Proliferation Inhibitory Activity

Determination of Cell Proliferation Inhibitory Activity $IC_{50}$ Value:

MIA PaCa-2 cells in an exponential growth phase were digested with trypsin-EDTA and plated in a 96-well plate at 2000-3000 cells per well and incubated overnight at 37° C. with 5% $CO_2$. A test compound was prepared as a mother liquor with DMSO, diluted with a DMEM growth medium in a concentration gradient and added to the 96-well plate and incubated for 72 hours at 37° C. in a 5% $CO_2$ incubator. After incubation, an equal volume of CellTiter-Glo detection reagent was added to each well and incubated after shaking, and a chemiluminescence value was measured by a microplate reader, and the $IC_{50}$ value for the inhibition of MIA PaCa-2 cell proliferation was fitted and calculated by GraphPad Prism software.

Wherein, "A" represents that the $IC_{50}$ value (nM) is less than 50; "B" represents that the $IC_{50}$ value (nM) is between 50 and 150 (excluding 150); "C" represents that the $IC_{50}$ value (nM) is between 150 and 300; and "D" represents that the $IC_{50}$ value (nM) is greater than 300.

The cell inhibitory activities of some representative compounds of the present invention are as follows.

| Compound No. | Cell proliferation inhibitory activity $IC_{50}$ value of MIA-PACA-2: |
|---|---|
| 3-2 | A |
| 3-6 | A |
| 3-2M | A |
| 3-6M | A |
| 3-17M | A |
| 3-19M | A |

3-2, 3-6, 3-2M, 3-6M, 3-17M, and 3-19M showed significant cell proliferation inhibitory activities against KRAS G12C mutant cells MIA PaCa-2.

2. Cell Proliferation Inhibitory Activity

Determination of Cell Proliferation Inhibitory Activity $IC_{50}$ Value:

NCI-H358 cells in an exponential growth phase were digested with trypsin-EDTA and plated in a 96-well plate at 2000-3000 cells per well and incubated overnight at 37° C. with 5% $CO_2$. A test compound was prepared as a mother liquor with DMSO, diluted with a RPMI 1640 growth medium in a concentration gradient and added to the 96-well plate and incubated for 72 hours at 37° C. in a 5% $CO_2$ incubator. After incubation, an equal volume of CellTiter-Glo detection reagent was added to each well and incubated after shaking, and a chemiluminescence value was measured by a microplate reader, and the $IC_{50}$ value for the inhibition of NCI-H358 cell proliferation was fitted and calculated by GraphPad Prism software.

Wherein, "A" represents that the $IC_{50}$ value (nM) is less than or equal to 50; and "B" represents that the $IC_{50}$ value (nM) is greater than 50.

| Compound No. | Cell proliferation inhibitory activity $IC_{50}$ value of H358 |
|---|---|
| 3-2 | A |
| 3-6 | A |
| 3-16M | A |
| 3-28M | A |
| 3-14 | A |
| 3-6B | A |
| 3-2M | A |
| 3-2P | B |
| 3-6M | A |
| 3-6P | B |

The experiment results showed that: compound 3-2, compound 3-6, compound 3-16M, compound 3-28M, compound 3-14, compound 3-6B, compound 3-2M, and compound 3-6M showed significant cell proliferation inhibitory activities against KRAS G12C mutant cells NCI-H358.

The cell proliferation inhibitory activity of the compound 3-2M with the axially chiral R-configuration against H358 was significantly better than that of the corresponding compound 3-2P thereof with the axially chiral S-configuration; and the cell proliferation inhibitory activity of the compound 3-2M with the R-configuration was more than five times that of the corresponding compound 3-2P thereof with the axially chiral S-configuration.

The cell proliferation inhibitory activity of the compound 3-6M with the axially chiral R-configuration was significantly better than that of the corresponding compound 3-6P with the axially chiral S-configuration.

3. Cell Proliferation Inhibitory Activity

The inhibitory effect of the compounds on the proliferation activity of H358 cells was tested with reference to the method of the biological test 2, and the results were as follows:

wherein "A" represents that the $IC_{50}$ value (nM) is less than 50; and "B" represents that the $IC_{50}$ value (nM) is greater than to 50.

| Compound No. | Cell proliferation inhibitory activity $IC_{50}$ value of H358 |
|---|---|
| 3-1MIS | A |
| 3-2MIS | A |
| 3-3MIS | A |
| 3-4MIS | A |
| 3-5MIS | A |
| 3-6MIS | A |
| 3-7MIS | A |
| 3-8MIS | A |

The experiment results showed that: compound 3-1MIS, compound 3-2MIS, compound 3-3MIS, compound 3-4MIS, compound 3-5MIS, compound 3-6MIS, compound 3-7MIS, and compound 3-8MIS showed significant cell proliferation inhibitory activities against KRAS G12C mutant cells H358.

4. Preliminary Safety Test of Compounds

Samples for testing: compound 3-2M and compound 3-6M.

Animal species and number: Balb/c; 3 animals per group.

Mode of administration: oral gavage.

Animal grouping and administration dose: solvent blank group and compound 3-2M group (400 mg/kg, 800 mg/kg); compound 3-6M group (400 mg/kg, 800 mg/kg).

Administration frequency: once a day, and administration for 3 days.

Test Procedure:

| Group | Day 1 | Day 2 | Day 3 |
|---|---|---|---|
| Solvent group | / | / | / |
| Compound 3-2M group | 400 mg/kg | 400 mg/kg | 800 mg/kg |
| Compound 3-6M group | 400 mg/kg | 400 mg/kg | 800 mg/kg |

Test results: during the administration period of compound 3-2M and compound 3-6M, the animals in all dose groups had normal water intake and feeding, normal activity and normal body weight, and no obvious abnormal performance. The maximum tolerated doses of the compound 3-2M and the compound 3-6M were tentatively suggested to be greater than 800 mg/kg.

5. Pharmacodynamic Test of CDX Model in Nude Mice

Model establishment and dosing solutions:

Animal species and number: Balb/c Nude.

Samples for testing: compound 3-2M and compound 3-6M.

Test groups: blank solvent control group; compound 3-2M (10 mg/kg, QD×15 days), and compound 3-6M (10 mg/kg, QD×15 days).

Animal model establishment: MIA-paca-2 cells were cultured in vitro and inoculated subcutaneously on the right side of the back of nude mice, and the tumor-bearing nude mice were randomly grouped. Subsequently, each group of animals was administered and the day of the first administration was defined as day 1 of the test.

Administration route and frequency: oral gavage; and once a day.

General state observation: observation time and frequency: once a day; observation index or content: including, but not limited to local administration, appearance and signs, general behavioral activities, mental status, death and other abnormal manifestations of the animals. The animals were euthanized at the end of the test.

Tumor volume calculation: V=½×long diameter×short diameter$^2$ ($mm^3$). Tumor growth inhibition ratio TGI (%) was used to evaluate the tumor suppressive efficacy of the compounds. TGI (%)=[1-(mean tumor volume at the end of administration of the treatment group−mean tumor volume at the beginning of administration of the treatment group)/(mean tumor volume at the end of administration of the control group−mean tumor volume at the beginning of administration of the control group)]×100%.

"+" represents that the tumor suppression ratio is less than 60%; "++" represents that the tumor suppression ratio is between 60% and 80%; and "++++" represents that the tumor suppression ratio is greater than 80%.

| Compound | Tumor suppression ratio (%) |
|---|---|
| 3-2M | +++ |
| 3-6M | +++ |

Test Results (1) Compound 3-2M and compound 3-6M showed significant inhibition of subcutaneous transplanted tumor growth of pancreatic cancer MIA-paca-2 cells in nude mice; and (2) in the test period of administration, the experimental animals had normal food and water intake, normal activities, and normal weight, and showed no toxicity.

6. In Vitro Isolated Heart Perfusion Test

Test method: influences of Langendorff isolated perfused heart test compounds on electrocardiogram, wherein the test method used in this test was as follows:

| Test system/method | Langendorff isolated perfused heart |
|---|---|
| Animals tested | Guinea pig |
| Test parameter | Heart Rate (HR) |
| Test concentration | 3.3 μM |

Test compounds: compound 3-2M and the compound in Example 41 of patent WO2018217651A1 (i.e., AMG510).

Test Results

| Compound | Concentration | HR (heart rate) change % |
|---|---|---|
| AMG510 | 3.3 μM | C |
| Compound 3-2M | 3.3 μM | A |

"A" represents that the heart rate decreases by less than 5%;

"B" represents that the heart rate decreases by greater than or equal to 5%, but less than 15%; and "C" represents that the heart rate decreases by greater than or equal to 15%.

This test showed that: compound 3-2M of the present invention had no obvious effect on the heart rate of the isolated heart, and AMG510 had a significant effect on reducing the heart rate. Compound 3-2M of the present invention has advantages over AMG510 in terms of the heart safety.

7. Testing of Compounds on Proliferation Activity Inhibition of NCI-H358 Cells

The inhibitory effect of the compounds on the proliferation activity of NCI-H358 cells was tested with reference to the method of the biological test 2, and the results were as follows.

Wherein "A" represents that the $IC_{50}$ value (nM) is less than 50; "B" represents that the $IC_{50}$ value (nM) is between 50 and 150; and "C" represents that the $IC_{50}$ value (nM) is greater than 150.

| Compound No. | Cell proliferation inhibitory activity $IC_{50}$ value of NCI-H358 |
|---|---|
| 3-6B | A |
| 3-28 | A |
| 3-29 | A |
| 3-31 | A |
| 3-32 | A |
| TM-1 | B |
| TM-2 | C |
| TM-3 | C |

The experiment results showed that: compound 3-6B, compound 3-28, compound 3-29, compound 3-31, and compound 3-32 showed significant cell proliferation inhibitory activities against KRAS G12C mutant cells NCI-H358.

8. Pharmacodynamics test of xenograft tumor model of tumor cells NCI-H358 in nude mice Model Establishment and Dosing Solutions:

Animal species and number: Balb/c Nude; 6 animals per group.

Samples for testing: compound 3-2M, compound 3-16M, TM-1, TM-3, and AMG510 (obtained by purchasing).

Test groups: blank solvent control group; compound 3-2M (100 mg/kg, QD×15 days), compound 3-16M (100 mg/kg, QD×15 days), TM-1 (100 mg/kg, QD×15 days), TM-3 (100 mg/kg, QD×15 days); and AMG510 (100 mg/kg, QD×15 days).

Animal model establishment: NCI-H358 tumor cells at logarithmic phase were cultured and collected in vitro, and inoculated subcutaneously on the right side of the back of nude mice at a quantity of $5\times10^6$ cells/each, and the tumor-bearing nude mice were randomly grouped when the tumor volume grew to 150-300 $mm^3$. Subsequently, each group of animals was administered and the day of the first administration was defined as day 1 of the test.

Administration route and frequency: oral gavage; and once a day.

General state observation: observation time and frequency: once a day; observation index or content: including, but is not limited to local administration, appearance and signs, general behavioral activities, mental status, death and other abnormal manifestations of the animals. The animals were euthanized at the end of the test.

Tumor volume calculation: V=½×long diameter× short $diameter^2$ ($mm^3$). Tumor growth inhibition ratio TGI (%) was used to evaluate the tumor suppressive efficacy of the compounds. TGI (%)=[1-(mean tumor volume at the end of administration of the treatment group−mean tumor volume at the beginning of administration of the treatment group)/(mean tumor volume at the end of administration of the control group−mean tumor volume at the beginning of administration of the control group)]×100%.

"+" represents that the tumor suppression ratio is less than 60%; "++" represents that the tumor suppression ratio is between 60% and 100%; "+++" represents that the tumor suppression ratio is between 101% and 140%; and "++++" represents that the tumor suppression ratio is greater than 140%.

| Compound | Tumor suppression ratio (%) |
|---|---|
| 3-2M | ++++ |
| 3-16M | ++++ |
| AMG510 | +++ |
| TM-1 | ++ |
| TM-3 | + |

Test results: compound 3-2M and compound 3-16M showed significant inhibitory effects on the subcutaneous transplanted tumor growth of lung cancer NCI-H358 cells in nude mice, and compound 3-2M and compound 3-16M showed better tumor inhibitory effects than AMG510, TM-1 and TM-3 at an administration dose of 100 mg/kg. 9. Cell proliferation inhibitory activity $IC_{50}$ value of NCI-H358 [3D model test]:

100 μl of high concentration agarose gel was spread in a 96-well plate as a bottom agarose gel layer; low concentration agarose and growth medium containing cells were mixed and spread on the bottom agarose gel layer, cooled and solidified and incubated overnight at 37° C.; a test compound was prepared into a mother liquor with DMSO, diluted with a RPMI 1640 growth medium in a concentration gradient, and the gradient diluted solution of the compound to be tested with different concentrations was added into 96 wells containing upper agarose gel cells, and solvent control wells were set and placed in a carbon dioxide incubator for culture. During the period, the drug-containing medium was changed to observe the cell growth. After the culture, the cells were stained with NBT, the number of colony formation was counted, and the $IC_{50}$ value of the compound inhibiting cell proliferation was obtained.

| Compound No. | Cell proliferation inhibitory activity $IC_{50}$ value of NCI-H358 [3D model test]: |
|---|---|
| 3-2M | 1.8 |
| 3-16M | 1.1 |
| AMG510 | 9.3 |

Compound 3-2M and compound 3-16M showed significant cell proliferation inhibitory activities against KRAS G12C mutant cells NCI-H358, and the inhibitory activities were better than AMG510.

10. Detecting Effects of Compounds on hERG Potassium Channels by Electrophysiological Manual Patch Clamp Preparation of test solution: the solution of test compound 3-16M was subjected to conventional ultrasound and oscillation to ensure complete dissolution of the compound.

Cell culture: the cell lines were derived from HEK-293 cells which overexpressed hERG potassium channel. The cells were cultured in a 5% $CO_2$ incubator at 37°. When a cell density reached 80% of a culture dish, the cells were pre-washed with a phosphate buffer solution (PBS), and then digested with trypsin/EDTA, and a cell culture medium was added to stop digestion. The cells were gently blown with a pipette and transferred to a centrifuge tube, centrifuged at 1000 rpm, the supernatant was poured out, and then the cell culture medium was added. The cells were gently blown and mixed evenly, then transferred to a culture dish for subculture, or the cells were dripped on a round slide and placed in a culture dish for the cells to adhere to the wall for test.

The hERG $IC_{50}$ value of the compound calculated by electrophysiology manual patch clamp system test was as follows:

| Compound | hERG $IC_{50}$ value (μM) |
|---|---|
| 3-16M | >100 |

Compound 3-16M had no blocking effect on hERG potassium channels in the test concentration range (IC50>100 M). However, it was recorded in the appendix supporting information material (Page 23) of the literature (The New England Journal of Medicine, 2020; 383:1207-1217; DOI: 10.1056/NEJMoa1917239) that the $IC_{50}$ value of AMG510 on hERG was 54.8 M. Compound 3-16M had a potentially heart safety better than AMG510.

11. Analysis of Therapeutic Safety Window

Continuous dosing safety tests revealed that animals in all dose groups fed and watered normally, moved normally, and had normal body weights without significant abnormalities in the three-day continuous dosing tests for compounds 3-2M and 3-6M, from a dose of 400 mg/kg to 800 mg/kg.

On the other hand, in vivo pharmacodynamic tests revealed that tumor suppression onset doses of compounds 3-2M and 3-6M were less than 10 mg/kg and that these compounds have a wide therapeutic safety window (a ratio of toxic dose to onset dose was greater than 80 times) and had significant potential for application.

12. Two-Week Repeated Dosing Safety Test

Samples for testing: compound 3-29; compound 3-16M; and compound 3-32.

Animal species and number: SD rats; 6 rats per group (half male and half female).

Mode of administration: oral gavage.

Animal grouping and administration dose: solvent blank group and compound 3-29 group (400 mg/kg); compound 3-16M group (400 mg/kg); and compound 3-32 group (400 mg/kg).

Administration frequency: once a day, and administration for 14 days.

Test Procedure:

After administration, a toxic reaction was observed by cages for 4 hours, and detailed clinical observation was made on animals with obvious abnormal performances. General clinical observation included twice a day during the duration of test (once in the morning and once in the afternoon). Death, morbidity, respiration, secretion, faeces, diet, drinking water, and other conditions were observed and weight changes of the rats during administration were recorded. Detailed clinical observations included but were not limited to behavioral activity, skin, coat, eyes, ears, nose, abdomen, external genitals, anus, extremities, feet, and respiration. After the administration, the animals in each group were euthanized, and all the animals were dissected and observed grossly.

Test results: during the administration period (14 days) of compound 3-29, compound 3-16M, and compound 3-32, the animals in all dose groups had normal water intake and feeding, normal activity and normal body weight, and no obvious abnormal performance.

13. Preliminary Study on Capsule Products of Compound 3-2M

Formulation Composition:

| Ingredient | Effect | Dosage per capsule(mg) |
|---|---|---|
| Compound 3-2M | Main drug | 100 |
| Mannitol | Diluent | 50 |
| Starch slurry | Binder | Proper amount |
| Sodium carboxymethyl starch | Disintegrant | 10 |
| Magnesium stearate | Lubricant | 2 |
| Gelatin hollow capsule | Capsule shell | 1 capsule |

Capsule Preparation Method:

The weighed compound 3-2M, mannitol and sodium carboxymethyl starch were added into a wet mixer granulator for mixing; under the condition of stirring with purified water, a proper amount of starch was slowly added, and stirred and dispersed evenly to prepare the binder—starch slurry. The wet mixer granulator was used to control a stirring speed and a shearing speed, and the starch slurry was slowly added, stirred and shorn to prepare a soft material. The prepared soft material was granulated using a 24-mesh sieve in an oscillating granulator to obtain wet granules. The wet granules were added to a fluidized bed granulator to obtain dry granules. The dry granules were sieved by a swing granulator for granulating and the granulated granules were weighed. The granulated granules were added into a three-dimensional multi-directional motion mixer, then added with magnesium stearate after mixing, and blended to obtain blended granules. The total blended granules were filled into No. 1 gelatin hollow capsules using a stower, and qualified capsules were screened out to prepare the capsules to be packaged.

The capsule samples with neat appearance were obtained, and the content uniformity of the capsule product met the requirements (A+2.2S≤15); and a cumulative solubility of the capsule product was greater than 75% in 1 hour in a dissolution medium with a pH of 2.0.

What is claimed is:

1. A compound represented by formula (II), or a stereoisomer, tautomer, or pharmaceutically acceptable salt thereof,

II

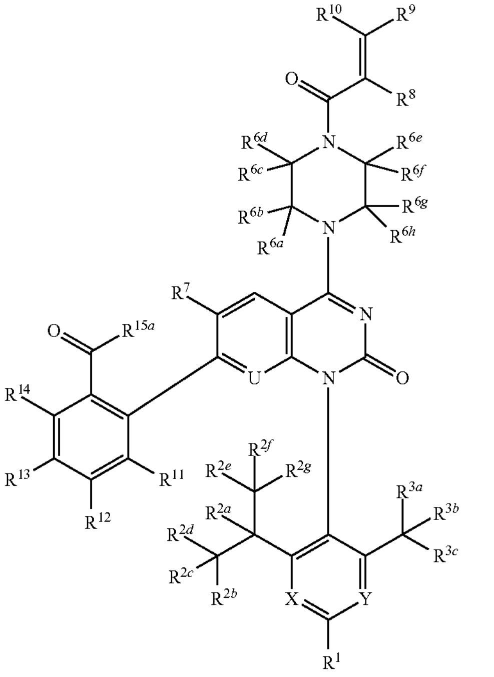

wherein, X is a nitrogen atom or $CR^4$, and Y is a nitrogen atom or $CR^5$;

U is a nitrogen atom or $CR^U$, wherein $R^U$ is hydrogen or deuterium;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{11}$, $R^{12}$, $R^{13}$, and $R^{14}$ are each independently selected from hydrogen, deuterium, halogen, alkyl or deuterated alkyl;

$R^{15a}$ is hydrogen or deuterium;

$R^{6a}$, $R^{6b}$, $R^{6c}$, $R^{6d}$, $R^{6e}$, $R^{6f}$, $R^{6g}$, and $R^{6h}$ are each independently selected from hydrogen, deuterium, methyl or trideuteriomethyl;

$R^7$ is fluorine or chlorine; and $R^8$, $R^9$, and $R^{10}$ are each independently selected from hydrogen, deuterium or fluorine;

wherein, the structural segment

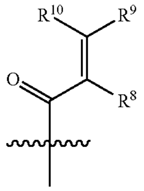

is selected from the following structures:

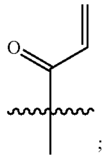

; or

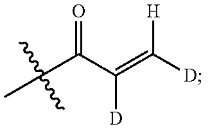

wherein, the structural segment

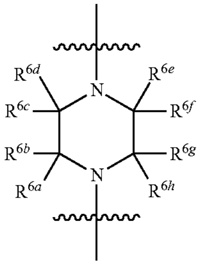

is selected from the following structures:

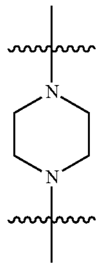

;

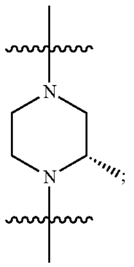

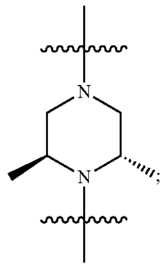

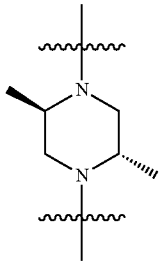

;

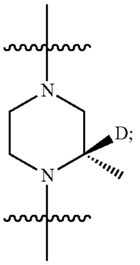

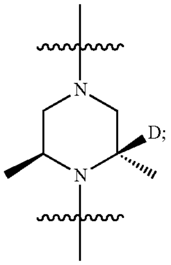

-continued
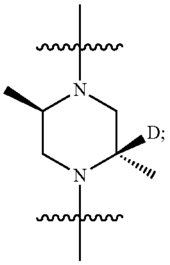
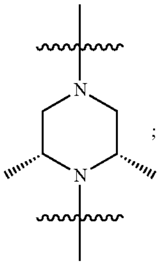
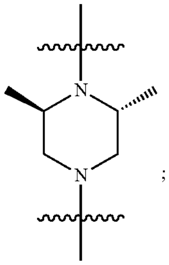
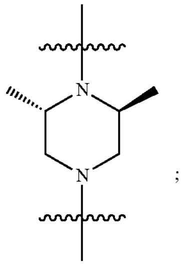
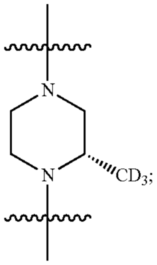
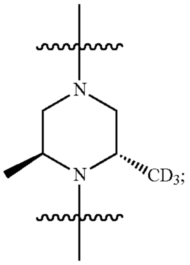
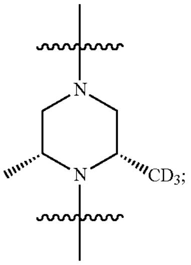
or
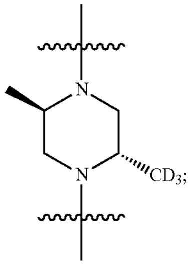
wherein, the structural segment
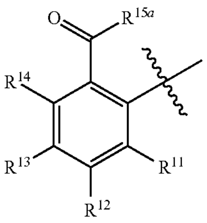
is selected from the following structures:
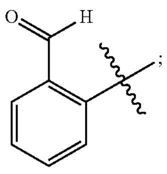
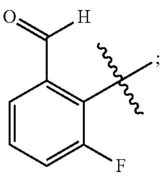
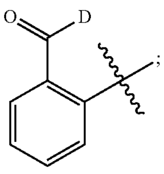
-continued
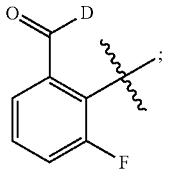
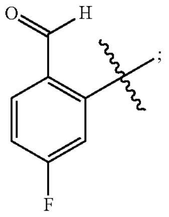
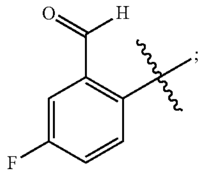
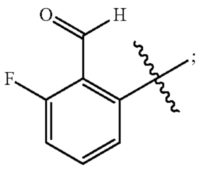
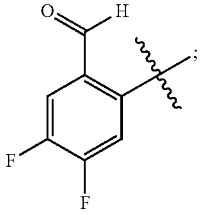
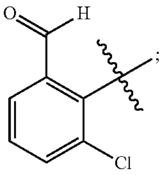
or
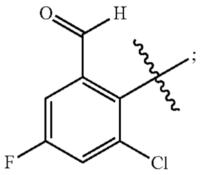
and
wherein, the structural segment
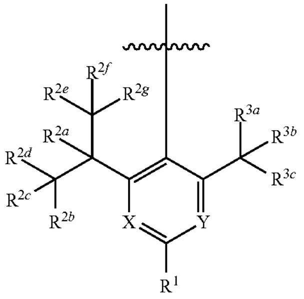
is selected from the following structures:
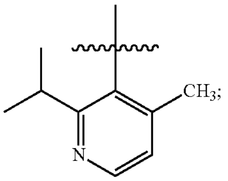
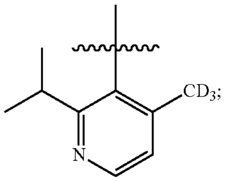
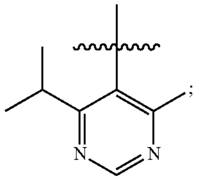
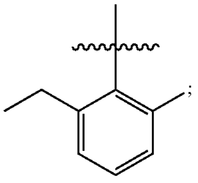

-continued

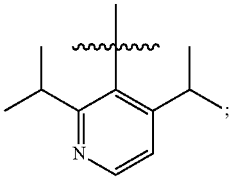;

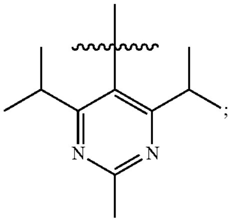;

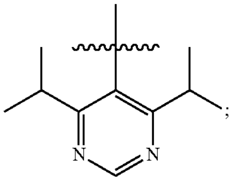;

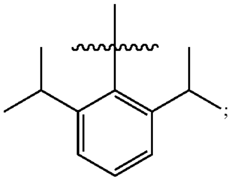;

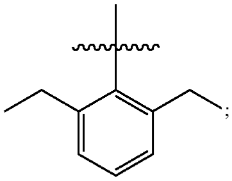;

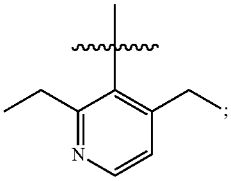;

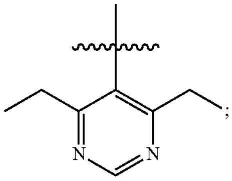; or

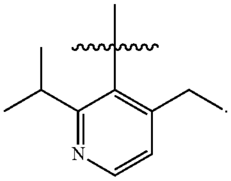.

2. The compound according to claim 1, wherein the compound is represented by formula (III), or a stereoisomer, tautomer, or pharmaceutically acceptable salt thereof,

III

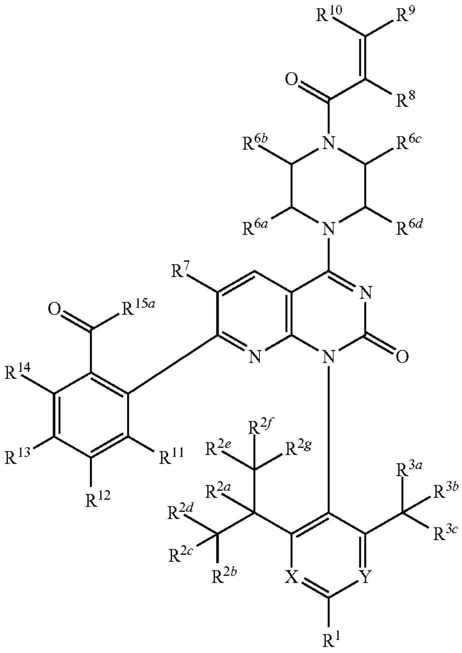

wherein, X is a nitrogen atom or $CR^4$, and Y is a nitrogen atom or $CR^5$;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{11}$, $R^{12}$, $R^{13}$, and $R^{14}$ are each independently selected from hydrogen, deuterium, halogen, alkyl or deuterated alkyl;

$R^{15a}$ is hydrogen or deuterium;

$R^{6a}$, $R^{6b}$, $R^{6c}$, and $R^{6d}$ are each independently selected from hydrogen, deuterium, methyl or trideuteriomethyl;

$R^7$ is fluorine or chlorine; and $R^8$, $R^9$, and $R^{10}$ are each independently selected from hydrogen, deuterium or fluorine;

wherein, the structural segment

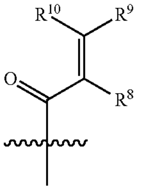

is selected from the following structures:

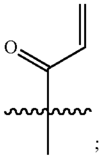;

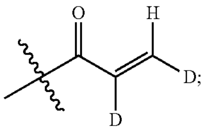

wherein, the structural segment

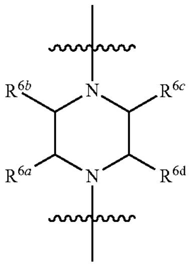

is selected from the following structures:

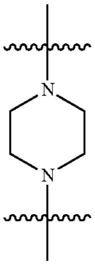;

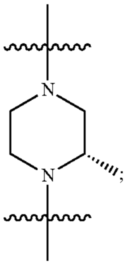;

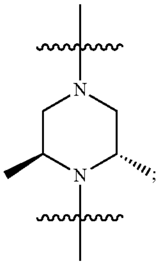;

-continued
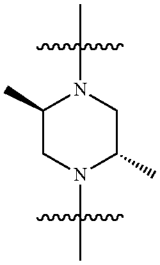 ; 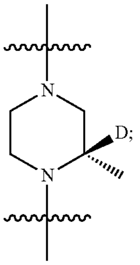 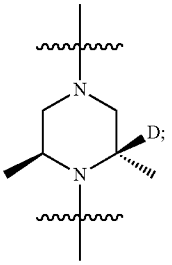
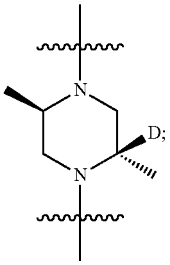 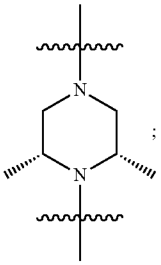 ;
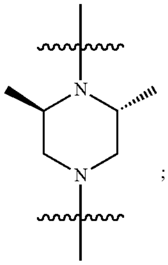 ; 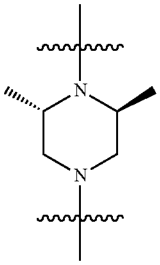 ; 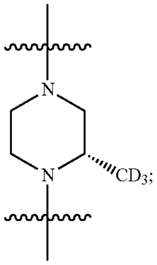
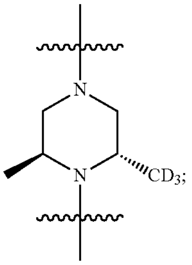 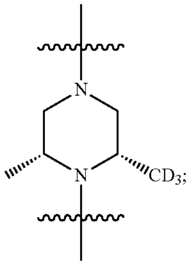 or
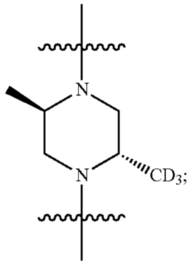
wherein, the structural segment
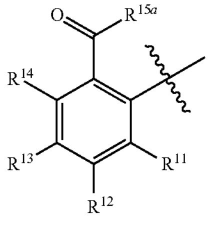
is selected from the following structures:
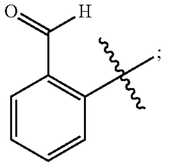 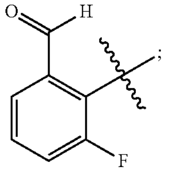 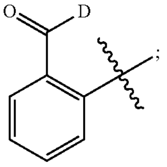
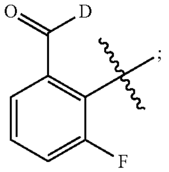 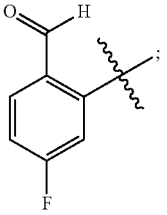
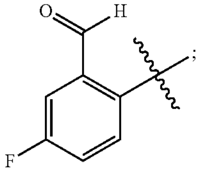
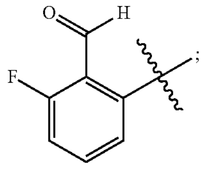 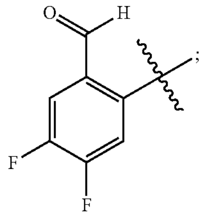
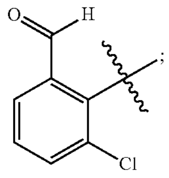 or 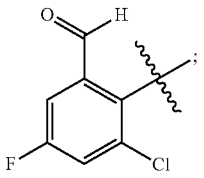
and
wherein, the structural segment
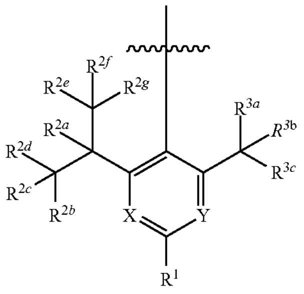

is selected from the following structures:
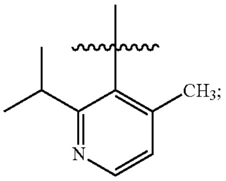
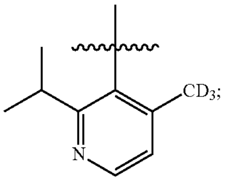
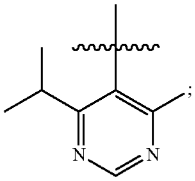
;
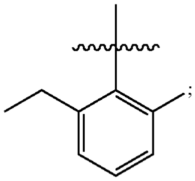
;
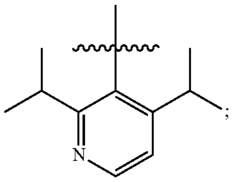
;
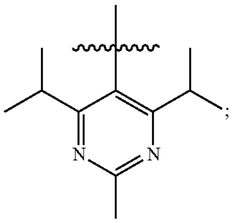
;
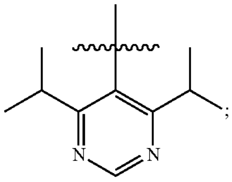
;
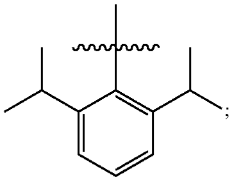
;
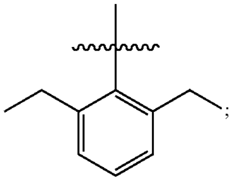
;
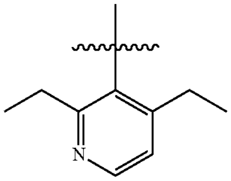
;
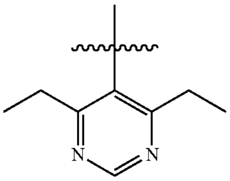
; or
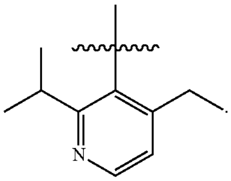
.
3. The compound represented according to claim 1, or a stereoisomer, tautomer, or pharmaceutically acceptable salt thereof, wherein the compound is selected from:
3-1
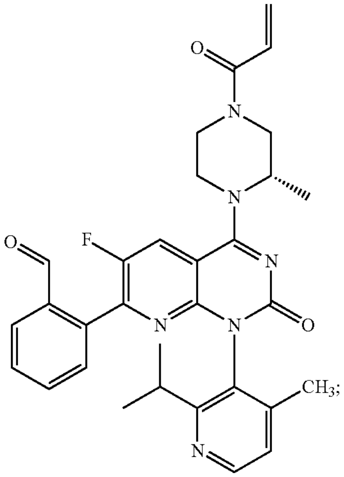
3-2
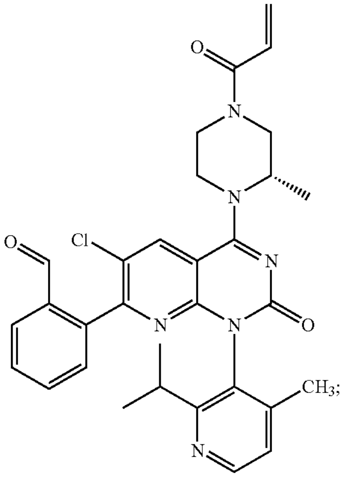
3-3
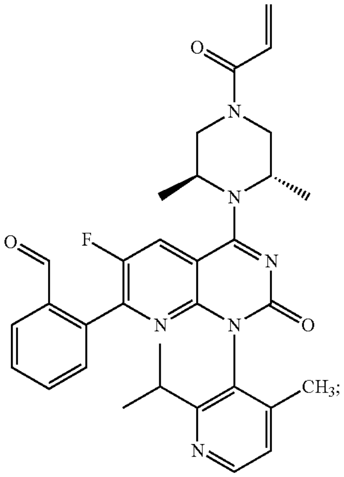

-continued
3-4
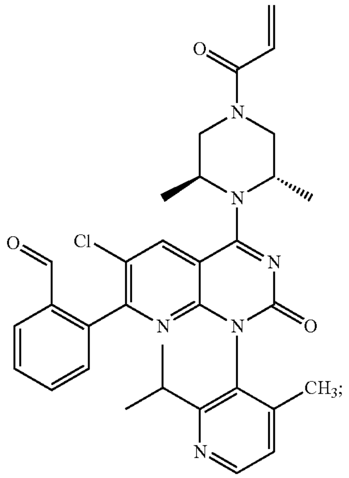
3-5
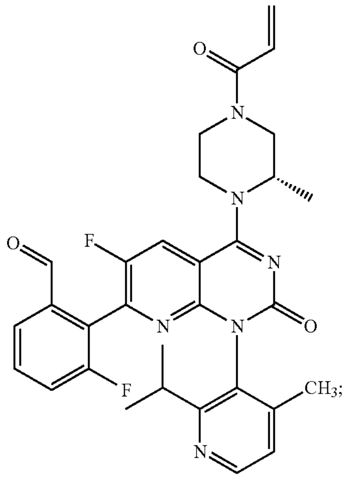
3-6
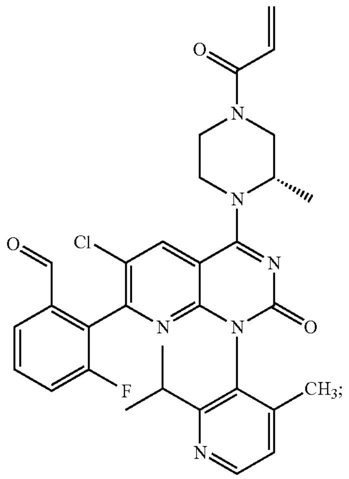
-continued
3-7
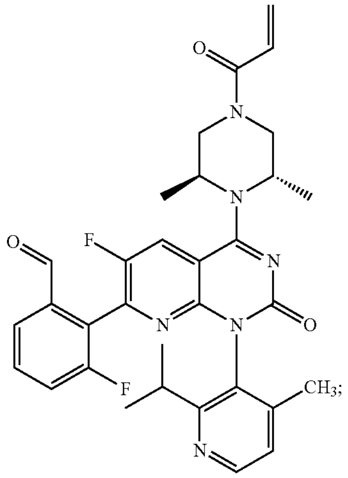
3-8
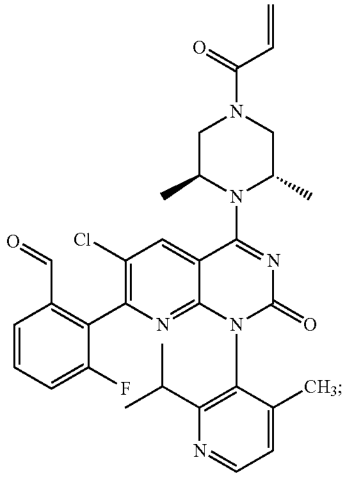
3-9
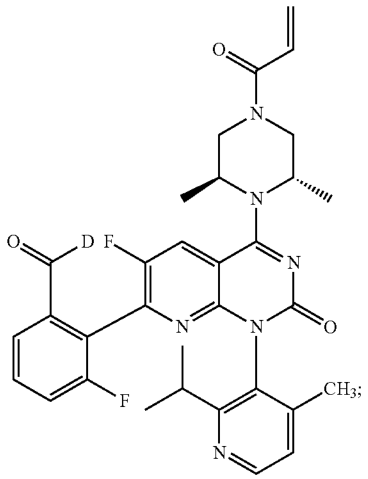

-continued
3-10
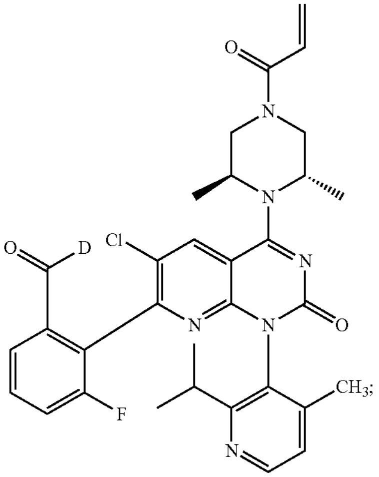
3-11
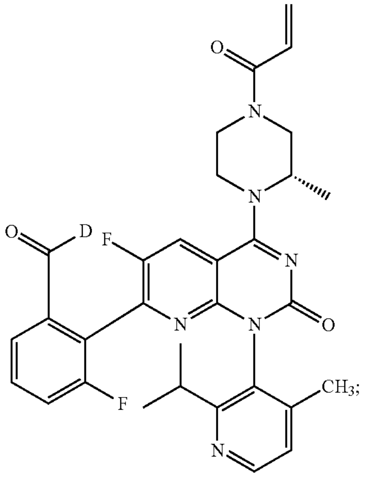
3-12
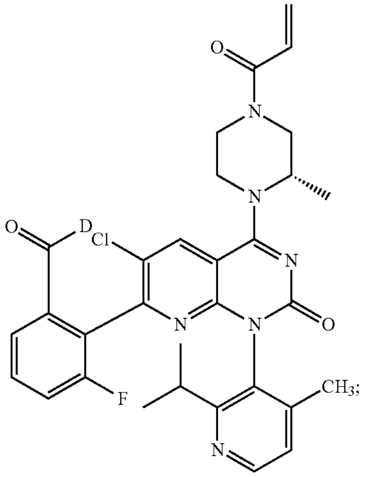
-continued
3-13
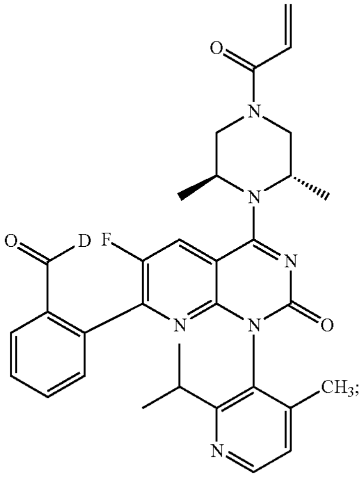
3-14
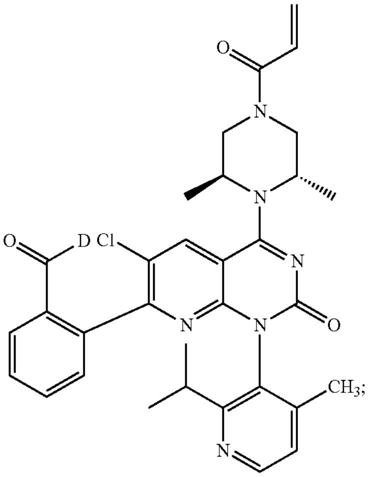
3-15
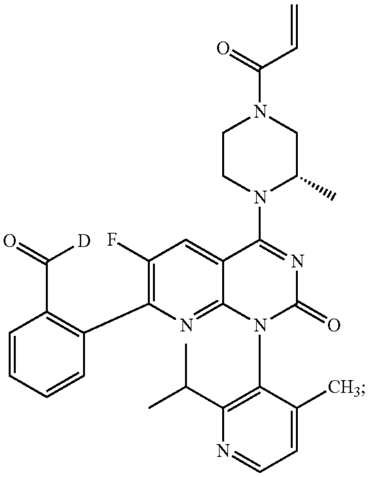

-continued
3-16
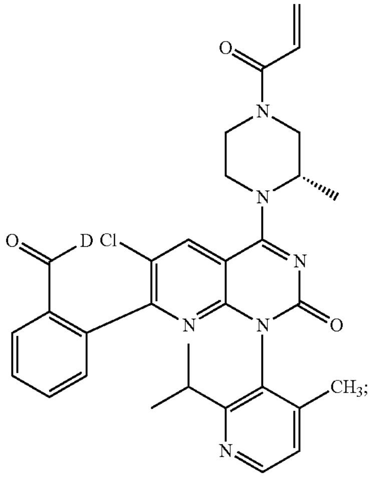
3-17
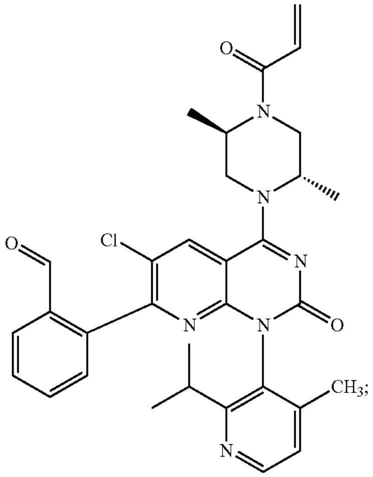
3-18
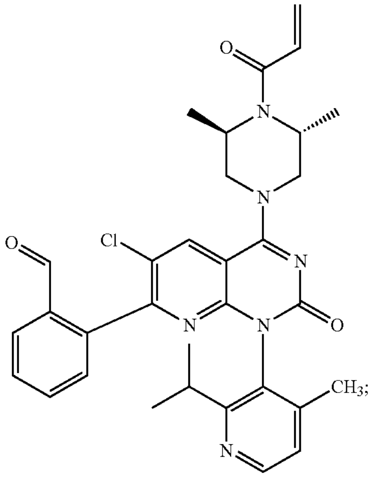
-continued
3-19
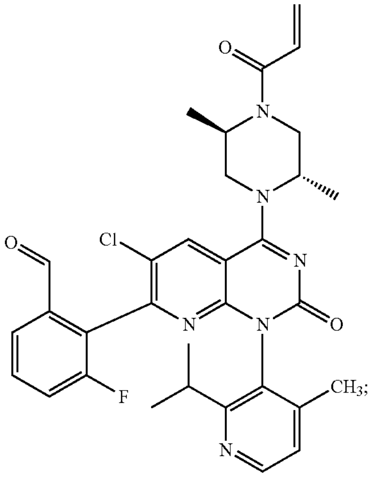
3-20
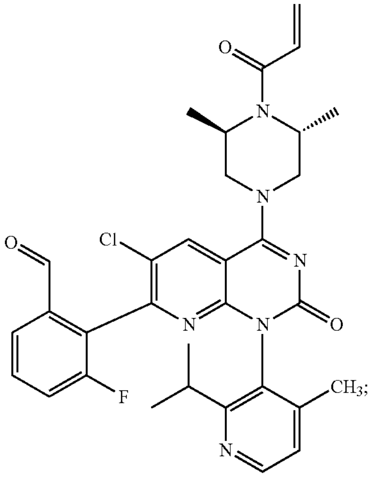
3-21
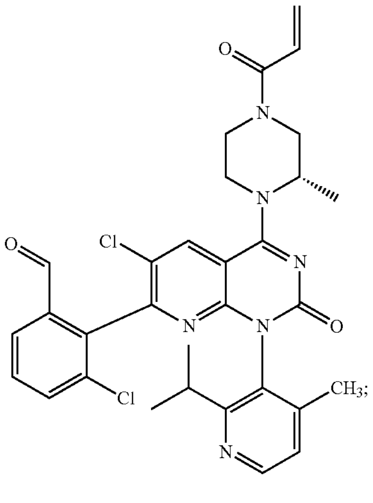

-continued
3-22
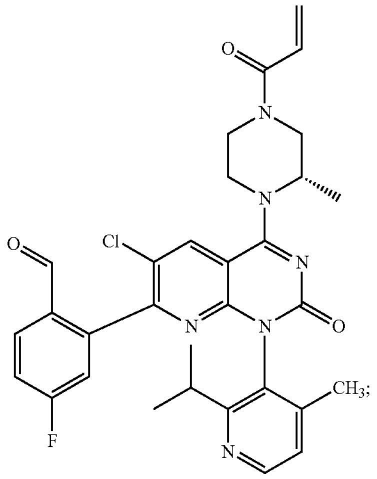
3-23
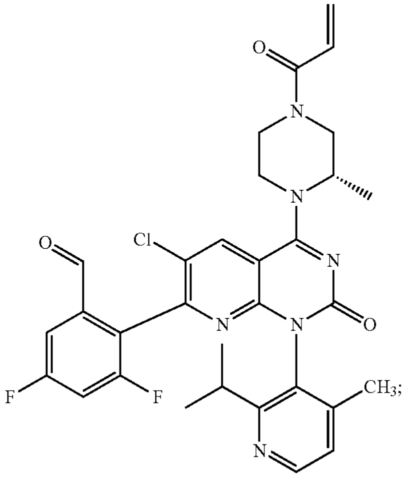
3-25
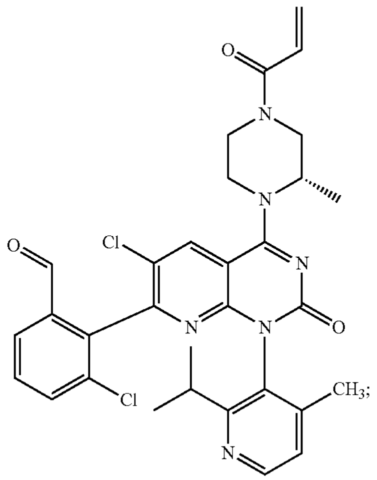
-continued
3-26
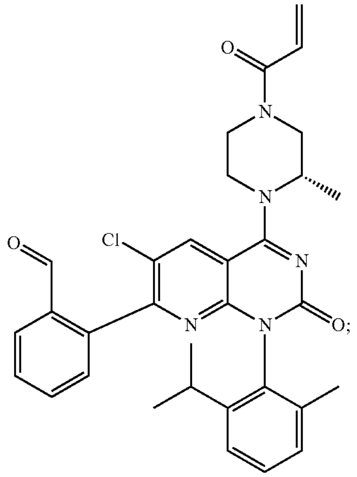
3-27
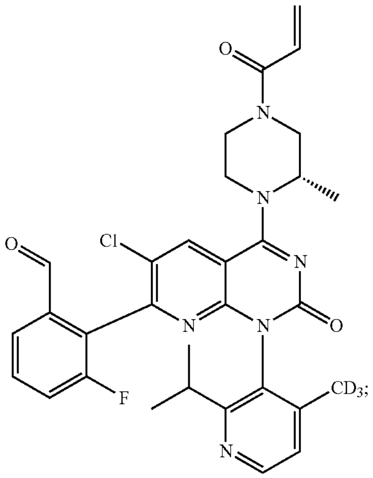
or
3-28
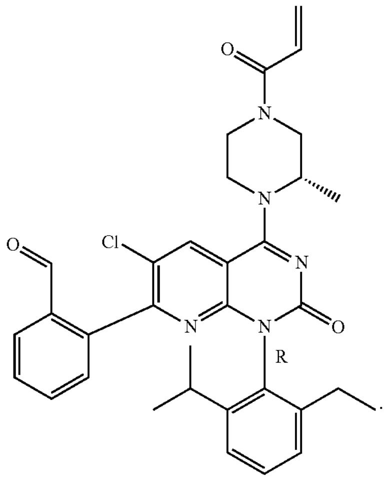

4. The compound according to claim 1, or a stereoisomer, tautomer, or pharmaceutically acceptable salt thereof, wherein the compound is selected from:
3-1B
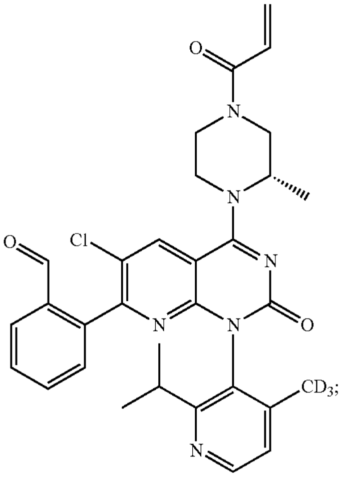
3-2B
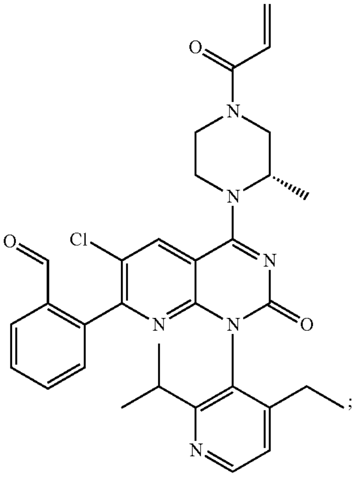
3-3B
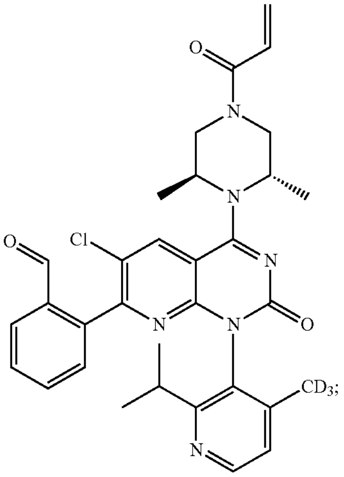
-continued
3-4B
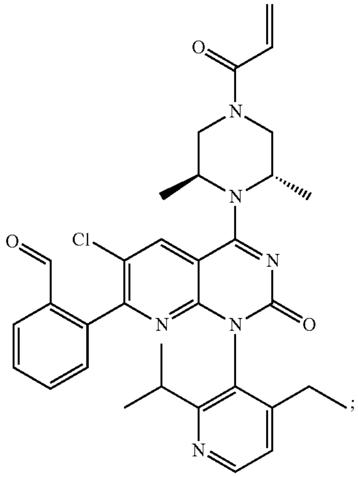
3-5B
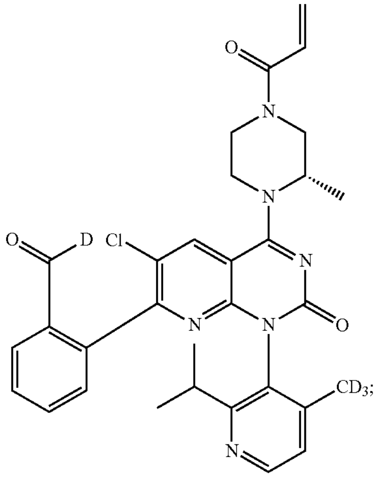
3-6B
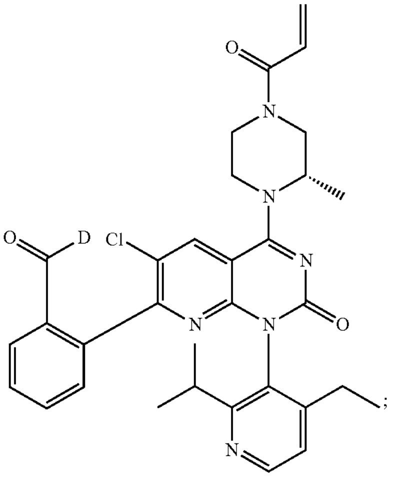

-continued
3-7B
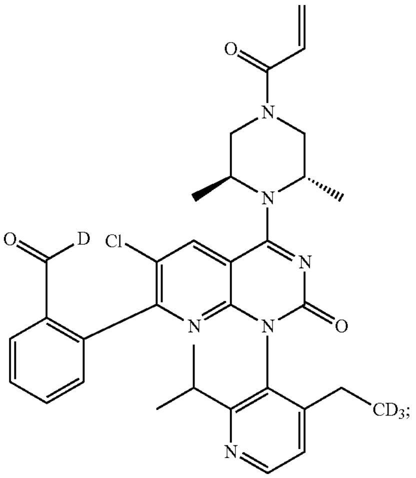
3-8B
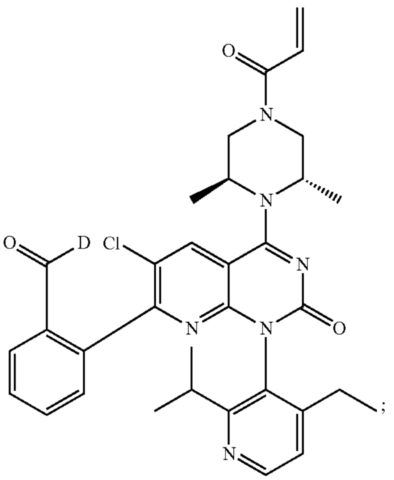
3-9B
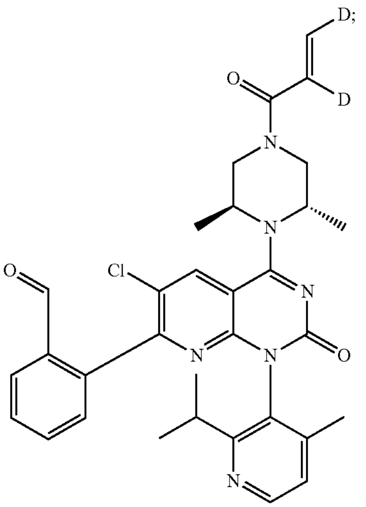
-continued
3-10B
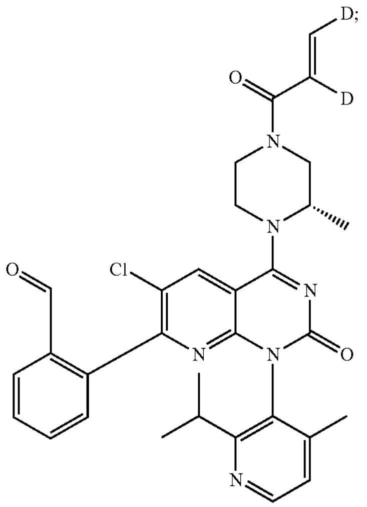
3-11B
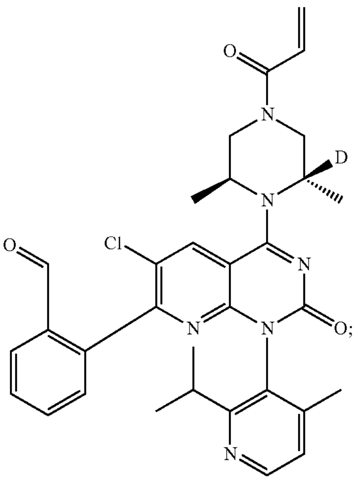
3-12B
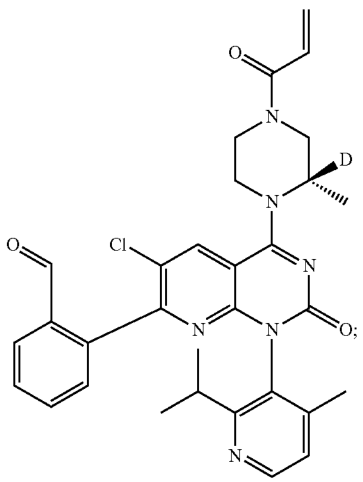

-continued
3-13B
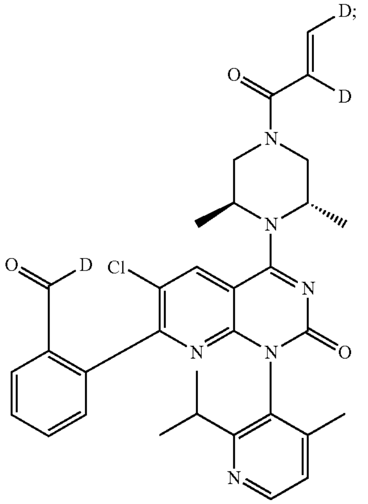
3-14B
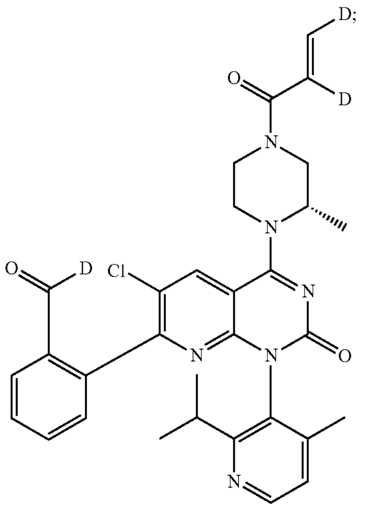
3-15B
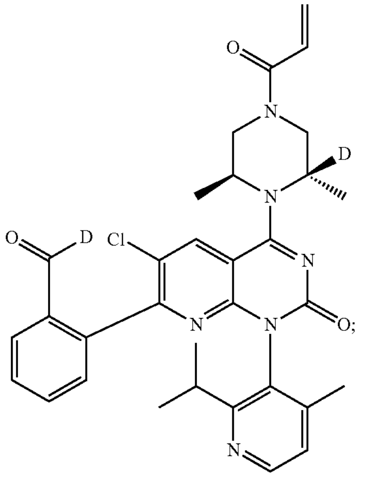
or
-continued
3-16B
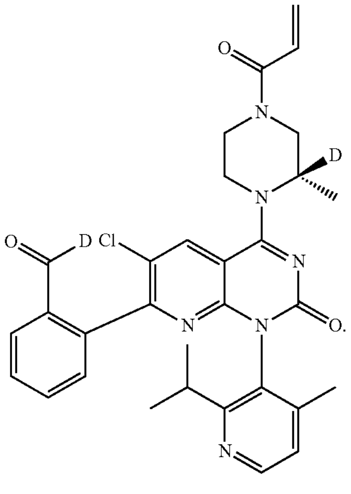
5. The compound according to claim 1, or a stereoisomer, tautomer, or pharmaceutically acceptable salt thereof, wherein the compound is selected from:
3-1MS
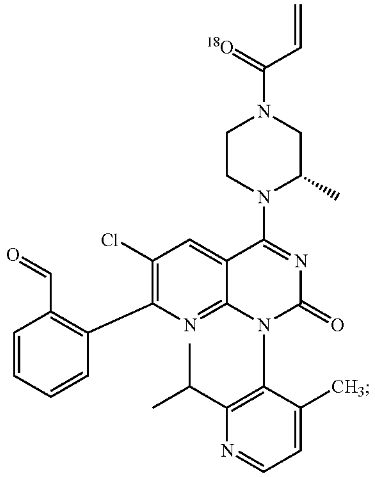
3-2MS
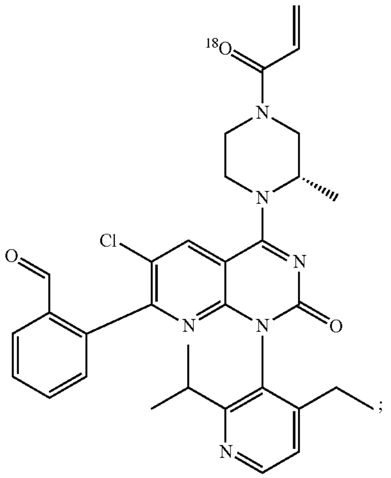

3-3MS
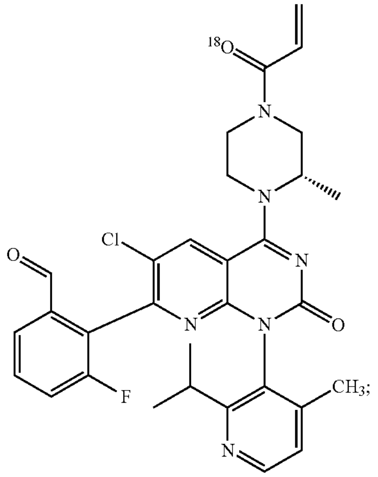
3-4MS
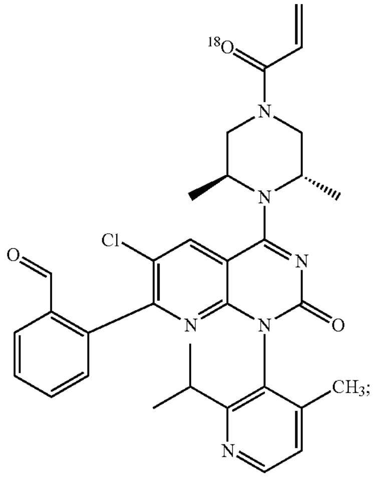
3-5MS
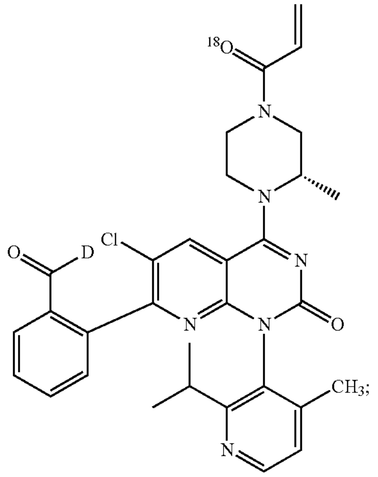
3-6MS
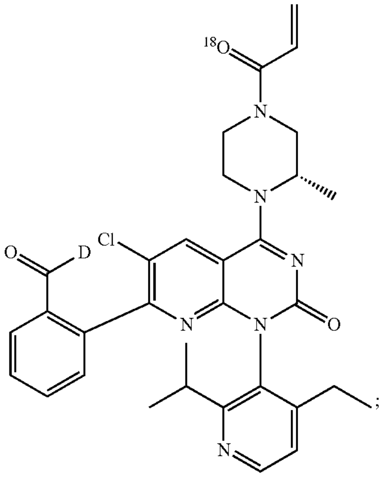
3-7MS
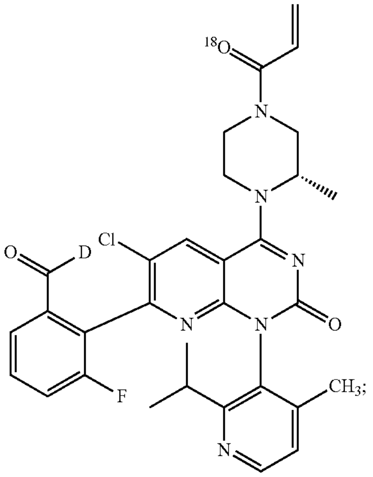
or
3-8MS
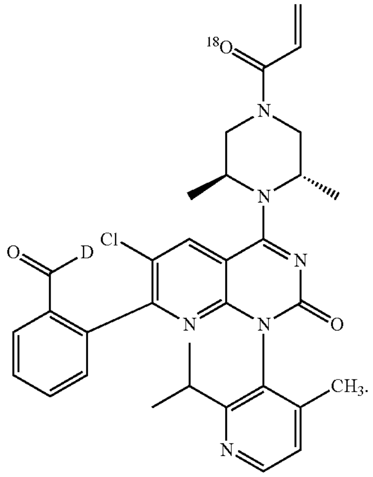
6. The compound according to claim 1, or a stereoisomer, tautomer, or pharmaceutically acceptable salt thereof, wherein the compound is selected from:

-continued
3K-1
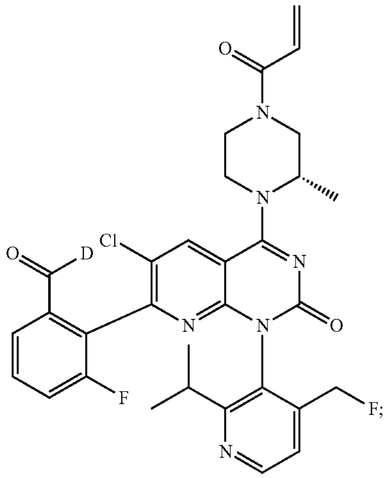
3K-2
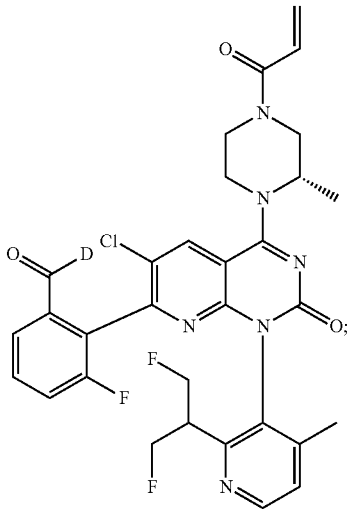
3K-3
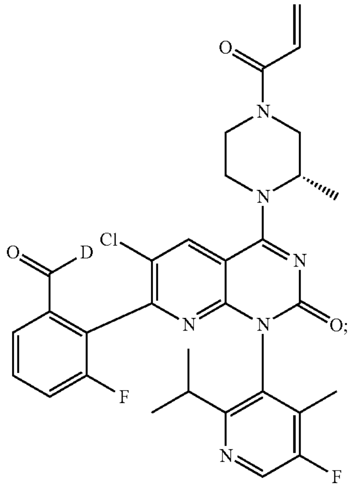
3K-5
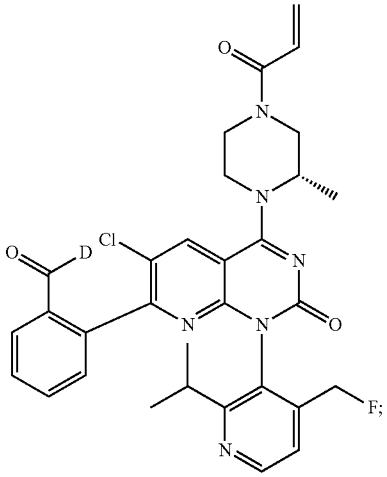
3K-6
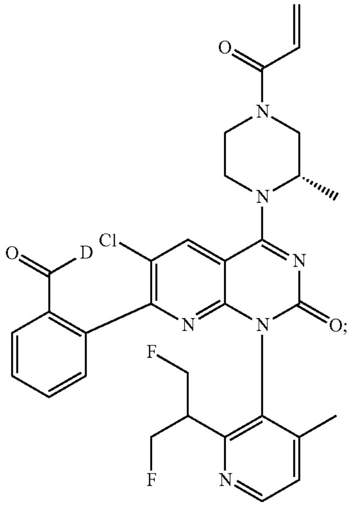
or
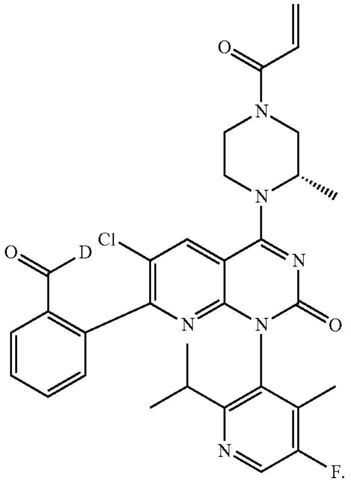 [SMILES: [2H]C(=O)c1ccccc1-c1nc2c(cc1Cl)c(N1CCN(C(=O)C=C)C[C@@H]1C)nc(=O)n2-c1c(C(C)C)ncc(F)c1C]
7. The compound according to claim 1, wherein the compound is represented by formula (IIIM), or a stereoisomer, tautomer, or pharmaceutically acceptable salt thereof,

IIIM

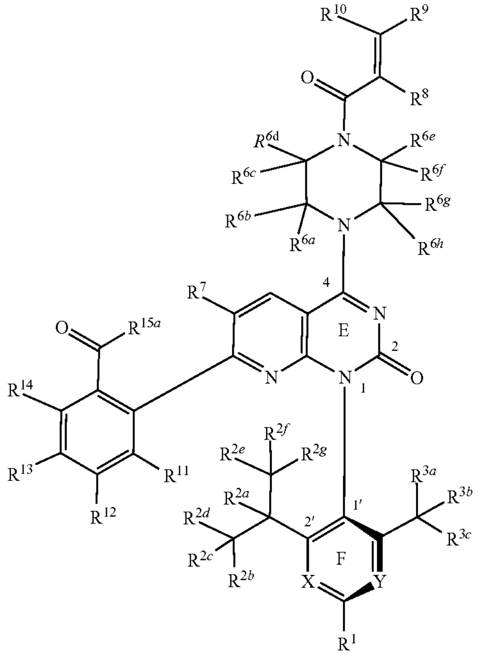

wherein, an axial chiral stereoconfiguration formed by connecting a nitrogen atom at the 1 position of the ring E with a carbon atom at the 1' position of the ring F is optically pure; and X is a nitrogen atom or $CR^4$, and Y is a nitrogen atom or $CR^5$;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{11}$, $R^{12}$, $R^{13}$, and $R^{14}$ are each independently selected from hydrogen, deuterium, alkyl or deuterated alkyl;

$R^{15a}$ is hydrogen or deuterium;

$R^{6a}$, $R^{6b}$, $R^{6c}$, $R^{6d}$, $R^{6e}$, $R^{6f}$, $R^{6g}$, and $R^{6h}$ are each independently selected from hydrogen, deuterium, methyl or trideuteriomethyl;

$R^7$ is fluorine or chlorine; and $R^8$, $R^9$, and $R^{10}$ are each independently selected from hydrogen, deuterium or fluorine;

wherein, the structural segment

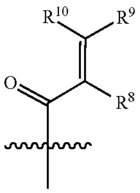

is selected from the following structures:

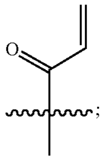 and 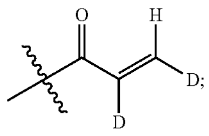

wherein, the structural segment

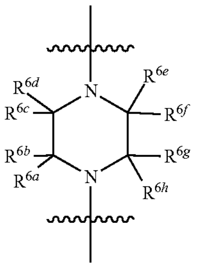

is selected from the following structures:

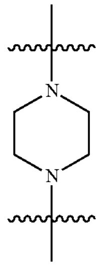 ; 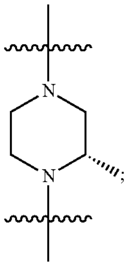 ; 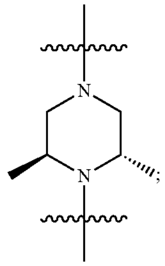

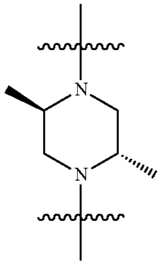 ; 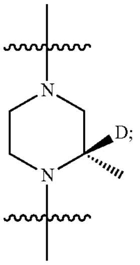 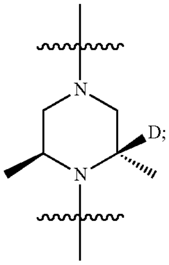

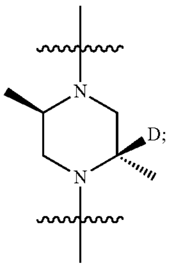 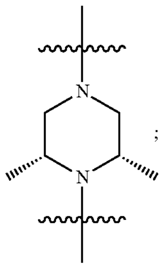 ;

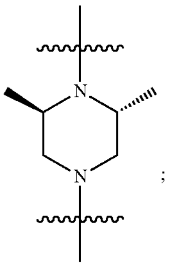 ; 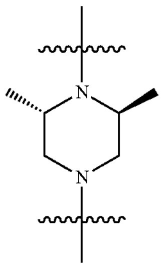 ; 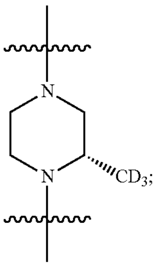

-continued
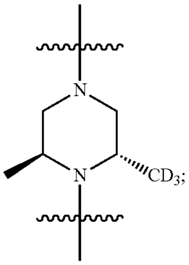
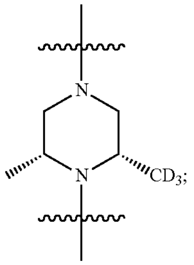
or
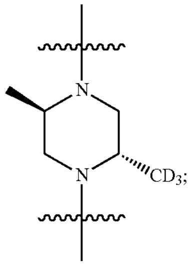
wherein, the structural segment
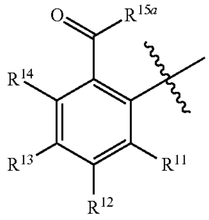
is selected from the following structures:
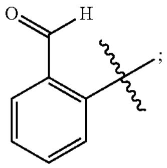
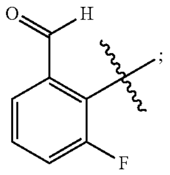
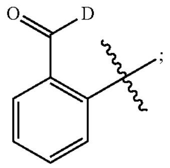
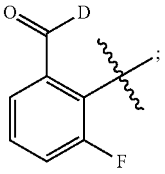
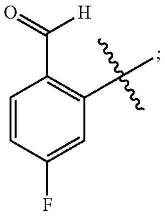
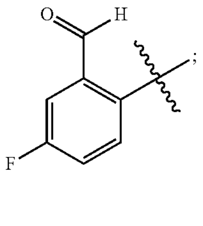
-continued
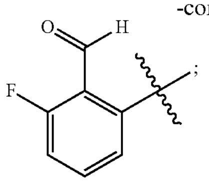
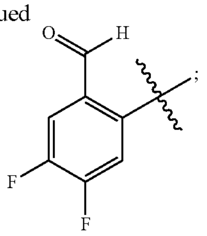
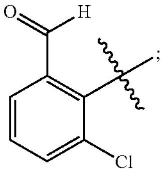
or
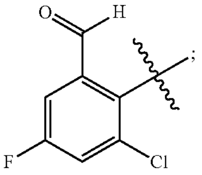
and
wherein, the structural segment
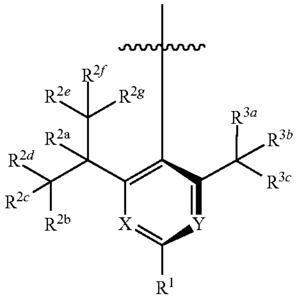
is selected from the following structures:
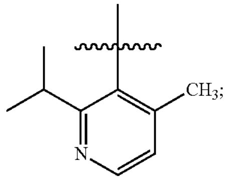
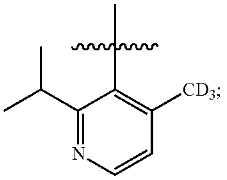
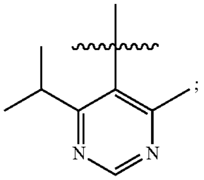
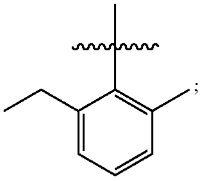
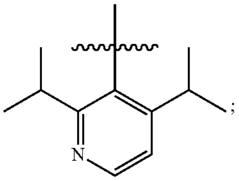
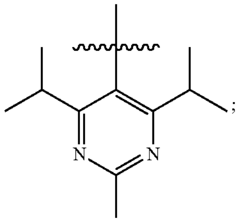
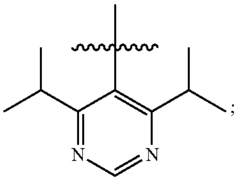
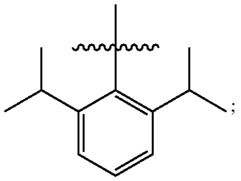

-continued

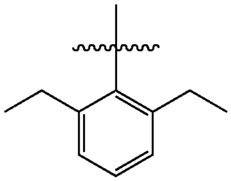

;

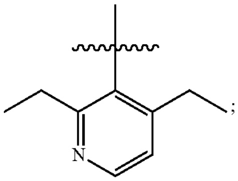

;

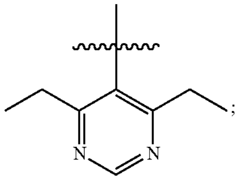

; or

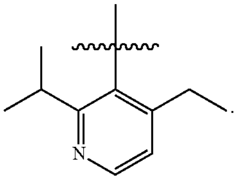

.

8. The compound according to claim 1, wherein the compound is represented by formula (IIIM-1), or a stereoisomer, tautomer, or pharmaceutically acceptable salt thereof,

IIIM-1

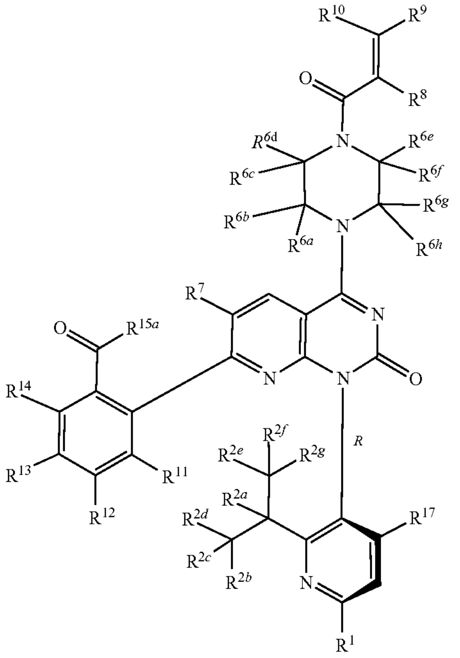

wherein:

$R^1$, $R^{2a}$, $R^{2b}$, $R^{2c}$, $R^{2d}$, $R^{2e}$, $R^{2f}$, $R^{2g}$, $R^{11}$, $R^{12}$, $R^{13}$, and $R^{14}$ are each independently selected from hydrogen, deuterium, alkyl or deuterated alkyl;

$R^{15a}$ is hydrogen or deuterium;

$R^{6a}$, $R^{6b}$, $R^{6c}$, $R^{6d}$, $R^{6e}$, $R^{6f}$, $R^{6g}$, and $R^{6h}$ are each independently selected from hydrogen, deuterium, methyl or trideuteriomethyl;

$R^7$ is fluorine or chlorine;

$R^8$, $R^9$, and $R^{10}$ are each independently selected from hydrogen, deuterium or fluorine; and $R^{17}$ is methyl, ethyl, deuterated methyl or deuterated ethyl;

wherein, the structural segment

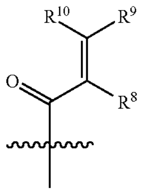

is selected from the following structures:

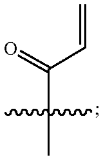

; or

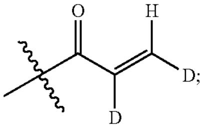

D;

wherein, the structural segment

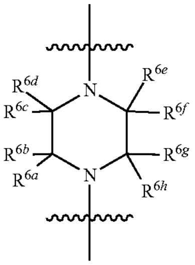

is selected from the following structures:

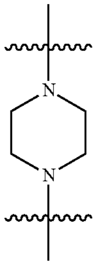

;

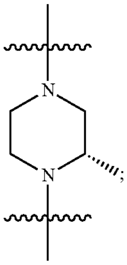

;

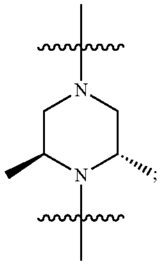

;

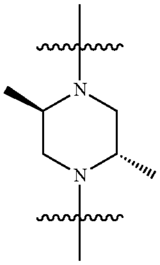

;

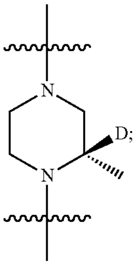

;

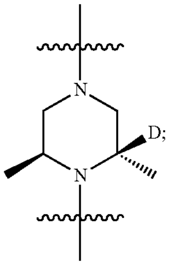

-continued
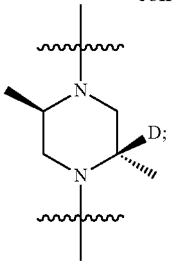
;
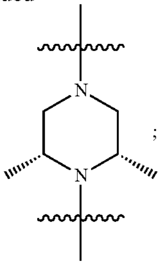
;
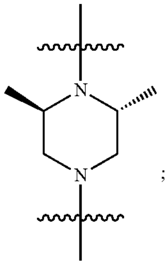
;
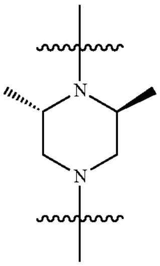
;
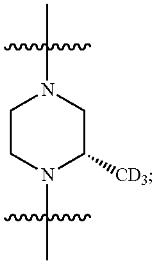
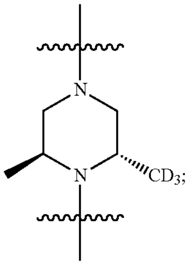
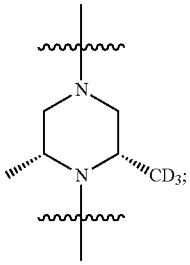
or
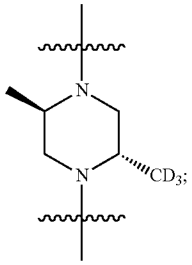
and
wherein, the structural segment
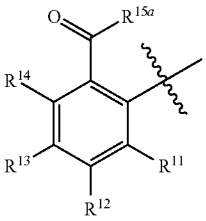
is selected from the following structures:
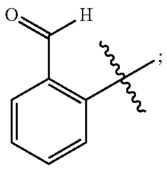
;
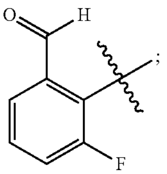
;
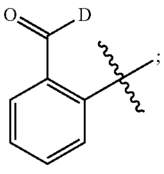
;
-continued
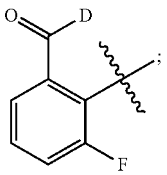
;
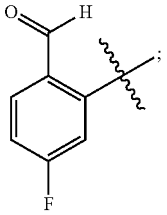
;
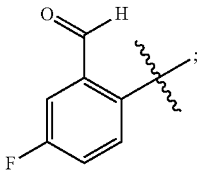
;
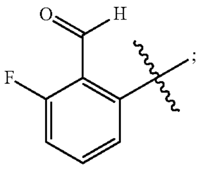
;
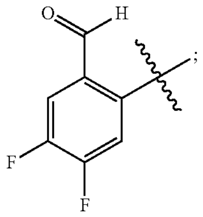
;
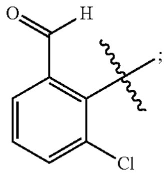
; or
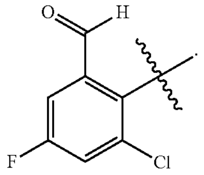
.
9. The compound according to claim 1, or a stereoisomer, tautomer, or pharmaceutically acceptable salt thereof, wherein the compound is selected from:
3-1M
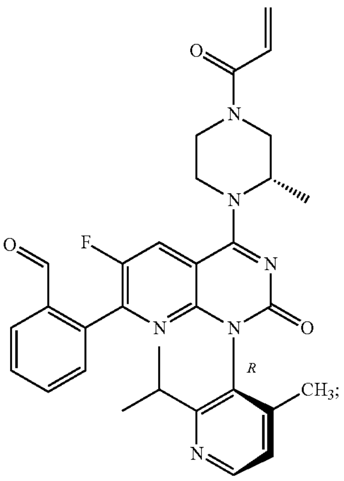

3-2M
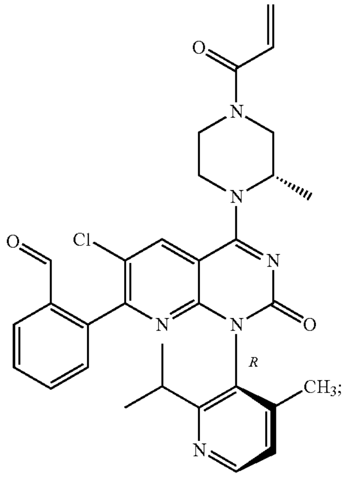
3-3M
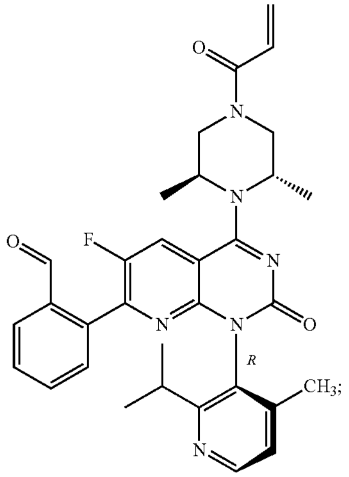
3-4M
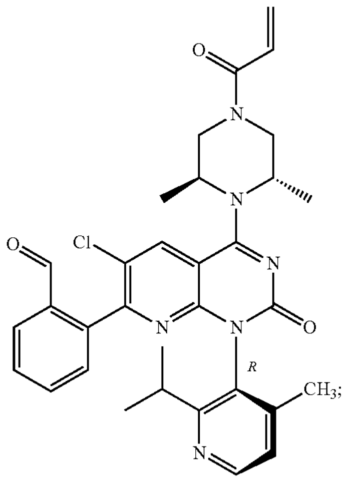
3-5M
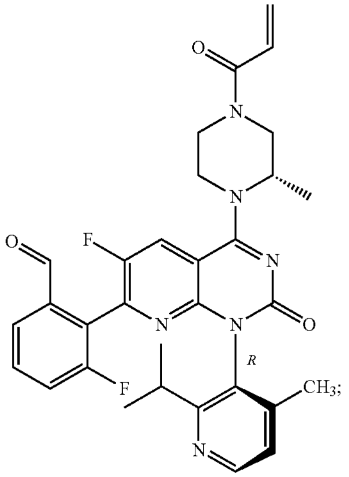
3-6M
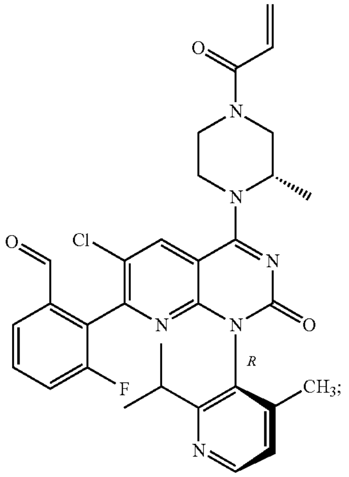
3-7M
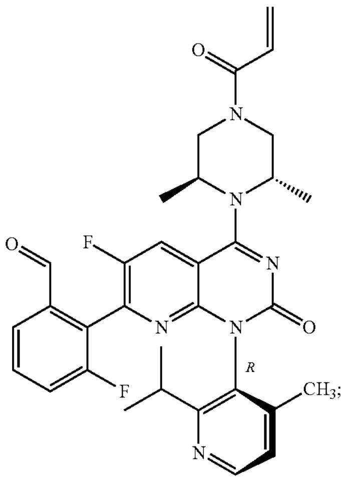

-continued
3-8M
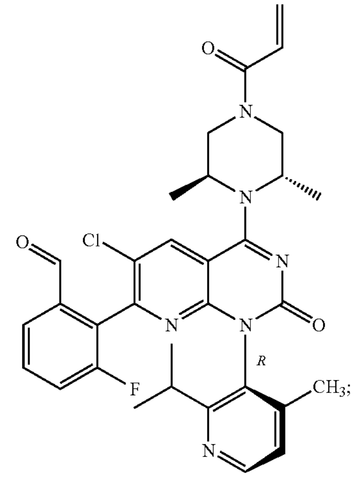
3-9M
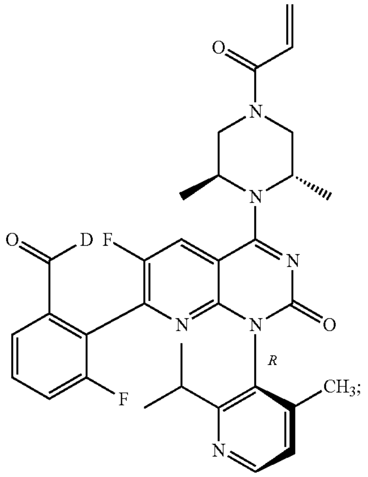
3-10M
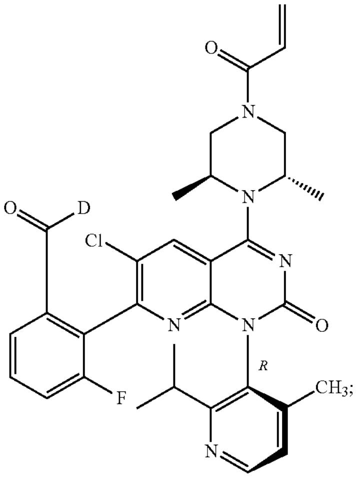
-continued
3-11M
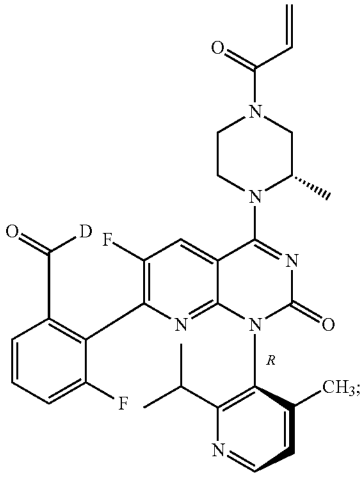
3-12M
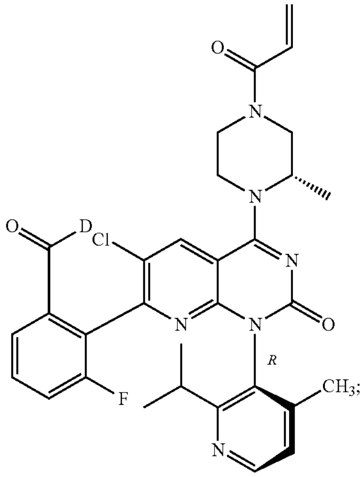
3-13M
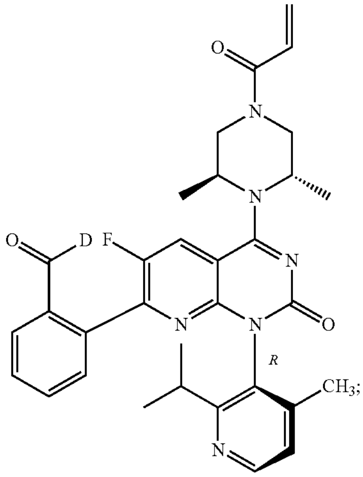

-continued
3-14M
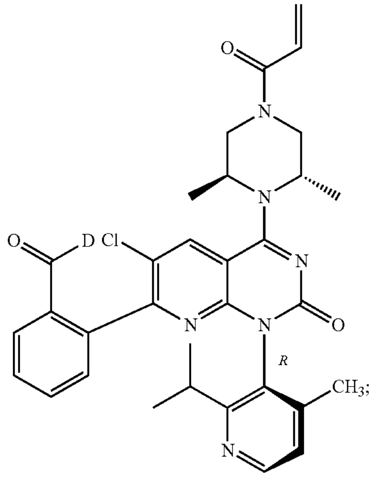
3-15M
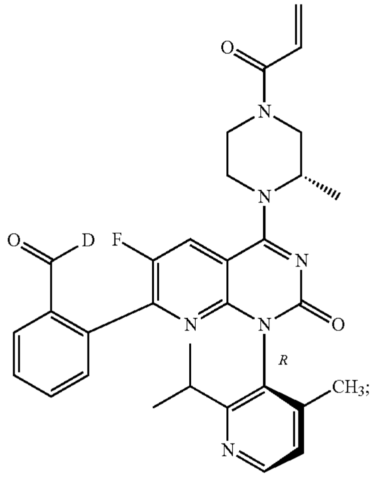
3-16M
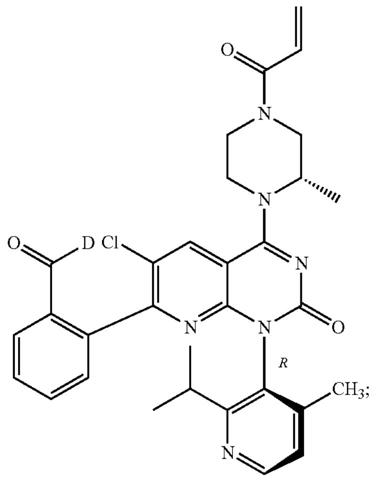
-continued
3-17M
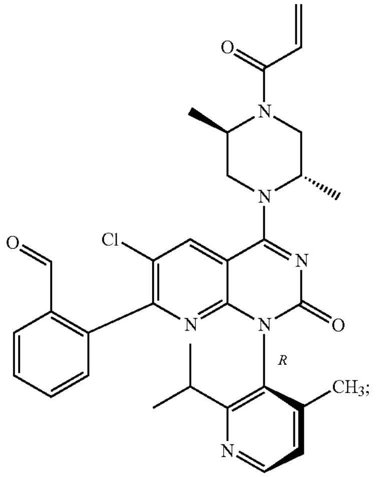
3-18M
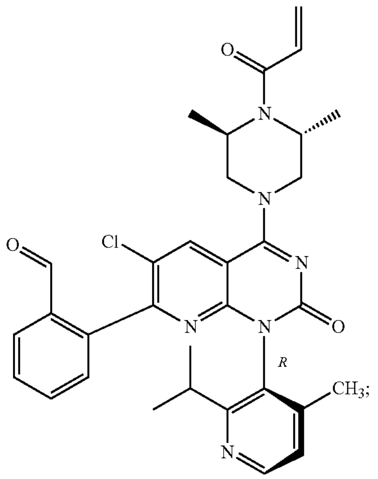
3-19M
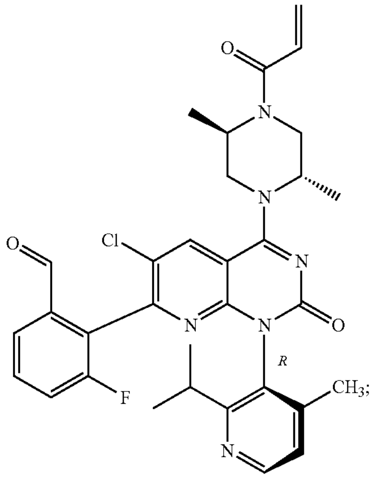

-continued
3-20M
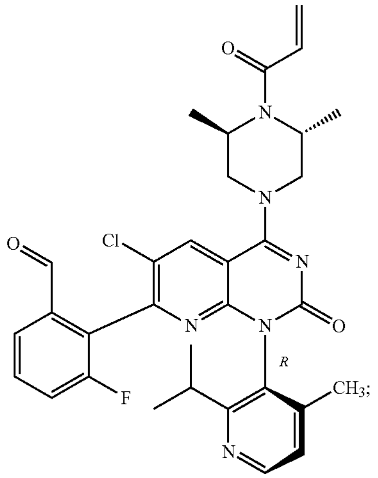
3-21M
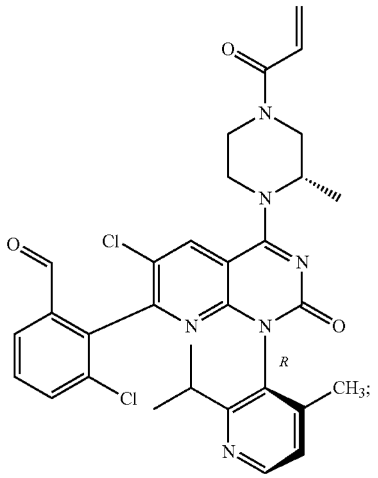
3-22M
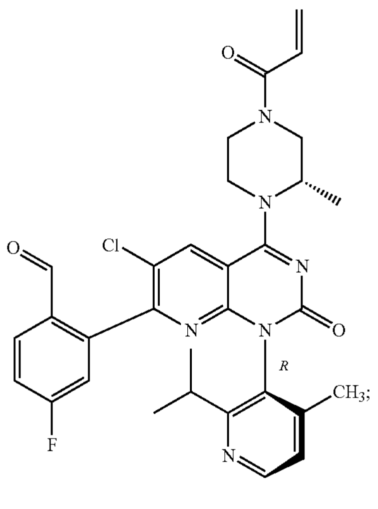
-continued
3-23M
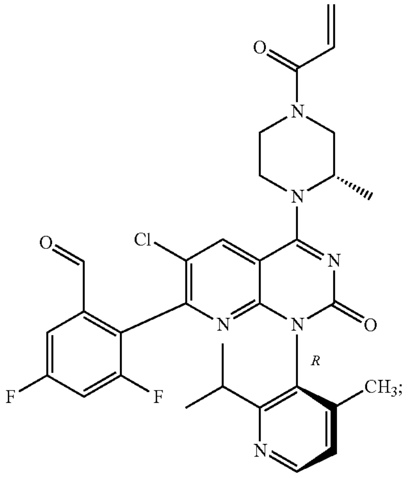
3-25M
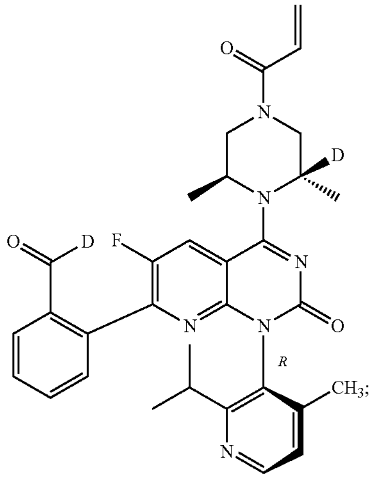
3-26M
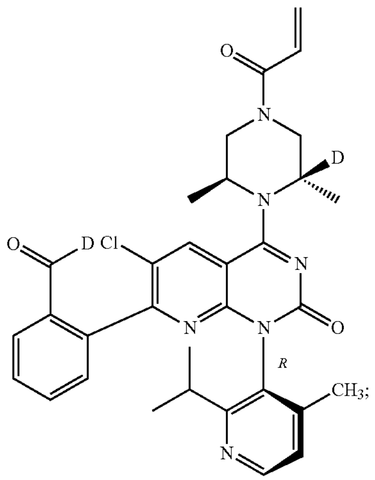

-continued
3-27M
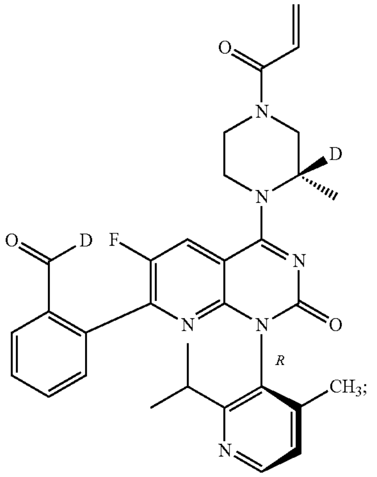
or
3-28M
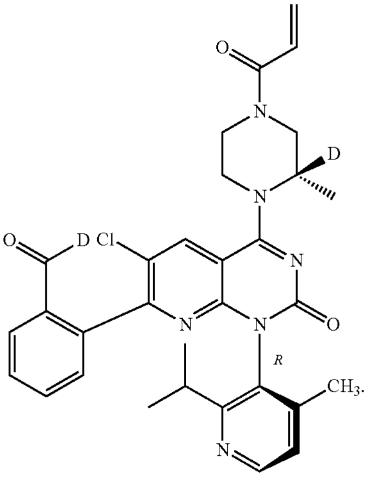
10. The compound according to claim 1, or a stereoisomer, tautomer, or pharmaceutically acceptable salt thereof, wherein the compound is selected from the following compounds with an axial chiral stereoconfiguration as R configuration:
3-1MIS
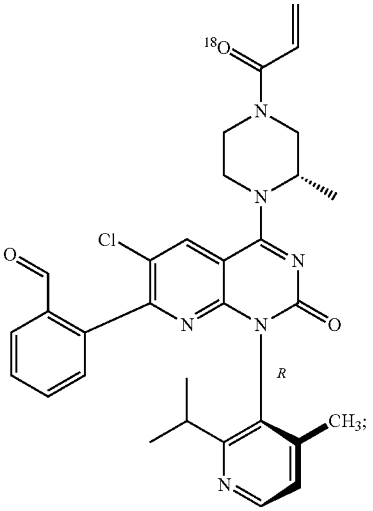
3-2MIS
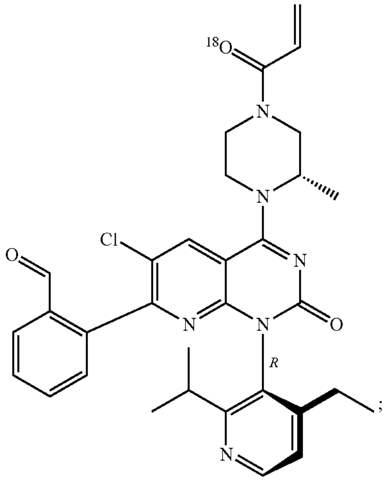
3-3MIS
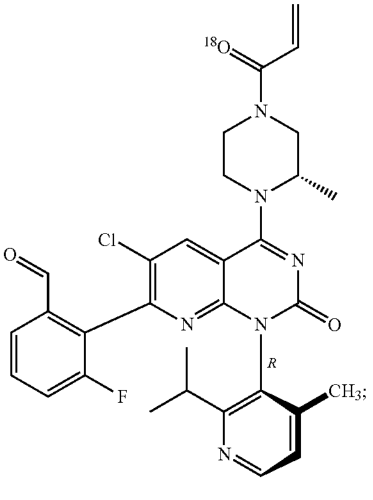

-continued
3-4MIS
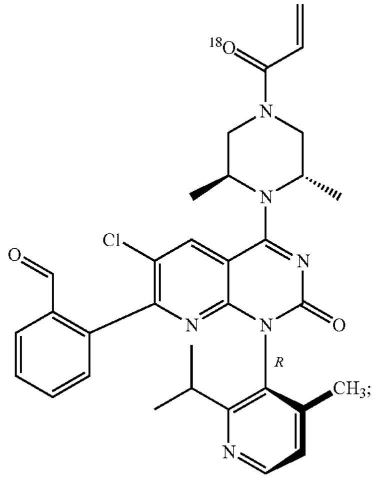
3-5MIS
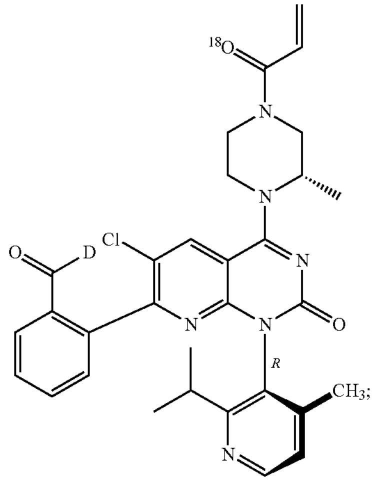
3-6MIS
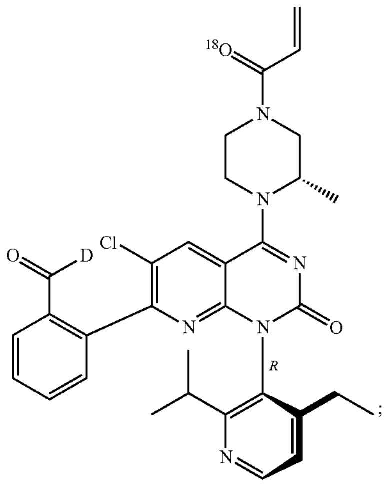
-continued
3-7MIS
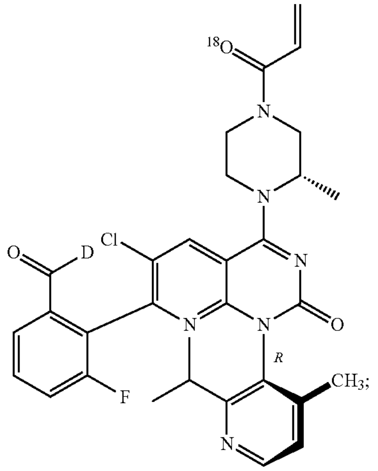
or
3-8MIS
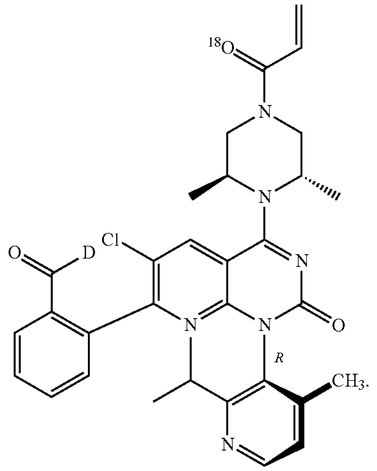
11. The compound according to claim 1, or a stereoisomer, tautomer, or pharmaceutically acceptable salt thereof, wherein the compound is selected from the following compounds with an axial chiral stereoconfiguration as R configuration:
3K-1M
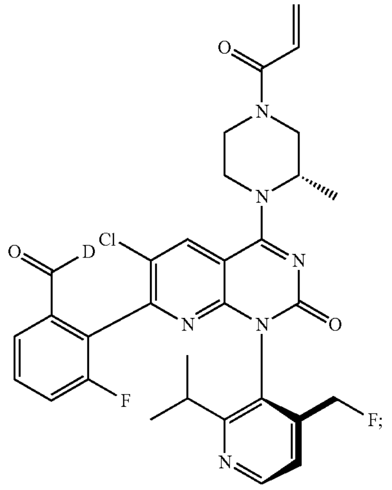

-continued
3K-2M
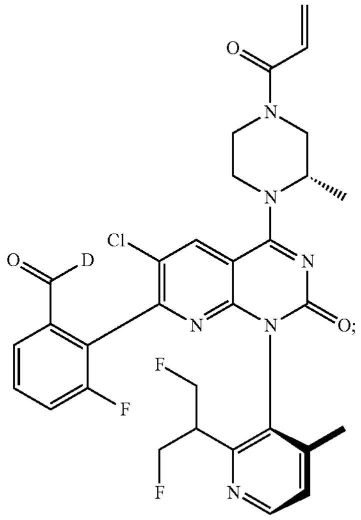
3K-3M
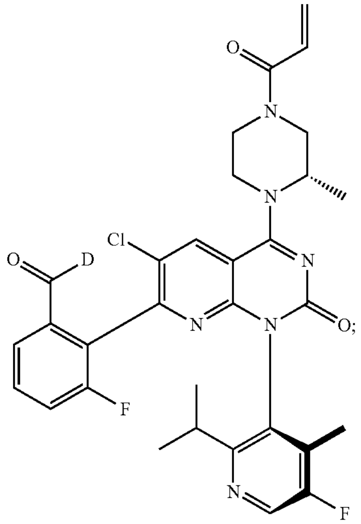
3K-5M
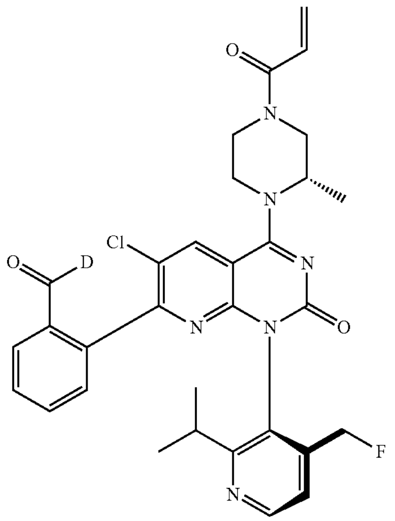
-continued
3K-6M
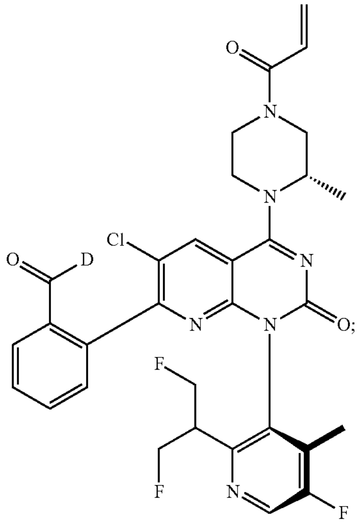
3K-7M
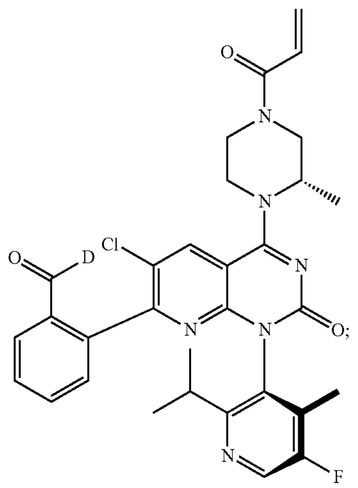
3K-9M
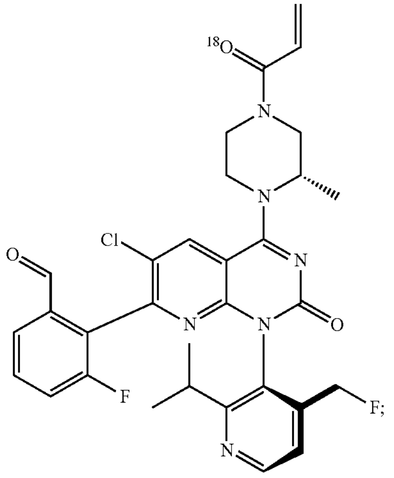

-continued
3K-10M
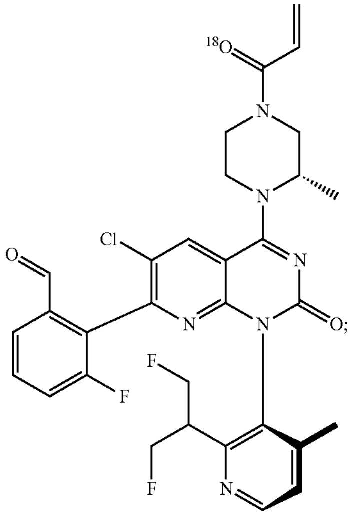
3K-11M
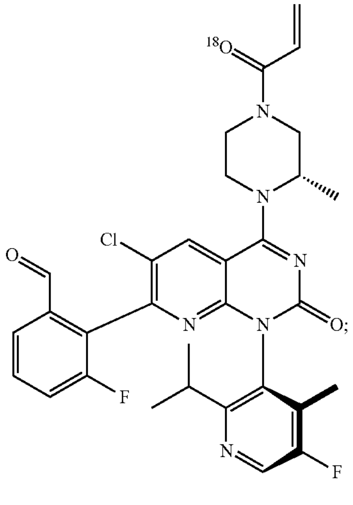
-continued
3K-13M
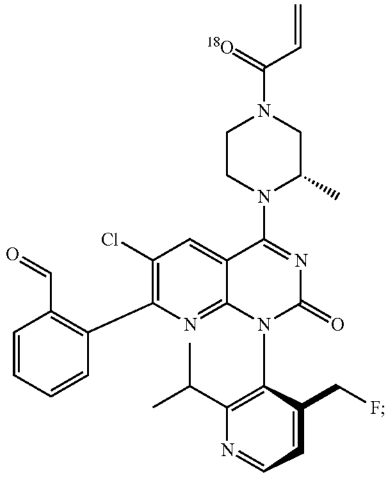
3K-14M
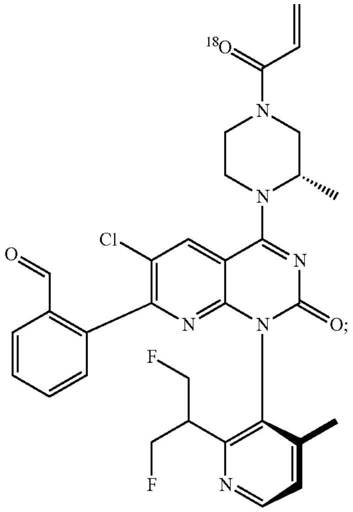
or -continued 3K-15M

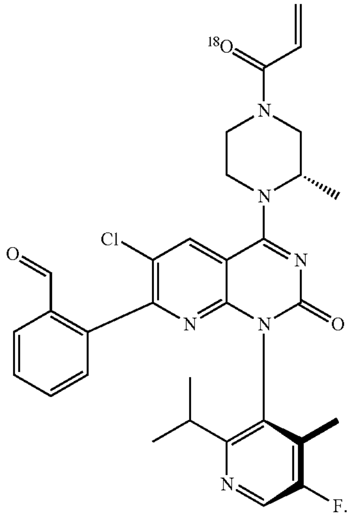

12. The compound according to claim 1, or a stereoisomer, tautomer, or pharmaceutically acceptable salt thereof, wherein the compound is selected from:

3-29

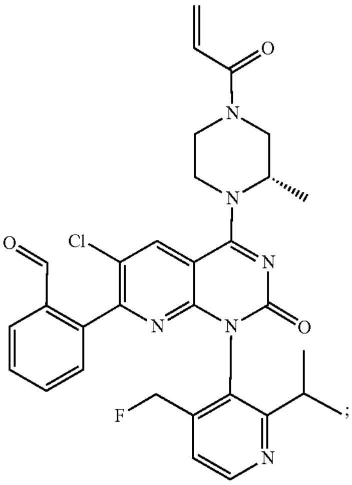

; or

-continued 3-31

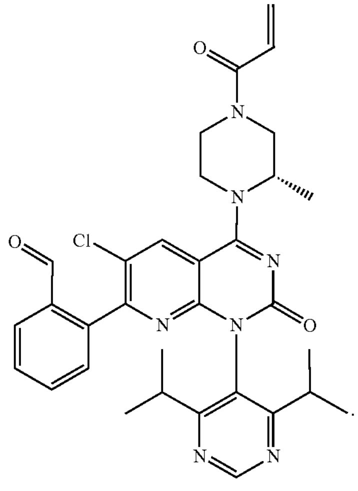

13. The compound according to claim 1, or a stereoisomer, tautomer, or pharmaceutically acceptable salt thereof, wherein the compound is axially chiral.

14. A pharmaceutical composition, comprising an effective dose of the compound, or the stereoisomer, the tautomer thereof, or the pharmaceutically acceptable salt thereof according to claim 1, and a pharmaceutically acceptable carrier.

15. A method for treating pancreatic cancer or lung cancer comprising administering a therapeutically effective amount of the compound or the pharmaceutically acceptable salt thereof according to claim 1, or a pharmaceutical composition comprising the compound or a pharmaceutically acceptable salt thereof, wherein the compound or the pharmaceutically acceptable salt thereof, or the pharmaceutical composition comprising the compound or the pharmaceutically acceptable salt thereof is capable of being used alone or in combination with other therapeutic methods comprising immunotherapy.

* * * * *